(12) United States Patent
Wathier et al.

(10) Patent No.: US 12,252,518 B2
(45) Date of Patent: Mar. 18, 2025

(54) METHODS OF TREATING NON-ARTERITIC ANTERIOR ISCHEMIC OPTIC NEUROPATHY

(71) Applicant: Life Biosciences, Inc., Boston, MA (US)

(72) Inventors: Michel Wathier, Boston, MA (US); Jennifer Cermak, Boston, MA (US); Joan Mannick, Boston, MA (US)

(73) Assignee: Life Biosciences, Inc., Boston, MA (US)

( * ) Notice: Subject to any disclaimer, the term of this patent is extended or adjusted under 35 U.S.C. 154(b) by 0 days.

(21) Appl. No.: 18/312,538

(22) Filed: May 4, 2023

(65) Prior Publication Data

US 2024/0228561 A1    Jul. 11, 2024

Related U.S. Application Data

(60) Provisional application No. 63/499,864, filed on May 3, 2023, provisional application No. 63/478,843, filed on Jan. 6, 2023.

(51) Int. Cl.
| | |
|---|---|
| *A61K 48/00* | (2006.01) |
| *A61K 31/65* | (2006.01) |
| *A61P 25/02* | (2006.01) |
| *C07K 14/47* | (2006.01) |
| *C12N 15/86* | (2006.01) |
| *C07H 21/04* | (2006.01) |

(52) U.S. Cl.
CPC .......... *C07K 14/4702* (2013.01); *A61K 31/65* (2013.01); *A61P 25/02* (2018.01); *C12N 15/86* (2013.01); *A61K 48/005* (2013.01); *A61K 48/0058* (2013.01); *C07H 21/04* (2013.01)

(58) Field of Classification Search
CPC .............. A61K 48/0016; A61K 48/005; A61K 48/0058; A61K 48/0075; C12N 15/79; C12N 15/85; C12N 15/86; C07H 21/04
See application file for complete search history.

(56) References Cited

U.S. PATENT DOCUMENTS

| | | |
|---|---|---|
| 5,928,941 A | 7/1999 | Lee et al. |
| 6,750,015 B2 | 6/2004 | Horwitz et al. |
| 7,851,595 B2 | 12/2010 | Duncan |
| 8,158,415 B2 | 4/2012 | Jo et al. |
| 8,252,901 B2 | 8/2012 | Duncan |
| 8,278,104 B2 | 10/2012 | Yamanaka et al. |
| 8,326,547 B2 | 12/2012 | Liu et al. |
| 8,609,373 B2 | 12/2013 | Liu et al. |
| 8,716,465 B2 | 5/2014 | Rossi et al. |
| 8,883,506 B2 | 11/2014 | Rossi et al. |
| 8,957,037 B2 | 2/2015 | Collard et al. |
| 9,228,204 B2 | 1/2016 | Pulst et al. |
| 9,580,689 B2 | 2/2017 | Kikyo et al. |
| 9,862,926 B2 | 1/2018 | Chin et al. |
| 9,862,930 B2 | 1/2018 | Dowdy et al. |
| 9,920,333 B2 | 3/2018 | Pulst et al. |
| 2002/0165180 A1 | 11/2002 | Weaver |
| 2003/0065157 A1 | 4/2003 | Lasek |
| 2003/0138772 A1 | 7/2003 | Gao et al. |
| 2003/0138799 A1 | 7/2003 | Ruppert et al. |
| 2003/0165921 A1 | 9/2003 | Tang et al. |
| 2004/0219579 A1 | 11/2004 | Aziz et al. |
| 2004/0235073 A1 | 11/2004 | Ruppert et al. |
| 2005/0064454 A1 | 3/2005 | Young et al. |
| 2005/0208496 A1 | 9/2005 | Ohtani et al. |
| 2006/0263774 A1 | 11/2006 | Clark et al. |
| 2007/0042392 A1 | 2/2007 | Tang et al. |
| 2007/0048301 A1 | 3/2007 | Bodary-winter et al. |
| 2007/0060743 A1 | 3/2007 | Tang et al. |
| 2007/0072175 A1 | 3/2007 | Cooper et al. |
| 2007/0161031 A1 | 7/2007 | Trinklein et al. |
| 2008/0050379 A1 | 2/2008 | Young et al. |
| 2008/0050393 A1 | 2/2008 | Tang et al. |
| 2008/0233648 A1 | 9/2008 | Sugaya et al. |
| 2010/0048678 A1 | 2/2010 | Smit et al. |
| 2010/0074864 A1 | 3/2010 | Achiron et al. |
| 2010/0099144 A1 | 4/2010 | Jo et al. |
| 2010/0150889 A1 | 6/2010 | Townes et al. |
| 2010/0190250 A1 | 7/2010 | Hu |
| 2010/0273220 A1 | 10/2010 | Yanik et al. |
| 2010/0285589 A1 | 11/2010 | Lowry et al. |
| 2011/0002940 A1 | 1/2011 | Piek et al. |
| 2011/0081708 A1 | 4/2011 | Liu et al. |
| 2012/0064048 A1 | 3/2012 | Collard et al. |

(Continued)

FOREIGN PATENT DOCUMENTS

| | | |
|---|---|---|
| EP | 1071776 A2 | 1/2001 |
| EP | 1358349 A2 | 11/2003 |

(Continued)

OTHER PUBLICATIONS

Kotterman et al., 2014 (Nature Reviews, vol. 15, p. 445-451).*
Shim et al., 2017 (Current Gene Therapy, vol. 17, No. 5, p. 1-18).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16).*
Bulcha et al., 2021 (Signal Transduction and Targeted Therapy, 6:53, p. 1-24).*

(Continued)

*Primary Examiner* — Shin Lin Chen
(74) *Attorney, Agent, or Firm* — Foley Hoag LLP; David E. Shore

(57) ABSTRACT

Disclosed herein are methods for preventing or treating non-arteritic anterior ischemic optic neuropathy in a subject by administering to the subject a nucleic acid molecule comprising a nucleic acid sequence encoding OCT4, a nucleic acid sequence encoding SOX2, and a nucleic acid sequence encoding KLF4.

30 Claims, 10 Drawing Sheets

Specification includes a Sequence Listing.

(56) References Cited

U.S. PATENT DOCUMENTS

| | | |
|---|---|---|
| 2012/0095188 A1 | 4/2012 | Jo et al. |
| 2012/0196328 A1 | 8/2012 | Liu et al. |
| 2012/0208278 A1 | 8/2012 | Yanik et al. |
| 2012/0225076 A1 | 9/2012 | Peeper et al. |
| 2012/0322864 A1 | 12/2012 | Rossi et al. |
| 2012/0322865 A1 | 12/2012 | Rossi et al. |
| 2013/0017596 A1 | 1/2013 | Townes et al. |
| 2013/0059752 A1 | 3/2013 | Bodary-winter et al. |
| 2013/0065791 A1 | 3/2013 | Rosenthal et al. |
| 2013/0130387 A1 | 5/2013 | Itskovitz-eldor et al. |
| 2014/0093486 A1 | 4/2014 | Chiou et al. |
| 2014/0128277 A1 | 5/2014 | Moller et al. |
| 2014/0170752 A1 | 6/2014 | Pulst et al. |
| 2015/0159143 A1 | 6/2015 | Dowdy et al. |
| 2015/0299701 A1 | 10/2015 | Collard et al. |
| 2016/0032393 A1 | 2/2016 | Achiron et al. |
| 2016/0076000 A1 | 3/2016 | Townes et al. |
| 2016/0102127 A1 | 4/2016 | Thepen et al. |
| 2017/0073639 A1 | 3/2017 | Eilertsen et al. |
| 2018/0155789 A1 | 6/2018 | Maeder et al. |
| 2018/0195047 A1 | 7/2018 | Jo |
| 2018/0216079 A1 | 8/2018 | Dowdy et al. |
| 2018/0299430 A1 | 10/2018 | Kuo et al. |
| 2018/0305689 A1 | 10/2018 | Sætrom et al. |
| 2019/0055518 A1 | 2/2019 | Young-ae |
| 2020/0283778 A1 | 9/2020 | Shah et al. |
| 2021/0403923 A1 | 12/2021 | Sinclair et al. |
| 2023/0048010 A1 | 2/2023 | Sinclair et al. |

FOREIGN PATENT DOCUMENTS

| | | |
|---|---|---|
| EP | 1394274 A2 | 3/2004 |
| EP | 1572987 A2 | 9/2005 |
| EP | 1578367 A2 | 9/2005 |
| EP | 1578996 A2 | 9/2005 |
| EP | 1888627 A2 | 2/2008 |
| EP | 2021499 A2 | 2/2009 |
| EP | 2126135 A2 | 12/2009 |
| EP | 2132225 A1 | 12/2009 |
| EP | 2191018 A2 | 6/2010 |
| EP | 2191840 A1 | 6/2010 |
| EP | 2388336 A1 | 11/2011 |
| EP | 2407488 A2 | 1/2012 |
| EP | 2421563 A1 | 2/2012 |
| EP | 2432881 A2 | 3/2012 |
| EP | 2478101 A1 | 7/2012 |
| EP | 2572000 A2 | 3/2013 |
| EP | 2638163 A1 | 9/2013 |
| EP | 2655621 A1 | 10/2013 |
| EP | 2675903 A1 | 12/2013 |
| EP | 2852671 A1 | 4/2015 |
| EP | 2931914 A1 | 10/2015 |
| EP | 3060237 A1 | 8/2016 |
| EP | 3194623 A1 | 7/2017 |
| EP | 3334755 A1 | 6/2018 |
| EP | 3385373 A1 | 10/2018 |
| WO | 9954460 A2 | 10/1999 |
| WO | 0069450 A1 | 11/2000 |
| WO | 0194629 A2 | 12/2001 |
| WO | 0244206 A2 | 6/2002 |
| WO | 2004073657 A2 | 9/2004 |
| WO | 2006123930 A2 | 11/2006 |
| WO | 2007078599 A2 | 7/2007 |
| WO | 2008081435 A2 | 7/2008 |
| WO | WO 2008/101233 A2 * | 8/2008 |
| WO | 2009028945 A2 | 3/2009 |
| WO | 2009061442 A1 | 5/2009 |
| WO | 2010104357 A2 | 9/2010 |
| WO | 2010123501 A1 | 10/2010 |
| WO | 2010135329 A2 | 11/2010 |
| WO | 2010138263 A2 | 12/2010 |
| WO | 2011017910 A1 | 2/2011 |
| WO | 2011034421 A1 | 3/2011 |
| WO | 2011144718 A2 | 11/2011 |
| WO | 2012014207 A2 | 2/2012 |
| WO | 2012040825 A1 | 4/2012 |
| WO | 2012065143 A1 | 5/2012 |
| WO | 2012087983 A1 | 6/2012 |
| WO | 2012120026 A1 | 9/2012 |
| WO | 2012136841 A1 | 10/2012 |
| WO | 2013177133 A2 | 11/2013 |
| WO | 2014191391 A1 | 12/2014 |
| WO | 2016170348 A2 | 10/2016 |
| WO | 2017026776 A1 | 2/2017 |
| WO | 2017173354 A2 | 10/2017 |
| WO | 2017180587 A2 | 10/2017 |
| WO | 2018041959 A1 | 3/2018 |
| WO | 2018204764 A1 | 11/2018 |
| WO | 2020069339 A1 | 4/2020 |
| WO | 2020069373 A1 | 4/2020 |
| WO | 2023250197 A2 | 12/2023 |

OTHER PUBLICATIONS

Drag et al., 2023 (IOVS, vol. 64, No. 7, article 39, p. 1-17).*
Cestari, Dean, 2023 (EyeWiki, American Academy of Ophthalmology, Non-Arteritic Anterior Ischemic Optic Neuropathy (NAION), p. 1-6).*
Maqbool et al., 2015 (Biochemical Society Transactions, vol. 43, No. 5, p. 1011-1017).*
Cruz et al., 2017 (Methods in Molecular Biology, vol. 1654, Chapter 5, pp. 55-75).*
Yan et al., 2023 (Computers in Biology and Medicine, 154: 106466, p. 1-12).*
Del Rio, Gabriel, 2021 (Computation, 9, 39, p. 1-11).*
Chen et al., 2010 (Geneseq Accession No. AYF61233, computer printout, pp. 1-2, For Seq Id No. 2).*
Anderson et al., 2012 (Geneseq Accession No. AZT11402, computer printout, pp. 1-2, For SEQ ID No. 4).*
Andrews et al., 2009 (Geneseq Accession No. AXF30774, computer printout, pp. 1-2, For SEQ ID No. 6).*
Wang et al., 2015 (Geneseq Accession No. BCN45139, computer printout, pp. 1-2, For SEQ ID No. 1).*
Anderson et al., 2012 (Geneseq Accession No. AZT11402, computer printout, pp. 1-2, For SEQ ID No. 3).*
Bancel et al., 2014 (Geneseq Accession No. BBI57915, computer printout, pp. 1-2, For SEQ ID No. 5).*
Tammam et al. (Jun. 21, 2016) "Nuclear Delivery of Recombinant OCT4 by Chitosan Nanoparticles for Transgene-Free Generation of Protein-Induced Pluripotent Stem Cells", Oncotarget, 7(25):37728-37739.
Hrit et al. (Oct. 16, 2018) "OGT Binds a Conserved C-Terminal Domain of TET1 to Regulate TET1 Activity and Function in Development", Elife, 7:e34870.
Kallunki et al. (Jul. 30, 2019 ) "How to Choose the Right Inducible Gene Expression System for Mammalian Studies?", Cells, 8(8):796.
Khani et al. (Sep. 2007) "AAV-Mediated Expression Targeting of Rod and Cone Photoreceptors with a Human Rhodopsin Kinase Promoter", Investigative Ophthalmology & Visual Science, 48(9):3954-3961.
Koch et al. (May 15, 2014) "ROCK2 Is a Major Regulator of Axonal Degeneration, Neuronal Death and Axonal Regeneration in The CNS", Cell Death and Disease, 5:e1225.
Koch et al. (Sep. 2014) "Viral Vector-Mediated Downregulation of Rhoa Increases Survival and Axonal Regeneration of Retinal Ganglion Cells", Frontiers in Cellular Neuroscience, 10 Pages.
Krishnan et al. (Dec. 15, 2016) "Overexpression of Soluble Fas Ligand following Adeno-Associated Virus Gene Therapy Prevents Retinal Ganglion Cell Death in Chronic and Acute Murine Models of Glaucoma", The Journal of Immunology, 197(12): 4626-4638.
Krueger et al. (Oct. 2004) "Tetracycline Derivatives: Alternative Effectors for Tet Transregulators", BioTechniques, 37.4:546-550.
Levine et al. (Apr. 17, 2018) "An Epigenetic Biomarker of Aging for Lifespan and Healthspan", Aging, 10(4):573-591.
Li et al. (Aug. 6, 2015) "Small-Molecule-Driven Direct Reprogramming of Mouse Fibroblasts into Functional Neurons", Cell Stem Cell, 17(2):195-203.

(56) References Cited

OTHER PUBLICATIONS

Liao et al. (Dec. 14, 2017) "In Vivo Target Gene Activation via CRISPR/Cas9- Mediated Trans-epigenetic Modulation", Cell, 171(7):1495-1507.
Lim et al. (Aug. 2016) "Neural Activity Promotes Long Distance, Target-Specific Regeneration of Adult Retinal Axons", Nature neuroscience, 19(8):1073-1084.
Liu et al. (Aug. 16, 2017) "A Sensitized IGF1 Treatment Restores Corticospinal Axon-Dependent Functions", Neuron, (95):817-833.
Liu et al. (Feb. 1, 2018) "CRISPR-Based Chromatin Remodeling of the Endogenous Oct4 or Sox2 Locus Enables Reprogramming to Pluripotency", Cell stem cell, 22(2): 252-261.
Long et al. (Oct. 2015) "Bromodeoxyuridine Promotes Full-Chemical Induction of Mouse Pluripotent Stem Cells", Cell Research, 25:1171-1174.
Lu et al. (2018) "In Vivo Cellular Reprogramming for Tissue Regeneration and Age Reversal", Innovation in Aging, 2 (Suppl 1):883.
Lu et al. (2020) "Reprogramming to Recover Youthful Epigenetic Information and Restore Vision", Nature, 588 (7836):124-129.
Lu et al. (2019) "Reversal of Ageing- and Injury-Induced Vision Loss by Tet-Dependent Epigenetic Reprogramming", BioRXiv, 51 pages.
Mai et al. (Jul. 16, 2018) "NKX3-1 is Required for Induced Pluripotent Stem Cell Reprogramming and can Replace OCT4 in Mouse and Human Ipsc Induction", Nature Cell Biology, 20(8):900-908.
Manukyan et al. (Apr. 25, 2014) "Epigenome Rejuvenation: HP1b Mobility as a Measure of Pluripotent and Senescent Chromatin Ground States", Scientific Reports, 4:4789.
Marsden et al. ( 2014) "How to Measure Distance Visual Acuity", Community Eye Health Journal, 27(85): 16.
McClellan et al. (Mar. 2014) "Ocular Surface Disease and Dacryoadenitis in Aging C57BL/6 Mice", The American Journal of Pathology, 184(3):631-643.
Miyazaki et al. (May 1, 2011) "Pigment Epithelium-Derived Factor Gene Therapy Targeting Retinal Ganglion Cell Injuries: Neuroprotection Against Loss of Function in Two Animal Models", Human gene therapy, 22(5):559-565.
Montana et al. (Jan. 14, 2013) "Reprogramming Of Adult Rod Photoreceptors Prevents Retinal Degeneration", Pnas, 110(5):1732-1737.
Moore et al. (Oct. 9, 2009) "KLF Family Members Regulate Intrinsic Axon Regeneration Ability", Science, 326 (5950):298-301.
Moreira et al. (Nov. 9, 2017) "Assessing Executive Dysfunction in Neurodegenerative Disorders: A Critical Review of Brief Neuropsychological Tools", Frontiers in aging neuroscience, 9(369):1-13.
Mosteiro et al. (Nov. 25, 2016) "Tissue Damage and Senescence Provide Critical Signals for Cellular Reprogramming in Vivo", Science, 12 Pages.
Mukaii et al. (Jan. 14, 2019) "Mouse Model of Ocular Hypertension with Retinal Ganglion Cell Degeneration", PLOS One, 14(1):e0208713.
Nieuwenhuis et al. (Jan. 13, 2023) "Improving Adeno-Associated Viral (AAV) Vector-Mediated Transgene Expression in Retinal Ganglion Cells: Comparison of Five Promoters", Gene Therapy, 30:503-519.
Norsworthy et al. (Jun. 21, 2017) "Sox11 Expression Promotes Regeneration of Some Retinal Ganglion Cell Types but Kills Others", Neuron, 94:1112-1120.
O'Donovan et al. (May 5, 2014) "B-RAF Kinase Drives Developmental Axon Growth and Promotes Axon Regeneration in the Injured Mature CNS", The Journal of Experimental Medicine, 211(5):801-814.
Oberdoerffer et al. (Sep. 2007) "The Role of Nuclear Architecture in Genomic Instability and Ageing", Nature Reviews Molecular Cell Biology, 8(9):692-702.
Zhao et al. (Dec. 17, 2015) "A Xen-like State Bridges Somatic Cells to Pluripotency during Chemical Reprogramming", Cell, 163:1678-1691.

Ocampo et al. (Dec. 15, 2016) "In Vivo Amelioration of Age-Associated Hallmarks by Partial Reprogramming", Cell, 167(7):1719-1733.
Park et al. (Nov. 7, 2008) "Promoting Axon Regeneration in the Adult CNS by Modulation of the PTEN/mTOR Pathway", Science, 322(5903):963-966.
Patel et al. (Feb. 2019) "Inhaled Nanoformulated mRNA Polyplexes for Protein Production in Lung Epithelium", Advanced Materials, 31(8): 1805116.
Qin et al. (Oct. 16, 2013) "Cross-Talk Between KLF4 and STAT3 Regulates Axon Regeneration", Nature Communications, 4:2633.
Ramachandran et al. (Feb. 1, 2017) "Evaluation of Dose and Safety of AAV7m8 and AAV8BP2 in the Non-Human Primate Retina", Human Gene Therapy, 28(2):154-167.
Ramamoorth et al. (Jan. 2015) "Non Viral Vectors in Gene Therapy-An Overview", Journal of Clinical and Diagnostic Research, 9(1):GE01-GE06.
Redmer et al. (May 27, 2011) "E-Cadherin Is Crucial for Embryonic Stem Cell Pluripotency and Can Replace OCT4 During Somatic Cell Reprogramming", EMBO reports, 12(7): 720-726.
Samiy, Nasrollah (Oct. 2014) "Gene Therapy for Retinal Diseases", Journal of Ophthalmic and Vision Research, 9 (4):506-509.
Senís et al. (Jul. 9, 2018) "AAV Vector-Mediated in Vivo Reprogramming Into Pluripotency", Nature Communications, 9(1):2651.
Shipley et al. (Feb. 17, 2016) "Differentiation of the SH-SY5Y Human Neuroblastoma Cell Line", Journal of Visualized Experiments, (108):53193.
Shu et al. (May 23, 2013) "Induction of Pluripotency in Mouse Somatic Cells with Lineage Specifiers", Cell, 153:963-975.
Siddiqui et al. (2022) "Small Molecule-Inducible Gene Regulatory Systems in Mammalian Cells: Progress and Design Principles", Current Opinion in Biotechnology, 78:102823.
Simpson et al. (Mar. 18, 2019) "New MiniPromoter Ple345 (NEFL) Drives Strong and Specific Expression in Retinal Ganglion Cells of Mouse and Primate Retina", Human gene therapy, 30(3):257-272.
Smalley, Eric (Nov. 9, 2017) "First AAV Gene Therapy Poised for Landmark Approval", Nature Biotechnology, 35:998-999.
Sun et al. (Aug. 2013) "Reversible Reactivity by Optic Nerve Astrocytes", Glia, 61(8): 1218-1235.
Takahashi et al. (Aug. 25, 2006) "Induction of Pluripotent Stem Cells from Mouse Embryonic and Adult Fibroblast Cultures by Defined Factors", Cell, 126(4):663-676.
Abad et al. (Sep. 2013) "Reprogramming in Vivo Produces Teratomas and iPS Cells with Totipotency Features", Nature, 502(7471):340-345.
Agha-Mohammadi et al. (Jul. 2014) "Second-Generation Tetracycline-Regulatable Promoter: Repositioned Tet Operator Elements Optimize Transactivator Synergy While Shorter Minimal Promoter Offers Tight Basal Leakiness", The Journal of Gene Medicine, 6(7):817-828.
Arsenijevic et al. (Jul. 31, 2022) "Lentiviral Vectors for Ocular Gene Therapy", Pharmaceutics, 14(8):1605.
Bareyre et al. (Apr. 12, 2011) "In Vivo Imaging Reveals a Phase-Specific Role of STAT3 During Central and Peripheral Nervous System Axon Regeneration", Proceedings of the National Academy of Sciences, 108(15): 6282-6287.
Bar-Nur et al. (Nov. 2014) "Small Molecules Facilitate Rapid and Synchronous IPSC Generation", Nature Methods, 11(11):1170-1176.
Baron et al. (2000) "Tet Repressor-Based System for Regulated Gene Expression in Eukaryotic Cells: Principles and Advances", Methods in Enzymology, 327:401-421.
Belin et al. (May 20, 2015) "Injury-Induced Decline of Intrinsic Regenerative Ability Revealed by Quantitative Proteomics", Neuron, 86(4):1000-1014.
Borkent et al. (May 10, 2016) "A Serial shRNA Screen for Roadblocks to Reprogramming Identifies the Protein Modifier SUMO2", Stem Cell Reports, 6(5):704-716.
Buck et al. (Jun. 12, 2020) "Recombinant Adeno-Associated Viral Vectors (rAAV)-Vector Elements in Ocular Gene Therapy Clinical Trials and Transgene Expression and Bioactivity Assays", International Journal of Molecular Sciences, 21(12):4197.

(56) References Cited

OTHER PUBLICATIONS

Bussian et al. (Oct. 2018) "Clearance of Senescent Glial Cells Prevents Tau-Dependent Pathology and Cognitive Decline", Nature, 562(7728):578-582.
Carey et al. (2008) "Reprogramming of Murine and Human Somatic Cells Using a Single Polycistronic Vector", Proceedings of the National Academy of Sciences of the United States of America, 106(1):157-162.
Chaffiol et al. (Nov. 1, 2017) "A New Promoter Allows Optogenetic Vision Restoration with Enhanced Sensitivity in Macaque Retina", Molecular Therapy, 25(11):2546-2560.
Choi et al. (Aug. 1, 2023) "Genome Editing in the Treatment of Ocular Diseases", Experimental and Molecular Medicine, 55(8):1678-1690.
Cieślar-Pobuda et al. (Apr. 28, 2017) "Transdifferentiation And Reprogramming: Overview of The Processes, Their Similarities and Differences", Molecular Cell Research, 1864(7):1359-1369.
Das et al. (Apr. 2004) "Viral Evolution as a Tool to Improve the Tetracycline-regulated Gene Expression System", The Journal Of Biological Chemistry, 279(18): 18776-82.
Database Genbank (May 28, 2019) "Homo Sapiens Kruppel Like Factor 4 (KLF4), Transcript Variant 1, mRNA", Accession No. NM_001314052.1, 5 pages.
Database Genbank (Nov. 18, 2018) "Homo Sapiens Kruppel Like Factor 4 (KLF4), Transcript Variant 2, mRNA", Accession No. NM_004235.5, 4 pages.
Database Genbank (Dec. 30, 2018) "Homo Sapiens MYC Proto-Oncogene, bHLH Transcription Factor (MYC), Transcript Variant 1, mRNA", Accession No. NM_002467.5, 5 pages.
Database Genbank (Jul. 31, 2023) "Homo Sapiens MYC Proto-Oncogene, bHLH Transcription Factor (MYC), Transcript Variant 2, mRNA", Accession No. NM_001354870.1, 7 pages.
Database Genbank (Jul. 31, 2023) "Homo Sapiens POU Class 5 Homeobox 1 (POU5F1), Transcript Variant 1, mRNA", Accession No. NM_002701, 5 pages.
Database Genbank (Jul. 31, 2023) "Homo Sapiens POU Class 5 Homeobox 1 (POU5F1), Transcript Variant 2, mRNA", Accession No. NM_203289, 4 pages.
Database Genbank (Jul. 31, 2023) "Homo Sapiens POU Class 5 Homeobox 1 (POU5F1), Transcript Variant 3, mRNA", Accession No. NM_001173531, 4 pages.
Database Genbank (Jul. 31, 2023) "Homo Sapiens POU Class 5 Homeobox 1 (POU5F1), Transcript Variant 4, mRNA", Accession No. NM_001285986, 4 pages.
Database Genbank (Jul. 31, 2023) "Homo Sapiens POU Class 5 Homeobox 1 (POU5F1), Transcript Variant 5, mRNA", Accession No. NM_001285987, 4 pages.
Database Genbank (Jul. 31, 2023) "Homo Sapiens SRY-box Transcription Factor 2 (SOX2), mRNA", Accession No. NM_003106.4, 4 pages.
Database Genbank (Jul. 13, 2023) "Krueppel-Like Factor 4 Isoform 1 [Homo sapiens]", Accession No. NP_001300981.1, 4 pages.
Database Genbank (Jul. 13, 2023) "Krueppel-Like Factor 4 Isoform 2 [Homo sapiens]", Accession No. NP_004226.3, 4 pages.
Database Genbank (Aug. 1, 2023) "Mus Musculus SRY (Sex Determining Region Y)-Box 2 (Sox2), mRNA", Accession No. NM_011443.4, 4 pages.
Database Genbank (Jul. 31, 2023) "Myc Proto-oncogene Protein Isoform 1 [Homo Sapiens]", Accession No. NP 002458.2, 5 pages.
Database Genbank (Jul. 31, 2023) "Myc Proto-oncogene Protein Isoform 2 [Homo Sapiens]", Accession No. NP_001341799.1, 5 pages.
Database Genbank (Jul. 31, 2023) "POU Domain, Class 5, Transcription Factor 1 Isoform 2 [Homo Sapiens]", Accession No. NP_976034.4, 3 pages.
Database Genbank (Jul. 31, 2023) "POU Domain, Class 5, Transcription Factor 1 Isoform 2 [Homo Sapiens]", Accession No. NP_001167002.1, 3 pages.
Database Genbank (Jul. 31, 2023) "POU Domain, Class 5, Transcription Factor 1 Isoform 3 [Homo Sapiens]", Accession No. NP_001272916.1, 3 pages.
Database Genbank (Jul. 31, 2023) "POU Domain, Class 5, Transcription Factor 1 Isoform 4 [Homo Sapiens]", Accession No. NP_001272915.1, 3 pages.
Database Genbank, (Jul. 31, 2023) "Transcription Factor SOX-2 [Homo sapiens]", Accession No. NP_003097.1, 3 pages.
Doshi et al. (Dec. 2020) "Small-molecule Inducible Transcriptional Control in Mammalian Cells", Crit Rev Biotechnol, 40(8):1131-1150.
Ebrahimi, Behnam, (Nov. 11, 2015) "Reprogramming Barriers and Enhancers: Strategies to Enhance the Efficiency And Kinetics of Induced Pluripotency", Cell Regeneration, 4:10.
Eguchi et al. (Dec. 5, 2016) "Reprogramming Cell Fate With a Genome-Scale Library of Artificial Transcription Factors", Proceedings of the National Academy of Sciences, 113(51):E8257-E8266.
Encinas et al. (Sep. 2000) "Sequential Treatment of SH-SY5Y Cells with Retinoic Acid and Brain-Derived Neurotrophic Factor Gives Rise to Fully Differentiated, Neurotrophic Factor-Dependent, Human Neuron-Like Cells", Journal of Neurochemistry, 75(3):991-1003.
Fortin et al. (Feb. 15, 2017) "Preprocessing, Normalization and Integration of the Illumina Humanmethylationepic Array with Minfi", Bioinformatics, 33(4):558-560.
Gao et al. (Apr. 2016) "Mice Homozygous for a Deletion in the Glaucoma Susceptibility Locus INK4 Show Increased Vulnerability of Retinal Ganglion Cells to Elevated Intraocular Pressure", The American Journal of Pathology, 186 (4):985-1005.
Gao et al. (Apr. 4, 2013) "Replacement of Oct4 by Tet1 During iPSC Induction Reveals an Important Role of DNA Methylation and Hydroxymethylation in Reprogramming", Cell Stem Cell, 12(4):453-469.
Geoffroy et al. (Mar. 31, 2016) "Evidence for an Age-Dependent Decline in Axon Regeneration in the Adult Mammalian Central Nervous System", Cell Reports, 15(2):238-246.
Ghoraba et al. (Jun. 3, 2022) "Ocular Gene Therapy: A Literature Review with Special Focus on Immune and Inflammatory Responses", Clinical Ophthalmology, 16:1753-1771.
Gossen et al. (Jun. 23, 1995) "Transcriptional Activation by Tetracyclines in Mammalian Cells", Science, 268 (5218):1766-1769.
Guo et al. (Apr. 29, 2011) "Hydroxylation of 5-Methylcytosine by TET1 Promotes Active DNA Demethylation in the Adult Brain", Cell, 145:423-434.
Hanlon et al. (Sep. 21, 2017) "A Novel Retinal Ganglion Cell Promoter for Utility in AAV Vectors", Frontiers in Neuroscience, 11:521.
Heng et al. (Feb. 5, 2010) "The Nuclear Receptor Nr5a2 Can Replace Oct4 in the Reprogramming of Murine Somatic Cells to Pluripotent Cells", Cell Stem Cell, 6: 167-174.
Horvath, Steve (Dec. 10, 2013) "DNA Methylation Age of Human Tissues and Cell Types", Genome Biology, 14:R115.
Horvath et al. (Jun. 2018) "DNA Methylation-Based Biomarkers and the Epigenetic Clock Theory of Ageing", Nature Reviews, 19(6):371-384.
Zhou et al. (May 8, 2009) "Generation of Induced Pluripotent Stem Cells Using Recombinant Proteins", Cell Stem Cell, 4(5):381-384.
Zhou et al. (Oct. 2006) "Optimization of the Tet-On System for Regulated Gene Expression Through Viral Evolution", Gene Therapy, 13:1382-1390.
Thompson et al. (Oct. 2018) "A Multi-Tissue Full Lifespan Epigenetic Clock for Mice", Aging, 10(10):2832-2854.
Triche Jr et al. (Apr. 1, 2013) "Low-Level Processing of Illumina Infinium DNA Methylation Beadarrays", Nucleic Acids Research, 41(7):e90.
Tyner et al. (Jan. 3, 2002) "P53 Mutant Mice that Display Early Ageing-Associated Phenotypes", Nature, 415:45-53.
Urlinger et al. (Jul. 5, 2000) "Exploring The Sequence Space for Tetracycline-Dependent Transcriptional Activators: Novel mutations Yield Expanded Range and Sensitivity", Proceedings of the National Academy of Sciences, 97(14):7963-7968.
Wang et al. (Sep. 4, 2018) "Lin28 Signaling Supports Mammalian PNS and CNS Axon Regeneration", Cell Reports, 24(10):2540-2552.

(56) References Cited

OTHER PUBLICATIONS

Wang et al. (May 13, 2020) "Mouse c-Synuclein Promoter-Mediated Gene Expression and Editing in Mammalian Retinal Ganglion Cells", The Journal of Neuroscience, 40(20):3896-3914.
Wang et al. (Feb. 14, 2019) "Ribosomal DNA Harbors an Evolutionarily Conserved Clock of Biological Aging", Genome Research, 29:325-333.
Wang et al. (Feb. 12, 2012) "Spatiotemporal Control of Gene Expression by a Light-Switchable Transgene System", Nature Methods, 9(3):266-269.
Wang et al. (Jan. 2009) "The Lysine Demethylase LSD1 (KDM1) Is Required for Maintenance of Global DNA Methylation", Nature Genetics, 41(1):125-129.
Ward et al. (Oct. 5, 2020) "Novel 199 Base Pair NEFH Promoter Drives Expression in Retinal Ganglion Cells", Scientific Reports, 10:16515.
Warren et al. (Nov. 5, 2010) "Highly Efficient Reprogramming to Pluripotency and Directed Differentiation of Human Cells with Synthetic Modified mRNA", Cell Stem Cell, 7(5):618-630.
Weltner et al. (Jul. 6, 2018) "Human Pluripotent Reprogramming with CRISPR Activators", Nature Communications, 9(1):2643.
Weng et al. (Apr. 19, 2017) "An Intrinsic Epigenetic Barrier for Functional Axon Regeneration", Neuron, 94:337-346.
Wright et al. (Jul. 1, 2005) "Identification of Factors that Contribute to Recombinant AAV2 Particle Aggregation and Methods to Prevent Its Occurrence during Vector Purification and Formulation", Molecular Therapy, 12(1): 171-178.
Xiao et al. (Jan. 4, 2018) "Endogenous Reprogramming of Alpha Cells into Beta Cells, Induced by Viral Gene Therapy, Reverses Autoimmune Diabetes", Cell Stem Cell, 22(1):78-90.
Yao et al. (Aug. 2018) "Restoration of Vision After De Novo Genesis of Rod Photoreceptors in Mammalian Retinas", Nature, 560(7719):484-488.
Yu et al. (Dec. 21, 2007) "Induced Pluripotent Stem Cell Lines Derived from Human Somatic Cells", Science, 318:1917-1920.
Yu et al. (Jun. 2015) "Tet3 Regulates Synaptic Transmission and Homeostatic Plasticity Via DNA Oxidation and Repair", Nature Neuroscience, 18(6):836-843.
Zahid et al. (Oct. 1, 2012) "Protein Transduction Domains: Applications for Molecular Medicine", Current Gene Therapy, 7 Pages.
Zhao et al. (Nov. 20, 2003) "A Coumermycin/Novobiocin-Regulated Gene Expression System", Human Gene Therapy, 14(17): 1619-1629.
Lipinski et al., Adv. Exp. Med. Biol. 1185:79-83 (2019).
Ralph GS et al., Clin. Sci. (London) 110(1); 37-46 (2006).
Balaggan KS et al., Gene Ther. 19(2):145-53 (2012).
Jiang et al., J Biol Chem., (20011130), vol. 276, No. 48, pp. 45168-74.
Hou et al., Science, (20130000), vol. 341, pp. 651-654.
Anokye-Danso et al., Cell Stem Cell, (20110000), vol. 8, pp. 633-638.
Blackmore et al., Proc Natl Acad Sci USA., (20120508), vol. 109, No. 19, pp. 7517-7522.
Mahmoudi et al., Biorxiv, (20180000).
Yao et al., "Restoration of vision after de novo genesis of rod photoreceptors in mammalian retinas", Nature, (20180000), vol. 560, No. 7719, pp. 484-488.
Crystal, Science, (19950000), vol. 270, pp. 404-410.
Park et al., Science, (20081100), vol. 322, No. 5903, pp. 963-966.
Mandal et al., Nat Protoc., (20130300), vol. 8, No. 3, pp. 568-582.
Goldberg et al., Science, (20020000), vol. 296, No. 5574, pp. 1860-1864.
Meer et al., Elife, (20180000), vol. 7.
Horvath et al., Aging, (20180000).
Loss of epigenetic information as a cause of mammalian aging. Yang J, Sinclair DA. Cell. Jan. 19, 2023; 186;2, 305-326.

Mohit, Gupta, et al. "Cellular Reprogramming, Transdifferentiation and Alleviation of the Aging Pathology." Research Journal of Biotechnology vol. 19 (2024): 2.
Sichani, Ali Saber, et al. "Partial Reprogramming as a Method for Regenerating Neural Tissues in Aged Organisms." Cellular Reprogramming 26.1 (2024): 10-23.
Yücel, A.D., Gladyshev, V.N. The long and winding road of reprogramming-induced rejuvenation. Nat Commun 15, 1941 (2024). https://doi.org/10.1038/s41467-024-46020-5.
Pico, Sara, et al. "Comparative analysis of mouse strains for in vivo reprogramming." bioRxiv (2024): 2024-03.
Xu, Lucy, et al. "Restoration of neuronal progenitors by partial reprogramming in the aged neurogenic niche." Nature Aging (2024): 1-22.
Hishida, Tomoaki, et al. "In vivo partial cellular reprogramming enhances liver plasticity and regeneration." Cell reports 39.4 (2022).
Puri, Deepika, and Wolfgang Wagner. "Epigenetic rejuvenation by partial reprogramming." Bioessays 45.4 (2023): 2200208.
Singh, Prim B., and Assem Zhakupova. "Age reprogramming: cell rejuvenation by partial reprogramming." Development 149.22 (2022).
Senís, E., Mosteiro, L., Wilkening, S et al. AAV vector-mediated in vivo reprogramming into pluripotency. Nat Commun 9, 2651 (2018). https://doi.org/10.1038/s41467-018-05059-x.
Karg, Margarete M., et al. "Sustained vision recovery by OSK gene therapy in a mouse model of glaucoma." Cellular Reprogramming 25.6 (2023): 288-299.
Macip, Carolina Cano, et al. "Gene Therapy-Mediated Partial Reprogramming Extends Lifespan and Reverses Age-Related Changes in Aged Mice." Cellular Reprogramming 26.1 (2024): 24-32.
Aasen, Trond, et al. "Efficient and rapid generation of induced pluripotent stem cells from human keratinocytes." Nature biotechnology 26.11 (2008): 1276-1284.
Agrawal, Nalini, et al. "Generation of recombinant skin in vitro by adeno-associated virus type 2 vector transduction." Tissue engineering 10.11-12 (2004): 1707-1715.
Deverman, Benjamin E., et al. "Cre-dependent selection yields AAV variants for widespread gene transfer to the adult brain." Nature biotechnology 34.2 (2016): 204-209.
Dugan et al. (Apr. 7, 2023) "Non-Arteritic Anterior Ischemic Optic Neuropathy (NAION)", American Academy of Ophthalmology, 6 pages.
Chen et al. (2014) "Reprogramming Adipose Tissue-Derived Mesenchymal Stem Cells into Pluripotent Stem Cells by a Mutant Adeno-Associated Viral Vector", Human Gene Therapy Methods, 25(1):72-82.
Ksander et al. (Jun. 2023) "Epigenetic Reprogi-Amming-A Novel Gene Therapy That Restores Vision Loss in A Nonhuman Primate Model of Naion", Arvo Annual Meeting Abstract, 64(474):2 pages.
Li et al. (Nov. 2010) "High-efficiency transduction of fibroblasts and mesenchymal stem cells by tyrosine-mutant AAV2 vectors for their potential use in cellular therapy", Human Gene Therapy, 21(11):1527-1543.
Maclaren et al. (Nov. 2006) "CNTF Gene Transfer Protects Ganglion Cells In Rat Retinae Undergoing Focal Injury And Branch Vessel Occlusion", Experimental Eye Research, 83(5):1118-1127.
Michaela et al. (Oct. 2014) "Ciliary Neurotrophic Factor (CNTF)-Mediated Ganglion Cell Survival In A Rodent Model Of Non-Arteritic Anterior Ischaemic Optic Neuropathy (NAION)", The British Journal of Ophthalmology, 99(1):133-137.
Randolph et al. (2017) "An All-in-one, Tet-on 3G Inducible PiggyBac System for Human Pluripotent Stem Cells and Derivatives", Scientific Reports, 7(1): 1549 (8 pages).
Rodda et al. (2005) "Transcriptional Regulation of Nanog By OCT4 and SOX2", The Journal of Biological Chemistry, 280(26):24731-7.
Takahashi et al. (Nov. 30, 2007) "Induction of Pluripotent Stem Cells from Adult Human Fibroblasts by Defined Factors" Cell, 131(5):861-872.

\* cited by examiner

METHODS OF TREATING NON-ARTERITIC ANTERIOR ISCHEMIC OPTIC NEUROPATHY

CROSS-REFERENCE TO RELATED APPLICATIONS

This application claims the right of priority to U.S. Provisional Patent Application No. 63/478,843, filed Jan. 6, 2023, and to U.S. Provisional Patent Application No. 63/499,864, filed May 3, 2023, the contents of each of which are hereby expressly incorporated by reference in their entirety.

INCORPORATION BY REFERENCE OF SEQUENCE LISTING

The instant application contains a Sequence Listing which has been submitted via EFS-Web. The content of the file named "061189-501001US_SequenceListing_ST26.xml", which was created on May 3, 2023 and is 86,016 bytes in size, is hereby incorporated by reference in its entirety.

TECHNICAL FIELD

The present patent application relates to methods of treating non-arteritic anterior ischemic optic neuropathy in a subject in need thereof using gene therapy.

BACKGROUND

Ischemic optic neuropathy is the most common acute optic nerve disorder in patients over age 50 years. Ischemic optic neuropathy is generally categorized as anterior (affecting the optic disc) versus posterior (retrobulbar), and as arteritic versus nonarteritic. Anterior involvement is usual with both arteritic and nonarteritic ischemic optic neuropathy.

Nonarteritic anterior ischemic optic neuropathy (NAION) is the most common form of ischemic optic neuropathy. It is an idiopathic, ischemic insult of the optic nerve head characterized by acute, monocular, painless visual loss with optic disc swelling. According to the American Academy of Ophthalmology, NAION affects between 2.3 and 10.3 people per 100,000 individuals per year making it the most common cause of acute optic neuropathy in patients over the age of 50. There are approximately 6000 new cases per year. Men and women are nearly equally affected. [www_eyewiki_aao_org/Non-Arteritic_Anterior_Ischemic_Optic_Neuropathy_(NAION)].

There are no known treatments for NAION that are proven to be effective. There have been many clinical trials studying over a dozen different therapies, but none have convincingly improved the visual outcome in patients with NAION. The present disclosure addresses the need for such a treatment.

SUMMARY

The present disclosure is directed to methods for preventing or treating non-arteritic anterior ischemic optic neuropathy in a subject by administering to the subject a nucleic acid molecule comprising a nucleic acid sequence encoding OCT4, a nucleic acid molecule comprising a nucleic acid sequence encoding SOX2, and a nucleic acid molecule comprising a nucleic acid sequence encoding KLF4. In some embodiments, the nucleic acid sequences encoding OCT4, SOX2, and KLF4 are on a single nucleic acid molecule. In certain aspects, an adeno-associated viral (AAV) vector comprises the nucleic acid molecule encoding OCT4, SOX2, and KLF4. In some embodiments, the nucleic acid molecule does not encode c-Myc and/or another transcription factors, such as Nanog.

In some embodiments, the methods further comprise administering to the subject a nucleic acid molecule comprising a nucleic acid sequence encoding a reverse tetracycline-controlled transactivator (rtTA). According to some embodiments of the methods, an AAV vector comprises the nucleic acid molecule encoding reverse tetracycline-controlled transactivator (rtTA). In some embodiments, the rtTA is rtTA3 or rtTA4. The AAV vector comprising the nucleic acid molecule encoding OCT4, SOX2, and KLF4 and the AAV vector comprising a nucleic acid molecule encoding reverse tetracycline-controlled transactivator (rtTA) may be present in a single AAV composition or as separate AAV compositions.

In some embodiments of the disclosed methods, the nucleic acid molecule comprising a nucleic acid sequence encoding OCT4, a nucleic acid sequence encoding SOX2, and a nucleic acid sequence encoding KLF4 is operably linked to an inducible promoter. In some embodiments, the inducible promoter comprises a tetracycline class antibiotic response element (TRE). In some embodiments, the tetracycline class antibiotic is doxycycline. In some embodiments, the inducible promoter is a TRE2 promoter.

In some embodiments of the disclosed methods, the nucleic acid molecule comprising a nucleic acid sequence encoding a rtTA is operably linked to a CMV promoter.

In some embodiments, the nucleic acid molecule comprising a nucleic acid sequence encoding OCT4, a nucleic acid sequence encoding SOX2, and a nucleic acid sequence encoding KLF4 is an adeno-associated viral (AAV) vector. In some embodiments, the AAV vector is serotype-2 (AAV2).

In some embodiments of the disclosed methods, the nucleic acid molecule comprising a nucleic acid sequence encoding OCT4, a nucleic acid sequence encoding SOX2, and a nucleic acid sequence encoding KLF4 does not comprise a nucleic acid sequence encoding c-Myc.

In some embodiments of the disclosed methods, the nucleic acid molecule comprising a nucleic acid sequence encoding OCT4, a nucleic acid sequence encoding SOX2, and a nucleic acid sequence encoding KLF4 comprises a nucleic acid sequence encoding self-cleaving peptide. In some embodiments, the self-cleaving peptide is a 2A peptide.

In some embodiments of the disclosed methods, the nucleic acid molecule encoding OCT4, SOX2, and KLF4 is flanked by inverted terminal repeats (ITRs), and wherein the distance between the ITRs is 4.7 kb or less.

In some embodiments, the methods further comprise administering to the subject an inducing agent.

In some embodiments of the disclosed methods, the nucleic acid molecule encoding reverse tetracycline-controlled transactivator (rtTA) is an AAV vector that does not comprise the nucleic acid molecule encoding OCT4, SOX2, and KLF4. The nucleic acid molecule encoding reverse tetracycline-controlled transactivator (rtTA) may be an AAV vector comprising SEQ ID NO: 36 or SEQ ID NO: 37.

In some embodiments of the disclosed methods, the nucleic acid molecule encoding OCT4, SOX2, and KLF4 comprises nucleic acid elements in the following order: a) a first inverted terminal repeat sequence (ITR) sequence; b) a TRE promoter sequence; c) a nucleic acid sequence encoding OCT4; d) a nucleic acid sequence encoding P2A; e) a nucleic acid sequence encoding SOX2; f) a nucleic acid sequence encoding T2A; g) a nucleic acid sequence encoding KLF4; h) an SV-40-derived terminator sequence; and i) a second inverted terminal repeat (ITR) sequence.

In some embodiments of the disclosed methods, the nucleic acid sequence encoding OCT4 comprises SEQ ID NO: 1. In some embodiments, the nucleic acid sequence encoding SOX2 comprises SEQ ID NO: 3. In some embodiments, the KLF4 is human KLF4 protein. In some embodiments, the nucleic acid sequence encoding KLF4 comprises SEQ ID NO: 5. In some embodiments, the nucleic acid sequence encoding P2A comprises SEQ ID NO: 8. In some embodiments, the P2A comprises the amino acid sequence of SEQ ID NO: 9. In some embodiments, the T2A comprises the amino acid sequence of SEQ ID NO: 11.

In some embodiments, the nucleic acid sequence encoding T2A is

```
                                          (SEQ ID NO: 10)
GAGGGCAGGGGAAGTCTTCTAACATGCGGGGACGTGGAGGAAAATCCCG
GCCCA.
```

In some embodiments, the TRE promoter sequence is SEQ ID NO: 7.

In some embodiments, the SV-40-derived terminator sequence is SEQ ID NO: 12.

In some embodiments, the first ITR sequence is SEQ ID NO: 16.

In some embodiments, the nucleic acid molecule encoding OCT4, SOX2, and KLF4 comprises SEQ ID NO: 13.

In some embodiments, the nucleic acid molecule encoding OCT4, SOX2, and KLF4 comprises SEQ ID NO:14.

In some embodiments, the nucleic acid molecule encoding OCT4, SOX2, and KLF4 and the nucleic acid molecule encoding rtTA are administered sequentially or simultaneously.

In some embodiments, the nucleic acid molecule encoding OCT4, SOX2, and KLF4 is administered intravitreally.

In some embodiments, the nucleic acid molecule encoding the rtTA is administered intravitreally.

In some embodiments, the nucleic acid molecule encoding OCT4, SOX2, and KLF4 and the nucleic acid molecule encoding rtTA are administered at a ratio of about 1:1.

In some embodiments, the AAV vector comprising the nucleic acid molecule encoding OCT4, SOX2, and KLF4 and the AAV vector comprising the nucleic acid molecule encoding rtTA are administered at a ratio of about 1:1 (vg:vg).

In some embodiments, the nucleic acid molecule encoding OCT4, SOX2, and KLF4 is AAV2-TRE-OSK vector and the nucleic acid molecule encoding rtTA is AAV2-CMV-rtTA3 or AAV2-CMV-rtTA4.

In some embodiments, the effective amount of the AAV2-TRE-OSK vector is in the range of from about $1\times10^9$ vg/eye to about $1\times10^{14}$ vg/eye.

In some embodiments, the effective amount of the AAV2-CMV-rtTA3 vector is in the range of from about $1\times10^9$ vg/eye to about $1\times10^{14}$ vg/eye.

In some embodiments, the effective amount of the AAV2-CMV-rtTA4 vector is in the range of from about $1\times10^9$ vg/eye to about $1\times10^{14}$ vg/eye.

In some embodiments, the nucleic acid molecule encoding OCT4, SOX2, and KLF4 is administered to the subject by oculus sinister (OS) injection, by oculus dexter (OS) injection, or by oculus uterque (OU) injection.

In some embodiments, the nucleic acid molecule encoding rtTA is administered to the subject by oculus sinister (OS) injection, by oculus dexter (OS) injection, or by oculus uterque (OU) injection.

In some embodiments, the methods further comprise administering to the subject an effective amount of an antibiotic. In some embodiments, the antibiotic is administered at least one day prior to administering the nucleic acid molecule encoding rtTA. In some embodiments, the antibiotic is administered when the nucleic acid molecule encoding rtTA is administered. In some embodiments, the antibiotic is administered at least one day following administration of the nucleic acid molecule encoding rtTA.

In certain aspects, provided herein are methods for recombinant preparation of an AAV, the method comprising introducing a vector into a cell under conditions whereby the AAV is produced, wherein the vector comprises one or more nucleic acid sequences encoding a) OCT4, SOX2, and KLF4. In some embodiments, the cell comprises a population of HEK293T cells.

Further provided herein are methods of generating an AAV comprising modifying a cell to express one or more plasmids comprising: one or more AAV2 Rep-Cap plasmids, one or more helper plasmids, and one or more transfer plasmids, wherein the one or more transfer plasmids comprise one or more nucleic acids encoding OCT4, SOX2, and KLF4. In some embodiments, the cell comprises a population of HEK293T cells.

In certain aspects, provided herein are methods for preventing or treating non-arteritic anterior ischemic optic neuropathy (NAION) in a subject in need thereof, the method comprising administering to the subject a pharmaceutically effective amount of a composition comprising an expression vector comprising a polynucleotide encoding OCT4, SOX2, and KLF4, but not c-Myc. In some embodiments, the polynucleotide further does not encode one or more transcription factors, such as Nanog.

In certain aspects, provided herein are methods for preventing or treating non-arteritic anterior ischemic optic neuropathy (NAION) in a subject in need thereof, the method comprising administering to the subject a pharmaceutically effective amount of a composition comprising an expression vector encoding three transcription factors, wherein the transcription factors consist of OCT4, SOX2, and KLF4.

In certain aspects, provided herein are methods for preventing or treating non-arteritic anterior ischemic optic neuropathy (NAION) in a subject in need thereof, the method comprising administering to the subject a composition comprising an expression vector comprising a polynucleotide encoding four or more transcription factors, wherein the transcription factors comprise OCT4, SOX2, and KLF4, but not c-Myc. In some embodiments, the polynucleotide further does not encode one or more transcription factors, such as Nanog.

In some embodiments, the composition does not reprogram the cell, tissue, or organ to a pluripotent state in the subject. In some embodiments, the composition rejuvenates at least one cell, tissue, or organ in the subject. In some embodiments, the composition does not induce c-Myc expression in the subject. In some embodiments, the composition does not induce expression of one or more transcription factors (e.g., Nanog) in the subject. In some embodiments, the composition does not induce expression of at least one stem cell marker in the subject. Such at least one stem cell marker may comprise Esub, Nanog, Lin28, TRA-1-60/TRA-1-81/TRA-2-54, SSEA1, SSEA4, or any combination thereof. In some embodiments, the composition induces expression of RBPMS, Bm3a, or a combination thereof in the subject. In some embodiments, rejuvenating at least one cell, tissue, or organ comprises increasing repair and/or regeneration in the cell, tissue, or organ. In some embodiments, rejuvenating at least one cell, tissue, or organ comprises restoring epigenetic information in the subject. In some embodiments, rejuvenating at least one cell, tissue, or organ comprises restoring epigenetic information lost due to aging, injury, disease, or any combination thereof in the cell, tissue, or organ. In some embodiments, rejuvenating at least one cell, tissue, or organ comprises reestablishing the epigenetic status of the cell, tissue, or organ to an epigenetic status closer to fertilization or final differentiation. In some embodiments, rejuvenating at least one cell, tissue, or organ comprises increasing the number of healthy axons in the subject. In some embodiments, rejuvenating at least one cell, tissue, or organ comprises preventing damages to healthy axons in the subject.

In some embodiments, the polynucleotide comprises DNA, RNA, or a combination thereof. In some embodiments, the DNA comprises a plasmid DNA. In some embodiments, the RNA comprises an mRNA. In some embodiments, the polynucleotide comprises an inducible promoter, such as a TRE3G promotor, a TRE2 promoter, a P tight promoter, and a tetracycline response element (TRE).

In some embodiments, the methods described herein further comprises administering to the subject an inducing agent to induce expression of OCT4, SOX2, and KLF4 in the subject. In some embodiments, the inducing agent comprises a tetracycline class antibiotic, such as doxycycline. In some embodiments, the inducing agent comprises a reverse tetracycline-controlled transactivator (rtTA) or a polynucleotide encoding the rtTA. In some embodiments, the polynucleotide encoding the rtTA is in an expression vector.

In some embodiments, the composition and the inducing agent is administered sequentially or simultaneously. In some embodiments, the composition is administered prior to administering the inducing agent. In some embodiments, the composition is administered after administering the inducing agent. In some embodiments, the composition is administered simultaneously with the inducing agent.

In some embodiments, the composition and the inducing agent is administered at a ratio of about 100:1, 50:1, 40:1, 30:1, 25;1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:25, 1:30, 1:40, 1:50 or 1:100. In some embodiments, the composition and the inducing agent is administered at a ratio of more than about 100:1. In some embodiments, the composition and the inducing agent is administered at a ratio of less about 1:100. In some embodiments, the composition and the inducing agent is administered at a ratio of about 1:1.

In some embodiments, the polynucleotide comprises a self-cleaving peptide, such as a 2A peptide.

In some embodiments, the polynucleotide comprises inverted terminal repeats (ITRs).

In some embodiments, the expression vector is a viral expression vector selected from a lentivirus, a retrovirus, an adenovirus, alphavirus, vaccinia virus, and an adeno-associated virus (AAV) vector. In some embodiments, the AAV vector is serotype-2 (AAV2).

In some embodiments, the polynucleotide comprises nucleic acid elements in the following order:
a. a first inverted terminal repeat sequence (ITR) sequence;
b. a TRE3G promoter sequence;
c. an OCT4 sequence;
d. a P2A cleavage sequence;
e. a SOX2 sequence;
f. a T2A cleavage sequence;
g. a KLF4 sequence;
h. an SV-40-derived terminator sequence; and
i. a second inverted terminal repeat (ITR) sequence.

In some embodiments,
i) OCT4 comprises an amino acid sequence having at least 70%, 75%, 80%, 85%, 90%, 91%, 92%, 93%, 94%, 95%, 96%, 97%, 98%, 99%, or more, identity to SEQ ID NO: 2;
ii) SOX2 comprises an amino acid sequence having at least 70%, 75%, 80%, 85%, 90%, 91%, 92%, 93%, 94%, 95%, 96%, 97%, 98%, 99%, or more, identity to SEQ ID NO: 4; and/or
iii) KLF4 comprises an amino acid sequence having at least 70%, 75%, 80%, 85%, 90%, 91%, 92%, 93%, 94%, 95%, 96%, 97%, 98%, 99%, or more, identity to SEQ ID NO: 6.

In some embodiments,
i) OCT4 comprises an amino acid sequence having at least 90% identity to SEQ ID NO: 2;
ii) SOX2 comprises an amino acid sequence having at least 90% identity to SEQ ID NO: 4; and/or
iii) KLF4 comprises an amino acid sequence having at least 90% identity to SEQ ID NO: 6.

In some embodiments,
i) OCT4 comprises an amino acid sequence having at least 95% identity to SEQ ID NO: 2;
ii) SOX2 comprises an amino acid sequence having at least 95% identity to SEQ ID NO: 4; and/or
iii) KLF4 comprises an amino acid sequence having at least 95% identity to SEQ ID NO: 6.

In some embodiments,
i) OCT4 comprises the amino acid sequence of SEQ ID NO: 2;
ii) SOX2 comprises the amino acid sequence of SEQ ID NO: 4; and/or
iii) KLF4 comprises the amino acid sequence of SEQ ID NO: 6.

In some embodiments,
i) the polynucleotide comprises a nucleic acid sequence having at least 70%, 75%, 80%, 85%, 90%, 91%, 92%, 93%, 94%, 95%, 96%, 97%, 98%, 99%, or more, identity to SEQ ID NO: 1;
ii) the polynucleotide comprises a nucleic acid sequence having at least 70%, 75%, 80%, 85%, 90%, 91%, 92%, 93%, 94%, 95%, 96%, 97%, 98%, 99%, or more, identity to SEQ ID NO: 3; and/or
iii) the polynucleotide comprises a nucleic acid sequence having at least 70%, 75%, 80%, 85%, 90%, 91%, 92%, 93%, 94%, 95%, 96%, 97%, 98%, 99%, or more, identity to SEQ ID NO: 5.

In some embodiments,
i) the polynucleotide comprises a nucleic acid sequence having at least 75% identity to SEQ ID NO: 1;
ii) the polynucleotide comprises a nucleic acid sequence having at least 75% identity to SEQ ID NO: 3; and/or
iii) the polynucleotide comprises a nucleic acid sequence having at least 75% identity to SEQ ID NO: 5.

In some embodiments,
i) the polynucleotide comprises a nucleic acid sequence having at least 90% identity to SEQ ID NO: 1;
ii) the polynucleotide comprises a nucleic acid sequence having at least 90% identity to SEQ ID NO: 3; and/or
iii) the polynucleotide comprises a nucleic acid sequence having at least 90% identity to SEQ ID NO: 5.

In some embodiments,
i) the polynucleotide comprises a nucleic acid sequence of SEQ ID NO: 1;
ii) the polynucleotide comprises a nucleic acid sequence of SEQ ID NO: 3; and/or
iii) the polynucleotide comprises a nucleic acid sequence of SEQ ID NO: 5.

In some embodiments, the composition is administered systematically. In some embodiments, the composition is administered locally to a tissue or organ. In some embodiments, the composition is administered intravitreally. In some embodiments, the composition is administered to the subject by oculus sinister (OS) injection, by oculus dexter (OD) injection, or by oculus uterque (OU) injection.

In some embodiments, administering the composition improves retinal ganglion cell (RGC) function and/or restores visual function in the subject.

In some embodiments, the preventing or treating NAION is measurable by electroretinogram (pERG). In some embodiments, the preventing or treating NAION is measured by electroretinogram (pERG).

BRIEF DESCRIPTION OF THE DRAWINGS

The summary, as well as the following detailed description, is further understood when read in conjunction with the appended drawings. For the purpose of illustrating the disclosed methods, there are shown in the drawings exemplary embodiments thereof; however, the methods are not limited to the specific embodiments disclosed. In the drawings:

FIG. 1A shows pERG data from both left (OS) and right (OD) eyes from experiments where the right eye received no treatment and the left eye was treated with vehicle (phosphate-buffered saline (PBS)) and subjected to induction of the NAION injury. Results show laser-induced decrease in peak amplitude (the left panel) and the absolute amplitude (the right panel) that is similar to that seen in NAION and is indicative of retinal ganglion cell (RGC) dysfunction. FIG. 1B shows pERG data from both left (OS) and right (OD) eyes from experiments where the right eye received no treatment (contralateral eye) and the left eye was injured with laser and administered the vehicle 1 day post-injury. Results show significant decreases in p50 amplitude (the left panel) and absolute amplitude from p50 to n95 (the right panel) indicating impairment of retinal ganglion cell (RGC) function.

DETAILED DESCRIPTION OF ILLUSTRATIVE EMBODIMENTS

Figure 1A:
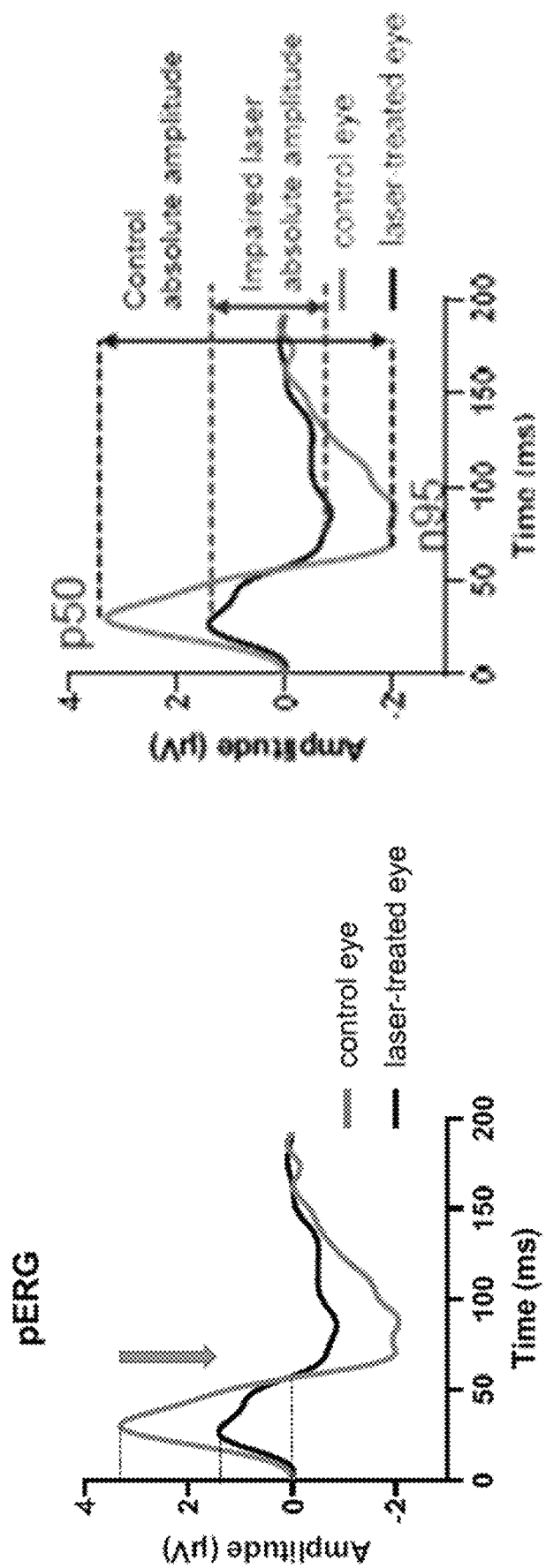
FIGS. 1A and 1B depict results from pattern electroretinogram (pERG) measurements showing induction of non-arteritic anterior ischemic optic neuropathy (NAION) results in decreased pERG signal. The pERG uses contrast reversing pattern stimuli (checkerboards) to assess macular retinal ganglion cell (RGC) activity. Changes in the pERG waveform are indicative of RGCs dysfunctions.

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

Unless specifically stated otherwise, any description as to a possible mechanism or mode of action or reason for improvement is meant to be illustrative only, and the disclosed methods are not to be constrained by the correctness or incorrectness of any such suggested mechanism or mode of action or reason for improvement.

Throughout this text, the description refers to compositions and methods of using the compositions. Where the disclosure describes or claims a feature or embodiment associated with a composition, such a feature or embodiment is equally applicable to the methods of using the composition. Likewise, where the disclosure describes or claims a feature or embodiment associated with a method of using a composition, such a feature or embodiment is equally applicable to the composition.

It is to be appreciated that certain features of the disclosed methods which are, for clarity, described herein in the context of separate embodiments, may also be provided in combination in a single embodiment. Conversely, various features of the disclosed methods that are, for brevity, described in the context of a single embodiment, may also be provided separately or in any subcombination.

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the disclosed methods. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The term "comprising" is intended to include examples encompassed by the terms "consisting essentially of" and "consisting of"; similarly, the term "consisting essentially of" is intended to include examples encompassed by the term "consisting of." The present disclosure also contemplates other embodiments "comprising," "consisting of," and "consisting essentially of" the embodiments or elements presented herein, whether explicitly set forth or not.

The singular forms "a," "and" and "the" include plural references unless the context clearly dictates otherwise.

For recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Some of the quantitative expressions given herein are not qualified with the term "about." It is understood that, whether the term "about" is used explicitly or not, every quantity given is intended to refer to the actual given value, and it is also meant to refer to the approximation to such given value that would reasonably be inferred based on the ordinary skill in the art, including approximations due to the experimental and/or measurement conditions for such value.

"AAV" or "adeno-associated virus" is a nonenveloped virus that is capable of carrying and delivering nucleic acids (e.g., engineered nucleic acids encoding OCT4; KLF4; SOX2; or any combination thereof) and belongs to the genus Dependoparvovirus. In some instances, an AAV is capable of delivering a nucleic acid encoding an inducing agent. In general, AAV does not integrate into the genome. The tissue-specific targeting capabilities of AAV is often determined by the AAV capsid serotype (see, e.g., Table 1 below for examples of AAV serotypes and their utility in tissue-specific delivery). Non-limiting serotypes of AAV include AAV1, AAV2, AAV3, AAV4, AAV5, AAV6, AAV7, AAV8, AAV9, AAV 10, AAV11, and variants thereof. In certain embodiments, the AAV serotype is a variant of AAV9 (e.g., AAV PHP.b).

TABLE 1

Non-limiting Examples of AAV Serotypes and their Use in Specific Tissues

| AAV Serotype | Relevant Tissue | | | | | | | | |
|---|---|---|---|---|---|---|---|---|---|
| | Liver | Heart | Muscle (e.g., Skeletal Muscle) | Eye | Central Nervous System (CNS) | Central Nervous System (Blood-brain barrier) | Pancreas | Lung | Immune System (T-cells, B-cells and Dendritic Cells) |
| AAV1 | | X | X | | X | | | | |
| AAV2 | X | | X | X | X | | | | |
| AAV3 | X | | X | X | | | | X | |
| AAV4 | | | X | X | X | | | | |
| AAV5 | | | X | X | X | | X | X | |
| AAV6 (e.g., AAV6.2) | | X | X | | | | | X | X |
| AAV7 | X | | X | | | | | | |
| AAV8 | X | | X | | X | | X | | |
| AAV9 | X | X | X | X | X | X | X | X | |
| AAV10 (e.g., AAVrh10) | X | X | X | X | X | X | X | X | |
| AAVDJ | X | | X | | X | | | | |
| AAVPHP.B | | | | | X | X | | | |

A "recombinant virus" is a virus (e.g., lentivirus, adenovirus, retrovirus, herpes virus, alphavirus, vaccinia virus or adeno-associated virus (AAV)) that has been isolated from its natural environment (e.g., from a host cell, tissue, or a subject) or is artificially produced.

The term "AAV vector" as used herein is a nucleic acid that comprises AAV inverted terminal repeats (ITRs) flanking an expression cassette (e.g., an expression cassette comprising a nucleic acid encoding OCT4, KLF4, and SOX2, each alone or in combination, or an expression cassette encoding rtTA or tTA). An AAV vector may further comprise a promoter sequence.

The terms "administer," "administering," or "administration," as used herein refers to introduction of any of the compositions described herein; any of the nucleic acids capable of inducing OCT4, KLF4, and/or SOX2 expression; any of the nucleic acids capable of inducing expression of one or more transcription factors selected from the group consisting of OCT4, KLF4, SOX2, and any combinations thereof; any of the engineered proteins described herein; any of the chemical agents activating (e.g., inducing expression of) OCT4, KLF4, and/or SOX2; any of the chemical agents activating (e.g., inducing expression of) one or more transcription factors selected from OCT4, KLF4, SOX2, and any combinations thereof; any of the antibodies activating (e.g., inducing expression of) OCT4, KLF4, and/or SOX2, and any combinations thereof; and/or any of the recombinant viruses (e.g., lentivirus, adenovirus, alphavirus, vaccinia virus, retrovirus, herpes virus, or AAV) described herein, alone, or in combination to any cell, tissue, organ, and/or subject. In some embodiments, a nucleic acid encoding an inducing agent, an engineered protein encoding an inducing agent, a chemical agent capable of modulating (e.g., activating or inhibiting) the activity of an inducing agent, and/or a recombinant virus encoding an inducing agent is also administered to the cell, tissue, organ and/or subject. Any of the compositions described herein, comprising any of the nucleic acids capable of inducing expression of one or more transcription factors selected from OCT4, KLF4, SOX2, and any combinations thereof; any of the chemical agents activating (e.g., inducing expression of, e.g., tetracyline) OCT4, KLF4, and/or SOX2; any of the engineered proteins encoding OCT4, SOX2, KLF4, or any combinations thereof; any of the chemical agents activating (e.g., inducing expression of, e.g., tetracyline) OCT4, KLF4, SOX2, or any combination thereof; any of the antibodies activating (e.g., inducing expression of) OCT4, KLF4, and/or SOX2; and/or any of the recombinant viruses (e.g., lentivirus, adenovirus, alphavirus, vaccinia virus, retrovirus, herpes virus, or AAV) described herein, alone, or in combination may be administered intravitreally, intraocularly, subconjuctivally, or subretinally. In other aspects, administration can be intravenously, intradermally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, systemically, injection, infusion, continuous infusion, localized perfusion bathing target cells directly, via a catheter, in creams, in lipid compositions (e.g., liposomes), or by other method or any combination of the forgoing as would be known to one of ordinary skill in the art (see, for example, Remington's Pharmaceutical Sciences (1990), incorporated herein by reference). In some embodiments, a composition comprising a nucleic acid encoding an inducing agent, an engineered protein encoding an inducing agent, a chemical agent capable of modulating (e.g., activating or inhibiting) the activity of an inducing agent, and/or a recombinant virus encoding an inducing agent is also administered to the cell, tissue, organ and/or subject using any suitable method such as intravitreally, intraocularly, subconjuctivally, or subretinally.

As used herein, the term "cell" is meant not only to include an individual cell but refers also to the particular tissue or organ from which it originates.

The term "gene expression" refers to the degree to which certain genes or all genes in a cell or tissue are transcribed into RNA. In some instances, the RNA is translated by the cell into a protein. The epigenome dictates gene expression patterns.

The terms "condition," "disease," and "disorder" are used interchangeably. As used herein, an "ocular disease" or "eye disease" is a disease or condition of the eye. An example of an ocular disease is Non-arteritic anterior ischemic optic neuropathy.

Any suitable method may be used to measure ocular function. Non-limiting examples include visual acuity tests, pattern electroretinograms (pERGs), and pathology.

"Cellular causes of aging" as used herein include loss or modification of epigenetic information.

The terms "c-Myc" or "Myc" refer to a nuclear phosphoprotein that has been implicated in cell cycle progression. c-Myc is capable of forming a heterodimer with the transcription factor MAX and the heterodimer is capable of binding to an E box consequence sequence on nucleic acids (e.g., engineered nucleic acids) to regulate transcription of target genes. In certain embodiments, a nucleotide sequence encoding c-Myc comprises a sequence that is at least 70% (e.g., at least 75%, 80%, 85%, 90%, 95%, 98%, 99%, or 100%) identical to a sequence as described in the NCBI RefSeq database under accession number NM_001354870.1 or NM_002467.5. In certain embodiments, an amino acid sequence encoding c-Myc comprises a sequence that is at least 70% (e.g., at least 75%, 80%, 85%, 90%, 95%, 98%, 99%, or 100%) identical to NP 002458.2 or NP 001341799.1. In certain embodiments, the methods comprise inducing expression of OCT4; KLF4; SOX2; or any combination thereof in the absence of inducing c-Myc expression or in the absence of activating c-Myc. Absence of inducing c-Myc expression may refer to absence of substantial induction of c-Myc expression over endogenous levels of c-Myc expression in a cell, tissue, subject, or any combination thereof. Absence of substantial induction of c-Myc expression as compared to endogenous levels of c-Myc expression in a cell, tissue, subject, or any combination thereof, may refer to increasing c-Myc expression by less than 70%, less than 60%, less than 50%, less than 40%, less than 30%, less than 20%, less than 10%, or any values in between as compared to endogenous levels of c-Myc expression in the cell, tissue, subject, or any combination thereof. Absence of activating c-Myc expression may refer to absence of substantial activation of c-Myc (e.g., activity) over endogenous c-Myc activity in a cell, tissue, subject, or any combination thereof. Absence of substantial induction of c-Myc activity as compared to endogenous c-Myc activity in a cell, tissue, subject, or any combination thereof, may refer to increasing c-Myc activity by less than 70%, less than 60%, less than 50%, less than 40%, less than 30%, less than 20%, less than 10%, or any values in between as compared to endogenous c-Myc activity in the cell, tissue, subject, or any combination thereof.

The terms "effective amount" and "therapeutically effective amount," as used herein, refer to the amount of a compound or composition, that, when administered to a subject, is effective to at least partially treat a condition from which the subject is suffering.

As used herein, a protein that is "functional" or "active" is one that retains its biological activity (e.g., capable of acting as a transcription factor or as an inducing agent). Conversely, a protein that is not functional or is inactive is one that is not capable of performing one or more of its wild-type functions.

The term "gene" refers to a nucleic acid fragment that expresses a protein, including regulatory sequences preceding (5 ' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Homolog" or "homologous" refers to sequences (e.g., nucleic acid or amino acid sequences) that share a certain percent identity (e.g., at least 5%, at least 10%, at least 15%, at least 20%, at least 25%, at least 30%, at least 35%, at least 40%, at least 45%, at least 50%, at least 55%, at least 60%, at least 65%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% percent identity). Homologous sequences include but are not limited to paralogous or orthologous sequences. Paralogous sequences arise from duplication of a gene within a genome of a species, while orthologous sequences diverge after a speciation event. A functional homolog retains one or more biological activities of a wild-type protein. In certain embodiments, a functional homolog of OCT4, KLF4, or SOX2 retains at least 10%, at least 20%, at least 30%, at least 40%, at least 50%, at least 60%, at least 70%, at least 80%, at least 90%, or at least 100% of the biological activity (e.g., transcription factor activity) of a wild-type counterpart.

"KLF4" may also be referred to as Kruppel-like factor 4, EZF, or GKLF and is a zinc-finger transcription factor. KLF4 has been implicated in regulation of differentiation and proliferation and is capable of interacting with co-activators, including members of the p300-CBP coactivator family. A KLF4 transcription factor, homolog (e.g., functional homolog), or variant thereof, as used herein, may be derived from any species, including humans. In certain embodiments, the nucleic acid encoding human KLF4 comprises a sequence that is at least 70% (e.g., at least 75%, 80%, 85%, 90%, 95%, 98%, 99%, or 100%) identical to a nucleic acid described in the NCBI RefSeq database under accession number NM_004235.5 or NM_001314052.1. Non-limiting examples of KLF4 variants include Kruppel-like factor 4 transcript variant 1 and Kruppel-like factor 4 transcript variant 2. In certain embodiments, KLF4 is encoded by a nucleic acid molecule comprising a nucleic acid sequence that is at least 70% (e.g., at least 75%, 80%, 85%, 90%, 95%, 98%, 99%, or 100%) identical to SEQ ID NO: 5. SEQ ID NO: 5 is a non-limiting example of a nucleotide sequence encoding human KLF4. In certain embodiments, KLF4 comprises an amino acid sequence that is at least 70% (e.g., at least 75%, 80%, 85%, 90%, 95%, 98%, 99%, or 100%) identical to NP_001300981.1 or NP_004226.3. In certain embodiments, KLF4 comprises an amino acid sequence that is at least 70% (e.g., at least 75%, 80%, 85%, 90%, 95%, 98%, 99%, or 100%) identical to SEQ ID NO: 6. SEQ ID NO: 6 is a non-limiting example of an amino acid sequence of human KLF4.

"Inverted terminal repeats" or "ITRs" are nucleic acid sequences that are reverse complements of one another. In general, in an AAV vector, ITRs are found on either side of a cassette (e.g., an expression cassette comprising a nucleic acid encoding OCT4; KLF4; SOX2; or any combination thereof). For example, the ITRs flanking the OSK cassette may comprise SEQ ID NOs: 16 and 32. Similarly, in some instances, the AAV2-CMV-rtTA3 vector disclosed herein can include ITRs comprising SEQ ID NOs: 22 and 33, and the AAV2-CMV-rtTA4 vector disclosed herein can include ITRs comprising SEQ ID NOs: 29 and 34. In some instances, the cassette encodes an inducing agent. AAV ITRs include ITRs from AAV1, AAV2, AAV3, AAV4, AAV5, AAV6, AAV7, AAV8, AAV9, AAV 10, AAV11, and AAV variants thereof.

The terms "nucleic acid," "polynucleotide", "nucleotide sequence", "nucleic acid molecule", "nucleic acid sequence", and "oligonucleotide" refer to a series of nucleotide bases (also called "nucleotides") in DNA and RNA, and mean any chain of two or more nucleotides. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids.

The nucleic acids described herein may be synthesized by standard methods known in the art, e.g., by use of an automated DNA synthesizer (such as those that are commercially available from Biosearch, Applied Biosystems, etc.). Such DNA sequences may be incorporated into a wide variety of vectors that incorporate suitable RNA polymerase promoters such as the T7 or SP6 polymerase promoters. A vector can be introduced in vivo such that it is taken up by a cell and directs the transcription of the nucleic acid molecule. Such a vector can remain episomal or become chromosomally integrated, as long as it can be transcribed. Such vectors can be constructed by recombinant DNA technology methods standard in the art. Vectors can be plasmid, viral, or others known in the art, used for replication and expression in mammalian cells. Expression of the sequence can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be administered to the subject.

The nucleic acid molecules may include natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5"- and 3"-non-coding regions, and the like. A "recombinant nucleic acid molecule" or "engineered nucleic acid molecule" is a nucleic acid molecule that has undergone a molecular biological manipulation, i.e., non-naturally occurring nucleic acid molecule or genetically engineered nucleic acid molecule. Furthermore, the terms "recombinant DNA molecule" or "engineered nucleic acid" refer to a nucleic acid sequence which is not naturally occurring, or can be made by the artificial combination of two otherwise separated segments of nucleic acid sequence, i.e., by ligating together pieces of DNA that are not normally contiguous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al, Molecular Cloning, second edition, Cold Spring Harbor Laboratory, Plainview, N.Y.; (1989), or Ausubel el al, Current Protocols in Molecular Biology, Current Protocols (1989), and DNA Cloning: A Practical Approach, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site-specific targets, e.g., promoters, DNA replication sites, regulation sequences, control sequences, open reading frames, or other useful features may be incorporated by design.

"OCT4" may also be referred to as Octamer-binding transcription factor 4, OCT3, OCT3/4, POU5F1, or POU class 5 homeobox 1 and is a transcription factor that has been implicated in embryonic development and determination of cell fate. Similar to other OCT transcription factors, OCT4 is characterized by a bipartite DNA binding domain called a POU domain. An OCT4 transcription factor, homolog, or variant thereof, as used herein, may be derived from any species, including humans. In certain embodiments, the nucleic acid encoding human OCT4 is at least 70% (e.g., at least 75%, 80%, 85%, 90%, 95%, 98%, 99%, or 100%) identical to a nucleic acid described in the NCBI RefSeq under accession number NM_002701, NM_203289, NM_001 173531, NM_001285986, or NM_001285987. In certain embodiments, the nucleic acid molecule encoding a human OCT4 comprises a nucleic acid sequence that is at least 70% (e.g., at least 75%, 80%, 85%, 90%, 95%, 98%, 99%, or 100%) identical to a nucleic acid sequence provided as SEQ ID NO: 1. SEQ ID NO: 1 is a non-limiting example of a nucleotide sequence encoding human OCT4. Non-limiting examples of OCT4 variants encompassed herein include POU5F1, transcript variant 1, POU5F1, transcript variant 2, POU5F1, transcript variant 3, POU5F1, transcript variant 4, and POU5F1 transcript variant 5. In certain embodiments, the nucleic acid molecule encodes an OCT4 comprising an amino acid sequence at least 70% (e.g., at least 75%, 80%, 85%, 90%, 95%, 98%, 99%, or 100%) identical to an amino acid sequence described in the NCBI RefSeq under accession number NP 001167002.1, NP_001272915.1, NP_001272916.1, NPJ302692.2, or NP_976034.4. In certain embodiments, the nucleic acid molecule encodes an OCT4 comprising an amino acid sequence that is at least 70% (e.g., at least 75%, 80%, 85%, 90%, 95%, 98%, 99%, or 100%) identical to SEQ ID NO: 2. SEQ ID NO: 2 is a non-limiting example of an amino acid sequence of human OCT4. Other OCT4 transcription factors (e.g., from other species) are known and nucleic acids encoding OCT4 transcription factors can be found in publicly available databases, including GenBank.

The term "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, activatable, repressible, tissue-specific, or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation of that sequence, expression of that sequence, or a combination thereof.

A promoter may promote ubiquitous expression or tissue-specific expression of an operably linked nucleic acid sequence from any species, including humans. In some embodiments, the promoter is a eukaryotic promoter. Non limiting examples of eukaryotic promoters include TDH3, PGK1, PKC1, TDH2, PYK1, TPI1, AT1, CMV, EF1 alpha, SV40, PGK1 (human or mouse), Ubc, human beta actin, CAG, TRE, UAS, Ac5, Polyhedrin, CaMKIIa, GAL1, GAL10, TEF1, GDS, ADH1, CaMV35S, Ubi, Hl, and U6, as would be known to one of ordinary skill in the art (see, e.g., Addgene website: blog. addgene.org/plasmids—101—the-promoter-region).

Non-limiting examples of ubiquitous promoters include tetracycline-responsive promoters (under the relevant conditions), CMV (e.g., SEQ ID NO: 17), EF1 alpha, a SV40 promoter, PGK1, Ubc, CAG, human beta actin gene promoter, a RSV promoter, an EFS promoter, and a promoter comprising an upstream activating sequence (UAS). In certain embodiments, the promoter is a mammalian promoter.

Non-limiting examples of tissue-specific promoters include eye-specific promoters. Non-limiting examples of eye-specific promoters include human GRK1 (rhodopsin kinase) promoter, human CRX (cone rod homeobox transcription factor) promoter, and human NRL promoter (neural retina leucine zipper transcription factor enhancer upstream of the human TK terminal promoter).

In some embodiments, a promoter of the present disclosure is suitable for use in AAV vectors. See, e.g., U.S. Patent Application Publication No. 2018/0155789, which is hereby incorporated by reference in its entirety for this purpose.

Non-limiting examples of constitutive promoters include CP1, CMV, EF1 alpha, SV40, PGK1, Ubc, human beta actin, beta tubulin, CAG, Ac5, Rosa26 promoter, COL1A1 promoter, polyhedrin, TEF1, GDS, CaM3 5S, Ubi, Hl, U6, red opsin promoter (red promoter), rhodopsin promoter (rho promoter), cone arrestin promoter (car promoter), rhodopsin kinase promoter (rk promoter). In some instances, the constitutive promoter is a Rosa26 promoter. In some instances, the constitutive promoter is a COL1A1 promoter. A tissue-specific promoter may be used to drive expression of an engineered nucleic acid, including e.g., a nucleic acid encoding a rtTA, tTA, OCT4, KLF4, SOX2, or any combination thereof. In some embodiments, a tissue-specific promoter is used to drive expression of a rtTA or a rTA. In some embodiments, a tissue-specific promoter is used to drive expression of OCT4, KLF4, and SOX2. In some embodiments, the SV40 promoter is used to drive expression of OCT4, KLF4, and SOX2.

"Tetracycline" refers to the tetracycline class of antibiotic compounds that includes, but is not limited to, tetracycline, chlortetracycline, oxytetracycline, demeclocyline, lymecycline, meclocycline, methacycline, minocycline, rolitetracycline, doxycycline, tigecycline, eravacycline, sarecycline, and omadacycline.

An "inducible promoter" is one that is characterized by initiating or enhancing transcriptional activity when in the presence of, influenced by, or contacted by an inducing agent. An inducing agent may be endogenous or a normally exogenous condition, compound, agent, or protein that contacts an engineered nucleic acid in such a way as to be active in inducing transcriptional activity from the inducible promoter. In certain embodiments, an inducing agent is a tetracycline-sensitive protein (e.g., tTA or rtTA, TetR family regulators).

Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (TetR, or TetRKRAB), a tetracycline operator sequence (tetO) and a tetracycline transactivator fusion protein (tTA), and a tetracycline operator sequence (tetO) and a reverse tetracycline transactivator fusion protein (rtTA)), steroid-regulated promoters (e.g., promoters based on the rat glucocorticoid receptor, human estrogen receptor, moth ecdysone receptors, and promoters from the steroid/retinoid/thyroid 25 receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), pH-regulated promoters, and light-regulated promoters. A non-limiting example of an inducible system that uses a light-regulated promoter is provided in Wang et al, Nat. Methods. 2012 Feb. 12; 9(3):266-9.

In certain embodiments, an inducible promoter comprises a tetracycline (Tet)-responsive element. For example, an inducible promoter may be a TRE3G promoter (e.g., a TRE3G promoter that comprises a sequence that is at least 70% (e.g., at least 75%, 80%, 85%, 90%, 95%, 98%, 99%, or 100%) identical to SEQ ID NO: 7). As an example, a TRE (e.g., TRE2) promoter may comprise a nucleic acid sequence that is at least 70% (e.g., at least 75%, 80%, 85%, 90%, 95%, 98%, 99%, or 100%) identical to SEQ ID NO: 7.

Additional non-limiting examples of inducible promoters include mifepristone-responsive promoters (e.g., GAL4-Elb promoter) and coumermycin-responsive promoters. See, e.g., Zhao et al., Hum Gene Ther. 2003 Nov. 20; 14(17): 1619-29.

A "reverse tetracycline transactivator" ("rtTA"), as used herein, is an inducing agent that binds to a TRE promoter (e.g., a TRE3G, a TRE2 promoter, or a P tight promoter) in the presence of a tetracycline (e.g., doxycycline) and is capable of driving expression of a transgene that is operably linked to the TRE promoter. rtTAs generally comprise a mutant tetracycline repressor DNA binding protein (TetR) and a transactivation domain (see, e.g., Gossen et al, Science. 1995 Jun. 23; 268(5218): 1766-9 and any of the transactivation domains listed herein). The mutant TetR domain is capable of binding to a TRE promoter when bound to tetracycline. See, e.g., US Publ. Appl. No. 2021-0403923 A, and the International Publ. No. WO2020/069339, entitled MUTANT REVERSE TETRACYCLINE TRANSACTIVATORS FOR EXPRESSION OF GENES, each of which is herein incorporated by reference in its entirety.

"SRY-box 2" or "SOX2" is a member of the SRY-related HMG-box (SOX) family of transcription factors. SOX2 has been implicated in promoting embryonic development. Members of the SOX (SRY-related HMG-box) family of transcription factors are characterized by a high mobility group 5 (HMG)-box DNA sequence. This HMG box is a DNA binding domain that is highly conserved throughout eukaryotic species. A SOX2 transcription factor, homolog or variant thereof, as used herein, may be derived from any species, including humans. In certain embodiments, the nucleic acid molecule encoding SOX2 comprises a sequence that is at least 70% (e.g., at least 75%, 80%, 85%, 90%, 95%, 98%, 99%, or 100%) identical to a nucleic acid described in the NCBI RefSeq under accession number NM_01 1443.4. In certain embodiments, the nucleic acid molecule encoding a human SOX2 comprises a sequence that is at least 70% (e.g., at least 75%, 80%, 85%, 90%, 95%, 98%, 99%, or 100%) identical to a nucleic acid molecule described in the NCBI RefSeq under accession number NM_003106.4. SEQ ID NO: 3 is a non-limiting example of a nucleotide sequence encoding human SOX2. In certain embodiments, the nucleic acid molecule encoding human SOX2 comprises a sequence that is at least 70% (e.g., at least 75%, 80%, 85%, 90%, 95%, 98%, 99%, or 100%) identical to SEQ ID NO: 3. According to some embodiments, the nucleic acid molecule encodes a SOX2 comprising an amino acid sequence that is at least 70% (e.g., at least 75%, 80%, 85%, 90%, 95%, 98%, 99%, or 100%) identical to the amino acid sequence described in the NCBI RefSeq under accession number NP_003097.1. According to some embodiments, the nucleic acid molecule encodes a SOX2 comprising the amino acid sequence described in the NCBI RefSeq under accession number NP_003097.1. In some instances, the nucleic acid molecule encodes a SOX2 comprising an amino acid sequence that is at least 70% (e.g., at least 75%, 80%, 85%, 90%, 95%, 98%, 99%, or 100%) identical to SEQ ID NO: 4. SEQ ID NO: 4 is a non-limiting example of an amino acid sequence of human SOX2.

A "multicistronic vector" is a vector that encodes more than one amino acid sequence (e.g., a vector encoding OCT4 and KLF4, OCT4 and SOX2, KLF4 and SOX2, or OCT4, SOX2, and KL4 (OSK)). A multicistronic vector allows for expression of multiple amino acid sequences from a nucleic acid sequence. Nucleic acid sequences encoding each transcription factor (e.g., OCT4, KLF4, or SOX2) may be connected or separated such that they produce unconnected proteins. For example, internal ribosome entry sites (IRES) or polypeptide cleavage signals may be placed between nucleic acid sequences encoding each transcription factor in a vector. Exemplary polypeptide cleavage signals include 2A peptides (e.g., T2A, P2A, E2A, and F2A). A T2A peptide may comprise a sequence that is at least 70% (e.g., at least 75%, 80%, 85%, 90%, 95%, 98%, 99%, or 100%) identical to SEQ ID NO: 10. A P2A peptide may comprise a sequence that is at least 70% (e.g., at least 75%, 80%, 85%, 90%, 95%, 98%, 99%, or 100%) identical to SEQ ID NO: 8.

In some embodiments, an expression vector of the present disclosure is a multicistronic expression vector.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds, such as chickens, ducks, geese, and/or turkeys). In certain embodiments, the animal is a mammal. The animal may be a male or female and at any stage of development. A non-human animal may be a transgenic animal.

A "terminator" or "terminator sequence," as used herein, is a nucleic acid (s, engineered nucleic acid) sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated.

The most commonly used type of terminator is a forward terminator. When placed downstream of a nucleic acid sequence that is usually transcribed, a forward transcriptional terminator will cause transcription to abort. In some embodiments, bidirectional transcriptional terminators may be used, which usually cause transcription to terminate on both the forward and reverse strand. In some embodiments, reverse transcriptional terminators may be used, which usually terminate transcription on the reverse strand only.

Non-limiting examples of mammalian terminator sequences include bovine growth hormone terminator, and viral termination sequences such as, for example, the SV40 terminator, spy, yejM, secG-leuU, thrLABC, rrnB Tl, his-LGDCBHAFI, metZWV, rrnC, xapR, aspA, and arcA terminator. In certain embodiments, the terminator sequence is SV40 and comprises a sequence that is at least 70% (e.g., at least 75%, 80%, 85%, 90%, 95%, 98%, 99%, or 100%) identical to SEQ ID NO: 12.

A "Tet-Off" system, as used herein, is a type of inducible system that is capable of repressing expression of a particular transgene in the presence of a tetracycline (e.g., doxycycline (DOX)). Conversely, a Tet-Off system is capable of inducing expression of a particular transgene in the absence of a tetracycline (e.g., doxycycline, DOX). In certain embodiments, a Tet-Off system comprises a tetracycline-responsive promoter operably linked to a transgene (e.g., encoding OCT4; KLF4; SOX2; or any combination thereof) and a tetracycline-controlled transactivator (tTA). The transgene with the tetracycline-responsive promoter (e.g., TRE3G, P tight, or TRE2) and the tetracycline-controlled transactivator may be encoded on the same vector or be encoded on separate vectors. See, e.g., US Publ. Appl. No. 2021-0403923 A, and the International Publ. No. WO2020/069339, entitled MUTANT REVERSE TETRACYCLINE TRANSACTIVATORS FOR EXPRESSION OF GENES, each of which is herein incorporated by reference in its entirety.

A "Tet-On" system, as used herein, is a type of inducible system that is capable of inducing expression of a particular transgene in the presence of a tetracycline (e.g., doxycycline (DOX)). In certain embodiments, a Tet-On system comprises a tetracycline-responsive promoter operably linked to a transgene (e.g., encoding OCT4; KLF4; SOX2; or any combination thereof) and a reverse tetracycline-controlled transactivator (rtTA). For example, the rtTA may be rtTA3, rtTA4, or variants thereof. In certain embodiments, a nucleic acid encoding rtTA3 comprises a sequence that is at least 70% (e.g., at least 75%, at least 80%, at least 85%, at least 90%, at least 95%, or at least 100%) identical to SEQ ID NO: 19. In certain embodiments, rtTA3 comprises an amino acid sequence that is at least 70% (e.g., at least 75%, at least 80%, at least 85%, at least 90%, at least 95%, at least 98%, at least 99%, or at least 100%) identical to SEQ ID NO: 20. In certain embodiments, a nucleic acid encoding rtTA4 comprises a sequence that is at least 70% (e.g., at least 75%, at least 80%, at least 85%, at least 90%, at least 95%, at least 98%, at least 99%, or at least 100%) identical to SEQ ID NO: 26. In certain embodiments, rtTA4 comprises an amino acid sequence that is at least 70% (e.g., at least 75%, at least 80%, at least 85%, at least 90%, at least 95%, at least 98%, at least 99%, or at least 100%) identical to SEQ ID NO: 27. The expression cassette encoding a tetracycline-responsive promoter (e.g., a promoter comprising a TRE, including TRE3G, P tight, and TRE2) and a reverse tetracycline-controlled transactivator may be encoded on the same vector or be encoded on separate vectors. See, e.g., US Publ. Appl. No. 2021-0403923 A, and the International Publ. No. WO2020/069339.

The term "tissue" refers to any biological tissue of a subject (including a group of cells, a body part, or an organ) or a part thereof, including blood and/or lymph vessels, which is the object to which a compound, particle, and/or composition as disclosed herein is delivered. A tissue may be an abnormal, damaged, or unhealthy tissue, which may need to be treated. A tissue may also be a normal or healthy tissue that is under a higher than normal risk of becoming abnormal or unhealthy, which may need to be prevented. In certain embodiments, the tissue is considered healthy but suboptimal for performance or survival in current or future conditions. In certain embodiments, the tissue is the central nervous system. In certain embodiments, the cell or tissue is from eye. In certain embodiments, the tissue is damaged (e.g., due to a congenital defect, an injury, an accident, or an iatrogenic injury), diseased, and/or aged. In certain embodiments, the tissue is a deep tissue that is reachable with a fiber optic probe.

As used herein, a "TRE promoter" is a promoter comprising a tetracycline-responsive element (TRE). As used herein, a TRE comprises at least one (e.g., at least 2, 3, 4, 5, 6, 7, 8, 9, 10, 11, 12, 13, 14, 15, 16, 17, 18, 19, or 20) Tet-O sequences. In some embodiments, a TRE promoter further comprises a minimal promoter located downstream of a tet-O sequence. A minimal promoter is a promoter that comprises the minimal elements of a promoter (e.g., TATA box and transcription initiation site), but is inactive in the absence of an upstream enhancer (e.g., sequences comprising Tet-O). As an example, a minimal promoter may be a minimal CMV promoter that comprises a sequence that is at least 70% (e.g., at least 75%, 80%, 85%, 90%, 95%, 98%, 99%, or 100%) identical to SEQ ID NO: 17 or 24. For example, a TRE promoter may be a TRE3G promoter (e.g., a TRE3G promoter that comprises a sequence that is at least 70% (e.g., at least 75%, 80%, 85%, 90%, 95%, 98%, 99%, or 100%) identical to SEQ ID NO: 7.

The term "tissue repair" in the context of damaged tissue refers to restoration of tissue architecture, function following tissue damage, or a combination thereof. Tissue repair includes tissue regeneration, cell growth, tissue replacement, and/or rewiring of existing tissue (reprogramming).

The term "tissue regeneration" refers to production of new tissue or cells within a tissue that are the same type as the tissue of interest (e.g., same type as the damaged tissue or cell). In some embodiments, the methods provided herein promote organ regeneration.

The term "tissue replacement" refers to production of a different type of tissue compared to the tissue of interest (e.g., connective tissue to replace damaged tissue).

As used herein, the terms "treatment," "treat," and "treating" refer to reversing, alleviating, delaying the onset of, or inhibiting the progress of a disease or disorder, or one or more symptoms thereof, as described herein. In certain embodiments, treatment may be administered after one or more symptoms have developed. In other embodiments, treatment may be administered in the absence of symptoms. In other embodiments, treatment may be administered to improve one or more of retinal perfusion, ocular pressure, thickness of retinal layers, survival of RGCs, retinal electrical response, macular nerve electrical response, optic nerve activity, retinal nerve light response, thickness of retinal layer (OCT), survival of retinal RGC cells, visual acuity, and the like. For example, treatment may be administered to a susceptible individual prior to the onset of symptoms. Treatment may also be continued after symptoms have resolved, for example, to prevent or delay their recurrence.

The term "variant" refers to a sequence that comprises a modification relative to a wild-type sequence. Non-limiting modifications in an amino acid sequence include insertions, deletions, and point mutations. Non-limiting modifications to nucleic acid sequences include frameshift mutations, nucleotide insertions, and nucleotide deletions.

The term "WPRE" refers to a Woodchuck Hepatitis Virus (WHP) Posttranscriptional Regulatory Element (WPRE). WPREs create tertiary structures in nucleic acids (e.g., expression vectors) and are capable of enhancing transgene expression (e.g., from a viral vector). In certain embodiments, a WPRE sequence is at least 70% (e.g., at least 75%, at least 80%, at least 85%, at least 90%, at least 95%, at least 98%, at least 99%, or at least 100%) identical to SEQ ID NO: 23 or 31.

Nucleic Acid Molecules

The present disclosure provides nucleic acid molecules that include a nucleic acid sequence encoding OCT4, a nucleic acid sequence encoding SOX2, a nucleic acid sequence encoding KLF4, or any combination thereof, and in the absence of an exogenous nucleic acid sequence encoding c-Myc. The nucleic acid molecule may be a vector, including for example an expression vector. In certain embodiments, the nucleic acid molecule includes a nucleic acid sequence encoding OCT4. In certain embodiments, the nucleic acid molecule includes a nucleic acid sequence encoding SOX2. In certain embodiments, the nucleic acid molecule includes a nucleic acid sequence encoding KLF4. In certain embodiments, the nucleic acid molecule includes any two of a nucleic acid sequence encoding OCT4, a nucleic acid sequence encoding SOX2, and a nucleic acid sequence encoding KLF4. In certain embodiments, the nucleic acid molecule includes a first nucleic acid sequence encoding OCT4, a second nucleic acid sequence encoding SOX2, and a third nucleic acid sequence encoding KLF4. In certain embodiments, OCT4 comprises an amino acid sequence at least 70% (e.g., at least 75%, 80%, 85%, 90%, 95%, 98%, 99%, or 100%) identical to SEQ ID NO: 2. In certain embodiments, the nucleic acid sequence encoding OCT4 is at least 70% (e.g., at least 75%, 80%, 85%, 90%, 95%, 98%, 99%, or 100%) identical to SEQ ID NO: 1. In certain embodiments, SOX2 comprises an amino acid sequence at least 70% (e.g., at least 75%, 80%, 85%, 90%, 95%, 98%, 99%, or 100%) identical to SEQ ID NO: 4. In certain embodiments, the nucleic acid sequence encoding SOX2 is at least 70% (e.g., at least 75%, 80%, 85%, 90%, 95%, 98%, 99%, or 100%) identical to SEQ ID NO: 3. In certain embodiments, KLF4 comprises an amino acid sequence at least 70% (e.g., at least 75%, 80%, 85%, 90%, 95%, 98%, 99%, or 100%) identical to SEQ ID NO: 6. In certain embodiments, the nucleic acid sequence encoding KLF4 is at least 70% identical (e.g., at least 75%, 80%, 85%, 90%, 95%, 98%, 99%, or 100%) to SEQ ID NO: 5. In certain embodiments, OCT4, SOX2, KLF4, or any combination thereof is a human protein. In certain embodiments, OCT4, SOX2, KLF4, or any combination thereof is a non-human protein, for example, a protein from one or more mammals including from one or more primates (e.g., cynomolgus monkeys, rhesus monkeys). If two or more of OCT4, SOX2, and KLF4 are on one nucleic acid molecule, they may be in any order. The words "first," "second," and "third" do not necessarily imply an order of the genes on the nucleic acid molecule.

In some embodiments, the nucleic acid molecule of the present disclosure includes an inducible promoter. In some embodiments, the nucleic acid molecule has one inducible promoter. In such instances, the expression of OCT4, SOX2, and KLF4 are under the control of the same inducible promoter. In some embodiments, the nucleic acid molecule has more than one inducible promoter. The inducible promoter may include a tetracycline-responsive element (TRE) (e.g., a TRE3G promoter, a TRE2 promoter, or a P tight promoter), mifepristone-responsive promoters (e.g., GAL4-Elb promoter), or a coumermycin-responsive). As an example, a TRE (e.g., TRE3G) promoter may comprise a nucleic acid sequence that is at least 70% (e.g., at least 75%, 80%, 85%, 90%, 95%, 98%, 99%, or 100%) identical to SEQ ID NO: 7. See, e.g., US Publ. Appl. No. 2021-0403923 A, and the International Publ. No. WO2020/069339.

In certain embodiments, the inducing agent is capable of inducing expression of the first (e.g., OCT4), second (e.g., SOX2), third (e.g., KLF4) nucleic acids, or any combination thereof from the inducible promoter in the presence of a tetracycline (e.g., doxycycline). In certain embodiments, the inducing agent is reverse tetracycline-controlled transactivator (rtTA) (e.g., M2-rtTA, rtTA3 or rtTA4). In certain embodiments, the rtTA is rtTA3 comprising an amino acid sequence that is at least 70% (e.g., at least 75%, 80%, 85%, 90%, 95%, 98%, 99%, or 100%) identical to SEQ ID NO: 20. In certain embodiments, rtTA3 is encoded by a nucleic acid sequence that is at least 70% (e.g., at least 75%, 80%, 85%, 90%, 95%, 98%, 99%, or 100%) identical to SEQ ID NO: 19. In certain embodiments, the rtTA is rtTA4 and comprises an amino acid sequence that is at least 70% (e.g., at least 75%, 80%, 85%, 90%, 95%, 98%, 99%, or 100%) identical to SEQ ID NO: 27. In certain embodiments, rtTA4 is encoded by a nucleic acid sequence that is at least 70% (e.g., at least 75%, 80%, 85%, 90%, 95%, 98%, 99%, or 100%) identical to SEQ ID NO: 26.

In certain embodiments, the inducing agent is capable of inducing expression of expression of the first nucleic acid (e.g., OCT4), second nucleic acid (e.g., SOX2), third nucleic (e.g., KLF4), or any combination thereof from the inducible promoter in the absence of a tetracycline (e.g., doxycycline).

In certain embodiments, the inducing agent is tetracycline-controlled transactivator (tTA).

In certain embodiments, the nucleic acid molecule of the present disclosure comprises a constitutive promoter, for example, one or more of CP1, CMV, EF1 alpha, SV40, PGK1, Ubc, human beta actin, CAG, Ac5, polyhedrin, TEF1, GDS, CaM3 5S, Ubi, H1, and/or U6 promoter. The constitutive promoter may be operably linked to nucleic acid sequences encoding OCT4, KLF4, SOX2, an inducing agent, or a combination thereof. In some embodiments, the nucleic acid molecule comprises one constitutive promoter. In some embodiments, the nucleic acid molecule comprises more than one constitutive promoter.

In certain embodiments, the nucleic acid molecule of the present disclosure comprises an SV40-derived terminator sequence. In certain embodiments, the SV40-derived sequence is at least 70% (e.g., at least 75%, 80%, 85%, 90%, 95%, 98%, 99%, or 100%) identical to SEQ ID NO: 12 or 30.

In certain embodiments, the nucleic acid molecule of the present disclosure comprises a separator sequence, which may be useful in producing two separate amino acid sequences from one transcript. The separator sequence may encode a self-cleaving peptide (e.g., 2A peptide, including a 2A peptide sequence that is at least 70% (e.g., at least 75%, 80%, 85%, 90%, 95%, 98%, 99%, or 100%) identical to SEQ ID NO: 8 or 10). In certain embodiments, the separator sequence is an Internal Ribosome Entry Site (IRES).

In certain embodiments, the nucleic acid molecule is a viral vector (e.g., a lentiviral, a retroviral, or an adeno-associated virus (AAV) vector). An AAV vector of the present disclosure generally comprises inverted terminal repeats (ITRs) flanking a transgene of interest (e.g., a nucleic acid sequence encoding OCT4, SOX2, KLF4, an inducing agent, or a combination thereof). In some embodiments, the distance between two inverted terminal repeats is less than 5.0 kilobases(kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb).

In certain embodiments, the nucleic acid molecule (e.g., an expression vector encoding OCT4, KLF4, SOX2, an inducing agent, or a combination thereof) of the present disclosure may further comprise a nucleic acid sequence encoding a selection agent (e.g., an antibiotic, including blasticidin, geneticin, hygromycin B, mycophenolic acid, puromycin, zeocin, actinomycin D, ampicillin, carbenicillin, kanamycin, and neomycin) and/or detectable marker (e.g., GFP, RFP, luciferase, CFP, mCherry, DsRed2FP, mKate, biotin, FLAG-tag, HA-tag, His-tag, Myc-tag, V5-tag, etc.).

In some embodiments, the expression vector encoding OCT4, KLF4, and SOX2 comprises the sequence provided in SEQ ID NO: 13, SEQ ID NO: 14, or SEQ ID NO: 15. In some embodiments, the expression vector encoding OCT4, KLF4, and SOX2 comprises the elements depicted in FIG. 2, or a combination thereof. The expression vector may be a viral vector. The viral vector may be an adeno-associated virus (AAV) vector, retroviral vector, lentiviral vector, herpes viral vector, and the like.

In another aspect, the present disclosure provides recombinant viruses. The recombinant viruses can include one or more lentivirus, adenovirus, retrovirus, herpes virus, alphavirus, vaccinia virus or adeno-associated virus (AAV) comprising any of the expression vectors described herein. In certain embodiments, the recombinant virus encodes a transcription factor selected from OCT4; KLF4; SOX2; and any combination thereof. In certain embodiments, the recombinant virus encodes two or more transcription factors selected from the group consisting of OCT4, KLF4, and SOX2. In certain embodiments, the recombinant virus encodes OCT4 and SOX2, OCT4 and KLF4, or SOX2 and KLF4. In certain embodiments, the recombinant virus encodes OCT4, KLF4, and SOX2. In certain embodiments, the recombinant virus encodes four or more transcription factors, for example OCT4, SOX2, KLF4, and another transcription factor.

Methods of Treatment of NAION

Further provided herein are methods for treating non-arteritic anterior ischemic optic neuropathy (NAION) in a subject in need thereof wherein the method includes administering to the subject one or more agents for upregulating OCT4, SOX2, KLF4, and/or one or more combinations thereof to the subject. The one or more agents do not upregulate c-Myc. The one or more agents for upregulating OCT4, SOX2, KLF4 (OSK) may include one or more means for inducing expression of OSK, including DNA, RNA, small molecules, and the like. In some embodiments, the methods include administering to the subject one or more nucleic acid molecules as contemplated herein. In some embodiments, the one or more nucleic acid molecules include a nucleic acid molecule system having at least two nucleic acid molecules.

In some embodiments of the methods for treating NAION in a subject, the agent for upregulating OSK expression includes at least one nucleic acid molecule encoding OSK as described herein above. The nucleic acid molecule encoding OSK does not comprise a nucleic acid sequence encoding c-myc. The nucleic acid molecule encoding OSK may be an adeno-associated viral (AAV) vector. According to some embodiments, the methods further comprise administering to the subject a nucleic acid molecule encoding a reverse tetracycline-controlled transactivator (rtTA). The nucleic acid molecule encoding a reverse tetracycline-controlled transactivator (rtTA) may be an AAV vector. In some embodiments, the AAV vector comprising a nucleic acid molecule encoding reverse tetracycline-controlled transactivator (rtTA) is not the same AAV vector as the AAV vector comprising a nucleic acid molecule encoding OCT4, SOX2, and KLF4.

The nucleic acid molecule encoding OCT4, SOX2, and KLF4 is operably linked to an inducible promoter. In some embodiments, the inducible promoter is induced by a tetracycline class antibiotic. Tetracycline class antibiotics are known in the art and include, for example, tetracycline, chlortetracycline, oxytetracycline, demeclocyline, lymecycline, meclocycline, methacycline, minocycline, rolitetracycline, doxycycline, tigecycline, eravacycline, sarecycline, and omadacycline. Doxycycline is an exemplary tetracycline class antibiotic. In some embodiments, the inducible promoter is a tetracycline class antibiotic response element (TRE) including for example a TRE2 promoter.

The reverse tetracycline-controlled transactivator (rtTA) may be rtTA3, rtTA4, or combinations thereof.

In some embodiments, the nucleic acid molecule encoding rtTA is operably linked to a constitutive promotor including one or more of CP1, CMV, EF1 alpha, SV40, PGK1, Ubc, human beta actin, CAG, Ac5, polyhedrin, TEF1, GDS, CaM3 5S, Ubi, Hl, and/or U6 promoter. In some embodiments, the nucleic acid molecule encoding rtTA is operably linked a CMV promoter.

In some embodiments, the AAV vector is serotype-2 (AAV2). In some embodiments, the AAV vector is a hybrid vector comprising capsid proteins from one or more serotypes including AAV1, AAV2, AAV5, AAV6, AAV7, AAV8 and AAV9 (e.g., AAV2/2, AAV2/6. AAV2/1, AAV2/5, AAV2/7, AAV2/8 and AAV2/9).

In some embodiments, the AAV vector comprising a nucleic acid molecule encoding OCT4, SOX2, and KLF4 comprises a self-cleaving peptide, for example a 2A peptide.

In some embodiments, the AAV vector comprising a nucleic acid molecule encoding OCT4, SOX2, and KLF4 comprises inverted terminal repeats (ITRs) flanking the first nucleic acid. In some embodiments, the AAV vector comprising a nucleic acid molecule encoding OCT4, SOX2, and KLF4 comprises inverted terminal repeats (ITRs) flanking the second nucleic acid. In some embodiments, the AAV vector comprising a nucleic acid molecule encoding OCT4, SOX2, and KLF4 comprises inverted terminal repeats (ITRs) flanking the third nucleic acid. In some embodiments, the AAV vector comprising a nucleic acid molecule encoding OCT4, SOX2, and KLF4 comprises inverted terminal repeats (ITRs) flanking one or more combinations of the first nucleic acid, the second nucleic acid, and/or the third nucleic acid. In some embodiments, the distance between two inverted terminal repeats (ITRs) is less than 5.0 kilobases(kb) (e.g., less than 4.9 kb, less than 4.8 kb, less than 4.7 kb, less than 4.6 kb, less than 4.5 kb, less than 4.4 kb, less than 4.3 kb, less than 4.2 kb, less than 4.1 kb, less than 4 kb, less than 3.5 kb, less than 3 kb, less than 2.5 kb, less than 2 kb, less than 1.5 kb, less than 1 kb, or less than 0.5 kb). In some embodiments, the distance between two ITRs is 4.7 kb or less.

The method can further include administering an inducing agent to the subject. The inducing agent can include for example a tetracycline-controlled transactivator (tTA). In certain aspects, the inducing agent is capable of inducing expression of expression of the first nucleic acid (e.g., OCT4), the second nucleic acid (e.g., SOX2), the third nucleic (e.g., KLF4), or any combination thereof from the inducible promoter in the absence of a tetracycline (e.g., doxycycline).

In some embodiments, the AAV-OSK vector comprising a nucleic acid molecule encoding OCT4, SOX2, and KLF4 comprises nucleic acid elements in a specific order. For example, the AAV vector comprising a nucleic acid molecule encoding OCT4, SOX2, and KLF4 can include elements in the following order: a) a first inverted terminal repeat sequence (ITR) sequence; b) a TRE2 promoter sequence; c) an OCT4 sequence; d) a P2A cleavage sequence; e) a SOX2 sequence; f) a T2A cleavage sequence; g) a KLF4 sequence; h) an SV-40-derived terminator sequence; and i) a second inverted terminal repeat (ITR) sequence, as described, for example in U.S. patent application Ser. No. 17/280,384, published as Intl. Publ. No. WO2020/069373 titled CELLULAR REPROGRAMMING TO REVERSE AGING AND PROMOTE ORGAN AND TISSUE REGENERATION, incorporated by reference herein in its entirety.

In certain embodiments, the encoded OCT4 comprises an amino acid sequence at least 70% (e.g., at least 75%, 80%, 85%, 90%, 95%, 98%, 99%, or 100%) identical to SEQ ID NO: 2. In certain embodiments, the nucleic acid sequence encoding OCT4 is at least 70% (e.g., at least 75%, 80%, 85%, 90%, 95%, 98%, 99%, or 100%) identical to SEQ ID NO: 1. In certain embodiments, the encoded SOX2 comprises an amino acid sequence at least 70% (e.g., at least 75%, 80%, 85%, 90%, 95%, 98%, 99%, or 100%) identical to SEQ ID NO: 4. In certain embodiments, the nucleic acid sequence encoding SOX2 is at least 70% (e.g., at least 75%, 80%, 85%, 90%, 95%, 98%, 99%, or 100%) identical to SEQ ID NO: 3. In certain embodiments, the encoded KLF4 comprises an amino acid sequence at least 70% (e.g., at least 75%, 80%, 85%, 90%, 95%, 98%, 99%, or 100%) identical to SEQ ID NO: 6. In certain embodiments, the nucleic acid sequence encoding KLF4 is at least 70% identical (e.g., at least 75%, 80%, 85%, 90%, 95%, 98%, 99%, or 100%) to SEQ ID NO: 5. In some embodiments, the nucleic acid sequence encoding OCT4 is SEQ ID NO: 1, the nucleic acid sequence encoding SOX2 is SEQ ID NO: 3, and the nucleic acid sequence encoding KLF4 is SEQ ID NO: 5.

In some embodiments, the P2A sequence encodes for a polypeptide with the sequence ATNFSLLKQAGDVEENPGP (SEQ ID NO: 9). In some embodiments, the P2A sequence is (SEQ ID NO: 8)
GCCACGAACTTCTCTCTGTTAAAGCAAGCAGGAGATGTTGAAGAAAACC
CCGGGCCT.

In some embodiments, the T2A sequence encodes a polypeptide of SEQ ID NO: 11. In some embodiments, the T2A sequence is (SEQ ID NO: 10)
GAGGGCAGGGGAAGTCTTCTAACATGCGGGGACGTGGAGGAAAATCCCG
GCCCA.

In some embodiments, the TRE2 promoter sequence is SEQ ID NO: 7. In some embodiments, the TRE2 promoter sequence comprises at least one minimal CMV promoter sequence. In some embodiments, the at least one minimal SV40 promoter sequence is SEQ ID NO: 12.

In some embodiments, the SV-40-derived terminator sequence is SEQ ID NO: 12.

In some embodiments, the ITR sequence is SEQ ID NO: 16.

In some embodiments, the nucleic acid molecule encoding OCT4, SOX2, and KLF4 comprises SEQ ID NO: 13 or 14. In some embodiments, the nucleic acid molecule encoding OCT4, SOX2, and KLF4 comprises SEQ ID NO: 15.

The AAV vector comprising a nucleic acid molecule encoding OCT4, SOX2, and KLF4 and the AAV vector comprising a nucleic acid molecule encoding rtTA are administered sequentially or simultaneously.

The nucleic acid molecules disclosed herein can be administered to a subject by any appropriate route including, without limitation, intravenous, intraperitoneal, subcutaneous, intramuscular, intranasal, topical, or intradermal routes. In certain embodiments, the composition is formulated for administration via intravenous injection or subcutaneous injection. In some embodiments, the dual vector system including an AAV vector comprising a nucleic acid molecule encoding OCT4, SOX2, and KLF4 and an AAV vector comprising a nucleic acid molecule encoding rtTA is administered intravitreally.

In some embodiments, the nucleic acid molecule encoding OCT4, SOX2, and KLF4 and the nucleic acid molecule encoding rtTA (e.g., rtTA3, rtTA4, etc.) are administered at a ratio (nucleic acid molecule:nucleic acid molecule) of about 1:20, 1:19, 1:18, 1:17, 1:16, 1:15, 1:14, 1:13, 1:12, 1:11, 1:10; 1:9; 1:8; 1:7; 1:6; 1:5; 1:4; 1:3; 1:2; 1:1; 1:0.5; 2:1; 3:1; 4:1; 5:1; 6:1, 7:1; 8:1; 9:1; 10:1, 11:1, 12:1, 13:1, 14:1, 15:1, 16:1, 17:1, 18:1, 19:1, or 20:1. In some embodiments, the nucleic acid molecule encoding OCT4, SOX2, and KLF4 and the nucleic acid molecule encoding rtTA (e.g., rtTA3, rtTA4, etc.) are administered at a ratio of about 1:2; 1:1.9; 1:1.8; 1:1.7; 1:1.6; 1:1.5; 1:1.4; 1:1.3; 1:1.2; 1:1.1; 1:1; 1:0.9; 1:0.8; 1:0.7; 1:0.6; 1:0.5; 1:0.4; 1:0.3; 1:0.2; 1:0.1; 0.1:1; 0.2:1; 0.3:1; 0.4:1; 0.5:1, 0.6:1; 0.7:1; 0.8:1; 0.9:1; 1:1; 1.1:1; 1.2:1; 1.3:1; 1.4:1; 1.5:1; 1.6:1; 1.7:1; 1.8:1; 1.9:1 or 2:1. In some embodiments, the nucleic acid molecule encoding OCT4, SOX2, and KLF4 and the nucleic acid molecule encoding rtTA are administered at an about 1:1 ratio.

In some embodiments, the AAV vector comprising a nucleic acid molecule encoding OCT4, SOX2, and KLF4 and the AAV vector comprising a nucleic acid molecule encoding rtTA (e.g., rtTA3, rtTA4, etc.) are administered at a ratio (vector genome:vector genome (vg:vg)) of about 1:20, 1:19, 1:18, 1:17, 1:16, 1:15, 1:14, 1:13, 1:12, 1:11, 1:10; 1:9; 1:8; 1:7; 1:6; 1:5; 1:4; 1:3; 1:2; 1:1; 1:0.5; 2:1; 3:1; 4:1; 5:1; 6:1, 7:1; 8:1; 9:1; 10:1, 11:1, 12:1, 13:1, 14:1, 15:1, 16:1, 17:1, 18:1, 19:1, or 20:1. In some embodiments, the AAV vector comprising a nucleic acid molecule encoding OCT4, SOX2, and KLF4 and the AAV vector comprising a nucleic acid molecule encoding rtTA are administered at an about 1:1 (vg:vg) ratio. In some embodiments, the AAV vector comprising a nucleic acid molecule encoding OCT4, SOX2, and KLF4 and the AAV vector comprising a nucleic acid molecule encoding rtTA (e.g., rtTA3, rtTA4, etc.) are administered at a ratio (vg/vg) of about 1:10; 1:9; 1:8; 1:7; 1:6; 1:5; 1:4; 1:3; 1:2; 1:1; 1:0.5; 2:1; 3:1; 4:1; 5:1; 6:1, 7:1; 8:1; 9:1; or 10:1. In some embodiments, the AAV vector comprising a nucleic acid molecule encoding OCT4, SOX2, and KLF4 and the AAV vector comprising a nucleic acid molecule encoding rtTA (e.g., rtTA3, rtTA4, etc.) are administered at a ratio (vg/vg) of about 1:2; 1:1.9; 1:1.8; 1:1.7; 1:1.6; 1:1.5; 1:1.4; 1:1.3; 1:1.2; 1:1.1; 1:1; 1:0.9; 1:0.8; 1:0.7; 1:0.6; 1:0.5; 1:0.4; 1:0.3; 1:0.2; 1:0.1; 0.1:1; 0.2:1; 0.3:1; 0.4:1; 0.5:1, 0.6:1; 0.7:1; 0.8:1; 0.9:1; 1:1; 1.1:1; 1.2:1; 1.3:1; 1.4:1; 1.5:1; 1.6:1; 1.7:1; 1.8:1; 1.9:1 or 2:1. In some embodiments, the AAV vector comprising a nucleic acid molecule encoding OCT4, SOX2, and KLF4 and the AAV vector comprising a nucleic acid molecule encoding rtTA are administered at an about 1:1 (vg/vg) ratio. According to some embodiments of the disclosed methods, the AAV vector comprising a nucleic acid molecule encoding OCT4, SOX2, and KLF4 comprises SEQ ID NO: 13, 14, or 35.

According to some embodiments, the AAV vector comprising a nucleic acid molecule encoding rtTA comprises SEQ ID NO: 19, 26, 36, or 37. According to some embodiments of the disclosed methods, the AAV vector comprising a nucleic acid molecule encoding OCT4, SOX2, and KLF4 comprises SEQ ID NO: 13, 14, or 35 and the AAV vector comprising a nucleic acid molecule encoding rtTA comprises SEQ ID NO: 19, 26, 36, or 37. According to some embodiments of the disclosed methods, the AAV vector comprising a nucleic acid molecule encoding OCT4, SOX2, and KLF4 comprises SEQ ID NO: 35 and the AAV vector comprising a nucleic acid molecule encoding rtTA comprises SEQ ID NO: 36 or 37.

In some embodiments, the AAV vector comprising a nucleic acid molecule encoding OCT4, SOX2, and KLF4 is an AAV2-TRE-OSK vector and the AAV vector comprising a nucleic acid molecule encoding rtTA is an AAV2-CMV-rtTA3. The AAV composition may include an AAV2-TRE-OSK vector and an AAV2-CMV-rtTA3 vector. The methods may include the AAV2-TRE-OSK vector and the AAV2-CMV-rtTA3 vector in the same or in separate compositions.

In some embodiments, the AAV vector comprising a nucleic acid molecule encoding OCT4, SOX2, and KLF4 is an AAV2-TRE-OSK vector and the AAV vector comprising a nucleic acid molecule encoding rtTA is an AAV2-CMV-rtTA4. The AAV composition may include an AAV2-TRE-OSK vector and an AAV2-CMV-rtTA4 vector. The methods may include the AAV2-TRE-OSK vector and the AAV2-CMV-rtTA4 vector in the same composition or in separate compositions.

The concentration of the AAV2-TRE-OSK vector to be administered in accordance with the disclosed methods includes an amount in the range of from about $1\times10^{10}$ vg/mL to about $2\times10^{13}$ vg/mL, for example, $1\times10^{12}$ vg/mL to about $2\times10^{12}$ vg/mL. For example, the effective amount of the AAV2-TRE-OSK vector can include from about $1.0\times10^{12}$ vg/mL to about $1.1\times10^{12}$ vg/mL, from about $1.1\times10^{12}$ vg/mL to about $1.2\times10^{12}$ vg/mL, from about $1.2\times10^{12}$ vg/mL to about $1.3\times10^{12}$ vg/mL, from about $1.3\times10^{12}$ vg/mL to about $1.4\times10^{12}$ vg/mL, from about $1.4\times10^{12}$ vg/mL to about $1.5\times10^{12}$ vg/mL, from about $1.5\times10^{12}$ vg/mL to about $1.6\times10^{12}$ vg/mL, from about $1.6\times10^{12}$ vg/mL to about $1.7\times10^{12}$ vg/mL, from about $1.7\times10^{12}$ vg/mL to about $1.8\times10^{12}$ vg/mL, from about $1.8\times10^{12}$ vg/mL to about $1.9\times10^{12}$ vg/mL, from about $1.9\times10^{12}$ vg/mL to about $2.0\times10^{12}$ vg/mL and any and all increments therebetween.

The concentration of the AAV2-CMV-rtTA3 vector administered in accordance with the disclosed methods includes an amount in the range of from about $1\times10^{10}$ vg/mL to about $2\times10^{13}$ vg/mL, for example, about $1\times10^{13}$ vg/mL to about $2\times10^{13}$ vg/mL. For example, the effective amount of the AAV2-CMV-rtTA3 vector can include from about $1.0\times10^{13}$ vg/mL to about $1.1\times10^{13}$ vg/mL, from about $1.1\times10^{13}$ vg/mL to about $1.2\times10^{13}$ vg/mL, from about $1.2\times10^{13}$ vg/mL to about $1.3\times10^{13}$ vg/mL, from about $1.3\times10^{13}$ vg/mL to about $1.4\times10^{13}$ vg/mL, from about $1.4\times10^{13}$ vg/mL to about $1.5\times10^{13}$ vg/mL, from about $1.5\times10^{13}$ vg/mL to about $1.6\times10^{13}$ vg/mL, from about $1.6\times10^{13}$ vg/mL to about $1.7\times10^{13}$ vg/mL, from about $1.7\times10^{13}$ vg/mL to about $1.8\times10^{13}$ vg/mL, from about $1.8\times10^{13}$ vg/mL to about $1.9\times10^{13}$ vg/mL, from about $1.9\times10^{13}$ vg/mL to about $2.0\times10^{13}$ vg/mL and any and all increments therebetween.

The concentration of the AAV2-CMV-rtTA4 vector administered in accordance with the disclosed methods includes an amount in the range of from about $1\times10^{10}$ vg/mL to about $2\times10^{13}$ vg/mL, for example, about $1\times10^{13}$ vg/mL to about $2\times10^{13}$ vg/mL. For example, the effective amount of the AAV2-CMV-rtTA4 vector can include from about $1.0\times10^{13}$ vg/mL to about $1.1\times10^{13}$ vg/mL, from about $1.1\times10^{13}$ vg/mL to about $1.2\times10^{13}$ vg/mL, from about $1.2\times10^{13}$ vg/mL to about $1.3\times10^{13}$ vg/mL, from about $1.3\times10^{13}$ vg/mL to about $1.4\times10^{13}$ vg/mL, from about $1.4\times10^{13}$ vg/mL to about $1.5\times10^{13}$ vg/mL, from about $1.5\times10^{13}$ vg/mL to about $1.6\times10^{13}$ vg/mL, from about $1.6\times10^{13}$ vg/mL to about $1.7\times10^{13}$ vg/mL, from about $1.7\times10^{13}$ vg/mL to about $1.8\times10^{13}$ vg/mL, from about $1.8\times10^{13}$ vg/mL to about $1.9\times10^{13}$ vg/mL, from about $1.9\times10^{13}$ vg/mL to about $2.0\times10^{13}$ vg/mL and any and all increments therebetween.

According to some embodiments, the effective dose of the AAV2-TRE-OSK vector administered in accordance with the disclosed methods includes the amount of vector administered per eye. The effective dose can include an amount of vector in the range of from about $1\times10^{9}$ vg/eye to about $1\times10^{14}$ vg/eye. In some embodiments, the effective dose of the AAV2-TRE-OSK vector can include an amount of vector in the range of from about $1\times10^{11}$ vg/eye to about $10\times10^{11}$ vg/eye. For example, the dose of the AAV2-TRE-OSK vector can include from about $1\times10^{11}$ vg/eye to about $2\times10^{11}$ vg/eye, from about $2\times10^{11}$ vg/eye to about $3\times10^{11}$ vg/eye, from about $3\times10^{11}$ vg/eye to about $4\times10^{11}$ vg/eye, from about $4\times10^{11}$ vg/eye to about $5\times10^{11}$ vg/eye, from about $5\times10^{11}$ vg/eye to about $6\times10^{11}$ vg/eye, from about $6\times10^{11}$ vg/eye to about $7\times10^{11}$ vg/eye, from about $7\times10^{11}$ vg/eye to about $8\times10^{11}$ vg/eye, from about $8\times10^{11}$ vg/eye to about $9\times10^{11}$ vg/eye, from about $9\times10^{11}$ vg/eye to about $10\times10^{11}$ vg/eye, including any and all increments therebetween. In some embodiments, the effective dose of the AAV2-TRE-OSK vector is about $3.06\times10^{11}$ vg/eye.

The effective dose of the AAV2-CMV-rtTA3 vector administered in accordance with the disclosed methods includes the amount of vector administered per eye. The effective dose the AAV2-CMV-rtTA3 vector can include an amount of vector in the range of from about $1\times10^{9}$ vg/eye to about $1\times10^{14}$ vg/eye. In some embodiments, the effective dose the AAV2-CMV-rtTA3 vector can include an amount of vector in the range of from about $1\times10^{11}$ vg/eye to about $10\times10^{11}$ vg/eye. For example, the dose the AAV2-CMV-rtTA3 vector can include from about $1\times10^{11}$ vg/eye to about $2\times10^{11}$ vg/eye, from about $2\times10^{11}$ vg/eye to about $3\times10^{11}$ vg/eye, from about $3\times10^{11}$ vg/eye to about $4\times10^{11}$ vg/eye, from about $4\times10^{11}$ vg/eye to about $5\times10^{11}$ vg/eye, from about $5\times10^{11}$ vg/eye to about $6\times10^{11}$ vg/eye, from about $6\times10^{11}$ vg/eye to about $7\times10^{11}$ vg/eye, from about $7\times10^{11}$ vg/eye to about $8\times10^{11}$ vg/eye, from about $8\times10^{11}$ vg/eye to about $9\times10^{11}$ vg/eye, from about $9\times10^{11}$ vg/eye to about $10\times10^{11}$ vg/eye, including any and all increments therebetween. In some embodiments, the effective dose of the AAV2-CMV-rtTA3 vector is about $2.66\times10^{11}$ vg/eye.

The effective dose of the AAV2-CMV-rtTA4 vector administered in accordance with the disclosed methods includes the amount of vector injected per eye. The effective dose can include an amount of vector in the range of from about $1\times10^9$ vg/eye to about $1\times10^{14}$ vg/eye. In some embodiments, the effective dose the AAV2-CMV-rtTA4 vector can include an amount of vector in the range of from about $1\times10^{11}$ vg/eye to about $10\times10^{11}$ vg/eye. For example, the dose the AAV2-CMV-rtTA4 vector can include from about $1\times10^{11}$ vg/eye to about $2\times10^{11}$ vg/eye, from about $2\times10^{11}$ vg/eye to about $3\times10^{11}$ vg/eye, from about $3\times10^{11}$ vg/eye to about $4\times10^{11}$ vg/eye, from about $4\times10^{11}$ vg/eye to about $5\times10^{11}$ vg/eye, from about $5\times10^{11}$ vg/eye to about $6\times10^{11}$ vg/eye, from about $6\times10^{11}$ vg/eye to about $7\times10^{11}$ vg/eye, from about $7\times10^{11}$ vg/eye to about $8\times10^{11}$ vg/eye, from about $8\times10^{11}$ vg/eye to about $9\times10^{11}$ vg/eye, from about $9\times10^{11}$ vg/eye to about $10\times10^{11}$ vg/eye, including any and all increments therebetween. In some embodiments, the effective dose of the AAV2-CMV-rtTA4 vector is about $2.66\times10^{11}$ vg/eye.

Embodiments of the methods include administering the AAV composition comprising an AAV vector including a nucleic acid molecule encoding OCT4, SOX2, and KLF4 and an AAV vector including a nucleic acid molecule encoding rtTA to the subject by one or more suitable routes including oculus sinister (OS) injection, oculus dexter (OD) injection, or oculus uterque (OU) injection. Administration may include one or more injections, for example, administration may include one injection comprising the AAV composition comprising an AAV vector including a nucleic acid molecule encoding OCT4, SOX2, and KLF4 and the AAV vector including a nucleic acid molecule encoding rtTA. In other aspects, the administration may include two (or more) injections, for example, one injection comprising the AAV composition comprising an AAV vector including a nucleic acid molecule encoding OCT4, SOX2, and KLF4 and one injection comprising the AAV vector including a nucleic acid molecule encoding rtTA. The injection comprising the AAV vector including a nucleic acid molecule encoding OCT4, SOX2, and KLF4 may be administered and the injection comprising the AAV vector including a nucleic acid molecule encoding rtTA may be administered simultaneously or sequentially. For example, the injection comprising the AAV composition comprising an AAV vector including a nucleic acid molecule encoding OCT4, SOX2, and KLF4 may be administered before, at the same time as, or after the injection comprising the AAV vector including a nucleic acid molecule encoding rtTA.

Embodiments of the methods further include administering to the subject an effective amount of an antibiotic. In some embodiments, the antibiotic includes tetracycline or doxycycline. In some embodiments, the antibiotic is administered at least one day prior to administering the AAV vector comprising a nucleic acid molecule encoding OCT4, SOX2, and KLF4 and the AAV vector comprising a nucleic acid molecule encoding rtTA.

The antibiotic may be administered when the AAV vector comprising a nucleic acid molecule encoding OCT4, SOX2, and KLF4 and the AAV vector comprising a nucleic acid molecule encoding rtTA are administered. The antibiotic may be administered at least one day following administration of the AAV composition comprising the AAV vector comprising a nucleic acid molecule encoding OCT4, SOX2, and KLF4 and the AAV vector comprising a nucleic acid molecule encoding rtTA. The antibiotic may be administered 2 days, 3 days, 4 days, 5 days, or more than 5 days following administration of the AAV composition comprising the AAV vector comprising a nucleic acid molecule encoding OCT4, SOX2, and KLF4 and the AAV vector comprising a nucleic acid molecule encoding rtTA.

The disclosed methods of treating NAION include methods of administering to a subject in need thereof an effective amount of an AAV genome including one or more polynucleotide sequences expressing OCT4, SOX2, and KLF4 and an AAV genome comprising a nucleic acid sequence encoding transactivator 3 or transactivator 4.

Methods of Preparing AAV-OSK Vectors

Provided herein are methods for recombinant preparation of an AAV. In some embodiments, the method comprises introducing one or more vectors as contemplated herein into a cell under conditions whereby the AAV is produced. The cell may include a population of cells. The population of cells may include any suitable cells as understood in the art, including for example HEK293 cells, HEK293T cells, COS cells, CHO cells, BHK cells, HeLa cells, and the like. The one or more vectors may be introduced into the cell using one or more suitable techniques including for example transfection, transduction, and/or infection. Exemplary methods for recombinant preparation of the AAV include transient transfection (e.g., with one or more transfer plasmids containing a first, and a second, and optionally a third vector as described herein), viral infection (e.g., with one or more recombinant helper viruses, such as a adenovirus, poxvirus (such as vaccinia virus), herpes virus (including HSV, cytomegalovirus, or baculovirus, containing a first, and a second, and optionally a third vector as described herein)), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV capsid proteins as described herein, and with an AAV genome as described herein being delivered in the form of a plasmid or a recombinant helper virus). The first vector may include one or more nucleic acid sequences expressing OCT4, SOX2, and/or KLF4 encoded by one or more of SEQ ID NOs: 13, 14, 15, and 35. The second vector may include one or more nucleic acid sequences expressing transactivator 3, for example SEQ ID NO: 21 or 36. Alternatively, the second vector may include one or more nucleic acid sequences expressing transactivator 4, for example SEQ ID NO: 28 or 37.

Further provided herein are methods for generating an AAV comprising modifying a cell to express one or more plasmids. The one or more plasmids may include one or more AAV2 Rep-Cap plasmids, one or more helper plasmids, and one or more transfer plasmids. The one or more transfer plasmids may include a first transfer plasmid including one or more nucleic acids encoding one or more of: OCT4, SOX2, and KLF4; a second transfer plasmid including one or more nucleic acids encoding transactivator 3; or a transfer plasmid including one or more nucleic acids encoding one or more of: OCT4, SOX2, KLF4, and transactivator 3. The one or more transfer plasmids may also include a first transfer plasmid including one or more nucleic acids encoding one or more of: OCT4, SOX2, and KLF4; a second transfer plasmid including one or more nucleic acids encoding trans activator 4; or a transfer plasmid including one or more nucleic acids encoding one or more of: OCT4, SOX2, KLF4, and transactivator 4.

EXAMPLES

Example 1—Methods of Producing Vectors

The present study set out to develop a method for manufacturing batches of vectors and to assess the stability of the prepared batches.

AAV Production Protocol
Materials
Cells:
HEK293T cells were used to produce the vectors as described herein. The cells were grown in DMEM media (Invitrogen, cat. no. 11995073) containing 10% fetal bovine serum (FBS) (Invitrogen HI FBS, cat. no. 16140), penicillin/streptomycin (Invitrogen, cat. no. 15140-122), Glutamine (Invitrogen cat. no. 25030).

Plasmids

Figure 2:
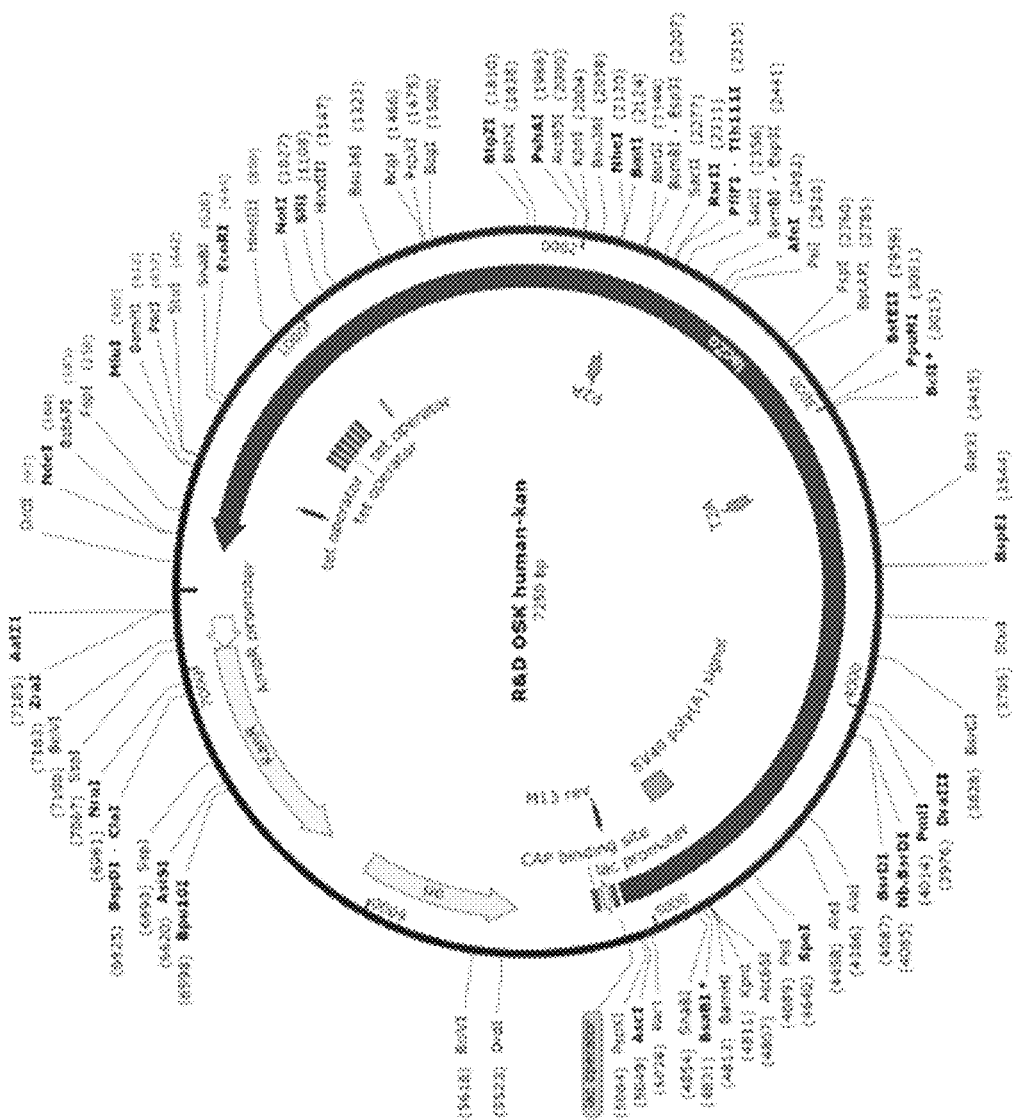
FIG. 2 is an illustrative vector map of TRE3G-OSK-SV40 pA, an AAV2 vector encoding OSK (SEQ ID NO: 15).

The recombinant AAV2-TRE-OSK plasmid (shown in FIG. 2) was prepared using the following components: (1) a nucleic acid sequence encoding an AAV2 capsid protein or a fragment thereof, (2) a nucleic encoding a functional rep gene, (3) a recombinant AAV transfer vector comprising AAV2 inverted terminal repeats (SEQ ID NO: 16, SEQ ID NO: 32) flanking a transgene encoding OCT4, KLF4, and SOX2 (SEQ ID NO: 13) operably linked to an inducible TRE promoter (TRE3G, SEQ ID NO: 7), and (4) a helper vector with rAAV2 Rep-Cap proteins. Plasmids were obtained from Stratagene/Agilent (Stratagene cat no: 240071). The AAV2 Rep-Cap plasmid included an pAAV-RC plasmid (Stratagene cat. no. 240071). In some cases, AAV2 hybrid vectors e.g., AAV2/1 AAV2/2, AAV2/5, AAV2/6, AAV2/7, AAV2/8 and AAV2/9 with capsid proteins from AAV1, 2, 3, 5, 6, 7, 8, and 9 serotypes. The helper plasmid included a pHelper plasmid (Stratagene, cat. no. 240071) and carried adenovirus-derived genes for introducing helper functions. As shown in FIG. 2 the entire AAV2-TRE3G-OSK-SV40 pA vector is 7250 base pairs in length, and two inverted terminal repeats (ITRs) flank the OSK sequences.

The first expression vector encoding OCT4, SOX2, and KLF4 includes the nucleic acid sequence set forth in SEQ ID NO: 15. The recombinant AAV vector can include a nucleic acid encoding an inducing agent.

Figure 3:
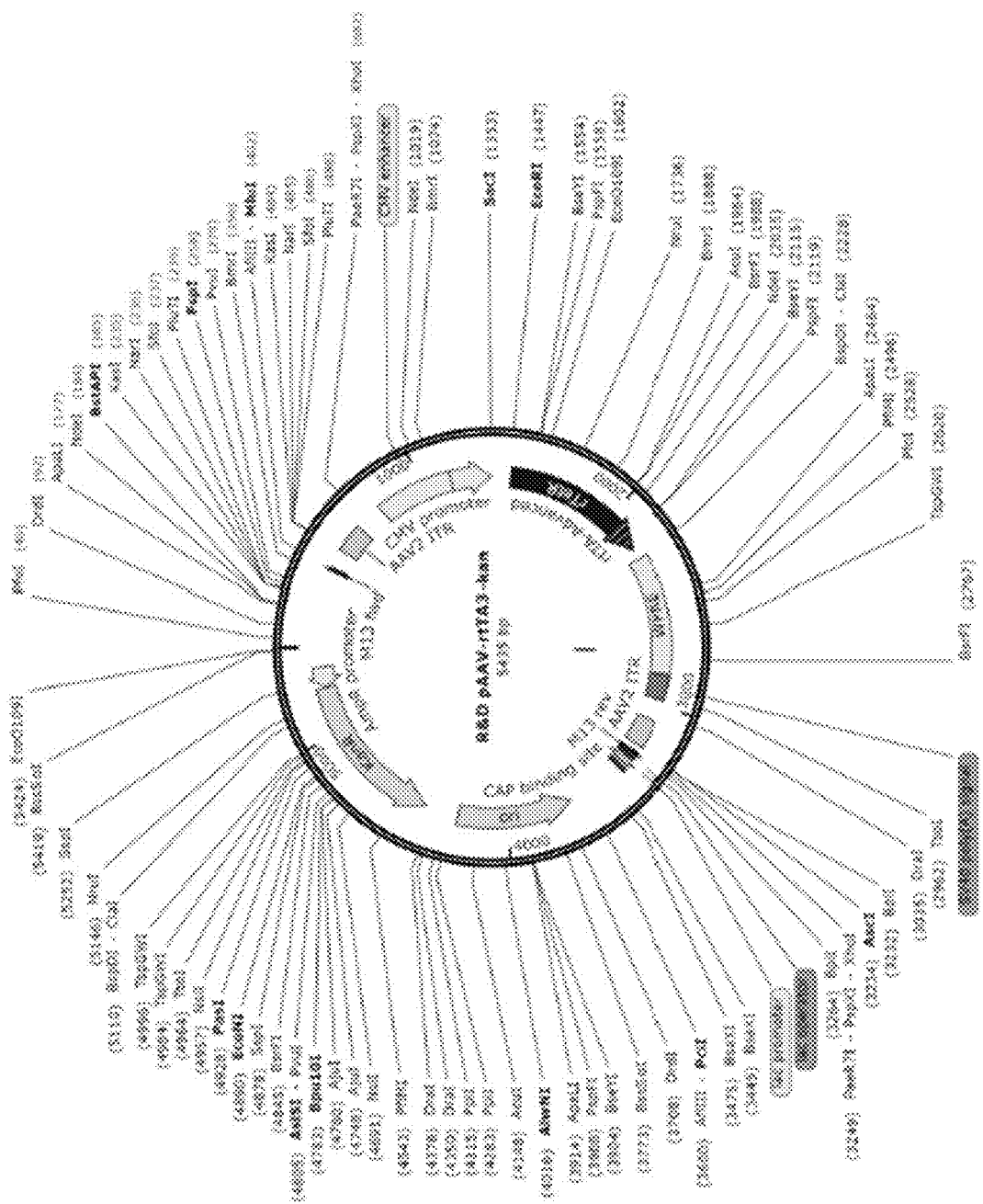
FIG. 3 depicts an illustrative vector map of pAAV2-CMV-rtTA3(VP16) (SEQ ID NO: 21). This vector is a non-limiting example of a vector encoding rtTA.
Figure 4:
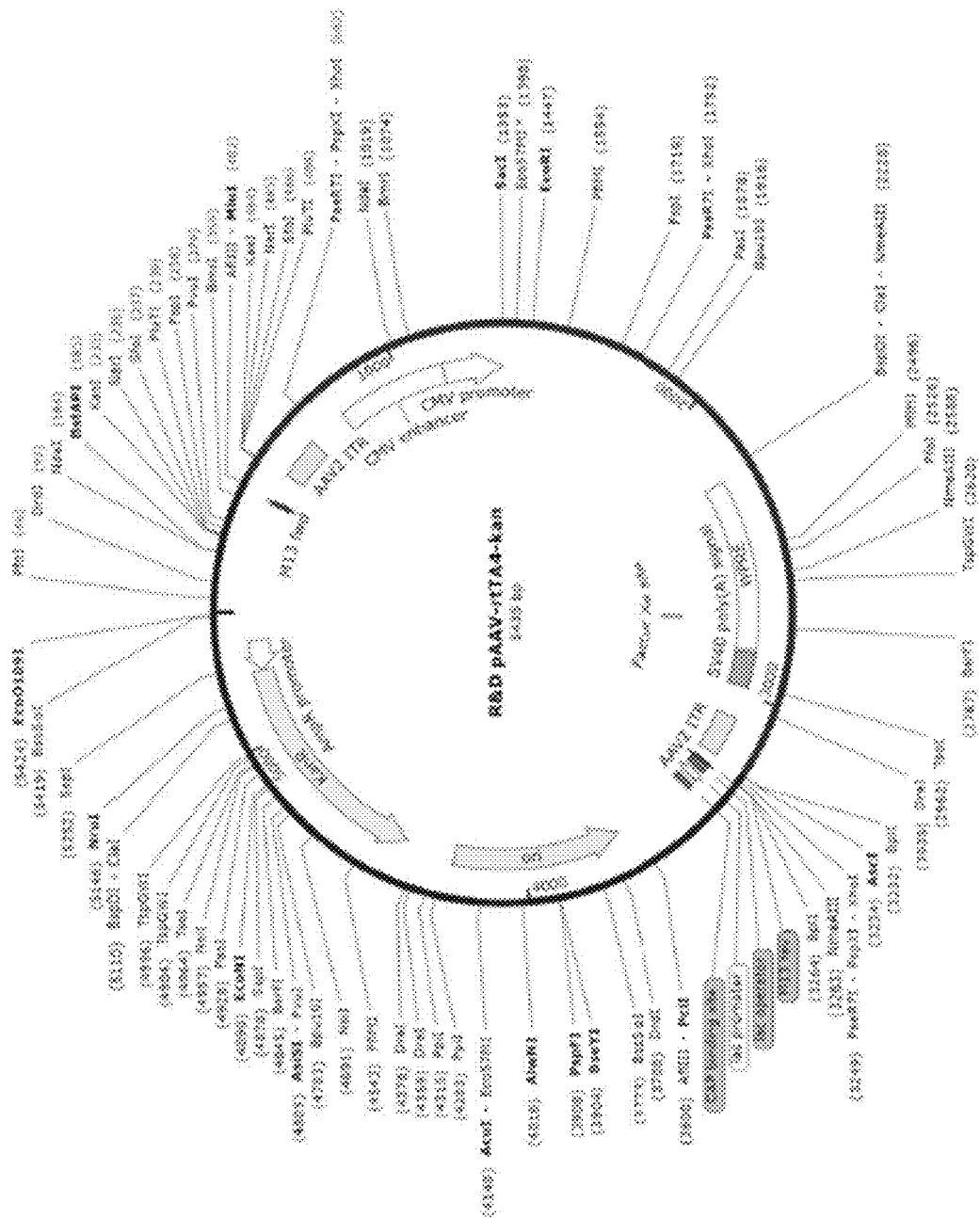
FIG. 4 depicts an illustrative vector map of pAAV2-CMV-rtTA4 (SEQ ID NO: 28). This vector is a non-limiting example of a vector encoding rtTA.
Figure 5:
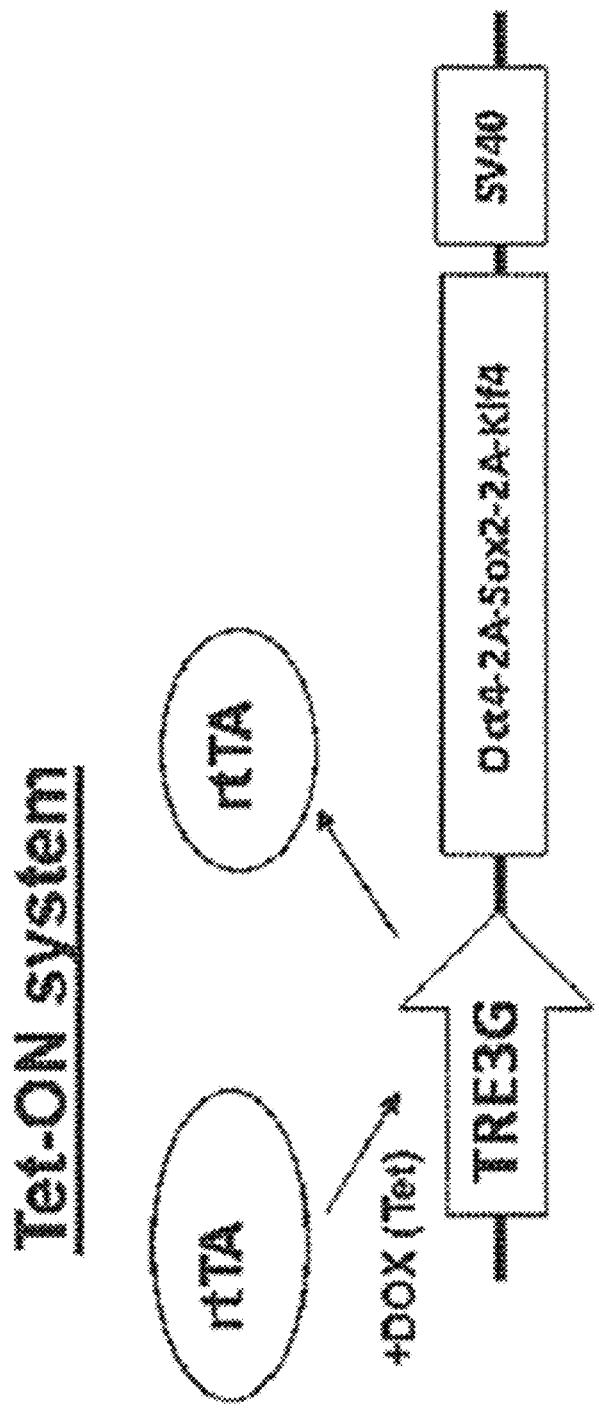
FIG. 5 depicts a schematic showing a non-limiting example of a Tet-ON system to express OCT4, SOX2, and KLF4 (OSK) in the presence of a tetracycline.

The recombinant pAAV2-CMV-rtTA, pAAV2-CMV-rtTA3(V16) (shown in FIG. 3), for the Tet-On plasmid was prepared using a similar approach to that described above but using a transfer plasmid with a CMV constitutive promoter (SEQ ID NO: 17) operably linked to rtTA3 (SEQ ID NO 19) inducing agent having 3 vp16 domains at the 3' end. An alternative recombinant pAAV2-CMV-rtTA, pAAV2-CMV-rtTA4(V16) (shown in FIG. 4), may be prepared in the same way.

Polyethyleneimine (PEI) Solution

PEI solution (1 µg/µl, Polysciences, cat. no. 23966-2) was prepared by dissolving PEI powder in H$_2$O that was heated to 80° C., cooled to room temperature, neutralized to pH 7.0, filter sterilized, aliquoted and stored at −20° C. The transfection efficiency was tested when each new batch was prepared.

Methods
Vector Production

On day 1, HEK293T cells were plated on 10 15-cm dishes before transfecting for 24 hours. Cells were seeded with 25 mL medium per 15-cm culture dish. Cells were split to a density of 70-90% (standard transfection density) ten times on 15 cm plates in order to provide a yield of 5E12 viral genomes (vg). Media was changed with 5% FBS to slow growth and reduce purification time one plate at a time in order to prevent cells from dying.

On day 2, 1 hour before transfection, medium was changed to 20 mL of freshly warmed medium. A DNA solution was prepared in a 50 mL FALCON™ tube. The amounts of DNA and reagents per dish are shown in the Table 2 below. Based on the size of inverted terminal repeat (ITR) plasmid, the amount of DNA was calculated. A tube of master mixture was prepared for 5 15-cm dishes. As shown in Table 2 below, all plasmids were diluted to 1 µg/µl in sterile H$_2$O.

A 10-mL sample of DMEM (without phenol red, Invitrogen cat. no. 31053-036) was prepared. A 785 µl aliquot of PEI solution was added, and the media was mixed. It was then incubated at room temperature for 20-30 minutes.

TABLE 2

Amounts of Reagents per Plate

| Plasmid | Plasmid size | Amount of Plasmid Per Plate | Amount of Plasmid Per 5 Plates | [plasmid] (µg/µl) | VOLUME |
|---|---|---|---|---|---|
| AAV2-RC | 7.3 kb | 15.2 µg | 76 µg | 1 µg/µl | 76 µl |
| HELPER | 11.6 kb | 24 µg | 120 µg | 1 µg/µl | 120 µl |
| ITR plasmid-Gene of Interest (e.g., OSK) | 6.3 kb | 13.117808 µg | 65.58904 µg | 1 µg/µl | 65.5 µl |

Next, 2 mL of DNA-PEI mixture was added to each of 10 15-cm dishes. The transfected cells were then incubated.

On Day 3, the medium was removed, and 25 mL of freshly warmed medium was added. Serum-containing medium was added for AAV2/2, AAV2/6. Serum-free medium was used for AAV2/1, AAV2/5, AAV2/7, AAV2/8 and AAV2/9.

On Day 5, cells were scraped with a cell scraper in their current medium and transferred to a 50 mL tube. The cell suspension was then spun at 1000 relative centrifugal force (rcf) for 5 minutes. The supernatant was then discarded.

Transfection Procedures

All cells were combined into 1 50-mL tube, washed with PBS, and spun at 1000 rpm for 5 minutes. The supernatant was then discarded.

The cell pellet was resuspended in a volume of hypotonic buffer five times the volume of the packed cell volume (approximately 25 mL). It was then incubated on ice for 10 minutes. A 0.11% by volume amount of 10× restore buffer was then added and mixed by pipetting (generally a volume of 3.3 mL).

The nuclei were then spun down at 2000 rcf for 10 minutes, generating a nuclear pellet of about 1 mL per 10 15-cm dishes. The pellet was stored at −80° C. for further purification.

Preparation of Solutions
5 M NaCl Salt Solution

A mass of 292.2 g NaCl was added to 200 of deionized (DI) water in a 2 L bottle. The mixture was shaken to mix, and poured into a large, graduated cylinder. DI water was then added up to 1 L and poured back into the 2 L bottle. A stir bar was added, and the volume was heated and stirred until dissolved. Alternatively, the volume was autoclaved. The solution was then cooled and sterile filtered through 0.2 µm filter.

40% PEG-8000, 2.5M NaCl (5× stock solution).

In a 1 L graduated cylinder, 400 g PEG-8000 and 500 mL 5 M NaCl were mixed. DI water was added to 1 L. This generally required about 100 mL of water. The solution was transferred to a 2 L flask and shaken to mix. A large stir bar was added, and the solution was heated overnight in a water bath at 55° C. The next day, the solution was sterile filtered with a 0.2 µm filter. This filtration step generally takes about 30 minutes.

Harvesting AAV from Media and Cells

The media and cells were harvested without use of trypsin. The media was collected with a pipetman and sterile filtered with a 0.2 μM filter. The cells were collected and spun down. Any remaining supernatant was added to the media sterile filtered with a 0.2 μm filter. The cells were harvested in one of several ways. Cells were collected with a cell scraper. Alternatively, cells were "blasted" with calcium- and magnesium-free PBS at a volume of 10 mL per 2 plates. A 40% solution of PEG 8000 adjusted to pH 7.4 was added to a final concentration of 12%. Approximately 25 mL per 100 mL of media/cells were used. The solution was stirred in a cold room for 1 hour and was either left to sit for 3 hours without spinning or was left overnight in cold room. The next day, the PEG mixture was spun at 3000×g for 20 minutes. The supernatant was discarded. The pellet was resuspended in less than about 7 mL of 1×PBS. The pellet was first suspended with about 5 mL and a volume of up to 2 mL was added once nearly suspended. A solution of benzonase at 1:10,000 was then added and the mixture was incubated for 45 minutes at 37° C. Optionally, the mixture was spun down at 2415xg for 10 minutes at 4° C. The supernatant was transferred to new tube.

Concentrating AAV with Ultracentrifugation

Preparation of Solutions

A 1 M MgCl2 stock solution was prepared which was at 1000× and was used for making MK buffer. A 2.5 M stock solution of KCl was prepared which was a 1000× and was also used for preparing MK buffer.

A 1 M solution of NaCl/phosphate-buffered saline (PBS) MK buffer was prepared by dissolving 58.4 g of NaCl in 1 mL of 1 M MgCl2 and 1 mL of 2.5 M KCl. Then, 1x PBS (Ca⁻ Mg⁻ Dulbecco's phosphate-buffered saline (DPBS), Gibco) was added to final volume of 1 L. The solution was sterilized by passing through a 0.22-μm filter and stored at 4° C. The solution was brought to final concentration of 1 M NaCl, 1 mM MgCl2, and 2.5 mM KCl.

A 1× PBS-MK buffer was prepared by dissolving 1 mL of 1 M MgCl2, and 1 mL 2.5 M KCl to 2×500 mL bottles of Ca— Mg— DPBS (Gibco). The solution was sterilized by passing through a 0.22 μm filter and stored at 4° C. The solution was brought to final concentrations of 1 mM MgCl2 and 2.5 mM KCl.

A 0.001% Pluronic-F68 (formulation buffer) solution was prepared by adding 500 μL of sterile 1000× Pluronic F-68 (1% solution) to 500 mL of 1× DPBS (Gibco, TC stock). The solution was stored at 4° C. for up to one month, or aliquoted and stored at −80° C. for up to one year.

A 0.001% PLURONIC™-F68+5% sorbitol (freezing buffer) solution was prepared by adding 25 g of sorbitol to 500 μL of sterile 1000× PLURONIC™ F-68 (1% solution) to 500 mL of 1× DPBS (Gibco, TC stock). The solution was stored at 4° C. for up to one month, or aliquoted and stored at −80° C. for up to one year.

As shown in Table 3, 15% iodixanol solution was prepared by mixing 30 mL of 60% iodixanol and 90 mL of 1 M NaCl/PBS-MK buffer. A 25% iodixanol solution was prepared by mixing 112.5 mL of 60% iodixanol, 157.5 mL of 1× PBS-MK buffer, and 900 μL of phenol red. A 40% iodixanol solution was prepared by mixing 202.5 mL of 60% iodixanol and 67.5 mL of 1× PBS-MK buffer. A 60% iodixanol solution was prepared by mixing 150 mL of 60% iodixanol and 675 μL of phenol red.

TABLE 3

| | | Iodixanol solutions | | |
|---|---|---|---|---|
| % soln | mL 60% iodixanol | mL 1M NaCl PBS-MK | mL PBS-MK | μL phenol red |
| 15 | 30 | 90 | 0 | 0 |
| 25 | 112.5 | 0 | 157.5 | 675 |
| 40 | 180 | 0 | 90 | 0 |
| 60 | 150 | 0 | 0 | 675 |

Note
all solutions were sterile-filtered with 0.2 um filters.

In order to create an ultra-gradient, the benzonased supernatants were added to Beckman optiseal tubes. If volumes were unequal, 1 M NaCl, PBS-MK mix was added to make them equal, to a final volume of approximately 7 mL.

The tubes were filled from the bottom using 10 mL syringes and long hypodermic needles. For each solution the same syringe was reused but the needles were changed after every sample in order to prevent cross-contamination between AAV preparations. 5 mL was the minimum volume for any layer.

The tubes were balanced to 5-10 μg. The tubes were balanced in pairs. They were first sorted so that the most similar tubes were paired, and then PBS was added to the lighter tube in each pairing. PBS was added by touching the tip to the side of the tube to prevent droplets from disturbing the layers. Caps were added and tubes were loaded into the ultracentrifuge.

The tubes were then spun in an ultracentrifuge using a VTi50 rotor for 1 hour at max speed (50,000 rpm=242,000 xg). The fractions were collected from the ultracentrifuged tubes by piercing the bottom with an 18-gauge needle. The black stopper was removed at the top before piercing with the needle, otherwise air bubbles were created that disturb the layers. The majority of the 60% fraction was removed. The remaining part of the 60% layer was then collected along with the 40% fraction in a 50 mL tube. Sample collection was complete when the color changed significantly, or the solution was cloudy Separation of Fractions on a Protein Gel Samples were denatured with 4× LDS with 2.5% (3-mercaptoethanol at 70° C. for 10 minutes. In order to prepare 200_, aliquots, 100_, of sample was combined with 5 μL of H₂O, 5 μL of LDS with 2.5% (3-mercaptoethanol. If necessary, extra running buffer (200 mL 10× Tris-Glycine SDS buffer, 1800 mL Millipure water) was prepared.

Samples were then loaded into a Tris Glycine gel. Either a 4-12% or 4-20% gradient gel was used. For AAV capsids, either is suitable.

The gel box was assembled, and the wells of the gel were loaded with 20 μL of sample per well. Gels were run at 225 V for 30-45 minutes, until the blue dye reached the bottom of the gel.

The gels were then stained with SYPRO™ red and imaged. First, a staining solution was prepared (7.5% acetic acid, SYPRO™ red is 5000×) by adding 10 μL of SYPRO™ red to 50 mL of stain solution. This was enough for 1 gel. Gels were stained for 1 hour while covered at room temperature on a slow rocker. The stain solution was then removed and acetic acid solution with no dye was added. The gels were incubated for 1 to 5 minutes in order to de-stain. The gels were images on a gel dock with EtBr settings (UV).

Good fractions were then combined and washed with 1×PBS with 0.001% F68. In some cases about 20 mL PBS+F68 was added to bring the final volume to just less than 30 mL in order to dilute the iodixanol which facilitates passing through the filter.

Samples were spun at 4700 g for 5 minutes. After everything flowed through, the samples were washed 3× more with 15 mL per wash in order to prepare a clear final solution. The samples were then aliquoted into labelled tubes (name of virus, payload, date) and stored at 4° C. for up to 1 week. For longer storage, the final elution was prepared with 1×PBS with 0.001% F68 and 5% sorbitol. Samples were frozen at −80° C.

Titering Virus with qPCR

Samples were prepared by aliquoting 12.5 µl Master Mix into tubes. Either fast advanced TAQMAN™ Master Mix from ThermoFisher or IDT Primetime Master Mix was used. To each tube, 0.0625 µl of primer 1, 0.0625 µl of primer 2, 0.125 µl of probe, 1 µl of virus, and 11.3 µl of $H_2O$ was added for a total volume of 25 µl.

Example 2—Method of Treating NAION in Non-Human Primates

This study set out to determine whether epigenetic reprogramming improves RGC function and restores visual function (pERG) in a nonhuman primate (NHP) model of NAION (Non-arteritic Anterior Ischemic Optic Neuropathy). The efficacy of the neuroprotective effect of the doxycycline responsive dual vector system AAV2-TRE-OSK (SEQ ID NO: 35)/AAV2-CMV-rtTA3V16 (SEQ ID NO: 36), in a photothrombotic experimental model of non-arteritic anterior ischemic optic neuropathy (NAION) was evaluated. The vector system was administered intravitreally (IVT) in African green monkeys induced by laser excitation of a systemically administered fluorophore at the optic nerve head (ONH).

Methods

Subject Recruitment

Monkeys with normal slit lamp and fundus exams, color fundus photographs (CFP), optical coherence tomography (OCT), confocal scanning laser ophthalmoscopy (cSLO), pattern electroretinograms (pERG), and pattern visual evoked potentials (pVEP) were recruited to the study. For baseline screening and all subsequent procedures, anesthesia was achieved with intramuscular ketamine (8 mg/kg) and xylazine (1.6 mg/kg) to effect, and pupil dilation with topical 10% phenylephrine and/or 1% cyclopentolate.

Test Article

Subjects were administered a composition comprising a dual vector system including a AAV2-TRE-OSK vector and a AAV2-CMV-rtTA3V16 vector. The AAV2-TRE-OSK vector was prepared to a concentration of approximately $1.53 \times 10^{12}$ vg/mL and administered at a dose of 200 µL per dose to the subject. The AAV2-CMV-rtTA3V16 vector was prepared to a concentration of approximately $1.33 \times 10^{13}$ vg/mL and administered at a dose of 20 µL per dose to the subject. Accordingly, the two vectors were administered in a ratio of 10:1 by volume (v/v) or a ratio of approximately 1:1 by viral genome ratio (vg/vg).

Intravitreal Dosing

Eyes received a single intravitreal (IVT) injection of test article or vehicle in accordance with the treatment assignment (Table 4). For IVT dosing a drop of proparacaine hydrochloride 0.5% was applied to the eye followed by a lid speculum and 5% Betadine solution, and a rinse with sterile 0.9% saline. Injections were administered to the central vitreous using a 31-gauge 0.375 inch needle inserted inferotemporally at the level of the or a serrata ~2.5 mm posterior to the limbus. Following injection, 1% topical atropine, a topical triple antibiotic neomycin, polymyxin, bacitracin ophthalmic ointment (or equivalent) was administered.

TABLE 4

Treatment Conditions

| Group | N | Eye | NAION Induction | Treatment | Route | Concentration (vg/mL) | Volume | Dose (vg/eye) | Test Article Required |
|---|---|---|---|---|---|---|---|---|---|
| 1A | 4 | OD | No Laser | No treatment | — | — | — | — | — |
|  |  | OS | Laser | Vehicle (PBS) 28 days pre-NAION induction | IVT | PBS | 220 | — | (220 µL + 66 µL overage) × 4 = 1144 µL |
| 1B | 4 | OD | No Laser | No treatment | — | — | — | — | — |
|  |  | OS | Laser | Vehicle 1 day post-NAION induction | IVT | PBS | 220 | — | (220 µL + 66 µL overage) × 4 = 1144 µL |
| 2 | 6 | OD | No Laser | No treatment | — | — | — | — | — |
|  |  | OS | Laser | Candidate #1 28 days pre-NAION induction | IVT | OSK: $1.53 \times 10^{12}$ rtTA3: $1.33 \times 10^{13}$ | 220 | OSK: $3.06 \times 10^{11}$ rtTA3: $2.66 \times 10^{11}$ | (220 µL + 66 µL overage) × 6 = 1716 µL |
| 3 | 6 | OD | No Laser | No treatment | — | — | — | — | — |
|  |  | OS | Laser | Candidate #1 1 day post-NAION induction | IVT | OSK: $1.53 \times 10^{12}$ rtTA3: $1.33 \times 10^{13}$ | 220 | OSK: $3.06 \times 10^{11}$ rtTA3: $2.66 \times 10^{11}$ | (220 µL + 66 µL overage) × 6 = 1716 µL |

Doxycycline Dosing

Monkeys received oral doxycycline (5 mg/kg) in a food item (banana slice) starting one day prior to dosing and continuing through study terminus (Table 5).

Vitreous Humor Collection

At designated time points (Table 5) vitreous humor (~170 μL) was collected OU with a 1.0 mL syringe with a 27-gauge needle introduced into the mid-vitreous by temporal scleral

TABLE 5

Dosing Schedule for Monkey Study

| Event | # | Eyes | Baseline* | −21 | −19 | −7 | 0 | 1 | 3 | 7 | 14 | 28 | 35 | 42 | 49 |
|---|---|---|---|---|---|---|---|---|---|---|---|---|---|---|---|
| CBC EDTA blood | 24 | — | X | — | — | — | — | — | — | — | — | — | — | — | — |
| DNA methylation blood | 20 | — | X | — | — | — | — | — | — | — | — | — | — | — | — |
| Serum | 20 | — | X | — | — | — | — | — | — | — | — | — | — | — | X |
| Photothrombosis | 20 | OS | — | — | — | — | X | — | — | X | — | — | — | — | — |
| IVT dosing Group 1A & 2 | 10 | OS | — | Gp1A & 2 | — | — | — | — | — | — | — | — | — | — | — |
| IVT dosing Group 1B & 3 | 10 | OS | — | — | — | — | — | Gp1B & 3 | — | — | — | — | — | — | — |
| Vitreous Tap | 10 | OS | — | X§ | — | — | — | X§ | — | — | — | — | — | — | — |
| Doxycycline** | 20 | — | — | X | X | X | X | X | X | X | X | X | X | X | X |
| Methylprednisolone | 20 | — | — | Gp1A & 2 | — | Gp1A & 2 | X | — | — | X | X | X | X | X | X |
| Body weights | 20 | — | X | X | — | X | X | — | — | X | X | — | X | — | X |
| Detailed clinical exams | 20 | — | X | — | — | — | — | — | — | — | — | — | — | — | — |
| Tonometry | 20 | OU | X | — | — | — | X | — | — | X | X | — | X | — | X |
| Slit lamp exams | 20 | OU | X | — | Gp1A & 2 | X | — | — | Gp1B & 3 | X | X | — | X | — | X |
| Fundus imaging | 20 | OU | X* | — | — | — | X | X | — | X | X | — | X | — | X |
| Spectralis cSLO | 20 | OU | X | — | — | — | X | X | — | X | X | — | X | — | X |
| Spectralis OCT | 20 | OU | X | — | — | — | X | X | — | X | X | — | X | — | X |
| Pattern ERG*** | 20 | OU | X | — | — | X | — | — | — | X | X | X | X | — | X |
| Pattern VEP*** | 20 | OU | X | — | — | X | — | — | — | X | X | X | X | — | X |
| ffERG*** | 20 | OU | — | — | — | — | — | — | — | — | — | — | — | X | X |
| Enucleation | 20 | OU | — | — | — | — | — | — | — | — | — | — | — | — | X |

X = event for all treatment groups; Gp1A = event for Group 1A; Gp1B = event for Group 1B; Gp2 = event for Group 2; Gp3 = event for Group 3.
*Baseline prescreen assessments will include evaluation of up to 24 monkeys to meet the targeted number of study recruits.
**Daily oral doxycycline dosing will begin at day −21 for all animals and continue until day 42.
***Exams will be completed within +−4 days.
§Vitreous tap done immediately prior to dosing Immunosuppression Monkeys received methylprednisolone (40 mg IM) weekly starting on Day 0 (Table 5). If inflammation exceeding 2+ anterior and/or vitreous cell was observed on subsequent exam subconjunctival dexamethasone (100 mL of 40 mg/mL) was administered, with repeat dosing guided by clinical observations. If inflammation did not respond to dexamethasone, methylprednisolone was increased to 80 mg IM weekly. Administered steroids were applied consistently across all treatment animals.

NAION Induction

Monkeys were divided by exam and weight criteria into two cohorts. After achieving mydriasis and placement of a saphenous vein catheter, rose bengal (2.5 mg/kg; 0.1 ml/kg of 25 mg/ml) were administered intravenously (IV), followed 25 seconds later by initiation of laser spot application to the ONH. Laser spots were applied with an Iridex Oculight TX 532 nm laser using a 0.9× contact laser lens. Four spots were placed in the four quadrants of the ONH, each of pulse duration 6 seconds, spot size 500 μm, power 100 mW. The first spot was applied in the superatemporal aspect of the ONH, the second in the inferotemporal, the third in the inferonasal, and the fourth in the superanasal. Branched retinal veins and arteries were avoided in the placement of each spot. Post-laser CFP imaging was performed immediately to document response to laser photothrombosis procedure.

Tonometry

Intraocular pressure (TOP) was measured oculus uterque (OU) or in both eyes using a TonoVet tonometer set to the dog (d) calibration setting. Three measures were taken from each eye at each ophthalmic examination time point (Table 8) and the mean TOP was defined.

puncture at the level of the or a serrata. Vitreous humor aliquots were transferred to pre-labeled cryotubes, flash frozen, and stored and shipped for analysis.

Full Field Electroretinography (ffERG)

At designated time points (Table 5), slit lamp biomicroscopy and retinoscopy were performed in both eyes (OU). employing an LKC UTAS full-field ERG apparatus and emWin software (Version 9.8.0). Immediately after sedation and topical instillation of 10% phenylephrine and 1% cyclopentolate, eyes were dark-adapted for 30 minutes. Additional mydriatic were administered prior to stimulus exposure. ffERGs were performed OD then OS (or OS then OD in random order). After placement of a DTL electrode (or Burian-Allen contact lens electrode), a subdermal reference electrode at the ipsilateral lateral canthus, and ground electrode in the upper limb for unilateral sequential testing a scotopic rod-specific response was elicited by a dim white flash in a LED Ganzfeld stimulator bowl. Mixed rod and cone responses were obtained using standard bright white flashes under scotopic conditions. To evaluate the photopic function of cone photoreceptors, monkeys were light-adapted to ambient room light for 10 minutes, after which a strobe white-flash stimulus was presented to the dilated eye using maximum flash intensity. The following ISCEV stimulus standards for toxicology studies were applied:

Scotopic 0.158 cd-s $m^2$ (−12 dB) stimulus (rod-driven response of on bipolar cells measured, b-wave)

Scotopic 2.51 cd-s $m^2$ (0 dB) stimulus (rod and cone-driven response of both photoreceptors, a-wave, and on bipolar cells, b-wave)

Photopic 2.51 cd-s $m^2$ (0 dB) stimulus (cone driven response of both photoreceptors, a-wave, and on and off bipolar cells, b-wave)

Photopic 30 Hz flicker stimulus at 2.51 cd-s m² (0 dB) stimulus (cone driven response)

Stimulus induction was denoted by a marker. The time integrated luminance of the stimulus and the background was recorded in absolute values. Monkeys underwent scotopic exams before photopic exams and underwent stimulus exposure order of increasing stimulus strength for a given adaptation. Single stimulus exposures preceded flicker stimulus exposure to avoid bleaching and loss of adaptation. Waveforms were analyzed for a- and b-wave amplitudes and latency. The amplitude of the b-wave was measured from the a-wave trough to the peak of the b-wave or, if no a-wave was present, from the pre-stimulus baseline to the peak of the b-wave. The amplitude of the a-wave was measured from the pre-stimulus baseline to the peak of the a-wave. A nonhuman primate ophthalmic scoring system was employed to assess ocular pathology changes in response to NAION induction and treatment intervention with a summary score derived from exam components. Incidence of papilledema and flame hemorrhage was also evaluated.

Imaging

Color anterior segment and fundus photography was performed using a Topcon TRC-50EX retinal camera with Canon 6D digital imaging hardware and New Vision Fundus Image Analysis System software.

Optical Coherence Tomography (OCT) and Confocal Scanning Laser Ophthalmoscopy (cSLO)

At designated time points (Table 5), cSLO and OCT were performed using a Heidelberg Spectralis HRA OCT with HEYEX image capture and analysis software. cSLO infrared (IR) and autofluorescence (AF) images were obtained at 30° field of view centered on the fovea and the follow-up imaging function referencing the baseline images. An overall OCT volume scan of the optic nerve and entire macula was performed by posterior pole. Images were qualitatively assessed with quantitative analysis of calculated retinal thickness. For the macula centered posterior pole scan, ganglion cell layer (GCL) and retinal nerve fiber layer (RNFL) thickness maps were generated, and the thickness data exported to an electronic spreadsheet. Peripapillary retinal nerve fiber layer thickness (pRNFL) thickness was determined in each quadrant (superior, inferior, temporal, nasal). HEYEX raw data files were generated for additional analyses.

Pattern ERG and VEP

At designated time points (Table 5), pattern ERGs (pERGs) and pattern VEP (pVEP) recordings were performed OU by positioning the monkeys with a DTL electrode and an additional active electrode placed in the inion in the midline at the posterior of the skull, with a ground electrode placed in the arm. A VERIS retinal projecting stimulator was used to project an alternating black and white checkerboard pattern at 2 Hz with a luminance of 100 cd/m2 at a contrast of 80% over a field of 45% generated by a VERIS multifocal ERG instrument. Grid size was varied in logarithmic steps, recordings at each grid size repeated twice and latencies and amplitudes determined. pVEP amplitude and pERG N95 amplitude were determined.

Clinical Observations

General wellbeing was assessed twice daily by cage side observation beginning one week prior to dosing and extending to study terminus.

Detailed Clinical Examination

Detailed clinical observations and physical exams were performed at designated time points (Table 5). Respiratory rate, heart rate, blood pressure, auscultation and integrity of the integument were also assessed. Body temperature was determined using a digital rectal thermometer.

Body Weights

Body weights were collected at ophthalmic exam intervals (Table 5).

CBC with Differential

Blood (0.5 mL) was transferred directly to K2EDTA lavender top vacutainer tubes (Greiner MiniCollect EDTA tubes REF #450475) and maintained on ice until CBC with differentials analysis on a Hemavet analyzer.

DNA Methylation Blood

Blood was transferred directly to K2EDTA anticoagulated 0.5 mL microcentrifuge tube. Samples will then be lysed, and DNA isolated on QIAMP MiniElute columns per the manufacturer's instructions (Qiagen). DNA samples were analyzed for DNA methylation measures of biologic age.

Serum

At designated time points (Table 5), blood (3 ml) was transferred directly to serum separator tubes (red top) and allowed to sit at room temperature for 30 to 60 minutes prior to centrifugation at 3000 rpm for 10 minutes at 4° C. Two serum aliquots (~0.5 mL×2) as available were carefully transferred to labeled 1.8 mL cryotubes and stored and shipped below −70° C. to a designated lab for nAb analysis.

Enucleation and Eye Processing

At study terminus (Table 5), after confirmation of the quality of in-life imaging and electrophysiology, monkeys were sedated with intramuscular ketamine (8 mg/kg) and xylazine (1.6 mg/kg) to effect, animals were then euthanized with sodium pentobarbital (100 mg/kg IV) to effect. Globes (OU) were enucleated after placing a suture marker at the 12 o'clock position. Globes with attached optic nerve were trimmed of excess tissue and placed in Davidson's fixative at room temperature for 24 hours with injection of ~300 µl of Davidson's fixative into the globe. The globes were transferred to phosphate buffered saline (PBS) with 0.05% sodium azide and stored and shipped in a container maintained at 4° C. to the designated histology lab for histological and immunohistochemical processing and analysis by a board-certified veterinary pathologist. Additional quantitative scoring of histology was conducted, guided by qualitative findings.

pERG Results

A NAION-like injury was induced on Day 0 in all NHPs (African Green monkeys; N=20) by iv rose bengal followed by laser treatment of the OS eye ONH. Pre-treated NHPs (n=6) received on Day −28 an intravitreal (IVT) injection of OSK (doxycycline-inducible AAV2-OSK; 1:1 ratio of AAV2-TRE-OSK+AAV2-CMV-rtTA3), or vehicle (n=4) into the OS eye. Post-treatment NHPs received on Day +1 an IVT injection of OSK (n=6), or vehicle (n=4) into the OS eye. All NHPs received daily oral doxycycline throughout the experiment. Both eyes were examined at baseline then at weekly intervals until Day +35 post-laser treatment (corresponding to Day 42) for multiple imaging and functional measures of retinal ganglion cells (RGCs).

Figure 1B:
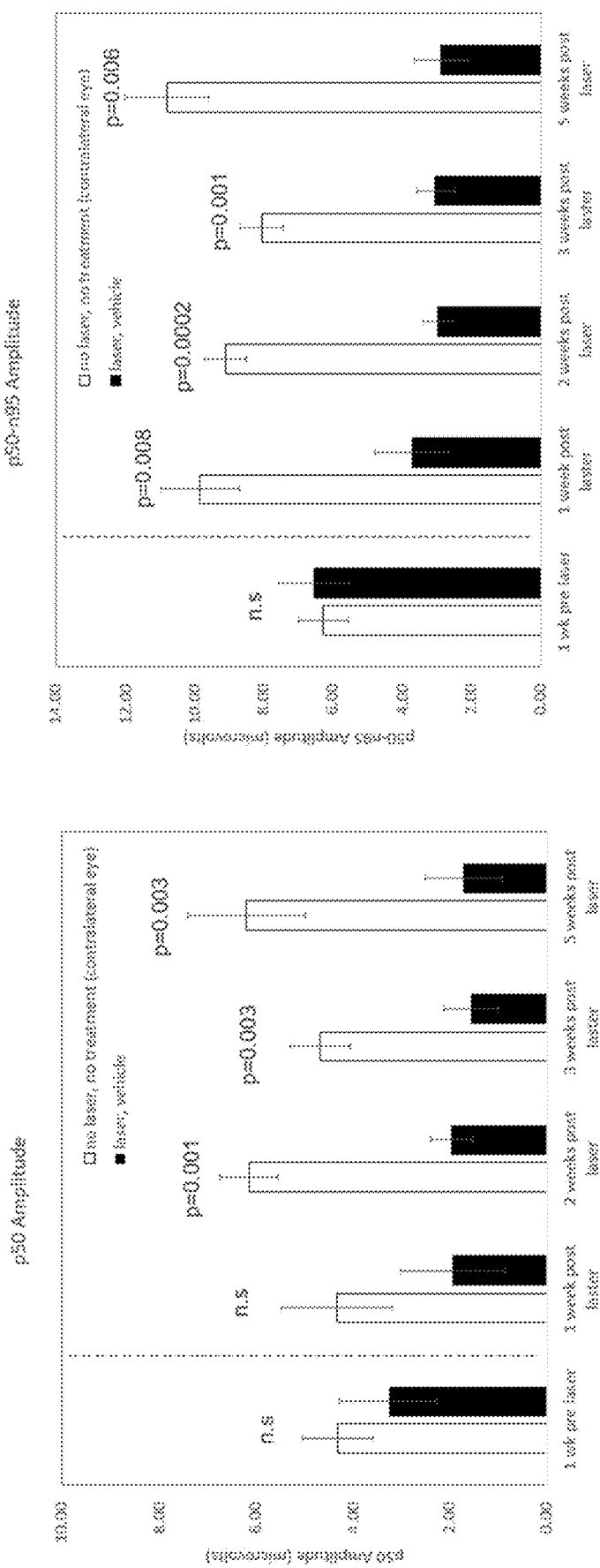
Figure 6:
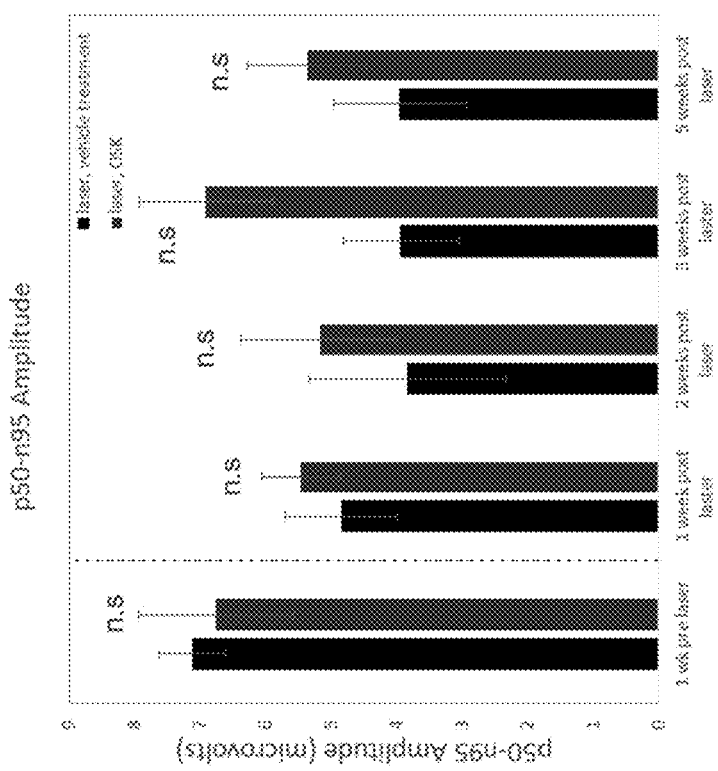
FIG. 6 depicts a schematic comparing the p50 peak amplitude (the left panel) or the absolute amplitude from p50 to n95 (the right panel) when treated with vehicle (the left bar at each time point) or OSK (controlled by Dox; as Tet-on system; the right bar at each time point) before laser treatment (i.e., prevention study). pERG signals were measured at different days and compared under different treatment.
Figure 6:
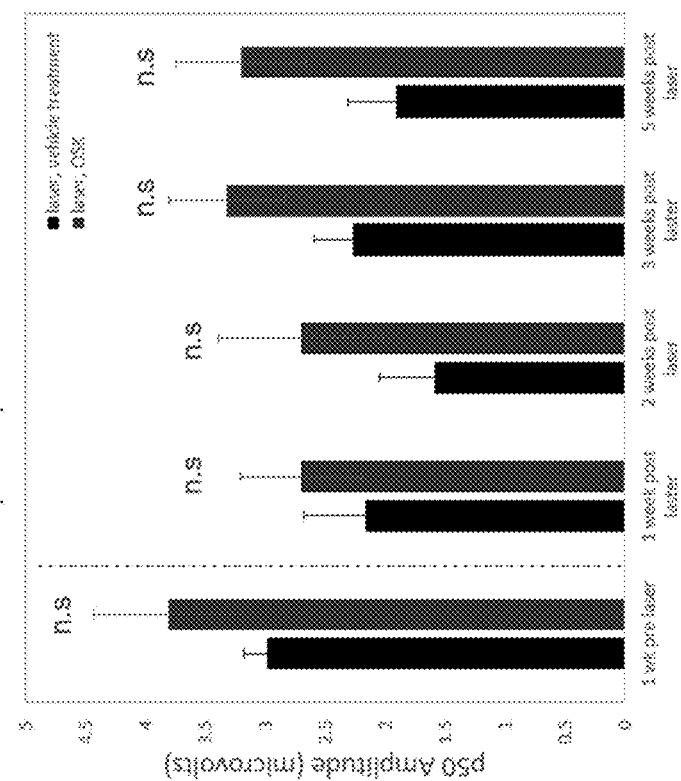
Figure 7:
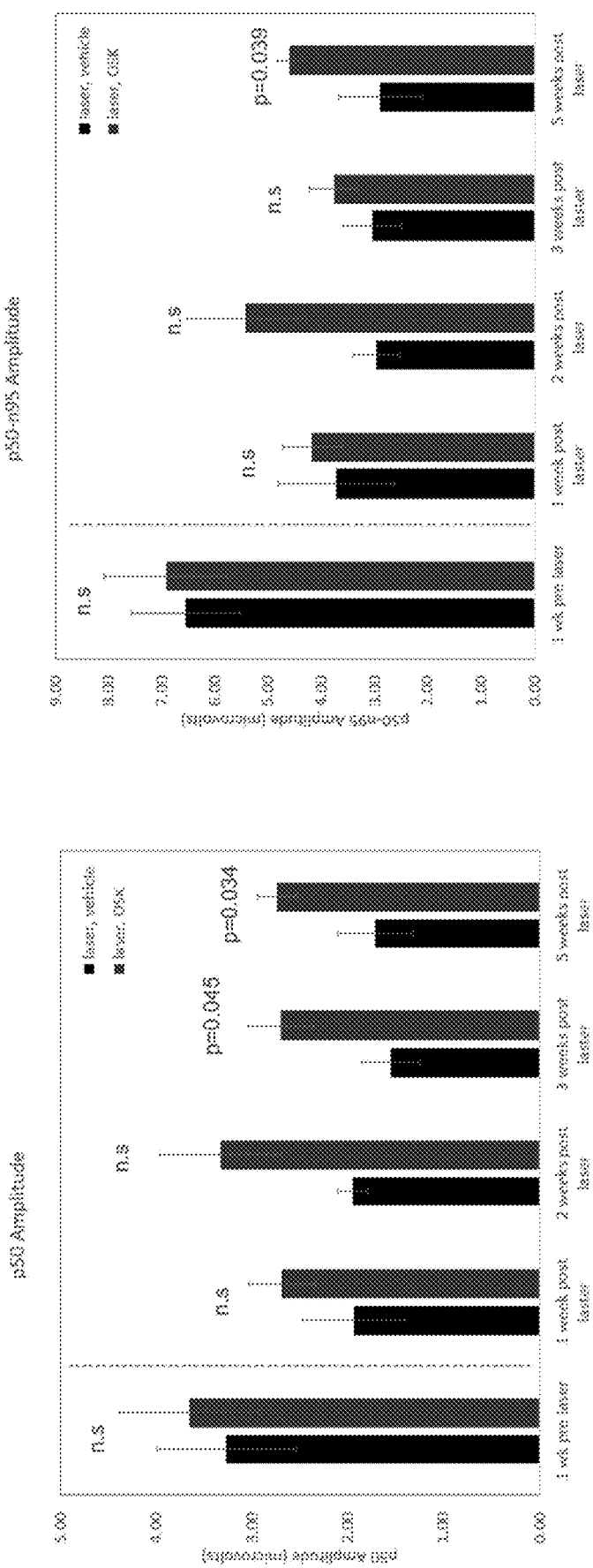
FIG. 7 depicts a schematic comparing the p50 peak amplitude (the left panel) or the absolute amplitude from p50 to n95 (the right panel) when treated with vehicle (the left bar at each time point) or OSK (controlled by Dox; as Tet-on system; the right bar at each time point) after laser treatment (i.e., rescue study). pERG signals were measured at different days and compared under different treatment.

Consistent with NAION pERG deficits in humans, the laser induced a NAION-like injury in vehicle treated OS eyes with a significant loss in pERG amplitude relative to OD (untreated) eyes (FIGS. 1A and 1B). Pretreatment with OSK in OS eyes increased pERG amplitude and partially reversed the NAION-like pERG deficits compared with vehicle-treated control eyes at the endpoint (p50-n95 amplitude: 5.36±0.91 vs 3.95±1.01, n.s., 5 weeks post-laser treatment; see FIG. 6). Post-treatment with OSK showed a significant recovery of pERG function by 5 weeks post-laser treatment (p50-n95 amplitude: 4.60±0.24 vs 2.89±0.79, P=0.039) (FIG. 7).

Results on Rescuing Axon Damage

Figure 8:
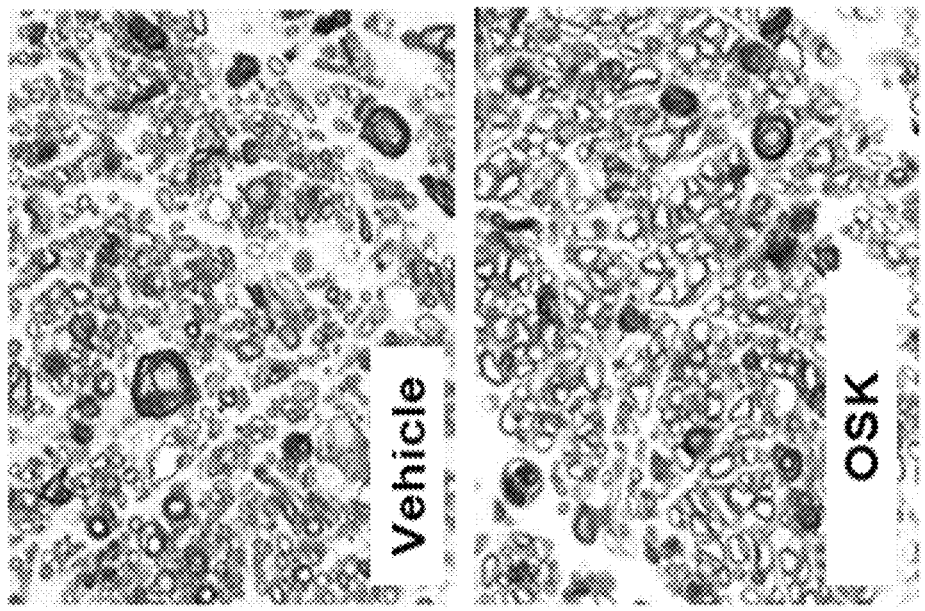
FIG. 8 depicts optic nerve myelin-specific axon stain microscopy results, which are used for axon counting by using AxonNet, for control ("no injury"; no laser treatment), or laser treatment followed by vehicle or OSK treatment.
Figure 8:
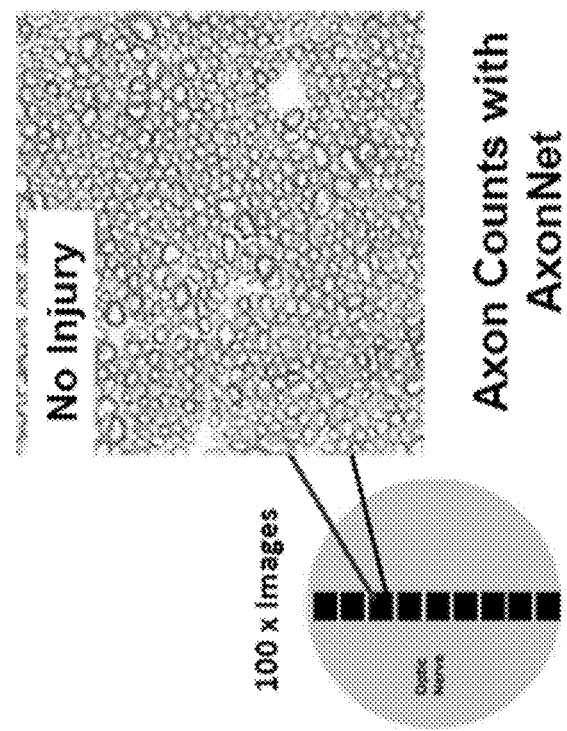
Figure 9:
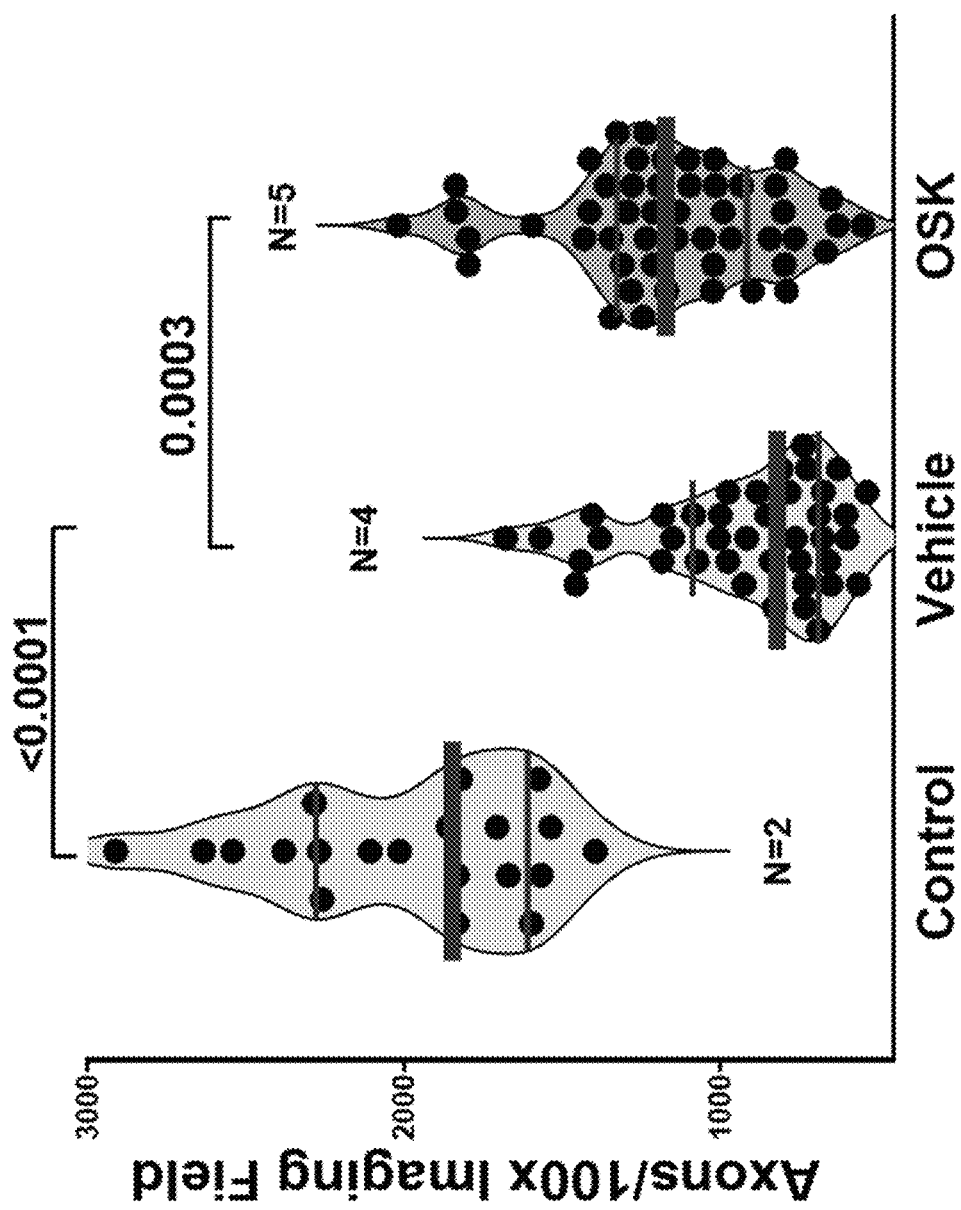
FIG. 9 depicts illustrative axon-counting results, from experiments as described in FIG. 8. Median values (middle bars) and interquartile ranges (top and bottom bars) are shown for each treatment/control.

Optic Nerve Myelin-Specific (PPD) Axon Stain was used to show the function of OSK expression to rescue axon damages subjected to induction of the NAION injury. As shown in FIG. 8, compared to vehicle treatment, post-expression of OSK rescued axon damages and increased axon numbers (counted with AxonNet; for a review of AxonNet, see Ehrlich and Rivera, AxonNet: A self-supervised Deep Neural Network for Intravoxel Structure Estimation from DW-MRI. ArXiv abs/2103.11006 (2021)). The enhancement of axon survival by OSK, compared to vehicle treatment, after laser-induced damage is further shown in FIG. 9.

As a summary for the NHP NAION study described herein, treatment with OSK improves RGC function, consistent with potential improvement in vision. In addition, treatment with OSK increases the number of healthy axons in the optic nerve, consistent with the potential for regeneration in the animals.

Equivalents and Incorporation by Reference

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

While various specific embodiments have been illustrated and described, it will be appreciated that various changes can be made without departing from the spirit and scope of the disclosure.

TABLE 6

AAV2-TRE-OSK Vector Sequences

| SEQ ID NO: | Component | Sequence |
|---|---|---|
| 1 | Human OCT4 nucleic acid sequence | ATGGCGGGACACCTGGCTTCGGATTTCGCCTTCTCGCCCCTCC AGGTGGTGGAGGTGATGGGCCAGGGGGGCCGGAGCCGGGCTG GGTTGATCCTCGGACCTGGCTAAGCTTCCAAGGCCCTCCTGGAG GGCCAGGAATCGGGCCGGGGGTTGGGCCAGGCTCTGAGGTGTG GGGGATTCCCCCATGCCCCCCGCCGTATGAGTTCTGTGGGGGGA TGGCGTACTGTGGGCCCCAGGTTGGAGTGGGGCTAGTGCCCCA AGGCGGCTTGGAGACCTCTCAGCCTGAGGGCGAAGCAGGAGTC GGGGTGGAGAGCAACTCCGATGGGGCCTCCCCGGAGCCCTGCA CCGTCACCCCTGGTGCCGTGAAGCTGGAGAAGGAGAAGCTGGA GCAAAACCCGGAGGAGTCCCAGGACATCAAAGCTCTGCAGAAA GAACTCGAGCAATTTGCCAAGCTCCTGAAGCAGAAGAGGATCA CCCTGGGATATACACAGGCCGATGTGGGGCTCACCCTGGGGGT TCTATTTGGGAAGGTATTCAGCCAAACGACCATCTGCCGCTTTG AGGCTCTGCAGCTTAGCTTCAAGAACATGTGTAAGCTGCGGCCC TTGCTGCAGAAGTGGGTGGAGGAAGCTGACAACAATGAAAATC TTCAGGAGATATGCAAAGCAGAAACCCTCGTGCAGGCCCGAAA GAGAAAGCGAACCAGTATCGAGAACCGAGTGAGAGGCAACCT GGAGAATTTGTTCCTGCAGTGCCCGAAACCCACACTGCAGCAG ATCAGCCACATCGCCCAGCAGCTTGGGCTCGAGAAGGATGTGG TCCGAGTGTGGTTCTGTAACCGGCGCCAGAAGGGCAAGCGATC AAGCAGCGACTATGCACAACGAGAGGATTTTGAGGCTGCTGGG TCTCCTTTCTCAGGGGGACCAGTGTCCTTTCCTCTGGCCCCAGG GCCCCATTTTGGTACCCCAGGCTATGGGAGCCCTCACTTCACTG CACTGTACTCCTCGGTCCCTTTCCCTGAGGGGGAAGCCTTTCCC CCTGTCTCTGTCACCACTCTGGGCTCTCCCATGCATTCAAAC |
| 2 | Human OCT4 amino acid sequence | MAGHLASDFAFSPPPGGGGDGPGGPEPGWVDPRTWLSFQGPPGGP GIGPGVGPGSEVWGIPPCPPPYEFCGGMAYCGPQVGVGLVPQGGL ETSQPEGEAGVGVESNSDGASPEPCTVTPGAVKLEKEKLEQNPEES QDIKALQKELEQFAKLLKQKRITLGYTQADVGLTLGVLFGKVFSQ TTICRFEALQLSFKNMCKLRPLLQKWVEEADNNENLQEICKAETLV QARKRKRTSIENRVRGNLENLFLQCPKPTLQQISHIAQQLGLEKDV VRVWFCNRRQKGKRSSSDYAQREDFEAAGSPFSGGPVSFPLAPGP HFGTPGYGSPHFTALYSSVPFPEGEAFPPVSVTTLGSPMHSN |
| 3 | Human SOX2 nucleic acid sequence | ATGTACAACATGATGGAGACGGAGCTGAAGCCGCCGGGCCCGC AGCAAACTTCGGGGGGCGGCGGCGGCAACTCCACCGCGGCGGC GGCCGGCGGCAACCAGAAAAACAGCCCGGACCGCGTCAAGCG GCCCATGAATGCCTTCATGGTGTGGTCCCGCGGGCAGCGGCGC AAGATGGCCCAGGAGAACCCCAAGATGCACAACTCGGAGATCA GCAAGCGCCTGGGCGCCGAGTGGAAACTTTTGTCGGAGACGGA GAAGCGGCCGTTCATCGACGAGGCTAAGCGGCTGCGAGCGCTG CACATGAAGGAGCACCCGGATTATAAATACCGGCCCCGGCGGA AAACCAAGACGCTCATGAAGAAGGATAAGTACACGCTGCCCGG CGGGCTGCTGGCCCCCGGCGGCAATAGCATGGCGAGCGGGGTC GGGGTGGGCGCCGGCCTGGGCGCGGGCGTGAACCAGCGCATGG ACAGTTACGCGCACATGAACGGCTGGAGCAACGGCAGCTACAG CATGATGCAGGACCAGCTGGGCTACCCGCAGCACCCGGGCCTC AATGCGCACGGCGCAGCGCAGATGCAGCCCATGCACCGCTACG ACGTGAGCGCCCTGCAGTACAACTCCATGACCAGCTCGCAGAC CTACATGAACGGCTCGCCCACCTACAGCATGTCCTACTCGCAGC |

TABLE 6-continued

AAV2-TRE-OSK Vector Sequences

| SEQ ID NO: | Component | Sequence |
|---|---|---|
| | | AGGGCACCCCTGGCATGGCTCTTGGCTCCATGGGTTCGGTGGTC AAGTCCGAGGCCAGCTCCAGCCCCCCTGTGGTTACCTCTTCCTC CCACTCCAGGGCGCCCTGCCAGGCCGGGGACCTCCGGGACATG ATCAGCATGTATCTCCCCGGCGCCGAGGTGCCGGAACCCGCCG CCCCCAGCAGACTTCACATGTCCCAGCACTACCAGAGCGGCCC GGTGCCCGGCACGGCCATTAACGGCACACTGCCCCTCTCACACA TG |
| 4 | Human SOX2 amino acid sequence | MYNMMETELKPPGPQQTSGGGGGNSTAAAAGGNQKNSPDRVKR PMNAFMVWSRGQRRKMAQENPKMHNSEISKRLGAEWKLLSETE KRPFIDEAKRLRALHMKEHPDYKYRPRRKTKTLMKKDKYTLPGG LLAPGGNSMASGVGVGAGLGAGVNQRMDSYAHMNGWSNGSYS MMQDQLGYPQHPGLNAHGAAQMPMHRYDVSALQYNSMTSSQ TYMNGSPTYSMSYSQQGTPGMALGSMGSVVKSEASSSPPVVTSSS HSRAPCQAGDLRDMISMYLPGAEVPEPAAPSRLHMSQHYQSGPVP GTAINGTLPLSHM |
| 5 | Human KLF4 nucleic acid sequence | ATGGCTGTCAGCGACGCGCTGCTCCCATCTTTCTCCACGTTCGC GTCTGGCCCGGCGGGAAGGGAGAAGACACTGCGTCAAGCAGGT GCCCCGAATAACCGCTGGCGGGAGGAGCTCTCCCACATGAAGC GACTTCCCCCAGTGCTTCCCGGCCGCCCCTATGACCTGGCGGCG GCGACCGTGGCCACAGACCTGGAGAGCGGCGGAGCCGGTGCGG CTTGCGGCGGTAGCAACCTGGCGCCCCTACCTCGGAGAGAGAC CGAGGAGTTCAACGATCTCCTGGACCTGGACTTTATTCTCTCCA ATTCGCTGACCCATCCTCCGGAGTCAGTGGCCGCCACCGTGTCC TCGTCAGCGTCAGCCTCCTCTTCGTCGTCGCCGTCGAGCAGCGG CCCTGCCAGCGCGCCCTCCACCTGCAGCTTCACCTATCCGATCC GGGCCGGGAACGACCCGGGCGTGGCGCCGGGCGGCACGGGCG GAGGCCTCCTCTATGGCAGGGAGTCCGCTCCCCCTCCGACGGCT CCCTTCAACCTGGCGGACATCAACGACGTGAGCCCCTCGGGCG GCTTCGTGGCCGAGCTCCTGCGGCCAGAATTGGACCCGGTGTAC ATTCCGCCGCAGCAGCCGCAGCCGCCAGGTGGCGGGCTGATGG GCAAGTTCGTGCTGAAGGCGTCGCTGAGCGCCCCTGGCAGCGA GTACGGCAGCCCGTCGGTCATCAGCGTCAGCAAAGGCAGCCCT GACGGCAGCCACCCGGTGGTGGTGGCGCCCTACAACGGCGGGC CGCCGCGCACGTGCCCCAAGATCAAGCAGGAGGCGGTCTCTTC GTGCACCCACTTGGGCGCTGGACCCCCTCTCAGCAATGGCCACC GGCCGGCTGCACACGACTTCCCCCTGGGGCGGCAGCTCCCCAG CAGGACTACCCCGACCCTGGGTCTTGAGGAAGTGCTGAGCAGC AGGGACTGTCACCCTGCCCTGCCGCTTCCTCCCGGCTTCCATCC CCACCCGGGGCCCAATTACCCATCCTTCCTGCCCGATCAGATGC AGCCGCAAGTCCCGCCGCTCCATTACCAAGAGCTCATGCCACCC GGTTCCTGCATGCCAGAGGAGCCCAAGCCAAAGAGGGGAAGAC GATCGTGGCCCCGGAAAAGGACCGCCACCCACACTTGTGATTA CGCGGGCTGCGGCAAAACCTACACAAAGAGTTCCCATCTCAAG GCACACCTGCGAACCCACACAGGTGAGAAACCTTACCACTGTG ACTGGGACGGCTGTGGATGGAAATTCGCCCGCTCAGATGAACT GACCAGGCACTACCGTAAACACACGGGGCACCGCCCGTTCCAG TGCCAAAAATGCGACCGAGCATTTTCCAGGTCGGACCACCTCGC CTTACACATGAAGAGGCATTTT |
| 6 | Human KLF4 amino acid sequence | MAVSDALLPSFSTFASGPAGREKTLRQAGAPNNRWREELSHMKRL PPVLPGRPYDLAAATVATDLESGGAGAACGGSNLAPLPRRETEEF NDLLDLDFILSNSLTHPPESVAATVSSSAS-ASSSSSPSSSGPASAPST CSFTYPIRAGNDPGVAPGGTGGGLLYGRESAPPPTAPFNLADINDV SPSGGFVAELLRPELDPVYIPPQQPQPPGGGLMGKFVLKASLSAPG SEYGSPSVISVSKGSPDGSHPVVVAPYNGGPPRTCP-KIKQEAVSSCT HLGAGPPLSNGHRPAAHDFPLGRQLPSRTTPTLGLEEVLSSRDCHP ALPLPPGFHPHPGPNYPSFLPDQMQPQVPPLHYQELMPPGSCMPEE PKPKRGRRSWPRKRTATHTCDYAGCGKTYTKSSHLKAHLRTHTG EKPYHCDWDGCGWKFARSDELTRHYRKHTGHRPFQCQKCDRAFS RSDHLALHMKRHF |
| 7 | TRE3G (TRE promoter) | TTTACTCCCTATCAGTGATAGAGAACGTATGAAGAGTTTACTCC CTATCAGTGATAGAGAACGTATGCAGACTTTACTCCCTATCAGT GATAGAGAACGTATAAGGAGTTTACTCCCTATCAGTGATAGAG AACGTATGACCAGTTTACTCCCTATCAGTGATAGAGAACGTATC TACAGTTTACTCCCTATCAGTGATAGAGAACGTATATCCAGTTT ACTCCCTATCAGTGATAGAGAACGTATAAGCTTTAGGCGTGTAC GGTGGGCGCCTATAAAAGCAGAGCTCGTTTAGTGAACCGTCAG ATCGCCTGGAGCAATTCCACAACACTTTTGTCTTATACCAACTT TCCGTACCACTTCCTACCCTCGTAAA |

TABLE 6-continued

AAV2-TRE-OSK Vector Sequences

| SEQ ID NO: | Component | Sequence |
|---|---|---|
| 8 | P2A peptide from porcine teschovirus-1 polyprotein | GCCACGAACTTCTCTCTGTTAAAGCAAGCAGGAGATGTTGAAG AAAACCCCGGGCCT |
| 9 | P2A amino acid | ATNFSLLKQAGDVEENPGP |
| 10 | T2A peptide from *Thosea asigna* virus capsid protein | GAGGGCAGGGGAAGTCTTCTAACATGCGGGGACGTGGAGGAAA ATCCCGGCCCA |
| 11 | T2A cleavage sequence amino acid | EGRGSLLTCGDVEENPGP |
| 12 | SV40 | AACTTGTTTATTGCAGCTTATAATGGTTACAAATAAAGCAATAG CATCACAAATTTCACAAATAAAGCATTTTTTTCACTGCATTCTA GTTGTGGTTTGTCCAAACTCATCAATGTATCTTATCATGTCTGGA TC |
| 13 | OCT4-2A-SOX2-2A-KLF4 (Whole insert sequence including Tet operators and SV40, minus ITRs) | CTATGCGGCATCAGAGCAGATTGTACTGAGAGTGCACCATATG CGGTGTGAAATACCGCACAGATGCGTAAGGAGAAAATACCGCA TCAGGCGCCATTCGCCATTCAGGCTGCGCAACTGTTGGGAAGG GCGATCGGTGCGGGCCTCTTCGCTATTACGCCAGCTGGCGAAAG GGGGATGTGCTGCAAGGCGATTAAGTTGGGTAACGCCAGGGTT TCCCCAGTCACGACGTTGTAAAACGACGGCCAGTGAATTGACG CGTATTGGGATCCATGATTACGCCAGATTTAATTAAGGCCTTAA TTAGGCTGCGCGCTCGCTCGCTCACTGAGGCCGCCCGGGCAAA GCCCGGGCGTCGGGCGACCTTTGGTCGCCCGGCCTCAGTGAGC GAGCGAGCGCGCAGAGAGGGAGTGGCCAACTCCATCACTAGGG GTTCCTTGTAGTTAATGATTAACCCGCCATGCTACTTATCTACGT AGCCATGCTCTAGGAAGATCGGAATTCTTTACTCCCTATCAGTG ATAGAGAACGTATGAAGAGTTTACTCCCTATCAGTGATAGAGA ACGTATGCAGACTTTACTCCCTATCAGTGATAGAGAACGTATAA GGAGTTTACTCCCTATCAGTGATAGAGAACGTATGACCAGTTTA CTCCCTATCAGTGATAGAGAACGTATCTACAGTTTACTCCCTAT CAGTGATAGAGAACGTATATCCAGTTTACTCCCTATCAGTGATA GAGAACGTATAAGCTTTAGGCGTGTACGGTGGGCGCCTATAAA AGCAGAGCTCGTTTAGTGAACCGTCAGATCGCCTGGAGCAATTC CACAACACTTTTGTCTTATACCAACTTTCCGTACCACTTCCTACC CTCGTAAAGCGGCCGCGCCACCATGGCGGGACACCTGGCTTCG GATTTCGCCTTCTCGCCCCCTCCAGGTGGTGGAGGTGATGGGCC AGGGGGGCCGGAGCCGGGCTGGGTTGATCCTCGGACCTGGCTA AGCTTCCAAGGCCCTCCTGGAGGGCCAGGAATCGGGCCGGGGG TTGGGCCAGGCTCTGAGGTGTGGGGGATTCCCCCATGCCCCCCG CCGTATGAGTTCTGTGGGGGGATGGCGTACTGTGGGCCCCAGGT TGGAGTGGGGCTAGTGCCCCAAGGCGGCTTGGAGACCTCTCAG CCTGAGGGCGAAGCAGGAGTCGGGGTGGAGAGCAACTCCGATG GGGCCTCCCCGGAGCCCTGCACCGTCACCCCTGGTGCCGTGAAG CTGGAGAAGGAGAAGCTGGAGCAAAACCCGGAGGAGTCCCAG GACATCAAAGCTCTGCAGAAAGAACTCGAGCAATTTGCCAAGC TCCTGAAGCAGAAGAGGATCACCCTGGGATATACACAGGCCGA TGTGGGGCTCACCCTGGGGGTTCTATTTGGGAAGGTATTCAGCC AAACGACCATCTGCCGCTTTGAGGCTCTGCAGCTTAGCTTCAAG AACATGTGTAAGCTGCGGCCCTTGCTGCAGAAGTGGGTGGAGG AAGCTGACAACAATGAAAATCTTCAGGAGATATGCAAAGCAGA AACCCTCGTGCAGGCCCGAAAGAGAAAGCGAACCAGTATCGAG AACCGAGTGAGAGGCAACCTGGAGAATTTGTTCCTGCAGTGCC CGAAACCCACACTGCAGCAGATCAGCCACATCGCCCAGCAGCT TGGGCTCGAGAAGGATGTGGTCCGAGTGTGGTTCTGTAACCGG CGCCAGAAGGGCAAGCGATCAAGCAGCGACTATGCACAACGAG AGGATTTTGAGGCTGCTGGGTCTCCTTTCTCAGGGGGACCAGTG TCCTTTCCTCTGGCCCCAGGGCCCCATTTTGGTACCCCAGGCTAT GGGAGCCCTCACTTCACTGCACTGTACTCCTCGGTCCCTTTCCCT GAGGGGGAAGCCTTTCCCCCTGTCTCTGTCACCACTCTGGGCTC TCCCATGCATTCAAACGCTAGCGGCAGCGGCGCCACGAACTTCT CTCTGTTAAAGCAAGCAGGAGATGTTGAAGAAAACCCCGGGCC TGCATGCATGTACAACATGATGGAGACGGAGCTGAAGCCGCCG GGCCCGCAGCAAACTTCGGGGGGCGGCGGCGGCAACTCCACCG |

TABLE 6-continued

AAV2-TRE-OSK Vector Sequences

| SEQ ID NO: | Component | Sequence |
|---|---|---|
| | | CGGCGGCGGCCGGCGGCAACCAGAAAAACAGCCCGGACCGCGT<br>CAAGCGGCCCATGAATGCCTTCATGGTGTGGTCCCGCGGGCAG<br>CGGCGCAAGATGGCCCAGGAGAACCCCAAGATGCACAACTCGG<br>AGATCAGCAAGCGCCTGGGCGCCGAGTGGAAACTTTTGTCGGA<br>GACGGAGAAGCGGCCGTTCATCGACGAGGCTAAGCGGCTGCGA<br>GCGCTGCACATGAAGGAGCACCCGGATTATAAATACCGGCCCC<br>GGCGGAAAACCAAGACGCTCATGAAGAAGGATAAGTACACGCT<br>GCCCGGCGGGCTGCTGGCCCCCGGCGGCAATAGCATGGCGAGC<br>GGGGTCGGGGTGGGCGCCGGCCTGGGCGCGGGCGTGAACCAGC<br>GCATGGACAGTTACGCGCACATGAACGGCTGGAGCAACGGCAG<br>CTACAGCATGATGCAGGACCAGCTGGGCTACCCGCAGCACCCG<br>GGCCTCAATGCGCACGGCGCAGCGCAGATGCAGCCCATGCACC<br>GCTACGACGTGAGCGCCCTGCAGTACAACTCCATGACCAGCTC<br>GCAGACCTACATGAACGGCTCGCCCACCTACAGCATGTCCTACT<br>CGCAGCAGGGCACCCCTGGCATGGCTCTTGGCTCCATGGGTTCG<br>GTGGTCAAGTCCGAGGCCAGCTCCAGCCCCCCTGTGGTTACCTC<br>TTCCTCCCACTCCAGGGCGCCCTGCCAGGCCGGGGACCTCCGGG<br>ACATGATCAGCATGTATCTCCCCGGCGCCGAGGTGCCGGAACC<br>CGCCGCCCCCAGCAGACTTCACATGTCCCAGCACTACCAGAGC<br>GGCCCGGTGCCCGGCACGGCCATTAACGGCACACTGCCCCTCTC<br>ACACATGGCATGCGGCTCCGGCGAGGGCAGGGGAAGTCTTCTA<br>ACATGCGGGGACGTGGAGGAAAATCCCGGCCCACTCGAGATGG<br>CTGTCAGCGACGCGCTGCTCCCATCTTTCTCCACGTTCGCGTCTG<br>GCCCGGCGGGAAGGGAGAAGACACTGCGTCAAGCAGGTGCCCC<br>GAATAACCGCTGGCGGGAGGAGCTCTCCCACATGAAGCGACTT<br>CCCCCAGTGCTTCCCGGCCGCCCCTATGACCTGGCGGCGGCGAC<br>CGTGGCCACAGACCTGGAGAGCGGCGGAGCCGGTGCGGCTTGC<br>GGCGGTAGCAACCTGGCGCCCCTACCTCGGAGAGAGACCGAGG<br>AGTTCAACGATCTCCTGGACCTGGACTTTATTCTCTCCAATTCGC<br>TGACCCATCCTCCGGAGTCAGTGGCCGCCACCGTGTCCTCGTCA<br>GCGTCAGCCTCCTCTTCGTCGTCGCCGTCGAGCAGCGGCCCTGC<br>CAGCGCGCCCTCCACCTGCAGCTTCACCTATCCGATCCGGGCCG<br>GGAACGACCCGGGCGTGGCGCCGGGCGGCACGGGCGGAGGCCT<br>CCTCTATGGCAGGGAGTCCGCTCCCCCTCCGACGGCTCCCTTCA<br>ACCTGGCGGACATCAACGACGTGAGCCCCTCGGGCGGCTTCGT<br>GGCCGAGCTCCTGCGGCCAGAATTGGACCCGGTGTACATTCCGC<br>CGCAGCAGCCGCAGCCGCCAGGTGGCGGGCTGATGGGCAAGTT<br>CGTGCTGAAGGCGTCGCTGAGCGCCCCTGGCAGCGAGTACGGC<br>AGCCCGTCGGTCATCAGCGTCAGCAAAGGCAGCCCTGACGGCA<br>GCCACCCGGTGGTGGTGGCGCCCTACAACGGCGGGCCGCCGCG<br>CACGTGCCCCAAGATCAAGCAGGAGGCGGTCTCTTCGTGCACC<br>CACTTGGGCGCTGGACCCCCTCTCAGCAATGGCCACCGGCCGGC<br>TGCACACGACTTCCCCCTGGGGCGGCAGCTCCCCAGCAGGACT<br>ACCCCGACCCTGGGTCTTGAGGAAGTGCTGAGCAGCAGGGACT<br>GTCACCCTGCCCTGCCGCTTCCTCCCGGCTTCCATCCCCACCCG<br>GGGCCCAATTACCCATCCTTCCTGCCCGATCAGATGCAGCCGCA<br>AGTCCCGCCGCTCCATTACCAAGAGCTCATGCCACCCGGTTCCT<br>GCATGCCAGAGGAGCCCAAGCCAAAGAGGGGAAGACGATCGT<br>GGCCCCGGAAAAGGACCGCCACCCACACTTGTGATTACGCGGG<br>CTGCGGCAAAACCTACACAAAGAGTTCCCATCTCAAGGCACAC<br>CTGCGAACCCACACAGGTGAGAAACCTTACCACTGTGACTGGG<br>ACGGCTGTGGATGGAAATTCGCCCGCTCAGATGAACTGACCAG<br>GCACTACCGTAAACACACGGGGCACCGCCCGTTCCAGTGCCAA<br>AAATGCGACCGAGCATTTTCCAGGTCGGACCACCTCGCCTTACA<br>CATGAAGAGGCATTTTTAAATGACTAGTGCGCGCAGCGGCCGA<br>CCATGGCCCAACTTGTTTATTGCAGCTTATAATGGTTACAAATA<br>AAGCAATAGCATCACAAATTTCACAAATAAAGCATTTTTTTCAC<br>TGCATTCTAGTTGTGGTTTGTCCAAACTCATCAATGTATCTTATC<br>ATGTCTGGATCTCGGTACCGGATCCAAATTCCCGATAAGGATCT<br>TCCTAGAGCATGCTACGTAGATAAGTAGCATGGCGGGTTAAT<br>CATTAACTACAAGGAACCCCTAGTGATGGAGTTGGCCACTCCCT<br>CTCTGCGCGCTCGCTCGCTCACTGAGGCCGGGCGACCAAAGGTC<br>GCCCGACGCCCGGGCTTTGCCCGGGCGGCCTCAGTGAGCGAGC<br>GAGCGCGCAGCCTTAATTAACCTAATTCATCCCAATGGCGCGCC<br>GAGCTTGGCTCGAGCATGGTCAT |
| 14 | OCT4-2A-<br>SOX2-2A-<br>KLF4<br>(Whole insert<br>sequence,<br>does not<br>include SV40 | ATGGCGGGACACCTGGCTTCGGATTTCGCCTTCTCGCCCCCTCC<br>AGGTGGTGGAGGTGATGGGCCAGGGGGCCGGAGCCGGGCTG<br>GGTTGATCCTCGGACCTGGCTAAGCTTCCAAGGCCCTCCTGGAG<br>GGCCAGGAATCGGGCCGGGGGTTGGGCAGGCTCTGAGGTGTG<br>GGGGATTCCCCCATGCCCCCGCCGTATAGAGTTCTGTGGGGGGA<br>TGGCCGTACTGTGGGCCCCAGGTTGGAGTGGGGCTAGTGCCCCA<br>AGGCGGCTTGGAGACCCTCTCAGCCTGAGGGCGAAGCAGGAGTC |

TABLE 6-continued

AAV2-TRE-OSK Vector Sequences

| SEQ ID NO: Component | Sequence |
|---|---|
| or Tet Operators) | GGGGTGGAGAGCAACTCCGATGGGGCCTCCCCGGAGCCCTGCA
CCGTCACCCCTGGTGCCGTGAAGCTGGAGAAGGAGAAGCTGGA
GCAAAACCCGGAGGAGTCCCAGGACATCAAAGCTCTGCAGAAA
GAACTCGAGCAATTTGCCAAGCTCCTGAAGCAGAAGAGGATCA
CCCTGGGATATACACAGGCCGATGTGGGCTCACCCTGGGGGT
TCTATTTGGGAAGGTATTCAGCCAAACGACCATCTGCCGCTTTG
AGGCTCTGCAGCTTAGCTTCAAGAACATGTGTAAGCTGCGGCCC
TTGCTGCAGAAGTGGGTGGAGGAAGCTGACAACAATGAAAATC
TTCAGGAGATATGCAAAGCAGAAACCCTCGTGCAGGCCCGAAA
GAGAAAGCGAACCAGTATCGAGAACCGAGTGAGAGGCAACCT
GGAGAATTTGTTCCTGCAGTGCCCGAAACCCACACTGCAGCAG
ATCAGCCACATCGCCCAGCAGCTTGGGCTCGAGAAGGATGTGG
TCCGAGTGTGGTTCTGTAACCGGCGCCAGAAGGGCAAGCGATC
AAGCAGCGACTATGCACAACGAGAGGATTTTGAGGCTGCTGGG
TCTCCTTTCTCAGGGGGACCAGTGTCCTTTCCTCTGGCCCCAGG
GCCCCATTTTGGTACCCCAGGCTATGGGAGCCCTCACTTCACTG
CACTGTACTCCTCGGTCCCTTTCCCTGAGGGGGAAGCCTTTCCC
CCTGTCTCTGTCACCACTCTGGGCTCTCCCATGCATTCAAACGCT
AGCGGCAGCGGCGCCACGAACTTCTCTCTGTTAAAGCAAGCAG
GAGATGTTGAAGAAAACCCCGGGCCTGCATGCATGTACAACAT
GATGGAGACGGAGCTGAAGCCGCCGGGCCCGCAGCAAACTTCG
GGGGGCGGCGGCGGCAACTCCACCGCGGCGGCGGCCGGCGGCA
ACCAGAAAAACAGCCCGGACCGCGTCAAGCGGCCCATGAATGC
CTTCATGGTGTGGTCCCGCGGGCAGCGGCGCAAGATGGCCCAG
GAGAACCCCAAGATGCACAACTCGGAGATCAGCAAGCGCCTGG
GCGCCGAGTGGAAACTTTTGTCGGAGACGGAGAAGCGGCCGTT
CATCGACGAGGCTAAGCGGCTGCGAGCGCTGCACATGAAGGAG
CACCCGGATTATAAATACCGGCCCCGGCGGAAAACCAAGACGC
TCATGAAGAAGGATAAGTACACGCTGCCCGGCGGGCTGCTGGC
CCCCGGCGGCAATAGCATGGCGAGCGGGGTCGGGGTGGGCGCC
GGCCTGGGCGCGGGCGTGAACCAGCGCATGGACAGTTACGCGC
ACATGAACGGCTGGAGCAACGGCAGCTACAGCATGATGCAGGA
CCAGCTGGGCTACCCGCAGCACCCGGGCCTCAATGCGCACGGC
GCAGCGCAGATGCAGCCCATGCACCGCTACGACGTGAGCGCCC
TGCAGTACAACTCCATGACCAGCTCGCAGACCTACATGAACGG
CTCGCCCACCTACAGCATGTCCTACTCGCAGCAGGGCACCCCTG
GCATGGCTCTTGGCTCCATGGGTTCGGTGGTCAAGTCCGAGGCC
AGCTCCAGCCCCCTGTGGTTACCTCTTCCTCCCACTCCAGGGC
GCCCTGCCAGGCCGGGGACCTCCGGGACATGATCAGCATGTAT
CTCCCCGGCGCCGAGGTGCCGGAACCCGCCGCCCCCAGCAGAC
TTCACATGTCCCAGCACTACCAGAGCGGCCCGGTGCCCGGCAC
GGCCATTAACGGCACACTGCCCCTCTCACACATGGCATGCGGCT
CCGGCGAGGGCAGGGGAAGTCTTCTAACATGCGGGGACGTGGA
GGAAAATCCCGGCCCACTCGAGATGGCTGTCAGCGACGCGCTG
CTCCCCATCTTTCTCCACGTTCGCGTCTGGCCCGGCGGGAAGGGA
GAAGACACTGCGTCAAGCAGGTGCCCCGAATAACCGCTGGCGG
GAGGAGCTCTCCCACATGAAGCGACTTCCCCCAGTGCTTCCCGG
CCGCCCCTATGACCTGGCGGCGGCGACCGTGGCCACAGACCTG
GAGAGCGGCGGAGCCGGTGCGGCTTGCGGCGGTAGCAACCTGG
CGCCCCTACCTCGGAGAGAGACCGAGGAGTTCAACGATCTCCT
GGACCTGGACTTTATTCTCTCCAATTCGCTGACCCATCCTCCGG
AGTCAGTGGCCGCCACCGTGTCCTCGTCAGCGTCAGCCTCCTCT
TCGTCGTCGCCGTCGAGCAGCGGCCCTGCCAGCGCGCCCTCCAC
CTGCAGCTTCACCTATCCGATCCGGGCCGGGAACGACCCGGGC
GTGGCGCCGGGCGGCACGGGCGGAGGCCTCCTCTATGGCAGGG
AGTCCGCTCCCCCCTCCGACGGCTCCCTTCAACCTGGCGGACATC
AACGACGTGAGCCCCTCGGGCGGCTTCGTGGCCGAGCTCCTGC
GGCCAGAATTGGACCCGGTGTACATTCCGCCGCAGCAGCCGCA
GCCGCCAGGTGGCGGGCTGATGGGCAAGTTCGTGCTGAAGGCG
TCGCTGAGCGCCCCTGGCAGCGAGTACGGCAGCCCGTCGGTCA
TCAGCGTCAGCAAAGGCAGCCCTGACGGCAGCCACCCGGTGGT
GGTGGCGCCCTACAACGGCGGGCCGCCGCGCACGTGCCCCAAG
ATCAAGCAGGAGGCGGTCTCTTCGTGCACCCACTTGGGCGCTGG
ACCCCCTCTCAGCAATGGCCACCGGCCGGCTGCACACGACTTCC
CCCTGGGGCGGCAGCTCCCCAGCAGGACTACCCCGACCCTGGG
TCTTGAGGAAGTGCTGAGCAGCAGGGACTGTCACCCTGCCCTGC
CGCTTCCTCCCGGCTTCCATCCCCACCCGGGGCCCAATTACCCA
TCCTTCCTGCCCGATCAGATGCAGCCGCAAGTCCCGCCGCTCCA
TTACCAAGAGCTCATGCCACCCGGTTCCTGCATGCAGAGGAGC
CCAAGCCAAAGAGGGGAAGACGATCGTGGCCCCGGAAAAGGA
CCGCCACCCACACTTGTGATTACGCGGGCTGCGGCAAAACCTAC
ACAAAGAGTTCCCATCTCAAGGCACACCTGCGAACCCACACAG
GTGAGAAACCTTACCACTGTGACTGGGACGGCTGTGGATGAA
ATTCGCCCGCTCAGATGAACTGACCAGGCACTACCGTAAACAC |

TABLE 6-continued

AAV2-TRE-OSK Vector Sequences

| SEQ ID NO: | Component | Sequence |
|---|---|---|
| | | ACGGGGCACCGCCCGTTCCAGTGCCAAAAATGCGACCGAGCAT<br>TTTCCAGGTCGGACCACCTCGCCTTACACATGAAGAGGCATTTT |
| 15 | pAAV2-TRE3G-OSK-SV40 (full plasmid sequence, including selection casettes) | TCGCGCGTTTCGGTGATGACGGTGAAAACCTCTGACACATGCAG<br>CTCCCGGAGACTGTCACAGCTTGTCTGTAAGCGGATGCCGGGA<br>GCAGACAAGCCCGTCAGGGCGCGTCAGCGGGTGTTGGCGGGTG<br>TCGGGGCTGGCTTAACTATGCGGCATCAGAGCAGATTGTACTGA<br>GAGTGCACCATATGCGGTGTGAAATACCGCACAGATGCGTAAG<br>GAGAAAATACCGCATCAGGCGCCATTCGCCATTCAGGCTGCGC<br>AACTGTTGGGAAGGGCGATCGGTGCGGGCCTCTTCGCTATTACG<br>CCAGCTGGCGAAAGGGGGATGTGCTGCAAGGCGATTAAGTTGG<br>GTAACGCCAGGGTTTTCCCAGTCACGACGTTGTAAAACGACGG<br>CCAGTGAATTGACGCGTATTGGGATCCATGATTACGCCAGATTT<br>AATTAAGGCCTTAATTAGGCTGCGCGCTCGCTCGCTCACTGAGG<br>CCGCCCGGGCAAAGCCCGGGCGTCGGGCGACCTTTGGTCGCCC<br>GGCCTCAGTGAGCGAGCGAGCGCGCAGAGAGGGAGTGGCCAA<br>CTCCATCACTAGGGGTTCCTTGTAGTTAATGATTAACCCGCCAT<br>GCTACTTATCTACGTAGCCATGCTCTAGGAAGATCGGAATTCTT<br>TACTCCCTATCAGTGATAGAGAACGTATGAAGAGTTTACTCCCT<br>ATCAGTGATAGAGAACGTATGCAGACTTTACTCCCTATCAGTGA<br>TAGAGAACGTATAAGGAGTTTACTCCCTATCAGTGATAGAGAA<br>CGTATGACCAGTTTACTCCCTATCAGTGATAGAGAACGTATCTA<br>CAGTTTACTCCCTATCAGTGATAGAGAACGTATATCCAGTTTAC<br>TCCCTATCAGTGATAGAGAACGTATAAGCTTTAGGCGTGTACGG<br>TGGGCGCCTATAAAAGCAGAGCTCGTTTAGTGAACCGTCAGAT<br>CGCCTGGAGCAATTCCACAACACTTTTGTCTTATACCAACTTTC<br>CGTACCACTTCCTACCCTCGTAAAGCGGCCGCGCCACCATGGCG<br>GGACACCTGGCTTCGGATTTCGCCTTCTCGCCCCCTCCAGGTGG<br>TGGAGGTGATGGCCAGGGGGGCCGGAGCCGGGCTGGGTTGAT<br>CCTCGGACCTGGCTAAGCTTCCAAGGCCCTCCTGGAGGGCCAG<br>GAATCGGGCCGGGGGTTGGGCCAGGCTCTGAGGTGTGGGGGAT<br>TCCCCCATGCCCCCCGCCGTATGAGTTCTGTGGGGGGATGGCGT<br>ACTGTGGGCCCCAGGTTGGAGTGGGGCTAGTGCCCCAAGGCGG<br>CTTGGAGACCTCTCAGCCTGAGGGCGAAGCAGGAGTCGGGGTG<br>GAGAGCAACTCCGATGGGGCCTCCCCGGAGCCCTGCACCGTCA<br>CCCCTGGTGCCGTGAAGCTGGAGAAGGAGAAGCTGGAGCAAAA<br>CCCGGAGGAGTCCCAGGACATCAAAGCTCTGCAGAAAGAACTC<br>GAGCAATTTGCCAAGCTCCTGAAGCAGAAGAGGATCACCCTGG<br>GATATACACAGGCCGATGTGGGGCTCACCCTGGGGGTTCTATTT<br>GGGAAGGTATTCAGCCAAACGACCATCTGCCGCTTTGAGGCTCT<br>GCAGCTTAGCTTCAAGAACATGTGTAAGCTGCGGCCCTTGCTGC<br>AGAAGTGGGTGGAGGAAGCTGACAACAATGAAAATCTTCAGGA<br>GATATGCAAAGCAGAAACCCTCGTGCAGGCCCGAAAGAGAAAG<br>CGAACCAGTATCGAGAACCGAGTGAGAGGCAACCTGGAGAATT<br>TGTTCCTGCAGTGCCCGAAACCCACACTGCAGCAGATCAGCCAC<br>ATCGCCCAGCAGCTTGGGCTCGAGAAGGATGTGGTCCGAGTGT<br>GGTTCTGTAACCGGCGCCAGAAGGGCAAGCGATCAAGCAGCGA<br>CTATGCACAACGAGAGGATTTTGAGGCTGCTGGGTCTCCTTTCT<br>CAGGGGGACCAGTGTCCTTTCCTCTGGCCCCAGGGCCCCATTTT<br>GGTACCCCAGGCTATGGGAGCCCTCACTTCACTGCACTGTACTC<br>CTCGGTCCCTTTCCCTGAGGGGGAAGCCTTTCCCCCTGTCTCTGT<br>CACCCACTCTGGGCTCTCCCATGCATTCAAACGCTAGCGGCAGCG<br>GCGCCACGAACTTCTCTCTGTTAAAGCAAGCAGGAGATGTTGA<br>AGAAAACCCCGGGCCTGCATGCATGTACAACATGATGGAGACG<br>GAGCTGAAGCCGCCGGGCCCGCAGCAAACTTCGGGGGGCGGCG<br>GCGGCAACTCCACCGCGGCGGCGGCCGGCGGCAACCAGAAAAA<br>CAGCCCGGACCGCGTCAAGCGGCCCATGAATGCCTTCATGGTGT<br>GGTCCCGCGGGCAGCGGCGCAAGATGGCCCAGGAGAACCCCAA<br>GATGCACAACTCGGAGATCAGCAAGCGCCTGGGCGCCGAGTGG<br>AAACTTTTGTCGGAGACGGAGAAGCGGCCGTTCATCGACGAGG<br>CTAAGCGGCTGCGAGCGCTGCACATGAAGGAGCACCCGGATTA<br>TAAATACCGGCCCCGGCGGAAAACCAAGACGCTCATGAAGAAG<br>GATAAGTACACGCTGCCCGGCGGGCTGCTGGCCCCCGGCGGCA<br>ATAGCATGGCGAGCGGGTCGGGGTGGGCGCCGGCCTGGGCGC<br>GGGCGTGAACCAGCGCATGGACAGTTACGCGCACATGAACGGC<br>TGGAGCAACGGCAGCTACAGCATGATGCAGGACCAGCTGGGCT<br>ACCCGCAGCACCCGGGCCTCAATGCGCACGGCGCAGCGCAGAT<br>GCAGCCCATGCACCGCTACGACGTGAGCGCCCTGCAGTACAAC<br>TCCATGACCAGCTCGCAGACCTACATGAACGGCTCGCCCACCTA<br>CAGCATGTCCTACTCGCAGCAGGGCACCCCTGGCATGGCTCTTG<br>GCTCCATGGGTTCGGTGGTCAAGTCCGAGGCCAGCTCCAGCCCC<br>CCTGTGGTTACCTCTTCCTCCCACTCCAGGGCGCCCTGCCAGGC<br>CGGGGACCTCCGGGACATGATCAGCATGTATCTCCCCGGCGCC<br>GAGGTGCCGGAACCCGCCGCCCCAGCAGACTTCACATGTCCC |

TABLE 6-continued

AAV2-TRE-OSK Vector Sequences

| SEQ ID NO: Component | Sequence |
|---|---|
| | AGCACTACCAGAGCGGCCCGGTGCCCGGCACGGCCATTAACGG |
| | CACACTGCCCCTCTCACACATGGCATGCGGCTCCGGCGAGGGC |
| | AGGGGAAGTCTTCTAACATGCGGGGACGTGGAGGAAAATCCCG |
| | GCCCACTCGAGATGGCTGTCAGCGACGCGCTGCTCCCATCTTTC |
| | TCCACGTTCGCGTCTGGCCCGGCGGGAAGGGAGAAGACACTGC |
| | GTCAAGCAGGTGCCCCGAATAACCGCTGGCGGGAGGAGCTCTC |
| | CCACATGAAGCGACTTCCCCCAGTGCTTCCCGGCCGCCCCTATG |
| | ACCTGGCGGCGGCGACCGTGGCCACAGACCTGGAGAGCGGCGG |
| | AGCCGGTGCGGCTTGCGGCGGTAGCAACCTGGCGCCCCTACCTC |
| | GGAGAGAGACCGAGGAGTTCAACGATCTCCTGGACCTGGACTT |
| | TATTCTCTCCAATTCGCTGACCCATCCTCCGGAGTCAGTGCCG |
| | CCACCGTGTCCTCGTCAGCGTCAGCCTCCTCTTCGTCGTCGCCGT |
| | CGAGCAGCGGCCCTGCCAGCGCGCCCTCCACCTGCAGCTTCACC |
| | TATCCGATCCGGGCCGGGAACGACCCGGGCGTGGCGCCGGGCG |
| | GCACGGGCGGAGGCCTCCTCTATGGCAGGGAGTCCGCTCCCCCT |
| | CCGACGGCTCCCTTCAACCTGGCGGACATCAACGACGTGAGCC |
| | CCTCGGGCGGCTTCGTGGCCGAGCTCCTGCGGCCAGAATTGGAC |
| | CCGGTGTACATTCCGCCGCAGCAGCCGCAGCCGCCAGGTGGCG |
| | GGCTGATGGGCAAGTTCGTGCTGAAGGCGTCGCTGAGCGCCCC |
| | TGGCAGCGAGTACGGCAGCCCGTCGGTCATCAGCGTCAGCAAA |
| | GGCAGCCCTGACGGCAGCCACCCGGTGGTGGTGGCGCCCTACA |
| | ACGGCGGGCCGCCGCGCACGTGCCCCAAGATCAAGCAGGAGGC |
| | GGTCTCTTCGTGCACCCACTTGGGCGCTGGACCCCCTCTCAGCA |
| | ATGGCCACCGGCCGGCTGCACACGACTTCCCCCTGGGGCGGCA |
| | GCTCCCCAGCAGGACTACCCCGACCCTGGGTCTTGAGGAAGTG |
| | CTGAGCAGCAGGGACTGTCACCCTGCCCTGCCGCTTCCTCCCGG |
| | CTTCCATCCCCACCCGGGGCCCAATTACCCATCCTTCCTGCCCG |
| | ATCAGATGCAGCCGCAAGTCCCGCCGCTCCATTACCAAGAGCTC |
| | ATGCCACCCGGTTCCTGCATGCCAGAGGAGCCCAAGCCAAAGA |
| | GGGGAAGACGATCGTGGCCCCGGAAAAGGACCGCCACCCACAC |
| | TTGTGATTACGCGGGCTGCGGCAAAACCTACACAAAGAGTTCC |
| | CATCTCAAGGCACACCTGCGAACCCACACAGGTGAGAAACCTT |
| | ACCACTGTGACTGGGACGGCTGTGGATGGAAATTCGCCCGCTC |
| | AGATGAACTGACCAGGCACTACCGTAAACACACGGGGCACCGC |
| | CCGTTCCAGTGCCAAAAATGCGACCGAGCATTTTCCAGGTCGGA |
| | CCACCTCGCCTTACACATGAAGAGGCATTTTTAAATGACTAGTG |
| | CGCGCAGCGGCCGACCATGGCCCAACTTGTTTATTGCAGCTTAT |
| | AATGGTTACAAATAAAGCAATAGCATCACAAATTTCACAAATA |
| | AAGCATTTTTTTCACTGCATTCTAGTTGTGGTTTGTCCAAACTCA |
| | TCAATGTATCTTATCATGTCTGGATCTCGGTACCGGATCCAAT |
| | TCCCGATAAGGATCTTCCTAGAGCATGGCTACGTAGATAAGTAG |
| | CATGGCGGGTTAATCATTAACTACAAGGAACCCCTAGTGATGG |
| | AGTTGGCCACTCCCTCTCTGCGCGCTCGCTCGCTCACTGAGGCC |
| | GGGCGACCAAAGGTCGCCCGACGCCCGGGCTTTGCCCGGGCGG |
| | CCTCAGTGAGCGAGCGAGCGCGCAGCCTTAATTAACCTAATTCA |
| | TCCCAATGGCGCGCCGAGCTTGGCTCGAGCATGGTCATAGCTGT |
| | TTCCTGTGTGAAATTGTTATCCGCTCACAATTCCACACAACATA |
| | CGAGCCGGAAGCATAAAGTGTAAAGCCTGGGGTGCCTAATGAG |
| | TGAGCTAACTCACATTAATTGCGTTGCGCTCACTGCCCGCTTTC |
| | CAGTCGGGAAACCTGTCGTGCCAGCTGCATTAATGAATCGGCC |
| | AACGCGCGGGGAGAGGCGGTTTGCGTATTGGGCGCTGTTCCGC |
| | TTCCTCGCTCACTGACTCGCTGCGCTCGGTCGTTCGGCTGCGGC |
| | GAGCGGTATCAGCTCACTCAAAGGCGGTAATACGGTTATCCAC |
| | AGAATCAGGGGATAACGCAGGAAAGAACATGTGAGCAAAAGG |
| | CCAGCAAAAGGCCAGGAACCGTAAAAAGGCCGCGTTGCTGGCG |
| | TTTTTCCATAGGCTCCGCCCCCCTGACGAGCATCACAAAAATCG |
| | ACGCTCAAGTCAGAGGTGGCGAAACCCGACAGGACTATAAAGA |
| | TACCAGGCGTTTCCCCCTGGAAGCTCCCTCGTGCGCTCTCCTGTT |
| | CCGACCCTGCCGCTTACCGGATACCTGTCCGCCTTTCTCCCTTCG |
| | GGAAGCGTGGCGCTTTCTCATAGCTCACGCTGTAGGTATCTCAG |
| | TTCGGTGTAGGTCGTTCGCTCCAAGCTGGGCTGTGTGCACGAAC |
| | CCCCCGTTCAGCCCGACCGCTGCGCCTTATCCGGTAACTATCGT |
| | CTTGAGTCCAACCCGGTAAGACACGACTTATCGCCACTGGCAGC |
| | AGCCACTGGTAACAGGATTAGCAGAGCGAGGTATGTAGGCGGT |
| | GCTACAGAGTTCTTGAAGTGGTGGCCTAACTACGGCTACACTAG |
| | AAGAACAGTATTTGGTATCTGCGCTCTGCTGAAGCCAGTTACCT |
| | TCGGAAAAAGAGTTGGTAGCTCTTGATCCGGCAAACAAACCAC |
| | CGCTGGTAGCGGTGGTTTTTTTGTTTGCAAGCAGCAGATTACGC |
| | GCAGAAAAAAAGGATCTCAAGAAGATCCTTTGATCTTTTCTACG |
| | GGGTCTGACGCTCAGTGGAACGAAAACTCACGTTAAGGGATTT |
| | TGGTCATGAGATTATCAAAAAGGATCTTCACCTAGATCCTTTTA |
| | AATTAAAAATGAAGTTTTAAATCAATCTAAAGTATATATGAGTA |
| | AACTTGGTCTGACAGTTAGAAAAACTCATCGAGCATCAAATGA |
| | AACTGCAATTTATTCATATCAGGATTATCAATACCATATTTTGA |

TABLE 6-continued

AAV2-TRE-OSK Vector Sequences

| SEQ ID NO: | Component | Sequence |
|---|---|---|
| | | AAAAGCCGTTTCTGTAATGAAGGAGAAAACTCACCGAGGCAGT TCCATAGGATGGCAAGATCCTGGTATCGGTCTGCGATTCCGACT CGTCCAACATCAATACAACCTATTAATTTCCCCTCGTCAAAAAT AAGGTTATCAAGTGAGAAATCACCATGAGTGACGACTGAATCC GGTGAGAATGGCAAAAGTTTATGCATTTCTTTCCAGACTTGTTC AACAGGCCAGCCATTACGCTCGTCATCAAAATCACTCGCATCAA CCAAACCGTTATTCATTCGTGATTGCGCCTGAGCGAAACGAAAT ACGCGATCGCTGTTAAAAGGACAATTACAAACAGGAATCGAAT GCAACCGGCGCAGGAACACTGCCAGCGCATCAACAATATTTTC ACCTGAATCAGGATATTCTTCTAATACCTGGAATGCTGTTTTCC CAGGGATCGCAGTGGTGAGTAACCATGCATCATCAGGAGTACG GATAAAATGCTTGATGGTCGGAAGAGGCATAAATTCCGTCAGC CAGTTTAGTCTGACCATCTCATCTGTAACATCATTGGCAACGCT ACCTTTGCCATGTTTCAGAAACAACTCTGGCGCATCGGGCTTCC CATACAATCGATAGATTGTCGCACCTGATTGCCCGACATTATCG CGAGCCCATTTATACCCATATAAATCAGCATCCATGTTGGAATT TAATCGCGGCCTAGAGCAAGACGTTTCCCGTTGAATATGGCTCA TACTCTTCCTTTTTCAATATTATTGAAGCATTTATCAGGGTTATT GTCTCATGAGCGGATACATATTTGAATGTATTTAGAAAAATAAA CAAATAGGGGTTCCGCGCACATTTCCCCGAAAAGTGCCACCTG ACGTCTAAGAAACCATTATTATCATGACATTAACCTATAAAAAT AGGCGTATCACGAGGCCCTTTTGTC |
| 16 | ITR - forward | CCTTAATTAGGCTGCGCGCTCGCTCGCTCACTGAGGCCGCCCGG GCAAAGCCCGGGCGTCGGGCGACCTTTGGTCGCCCGGCCTCAG TGAGCGAGCGAGCGCGCAGAGAGGGAGTGGCCAACTCCATCAC TAGGGGTTCCT |
| 32 | ITR - reverse | AGGAACCCCTAGTGATGGAGTTGGCCACTCCCTCTCTGCGCGCT CGCTCGCTCACTGAGGCCGGGCGACCAAAGGTCGCCCGACGCC CGGGCTTTGCCCGGGCGGCCTCAGTGAGCGAGCGAGCGCGCAG CTGCCTGCAGG |
| 35 | OCT4-2A-SOX2-2A-KLF4 (Whole insert sequence including Tet operators, SV40, and ITRs) | CCTTAATTAGGCTGCGCGCTCGCTCGCTCACTGAGGCCGCCCGG GCAAAGCCCGGGCGTCGGGCGACCTTTGGTCGCCCGGCCTCAG TGAGCGAGCGAGCGCGCAGAGAGGGAGTGGCCAACTCCATCAC TAGGGGTTCCTTGTAGTTAATGATTAACCCGCCATGCTACTTAT CTACGTAGCCATGCTCTAGGAAGATCGGAATTCTTTACTCCCTA TCAGTGATAGAGAACGTATGAAGAGTTTACTCCCTATCAGTGAT AGAGAACGTATGCAGACTTTACTCCCTATCAGTGATAGAGAAC GTATAAGGAGTTTACTCCCTATCAGTGATAGAGAACGTATGACC AGTTTACTCCCTATCAGTGATAGAGAACGTATCTACAGTTTACT CCCTATCAGTGATAGAGAACGTATATCCAGTTTACTCCCTATCA GTGATAGAGAACGTATAAGCTTTAGGCGTGTACGGTGGGCGCC TATAAAAGCAGAGCTCGTTTAGTGAACCGTCAGATCGCCTGGA GCAATTCCACAACACTTTTGTCTTATACCAACTTTCCGTACCACT TCCTACCCTCGTAAAGCGGCCGCGCCACCATGGCGGGACACCT GGCTTCGGATTTCGCCTTCTCGCCCCCTCCAGGTGGTGGAGGTG ATGGGCCAGGGGGGCCGGAGCCGGGCTGGGTTGATCCTCGGAC CTGGCTAAGCTTCCAAGGCCCTCCTGGAGGGCCAGGAATCGGG CCGGGGGTTGGGCCAGGCTCTGAGGTGTGGGGGATTCCCCCAT GCCCCCCGCCGTATGAGTTCTGTGGGGGATGGCGTACTGTGGG CCCCAGGTTGGAGTGGGCTAGTGCCCCAAGGCGGCTTGGAGA CCTCTCAGCCTGAGGGCGAAGCAGGAGTCGGGGTGGAGAGCAA CTCCGATGGGGCCTCCCCGGAGCCCTGCACCGTCACCCCTGGTG CCGTGAAGCTGGAGAAGGAGAAGCTGGAGCAAAACCCGGAGG AGTCCCAGGACATCAAAGCTCTGCAGAAAGAACTCGAGCAATT TGCCAAGCTCCTGAAGCAGAAGAGGATCACCCTGGGATATACA CAGGCCGATGTGGGGCTCACCCTGGGGGTTCTATTTGGGAAGGT ATTCAGCCAAACGACCATCTGCCGCTTTGAGGCTCTGCAGCTTA GCTTCAAGAACATGTGTAAGCTGCGGCCCTTGCTGCAGAAGTG GGTGGAGGAAGCTGACAACAATGAAAATCTTCAGGAGATATGC AAAGCAGAAACCCTCGTGCAGGCCCGAAAGAGAAAGCGAACC AGTATCGAGAACCGAGTGAGAGGCAACCTGGAGAATTTGTTCC TGCAGTGCCCGAAACCCACACTGCAGCAGATCAGCCACATCGC CCAGCAGCTTGGGCTCGAGAAGGATGTGGTCCGAGTGTGGTTCT GTAACCGGCGCCAGAAGGGCAAGCGATCAAGCAGCGACTATGC ACAACGAGAGGATTTTGAGGCTGCTGGGTCTCCTTTCTCAGGGG GACCAGTGTCCTTTCCTCTGGCCCCAGGGCCCCATTTTGGTACC CCAGGCTATGGGAGCCCTCACTTCACTGCACTGTACTCCTCGGT |

TABLE 6-continued

AAV2-TRE-OSK Vector Sequences

| SEQ ID NO: Component | Sequence |
|---|---|
| | CCCTTTCCCTGAGGGGGAAGCCTTTCCCCCTGTCTCTGTCACCA |
| | CTCTGGGCTCTCCCATGCATTCAAACGCTAGCGGCAGCGGCGCC |
| | ACGAACTTCTCTCTGTTAAAGCAAGCAGGAGATGTTGAAGAAA |
| | ACCCCGGGCCTGCATGCATGTACAACATGATGGAGACGGAGCT |
| | GAAGCCGCCGGGCCCGCAGCAAACTTCGGGGGCGGCGGCGGC |
| | AACTCCACCGCGGCGGCGGCCGGCGGCAACCAGAAAAACAGCC |
| | CGGACCGCGTCAAGCGGCCCATGAATGCCTTCATGGTGTGGTCC |
| | CGCGGGCAGCGGCGCAAGATGGCCCAGGAGAACCCCAAGATGC |
| | ACAACTCGGAGATCAGCAAGCGCCTGGGCGCCGAGTGGAAACT |
| | TTTGTCGGAGACGGAGAAGCGGCCGTTCATCGACGAGGCTAAG |
| | CGGCTGCGAGCGCTGCACATGAAGGAGCACCCGGATTATAAAT |
| | ACCGGCCCCGGCGGAAAACCAAGACGCTCATGAAGAAGGATAA |
| | GTACACGCTGCCCGGCGGGCTGCTGGCCCCGGCGGCAATAGC |
| | ATGGCGAGCGGGGTCGGGGTGGGCGCCGGCCTGGGCGCGGGCG |
| | TGAACCAGCGCATGGACAGTTACGCGCACATGAACGGCTGGAG |
| | CAACGGCAGCTACAGCATGATGCAGGACCAGCTGGGCTACCCG |
| | CAGCACCCGGGCCTCAATGCGCACGGCGCAGCGCAGATGCAGC |
| | CCATGCACCGCTACGACGTGAGCGCCCTGCAGTACAACTCCATG |
| | ACCAGCTCGCAGACCTACATGAACGGCTCGCCCACCTACAGCA |
| | TGTCCTACTCGCAGCAGGGCACCCCTGGCATGGCTCTTGGCTCC |
| | ATGGGTTCGGTGGTCAAGTCCGAGGCCAGCTCCAGCCCCCCTGT |
| | GGTTACCTCTTCCTCCCACTCCAGGGCGCCCTGCCAGGCCGGGG |
| | ACCTCCGGGACATGATCAGCATGTATCTCCCCGGCGCCGAGGTG |
| | CCGGAACCCGCCGCCCCCAGCAGACTTCACATGTCCCAGCACTA |
| | CCAGAGCGGCCCGGTGCCCGGCACGGCCATTAACGGCACACTG |
| | CCCCTCTCACACATGGCATGCGGCTCCGGCGAGGGCAGGGGAA |
| | GTCTTCTAACATGCGGGGACGTGGAGGAAAATCCCGGCCCACT |
| | CGAGATGGCTGTCAGCGACGCGCTGCTCCCATCTTTCTCCACGT |
| | TCGCGTCTGGCCCGGCGGGAAGGGAGAAGACACTGCGTCAAGC |
| | AGGTGCCCCGAATAACCGCTGGCGGGAGGAGCTCTCCCACATG |
| | AAGCGACTTCCCCCAGTGCTTCCCGGCCGCCCCTATGACCTGGC |
| | GGCGGCGACCGTGGCCACAGACCTGGAGAGCGGCGGAGCCGGT |
| | GCGGCTTGCGGCGGTAGCAACCTGGCGCCCCTACCTCGGAGAG |
| | AGACCGAGGAGTTCAACGATCTCCTGGACCTGGACTTTATTCTC |
| | TCCAATTCGCTGACCCATCCTCCGGAGTCAGTGGCCGCCACCGT |
| | GTCCTCGTCAGCGTCAGCCTCCTCTTCGTCGTCGCCGTCGAGCA |
| | GCGGCCCTGCCAGCGCGCCCTCCACCTGCAGCTTCACCTATCCG |
| | ATCCGGGCCGGGAACGACCCGGGCGTGGCGCCGGGCGGCACGG |
| | GCGGAGGCCTCCTCTATGGCAGGGAGTCCGCTCCCCCTCCGACG |
| | GCTCCCTTCAACCTGGCGGACATCAACGACGTGAGCCCCTCGGG |
| | CGGCTTCGTGGCCGAGCTCCTGCGGCCAGAATTGGACCCGGTGT |
| | ACATTCCGCCGCAGCAGCCGCAGCCGCCAGGTGGCGGGCTGAT |
| | GGGCAAGTTCGTGCTGAAGGCGTCGCTGAGCGCCCCTGGCAGC |
| | GAGTACGGCAGCCCGTCGGTCATCAGCGTCAGCAAAGGCAGCC |
| | CTGACGGCAGCCACCCGGTGGTGGTGGCGCCCTACAACGGCGG |
| | GCCGCCGCGCACGTGCCCCAAGATCAAGCAGGAGGCGGTCTCT |
| | TCGTGCACCCACTTGGGCGCTGGACCCCCTCTCAGCAATGGCCA |
| | CCGGCCGGCTGCACACGACTTCCCCCTGGGGCGGCAGCTCCCCA |
| | GCAGGACTACCCCGACCCTGGGTCTTGAGGAAGTGCTGAGCAG |
| | CAGGGACTGTCACCCTGCCCTGCCGCTTCCTCCCGGCTTCCATC |
| | CCCACCCGGGGCCCAATTACCCATCCTTCCTGCCCGATCAGATG |
| | CAGCCGCAAGTCCCGCCGCTCCATTACCAAGAGCTCATGCCACC |
| | CGGTTCCTGCATGCCAGAGGAGCCCAAGCCAAAGAGGGGAAGA |
| | CGATCGTGGCCCCGGAAAAGGACCGCCACCCACACTTGTGATT |
| | ACGCGGGCTGCGGCAAAACCTACACAAAGAGTTCCCATCTCAA |
| | GGCACACCTGCGAACCCACACAGGTGAGAAACCTTACCACTGT |
| | GACTGGGACGGCTGTGGATGGAAATTCGCCCGCTCAGATGAAC |
| | TGACCAGGCACTACCGTAAACACACGGGGCACCGCCCGTTCCA |
| | GTGCCAAAAATGCGACCGAGCATTTTCCAGGTCGGACCACCTC |
| | GCCTTACACATGAAGAGGCATTTTTAAATGACTAGTGCGCGCAG |
| | CGGCCGACCATGGCCCAACTTGTTTATTGCAGCTTATAATGGTT |
| | ACAAATAAAGCAATAGCATCACAAATTTCACAAATAAAGCATT |
| | TTTTTCACTGCATTCTAGTTGTGGTTTGTCCAAACTCATCAATGT |
| | ATCTTATCATGTCTGGATCTCGGTACCGGATCCAAATTCCCGAT |
| | AAGGATCTTCCTAGAGCATGGCTACGTAGATAAGTAGCATGGC |
| | GGGTTAATCATTAACTACAAGGAACCCCTA |

TABLE 7

AAV2-CMV-rtTA3V16 Vector Sequences

| SEQ ID NO: | Component | Sequence |
|---|---|---|
| 17 | CMV promoter | GTGATGCGGTTTTGGCAGTACATCAATGGGCGTGGATAGCG GTTTGACTCACGGGGATTTCCAAGTCTCCACCCCATTGACG TCAATGGGAGTTTGTTTTGGCACCAAAATCAACGGGACTTT CCAAAATGTCGTAACAACTCCGCCCCATTGACGCAAATG GCGGTAGGCGTGTACGGTGGGAGGTCTATATAAGCAGAGC T |
| 18 | CMV enhancer | GACATTGATTATTGACTAGTTATTAATAGTAATCAATTACG GGGTCATTAGTTCATAGCCCATATATGGAGTTCCGCGTTAC ATAACTTACGGTAAATGGCCCGCCTGGCTGACCGCCCAACG ACCCCCGCCCATTGACGTCAATAATGACGTATGTTCCCATA GTAACGCCAATAGGGACTTTCCATTGACGTCAATGGGTGGA GTATTTACGCTAAACTGCCCACTTGGCAGTACATCAAGTGT ATCATATGCCAAGTACGCCCCCTATTGACGTCAATGACGGT AAATGGCCCGCCTGGCATTATGCCCAGTACATGACCTTATG GGACTTTCCTACTTGGCAGTACATCTACGTATTAGTCATCG CTATTACCATG |
| 19 | rtTA3 Advanced nucleic acid sequence | ATGTCTAGACTGGACAAGAGCAAAATCATAAACAGCGCTC TGGAATTACTCAATGGAGTCGGTATCGAAGGCCTGACGAC AAGGAAACTCGCTCAAAAGCTGGGAGTTGAGCAGCCTACC CTGTACTGGCACGTGAAGAACAAGCGGGCCCTGCTCGATG CCCTGCCAATCGAGATGCTGGACAGGCATCATACCCACAG CTGCCCCCTGGAAGGCGAGTCATGGCAAGACTTTCTGCGGA ACAACGCCAAGTCATACCGCTGTGCTCTCCTCTCACATCGC GACGGGGCTAAAGTGCATCTCGGCACCCGCCCAACAGAGA AACAGTACGAAACCCTGGAAAATCAGCTCGCGTTCCTGTGT CAGCAAGGCTTCTCCCTGGAGAACGCACTGTACGCTCTGTC CGCCGTGGGCCACTTTACACTGGGCTGCGTATTGGAGGAAC AGGAGCATCAAGTAGCAAAAGAGGAAAGAGAGACACCTA CCACCGATTCTATGCCCCCACTTCTGAAGCAAGCAATTGAG CTGTTCGACCGGCAGGGAGCCGAACCTGCCTTCCTTTTCGG CCTGGAACTAATCATATGTGGCCTGGAGAAACAGCTAAAG TGCGAAAGCGGCGGGCCGACCGACGCCCTTGACGATTTTG ACTTAGACATGCTCCCAGCCGATGCCCTTGACGACTTTGAC CTTGATATGCTGCCTGCTGACGCTCTTGACGATTTTGACCTT GACATGCTCCCCGGGTAA |
| 20 | rtTA3 Advanced amino acid | MSRLDKSKIINSALELLNGVGIEGLTTRKLAQKLGVEQPTLYW HVKNKRALLDALPIEMLDRHHTHSCPLEGESWQDFLRNNAKS YRCALLSHRDGAKVHLGTRPTEKQYETLENQLAFLCQQGFSL ENALYALSAVGHFTLGCVLEEQEHQVAKEERETPTTDSMPPL LKQAIELFDRQGAEPAFLFGLELIICGLEKQLKCESGGPTDALD DFDLDMLPADALDDFDLDMLPADALDDFDLDMLPG* |
| 21 | AAV2-CMV-rtTA3V16 (full plasmid sequence) | TCGCGCGTTTCGGTGATGACGGTGAAAACCTCTGACACATG CAGCTCCCGGAGACTGTCACAGCTTGTCTGTAAGCGGATGC CGGGAGCAGACAAGCCCGTCAGGGCGCGTCAGCGGGTGTT GGCGGGTGTCGGGGCTGGCTTAACTATGCGGCATCAGAGC AGATTGTACTGAGAGTGCACCATATGCGGTGTGAAATACC GCACAGATGCGTAAGGAGAAAATACCGCATCAGGCGCCAT TCGCCATTCAGGCTGCGCAACTGTTGGGAAGGGCGATCGGT GCGGGCCTCTTCGCTATTACGCCAGCTGGCGAAAGGGGGA TGTGCTGCAAGGCGATTAAGTTGGGTAACGCCAGGGTTTTC CCAGTCACGACGTTGTAAAACGACGGCCAGTGAATTGACG CGTATTGGGATACTATGGTTGCTTTGACGTATGCGGTGTGA ATACCGCACAGATGCGTAAGGAGAAAATACCGCATCAGG CGCCCCTGCAGGCAGCTGCGCGCTCGCTCGCTCACTGAGGC CGCCCGGGCAAAGCCCGGGCGTCGGGCGACCTTTGGTCGC CCGGCCTCAGTGAGCGAGCGAGCGCGCAGAGAGGGAGTGG CCAACTCCATCACTAGGGGTTCCTGCGGCCGCTCGGTCCGC ACGATCTCAATTCGGCCATTACGGCCGGATCCGGCTCGAGG AGCTTGGCCCATTGCATACGTTGTATCCATATCATAATATG TACATTTATATTGGCTCATGTCCAACATTACCGCCATGTTG ACATTGATTATTGACTAGTTATTAATAGTAATCAATTACGG GGTCATTAGTTCATAGCCCATATATGGAGTTCCGCGTTACA TAACTTACGGTAAATGGCCCGCCTGGCTGACCGCCCAACGA CCCCCGCCCATTGACGTCAATAATGACGTATGTTCCCATAG TAACGCCAATAGGGACTTTCCATTGACGTCAATGGGTGGAG TATTTACGCTAAACTGCCCACTTGGCAGTACATCAAGTGTA TCATATGCCAAGTACGCCCCCTATTGACGTCAATGACGGTA AATGGCCCGCCTGGCATTATGCCCAGTACATGACCTTATGG GACTTTCCTACTTGGCAGTACATCTACGTATTAGTCATCGCT ATTACCATGGTGATGCGGTTTTGGCAGTACATCAATGGGCG TGGATAGCGGTTTGACTCACGGGGATTTCCAAGTCTCCACC |

TABLE 7-continued

AAV2-CMV-rtTA3V16 Vector Sequences

| SEQ ID NO: | Component | Sequence |
|---|---|---|
| | | CCATTGACGTCAATGGGAGTTTGTTTTGGCACCAAAATCAA |
| | | CGGGACTTTCCAAAATGTCGTAACAACTCCGCCCCATTGAC |
| | | GCAAATGGGCGGTAGGCGTGTACGGTGGGAGGTCTATATA |
| | | AGCAGAGCTCGTTTAGTGAACCGTCAGATCGCCTGGAGAC |
| | | GCCATCCACGCTGTTTTGACCTCCATAGAAGACACCGGGAC |
| | | CGATCCAGCCTCCGCGGCCCCGAATTCACCATGTCTAGACT |
| | | GGACAAGAGCAAAATCATAAACAGCGCTCTGGAATTACTC |
| | | AATGGAGTCGGTATCGAAGGCCTGACGACAAGGAAACTCG |
| | | CTCAAAAGCTGGGAGTTGAGCAGCCTACCCTGTACTGGCAC |
| | | GTGAAGAACAAGCGGGCCCTGCTCGATGCCCTGCCAATCG |
| | | AGATGCTGGACAGGCATCATACCCACAGCTGCCCCCTGGA |
| | | AGGCGAGTCATGGCAAGACTTTCTGCGGAACAACGCCAAG |
| | | TCATACCGCTGTGCTCTCCTCTCACATCGCGACGGGGCTAA |
| | | AGTGCATCTCGGCACCCGCCCAACAGAGAAACAGTACGAA |
| | | ACCCTGGAAAATCAGCTCGCGTTCCTGTGTCAGCAAGGCTT |
| | | CTCCCTGGAGAACGCACTGTACGCTCTGTCCGCCGTGGGCC |
| | | ACTTTACACTGGGCTGCGTATTGGAGGAACAGGAGCATCA |
| | | AGTAGCAAAAGAGGAAAGAGAGACACCTACCACCGATTCT |
| | | ATGCCCCCACTTCTGAAGCAAGCAATTGAGCTGTTCGACCG |
| | | GCAGGGAGCCGAACCTGCCTTCCTTTTCGGCCTGGAACTAA |
| | | TCATATGTGGCCTGGAGAAACAGCTAAAGTGCGAAAGCGG |
| | | CGGGCCGACCGACGCCCTTGACGATTTTGACTTAGACATGC |
| | | TCCCAGCCGATGCCCTTGACGACTTTGACCTTGATATGCTG |
| | | CCTGCTGACGCTCTTGACGATTTTGACCTTGACATGCTCCCC |
| | | GGGTAACTAAGTAAGGATCATCTTAATTAAATCGATAAGG |
| | | ATCTGGCCGCCTCGGCCTAATCAACCTCTGGATTACAAAAT |
| | | TTGTGAAAGATTGACTGGTATTCTTAACTATGTTGCTCCTTT |
| | | TACGCTATGTGGATACGCTGCTTTAATGCCTTTGTATCATGC |
| | | TATTGCTTCCCGTATGGCTTTCATTTTCTCCTCCTTGTATAA |
| | | ATCCTGGTTGCTGTCTCTTTATGAGGAGTTGTGGCCCGTTGT |
| | | CAGGCAACGTGGCGTGGTGTGCACTGTGTTTGCTGACGCAA |
| | | CCCCCACTGGTTGGGGCATTGCCACCACCTGTCAGCTCCTT |
| | | TCCGGGACTTTCGCTTTCCCCCTCCCTATTGCCACGGCGGA |
| | | ACTCATCGCCGCCTGCCTTGCCCGCTGCTGGACAGGGGCTC |
| | | GGCTGTTGGGCACTGACAATTCCGTGGTGTTGTCGGGGAAA |
| | | TCATCGTCCTTTCCTTGGCTGCTCGCCTGTGTTGCCACCTGG |
| | | ATTCTGCGCGGGACGTCCTTCTGCTACGTCCCTTCGGCCCTC |
| | | AATCCAGCGGACCTTCCTTCCCGCGGCCTGCTGCCGGCTCT |
| | | GCGGCCTCTTCCGCGTCTTCGCCTTCGCCCTCAGACGAGTC |
| | | GGATCTCCCTTTGGGCCGCCTCCCCGCCAGACATGATAAGA |
| | | TACATTGATGAGTTTGGACAAACCACAACTAGAATGCAGT |
| | | GAAAAAAATGCTTTATTTGTGAAATTTGTGATGCTATTGCT |
| | | TTATTTGTAACCATTATAAGCTGCAATAAACAAGTTAACAA |
| | | CAACAATTGCATTCATTTTATGTTTCAGGTTCAGGGGGAGA |
| | | TGTGGGAGGTTTTTTAAAGCAAGTAAAACCTCTACAAATGT |
| | | GGTAACTAGCGCGTGCGGCCGCAGGAACCCCTAGTGATGG |
| | | AGTTGGCCACTCCCTCTCTGCGCGCTCGCTCGCTCACTGAG |
| | | GCCGGGCGACCAAAGGTCGCCCGACGCCCGGGCTTTGCCC |
| | | GGGCGGCCTCAGTGAGCGAGCGAGCGCGCAGCTGCCTGCA |
| | | GGATCCCAATGGCGCGCCGAGCTTGGCTCGAGCATGGTCAT |
| | | AGCTGTTTCCTGTGTGAAATTGTTATCCGCTCACAATTCCAC |
| | | ACAACATACGAGCCGGAAGCATAAAGTGTAAAGCCTGGGG |
| | | TGCCTAATGAGTGAGCTAACTCACATTAATTGCGTTGCGCT |
| | | CACTGCCCGCTTTCCAGTCGGGAAACCTGTCGTGCCAGCTG |
| | | CATTAATGAATCGGCCAACGCGCGGGGAGAGGCGGTTTGC |
| | | GTATTGGGCGCTGTTCCGCTTCCTCGCTCACTGACTCGCTGC |
| | | GCTCGGTCGTTCGGCTGCGGCGAGCGGTATCAGCTCACTCA |
| | | AAGGCGGTAATACGGTTATCCACAGAATCAGGGGATAACG |
| | | CAGGAAAGAACATGTGAGCAAAAGGCCAGCAAAAGGCCA |
| | | GGAACCGTAAAAAGGCCGCGTTGCTGGCGTTTTTCCATAGG |
| | | CTCCGCCCCCCTGACGAGCATCACAAAAATCGACGCTCAA |
| | | GTCAGAGGTGGCGAAACCCGACAGGACTATAAAGATACCA |
| | | GGCGTTTCCCCCTGGAAGCTCCCTCGTGCGCTCTCCTGTTCC |
| | | GACCCTGCCGCTTACCGGATACCTGTCCGCCTTTCTCCCTTC |
| | | GGGAAGCGTGGCGCTTTCTCATAGCTCACGCTGTAGGTATC |
| | | TCAGTTCGGTGTAGGTCGTTCGCTCCAAGCTGGGCTGTGTG |
| | | CACGAACCCCCCGTTCAGCCCGACCGCTGCGCCTTATCCGG |
| | | TAACTATCGTCTTGAGTCCAACCCGGTAAGACACGACTTAT |
| | | CGCCACTGGCAGCAGCCACTGGTAACAGGATTAGCAGAGC |
| | | GAGGTATGTAGGCGGTGCTACAGAGTTCTTGAAGTGGTGG |
| | | CCTAACTACGGCTACACTAGAAGAACAGTATTTGGTATCTG |
| | | CGCTCTGCTGAAGCCAGTTACCTTCGGAAAAAGAGTTGGTA |
| | | GCTCTTGATCCGGCAAACAAACCACCGCTGGTAGCGGTGGT |
| | | TTTTTTGTTTGCAAGCAGCAGATTACGCGCAGAAAAAAAGG |
| | | ATCTCAAGAAGATCCTTTGATCTTTTCTACGGGGTCTGACG |

TABLE 7-continued

AAV2-CMV-rtTA3V16 Vector Sequences

| SEQ ID NO: | Component | Sequence |
|---|---|---|
| | | CTCAGTGGAACGAAAACTCACGTTAAGGGATTTTGGTCATG AGATTATCAAAAAGGATCTTCACCTAGATCCTTTTAAATTA AAAATGAAGTTTTAAATCAATCTAAAGTATATATGAGTAAA CTTGGTCTGACAGTTAGAAAAACTCATCGAGCATCAAATGA AACTGCAATTTATTCATATCAGGATTATCAATACCATATTTT TGAAAAAGCCGTTTCTGTAATGAAGGAGAAAACTCACCGA GGCAGTTCCATAGGATGGCAAGATCCTGGTATCGGTCTGCG ATTCCGACTCGTCCAACATCAATACAACCTATTAATTTCCC CTCGTCAAAAATAAGGTTATCAAGTGAGAAATCACCATGA GTGACGACTGAATCCGGTGAGAATGGCAAAAGTTTATGCA TTTCTTTCCAGACTTGTTCAACAGGCCAGCCATTACGCTCGT CATCAAAATCACTCGCATCAACCAAACCGTTATTCATTCGT GATTGCGCCTGAGCGAAACGAAATACGCGATCGCTGTTAA AAGGACAATTACAAACAGGAATCGAATGCAACCGGCGCAG GAACACTGCCAGCGCATCAACAATATTTTCACCTGAATCAG GATATTCTTCTAATACCTGGAATGCTGTTTTCCCAGGGATC GCAGTGGTGAGTAACCATGCATCATCAGGAGTACGGATAA AATGCTTGATGGTCGGAAGAGGCATAAATTCCGTCAGCCA GTTTAGTCTGACCATCTCATCTGTAACATCATTGGCAACGC TACCTTTGCCATGTTTCAGAAACAACTCTGGCGCATCGGGC TTCCCATACAATCGATAGATTGTCGCACCTGATTGCCCGAC ATTATCGCGAGCCCATTTATACCCATATAAATCAGCATCCA TGTTGGAATTTAATCGCGGCCTAGAGCAAGACGTTTCCCGT TGAATATGGCTCATACTCTTCCTTTTTCAATATTATTGAAGC ATTTATCAGGGTTATTGTCTCATGAGCGGATACATATTTGA ATGTATTTAGAAAAATAAACAAATAGGGGTTCCGCGCACA TTTCCCCGAAAAGTGCCACCTGACGTCAAGAAACCATTAT TATCATGACATTAACCTATAAAAATAGGCGTATCACGAGGC CCTTTTGTC |
| 22 | ITR - forward | CCTGCAGGCAGCTGCGCGCTCGCTCGCTCACTGAGGCCGCC CGGGCAAAGCCCGGGCGTCGGGCGACCTTTGGTCGCCCGG CCTCAGTGAGCGAGCGAGCGCGCAGAGAGGGAGTGGCCAA CTCCATCACTAGGGGTTCCT |
| 33 | ITR - reverse | AGGAACCCCTAGTGATGGAGTTGGCCACTCCCTCTCTGCGC GCTCGCTCGCTCACTGAGGCCGGGCGACCAAAGGTCGCCC GACGCCCGGGCTTTGCCCGGGCGGCCTCAGTGAGCGAGCG AGCGCGCAGCTGCCTGCAGG |
| 23 | WPRE | AATCAACCTCTGGATTACAAAATTTGTGAAAGATTGACTGG TATTCTTAACTATGTTGCTCCTTTTACGCTATGTGGATACGC TGCTTTAATGCCTTTGTATCATGCTATTGCTTCCCGTATGGC TTTCATTTTCTCCTCCTTGTATAAATCCGGTTGCTGTCTCTT TATGAGGAGTTGTGGCCCGTTGTCAGGCAACGTGGCGTGGT GTGCACTGTGTTTGCTGACGCAACCCCCACTGGTTGGGGCA TTGCCACCACCTGTCAGCTCCTTTCCGGGACTTTCGCTTTCC CCCTCCCTATTGCCACGGCGGAACTCATCGCCGCCTGCCTT GCCCGCTGCTGGACAGGGGCTCGGCTGTTGGGCACTGACA ATTCCGTGGTGTTGTCGGGGAAATCATCGTCCTTTCCTTGG CTGCTCGCCTGTGTTGCCACCTGGATTCTGCGCGGGACGTC CTTCTGCTACGTCCCTTCGGCCCTCAATCCAGCGGACCTTCC TTCCCGCGGCCTGCTGCCGGCTCTGCGGCCTCTTCCGCGTCT TCGCCTTCGCCCTCAGACGAGTCGGATCTCCCTTTGGGCCG CCTCCCCGC |
| 36 | Full CMV-rtTA3V16 sequence (including ITRs) | CCTGCAGGCAGCTGCGCGCTCGCTCGCTCACTGAGGCCGCC CGGGCAAAGCCCGGGCGTCGGGCGACCTTTGGTCGCCCGG CCTCAGTGAGCGAGCGAGCGCGCAGAGAGGGAGTGGCCAA CTCCATCACTAGGGGTTCCTGCGGCCGCTCGGTCCGCACGA TCTCAATTCGGCCATTACGGCCGGATCCGGCTCGAGGAGCT TGGCCCATTGCATACGTTGTATCCATATCATAATATGTACA TTTATATTGGCTCATGTCCAACATTACCGCCATGTTGACATT GATTATTGACTAGTTATTAATAGTAATCAATTACGGGGTCA TTAGTTCATAGCCCATATATGGAGTTCCGCGTTACATAACT TACGGTAAATGGCCCGCCTGGCTGACCGCCCAACGACCCCC GCCCATTGACGTCAATAATGACGTATGTTCCCATAGTAACG CCAATAGGGACTTTCCATTGACGTCAATGGGTGGAGTATTT ACGCTAAACTGCCCACTTGGCAGTACATCAAGTGTATCATA TGCCAAGTACGCCCCCTATTGACGTCAATGACGGTAAATGG CCCGCCTGGCATTATGCCCAGTACATGACCTTATGGGACTT TCCTACTTGGCAGTACATCTACGTATTAGTCATCGCTATTAC CATGGTGATGCGGTTTTGGCAGTACATCAATGGGCGTGGAT AGCGGTTTGACTCACGGGGATTTCCAAGTCTCCACCCCATT GACGTCAATGGGAGTTTGTTTTGGCACCAAAATCAACGGG |

TABLE 7-continued

AAV2-CMV-rtTA3V16 Vector Sequences

| SEQ ID NO: | Component | Sequence |
|---|---|---|
| | | ACTTTCCAAAATGTCGTAACAACTCCGCCCCATTGACGCAA
ATGGGCGGTAGGCGTGTACGGTGGGAGGTCTATATAAGCA
GAGCTCGTTTAGTGAACCGTCAGATCGCCTGGAGACGCCAT
CCACGCTGTTTTGACCTCCATAGAAGACACCGGGACCGATC
CAGCCTCCGCGGCCCCGAATTCACCATGTCTAGACTGGACA
AGAGCAAAATCATAAACAGCGCTCTGGAATTACTCAATGG
AGTCGGTATCGAAGGCCTGACGACAAGGAAACTCGCTCAA
AAGCTGGGAGTTGAGCAGCCTACCCTGTACTGGCACGTGA
AGAACAAGCGGGCCCTGCTCGATGCCCTGCCAATCGAGAT
GCTGGACAGGCATCATACCCACAGCTGCCCCTGGAAGGC
GAGTCATGGCAAGACTTTCTGCGGAACAACGCCAAGTCAT
ACCGCTGTGCTCTCCTCTCACATCGCGACGGGGCTAAAGTG
CATCTCGGCACCCGCCCAACAGAGAAACAGTACGAAACCC
TGGAAAATCAGCTCGCGTTCCTGTGTCAGCAAGGCTTCTCC
CTGGAGAACGCACTGTACGCTCTGTCCGCCGTGGGCCACTT
TACACTGGGCTGCGTATTGGAGGAACAGGAGCATCAAGTA
GCAAAGAGGAAAGAGAGACACCTACCACCGATTCTATGC
CCCCACTTCTGAAGCAAGCAATTGAGCTGTTCGACCGGCAG
GGAGCCGAACCTGCCTTCCTTTTCGGCCTGGAACTAATCAT
ATGTGGCCTGGAGAAACAGCTAAAGTGCGAAAGCGGCGGG
CCGACCGACGCCCTTGACGATTTTGACTTAGACATGCTCCC
AGCCGATGCCCTTGACGACTTTGACCTTGATATGCTGCCTG
CTGACGCTCTTGACGATTTTGACCTTGACATGCTCCCCGGG
TAACTAAGTAAGGATCATCTTAATTAAATCGATAAGGATCT
GGCCGCCTCGGCCTAATCAACCTCTGGATTACAAAATTTGT
GAAAGATTGACTGGTATTCTTAACTATGTTGCTCCTTTTACG
CTATGTGGATACGCTGCTTTAATGCCTTTGTATCATGCTATT
GCTTCCCGTATGGCTTTCATTTTCTCCTCCTTGTATAAATCC
TGGTTGCTGTCTCTTTATGAGGAGTTGTGGCCCGTTGTCAG
GCAACGTGGCGTGGTGTGCACTGTGTTTGCTGACGCAACCC
CCACTGGTTGGGGCATTGCCACCACCTGTCAGCTCCTTTCC
GGGACTTTCGCTTTCCCCCTCCCTATTGCCACGGCGGAACT
CATCGCCGCCTGCCTTGCCCGCTGCTGGACAGGGGCTCGGC
TGTTGGGCACTGACAATTCCGTGGTGTTGTCGGGGAAATCA
TCGTCCTTTCCTTGGCTGCTCGCCTGTGTTGCCACCTGGATT
CTGCGCGGGACGTCCTTCTGCTACGTCCCTTCGGCCCTCAA
TCCAGCGGACCTTCCTTCCCGCGGCCTGCTGCCGGCTCTGC
GGCCTCTTCCGCGTCTTCGCCTTCGCCCTCAGACGAGTCGG
ATCTCCCTTTGGGCCGCCTCCCCGCCAGACATGATAAGATA
CATTGATGAGTTTGGACAAACCACAACTAGAATGCAGTGA
AAAAAATGCTTTATTTGTGAAATTTGTGATGCTATTGCTTTA
TTTGTAACCATTATAAGCTGCAATAAACAAGTTAACAACAA
CAATTGCATTCATTTTATGTTTCAGGTTCAGGGGGAGATGT
GGGAGGTTTTTTAAAGCAAGTAAAACCTCTACAAATGTGGT
AACTAGCGCGTGCGGCCGCAGGAACCCCTAGTGATGGAGT
TGGCCACTCCCTCTCTGCGCGCTCGCTCGCTCACTGAGGCC
GGGCGACCAAAGGTCGCCCGACGCCCGGGCTTTGCCCGGG
CGGCCTCAGTGAGCGAGCGAGCGCGCAGCTGCCTGCAGG |

TABLE 8

AAV2-CMV-rtTA4 V16 Vector Sequences

| SEQ ID NO: | Component | Sequence |
|---|---|---|
| 24 | CMV promoter | GTGATGCGGTTTTGGCAGTACATCAATGGGCGTGGATAGCGGT
TTGACTCACGGGGATTTCCAAGTCTCCACCCCATTGACGTCAAT
GGGAGTTTGTTTTGGCACCAAAATCAACGGGACTTTCCAAAAT
GTCGTAACAACTCCGCCCCATTGACGCAAATGGGCGGTAGGCG
TGTACGGTGGGAGGTCTATATAAGCAGAGCT |
| 25 | CMV enhancer | GACATTGATTATTGACTAGTTATTAATAGTAATCAATTACGGG
GTCATTAGTTCATAGCCCATATATGGAGTTCCGCGTTACATAAC
TTACGGTAAATGGCCCGCCTGGCTGACCGCCCAACGACCCCCG
CCCATTGACGTCAATAATGACGTATGTTCCCATAGTAACGCCA
ATAGGGACTTTCCATTGACGTCAATGGGTGGAGTATTTACGCT
AAACTGCCCACTTGGCAGTACATCAAGTGTATCATATGCCAAG
TACGCCCCCTATTGACGTCAATGACGGTAAATGGCCCGCCTGG
CATTATGCCCAGTACATGACCTTATGGGACTTTCCTACTTGGCA
GTACATCTACGTATTAGTCATCGCTATTACCATG |

TABLE 8-continued

AAV2-CMV-rtTA4 V16 Vector Sequences

| SEQ ID NO: | Component | Sequence |
|---|---|---|
| 26 | rtTA4 Advanced nucleic acid sequence | ATGTCCCGCTTGGATAAGAGCAAGGTAATAAATAGCGCACTCG AACTCCTCAACGGCGTGGGCATCGAAGGTCTGACTACTCGAAA GCTCGCCCAGAAATTGGGTGTGGAGCAACCTACATTGTATTG CATGTCAAGAACAAAAGAGCCCTGCTGGACGCTCTTCCTATTG AAATGCTTGACAGGCATCACACTCATTCCTGCCCCCTTGAGGT CGAGAGTTGGCAAGATTTTCTCCGAAACAATGCAAAGTCCTAC CGCTGCGCACTTTTGTCCCATAGGGATGGAGCAAAAGTGCACC TGGGAACCAGGCCAACAGAGAAACAATACGAGACTCTCGAGA ACCAGTTGGCTTTCTTGTGCCAACAGGGGTTCTCACTTGAAAAT GCCCTTTACGCACTGTCAGCCGTTGGACATTTTACCCTGGGGTG CGTTCTTGAGGAGCAAGAACATCAGGTTGCTAAGGAGGAGCG CGAGACTCCAACCACTGATTCTATGCCACCTTTGCTGAAACAG GCCATTGAACTTTTCGATAGACAGGGTGCTGAACCTGCCTTTCT CTTCGGGTTGGAGCTGATTATTTGTGGTCTCGAAAAACAGCTG AAATGTGAAAGTGGTGGCCCTACTGACGCCCTCGATGATTTCG ACCTGGATATGCTGCCAGCCGATGCACTTGATGATTTCGATTTG GATATGCTTCCAGCCGACGCACTGGACGACTTCGATTTGGACA TGCTTCCCGGTTAA |
| 27 | rtTA4 Advanced amino acid sequence | MSRLDKSKVINSALELLNGVGIEGLTTRKLAQKLGVEQPTLYWH VKNKRALLDALPIEMLDRHHTHSCPLEVESWQDFLRNNAKSYRC ALLSHRDGAKVHLGTRPTEKQYETLENQLAFLCQQGFSLENALY ALSAVGHFTLGCVLEEQEHQVAKEERETPTTDSMPPLLKQAIELF DRQGAEPAFLFGLELIICGLEKQLKCESGGPTDALDDFDLDMLPA DALDDFDLDMLPADALDDFDLDMLPG |
| 28 | AAV2-CMV-rtTA4V16 | TCGCGCGTTTCGGTGATGACGGTGAAAACCTCTGACACATGCA GCTCCCGGAGACTGTCACAGCTTGTCTGTAAGCGGATGCCGGG AGCAGACAAGCCCGTCAGGGCGCGTCAGCGGGTGTTGGCGGG TGTGCGGGGCTGGCTTAACTATGCGGCATCAGAGCAGATTGTAC TGAGAGTGCACCATATGCGGTGTGAAATACCGCACAGATGCGT AAGGAGAAAATACCGCATCAGGCGCCATTCGCCATTCAGGCTG CGCAACTGTTGGGAAGGGCGATCGGTGCGGGCCTCTTCGCTAT TACGCCAGCTGGCGAAAGGGGGATGTGCTGCAAGGCGATTAA GTTGGGTAACGCCAGGGTTTTCCCAGTCACGACGTTGTAAAAC GACGGCCAGTGAATTGACGCGTATTGGGATACTATGGTTGCTT TGACGTATGCGGTGTGAAATACCGCACAGATGCGTAAGGAGA AAATACCGCATCAGGCGCCCCTGCAGGCAGCTGCGCGCTCGCT CGCTCACTGAGGCCGCCCGGGCAAAGCCCGGGCGTCGGGCGA CCTTTGGTCGCCCGGCCTCAGTGAGCGAGCGAGCGCGCAGAGA GGGAGTGGCCAACTCCATCACTAGGGGTTCCTGCGGCCGCTCG GTCCGCACGATCTCAATTCGGCCATTACGCCGGATCCGGCTC GAGGAGCTTGGCCCATTGCATACGTTGTATCCATATCATAATA TGTACATTTATATTGGCTCATGTCCAACATTACCGCCATGTTGA CATTGATTATTGACTAGTTATTAATAGTAATCAATTACGGGGTC ATTAGTTCATAGCCCATATATGGAGTTCCGCGTTACATAACTTA CGGTAAATGGCCCGCCTGGCTGACCGCCCAACGACCCCCGCCC ATTGACGTCAATAATGACGTATGTTCCCATAGTAACGCCAATA GGGACTTTCCATTGACGTCAATGGGTGGAGTATTTACGCTAAA CTGCCCACTTGGCAGTACATCAAGTGTATCATATGCCAAGTAC GCCCCCTATTGACGTCAATGACGGTAAATGGCCCGCCTGGCAT TATGCCCAGTACATGACCTTATGGGACTTTCCTACTTGGCAGTA CATCTACGTATTAGTCATCGCTATTACCATGGTGATGCGGTTTT GGCAGTACATCAATGGGCGTGGATAGCGGTTTGACTCACGGGG ATTTCCAAGTCTCCACCCCATTGACGTCAATGGGAGTTTGTTTT GGCACCAAAATCAACGGGACTTTCCAAAATGTCGTAACAACTC CGCCCCATTGACGCAAATGGGCGGTAGGCGTGTACGGTGGGA GGTCTATATAAGCAGAGCTCGTTTAGTGAACCGTCAGATCGCC TGGAGACGCCATCCACGCTGTTTTGACCTCCATAGAAGACACC GGGACCGATCCAGCCTCCGCGGCCCCGAATTCACCATGTCCCG CTTGGATAAGAGCAAGGTAATAAATAGCGCACTCGAACTCCTC AACGGCGTGGGCATCGAAGGTCTGACTACTCGAAAGCTCGCCC AGAAATTGGGTGTGGAGCAACCTACATTGTATTGGCATGTCAA GAACAAAAGAGCCCTGCTGGACGCTCTTCCTATTGAAATGCTT GACAGGCATCACACTCATTCCTGCCCCCTTGAGGTCGAGAGTT GGCAAGATTTTCTCCGAAACAATGCAAAGTCCTACCGCTGCGC ACTTTTGTCCCATAGGGATGGAGCAAAAGTGCACCTGGGAACC AGGCCAACAGAGAAACAATACGAGACTCTCGAGAACCAGTTG GCTTTCTTGTGCCAACAGGGGTTCTCACTTGAAAATGCCCTTTA CGCACTGTCAGCCGTTGGACATTTTACCCTGGGGTGCGTTCTTG AGGAGCAAGAACATCAGGTTGCTAAGGAGGAGCGCGAGACTC CAACCACTGATTCTATGCCACCTTTGCTGAAACAGGCCATTGA ACTTTTCGATAGACAGGGTGCTGAACCTGCCTTTCTCTTCGGGT TGGAGCTGATTATTTGTGGTCTCGAAAAACAGCTGAAATGTGA AAGTGGTGGCCCTACTGACGCCCTCGATGATTTCGACCTGGAT |

TABLE 8-continued

AAV2-CMV-rtTA4 V16 Vector Sequences

| SEQ ID NO: | Component | Sequence |
|---|---|---|
| | | ATGCTGCCAGCCGATGCACTTGATGATTTCGATTTGGATATGCT
TCCAGCCGACGCACTGGACGACTTCGATTTGGACATGCTTCCC
GGTTAACTAAGTAAGGATCATCTTAATTAAATCGATAAGGATC
TGGCCGCCTCGGCCTAATCAACCTCTGGATTACAAAATTTGTG
AAAGATTGACTGGTATTCTTAACTATGTTGCTCCTTTTACGCTA
TGTGGATACGCTGCTTTAATGCCTTTGTATCATGCTATTGCTTC
CCGTATGGCTTTCATTTTCTCCTCCTTGTATAAATCCTGGTTGCT
GTCTCTTTATGAGGAGTTGTGGCCCGTTGTCAGGCAACGTGGC
GTGGTGTGCACTGTGTTTGCTGACGCAACCCCCACTGGTTGGG
GCATTGCCACCACCTGTCAGCTCCTTTCCGGGACTTTCGCTTTC
CCCCTCCCTATTGCCACGGCGGAACTCATCGCCGCCTGCCTTGC
CCGCTGCTGGACAGGGGCTCGGCTGTTGGGCACTGACAATTCC
GTGGTGTTGTCGGGGAAATCATCGTCCTTTCCTTGGCTGCTCGC
CTGTGTTGCCACCTGGATTCTGCGCGGGACGTCCTTCTGCTACG
TCCCTTCGGCCCTCAATCCAGCGGACCTTCCTTCCCGCGGCCTG
CTGCCGGCTCTGCGGCCTCTTCCGCGTCTTCGCCTTCGCCCTCA
GACGAGTCGGATCTCCCTTTGGGCCGCCTCCCCGCCAGACATG
ATAAGATACATTGATGAGTTTGGACAAACCACAACTAGAATGC
AGTGAAAAAAATGCTTTATTTGTGAAATTTGTGATGCTATTGCT
TTATTTGTAACCATTATAAGCTGCAATAAACAAGTTAACAACA
ACAATTGCATTCATTTTATGTTTCAGGTTCAGGGGGAGATGTG
GGAGGTTTTTTAAAGCAAGTAAAACCTCTACAAATGTGGTAAC
TAGCGCGTGCGGCCGCAGGAACCCCTAGTGATGGAGTTGGCCA
CTCCCTCTCTGCGCGCTCGCTCGCTCACTGAGGCCGGGCGACC
AAAGGTCGCCCGACGCCCGGGCTTTGCCCGGGCGGCCTCAGTG
AGCGAGCGAGCGCGCAGCTGCCTGCAGGATCCCAATGGCGCG
CCGAGCTTGGCTCGAGCATGGTCATAGCTGTTTCCTGTGTGAA
ATTGTTATCCGCTCACAATTCCACACAACATACGAGCCGGAAG
CATAAAGTGTAAAGCCTGGGGTGCCTAATGAGTGAGCTAACTC
ACATTAATTGCGTTGCGCTCACTGCCCGCTTTCCAGTCGGGAA
ACCTGTCGTGCCAGCTGCATTAATGAATCGGCCAACGCGCGGG
GAGAGGCGGTTTGCGTATTGGGCGCTGTTCCGCTTCCTCGCTCA
CTGACTCGCTGCGCTCGGTCGTTCGGCTGCGGCGAGCGGTATC
AGCTCACTCAAAGGCGGTAATACGGTTATCCACAGAATCAGGG
GATAACGCAGGAAAGAACATGTGAGCAAAAGGCCAGCAAAAG
GCCAGGAACCGTAAAAAGGCCGCGTTGCTGGCGTTTTTCCATA
GGCTCCGCCCCCCTGACGAGCATCACAAAAATCGACGCTCAAG
TCAGAGGTGGCGAAACCCGACAGGACTATAAAGATACCAGGC
GTTTCCCCCTGGAAGCTCCCTCGTGCGCTCTCCTGTTCCGACCC
TGCCGCTTACCGGATACCTGTCCGCCTTTCTCCCTTCGGGAAGC
GTGGCGCTTTCTCATAGCTCACGCTGTAGGTATCTCAGTTCGGT
GTAGGTCGTTCGCTCCAAGCTGGGCTGTGTGCACGAACCCCCC
GTTCAGCCCGACCGCTGCGCCTTATCCGGTAACTATCGTCTTGA
GTCCAACCCGGTAAGACACGACTTATCGCCACTGGCAGCAGCC
ACTGGTAACAGGATTAGCAGAGCGAGGTATGTAGGCGGTGCT
ACAGAGTTCTTGAAGTGGTGGCCTAACTACGGCTACACTAGAA
GAACAGTATTTGGTATCTGCGCTCTGCTGAAGCCAGTTACCTTC
GGAAAAAGAGTTGGTAGCTCTTGATCCGGCAAACAAACCACC
GCTGGTAGCGGTGGTTTTTTTGTTTGCAAGCAGCAGATTACGC
GCAGAAAAAAAGGATCTCAAGAAGATCCTTTGATCTTTTCTAC
GGGGTCTGACGCTCAGTGGAACGAAAACTCACGTTAAGGGATT
TTGGTCATGAGATTATCAAAAAGGATCTTCACCTAGATCCTTTT
AAATTAAAAATGAAGTTTTAAATCAATCTAAAGTATATATGAG
TAAACTTGGTCTGACAGTTAGAAAAACTCATCGAGCATCAAAT
GAAACTGCAATTTATTCATATCAGGATTATCAATACCATATTTT
TGAAAAAGCCGTTTCTGTAATGAAGGAGAAAACTCACCGAGG
CAGTTCCATAGGATGGCAAGATCCTGGTATCGGTCTGCGATTC
CGACTCGTCCAACATCAATACAACCTATTAATTTCCCCTCGTCA
AAAATAAGGTTATCAAGTGAGAAATCACCATGAGTGACGACT
GAATCCGGTGAGAATGGCAAAAGTTTATGCATTTCTTTCCAGA
CTTGTTCAACAGGCCAGCCATTACGCTCGTCATCAAAATCACT
CGCATCAACCAAACCGTTATTCATTCGTGATTGCGCCTGAGCG
AAACGAAATACGCGATCGCTGTTAAAAGGACAATTACAAACA
GGAATCGAATGCAACCGGCGCAGGAACACTGCCAGCGCATCA
ACAATATTTTCACCTGAATCAGGATATTCTTCTAATACCTGGAA
TGCTGTTTTCCCAGGGATCGCAGTGGTGAGTAACCATGCATCA
TCAGGAGTACGGATAAAATGCTTGATGGTCGGAAGAGGCATA
AATTCCGTCAGCCAGTTTAGTCTGACCATCTCATCTGTAACATC
ATTGGCAACGCTACCTTTGCCATGTTTCAGAAACAACTCTGGC
GCATCGGGCTTCCCATACAATCGATAGATTGTCGCACCTGATT
GCCCGACATTATCGCGAGCCCATTTATACCCATATAAATCAGC
ATCCATGTTGGAATTTAATCGCGGCCTAGAGCAAGACGTTTCC
CGTTGAATATGGCTCATACTCTTCCTTTTTCAATATTATTGAAG
CATTTATCAGGGTTATTGTCTCATGAGCGGATACATATTTGAAT
GTATTTAGAAAAATAAACAAATAGGGGTTCCGCGCACATTTCC |

TABLE 8-continued

AAV2-CMV-rtTA4 V16 Vector Sequences

| SEQ ID NO: | Component | Sequence |
|---|---|---|
|  |  | CCGAAAAGTGCCACCTGACGTCTAAGAAACCATTATTATCATG<br>ACATTAACCTATAAAAATAGGCGTATCACGAGGCCCTTTTGTC |
| 29 | ITR - forward | CCTGCAGGCAGCTGCGCGCTCGCTCGCTCACTGAGGCCGCCCG<br>GGCAAAGCCCGGGCGTCGGGCGACCTTTGGTCGCCCGGCCTCA<br>GTGAGCGAGCGAGCGCGCAGAGAGGGAGTGGCCAACTCCATC<br>ACTAGGGGTTCCT |
| 34 | ITR-reverse | AGGAACCCCTAGTGATGGAGTTGGCCACTCCCTCTCTGCGCGC<br>TCGCTCGCTCACTGAGGCCGGGCGACCAAAGGTCGCCCGACGC<br>CCGGGCTTTGCCCGGGCGGCCTCAGTGAGCGAGCGAGCGCGCA<br>GCTGCCTGCAGG |
| 30 | SV40p | TAAGATACATTGATGAGTTTGGACAAACCACAACTAGAATGCA<br>GTGAAAAAAATGCTTTATTTGTGAAATTTGTGATGCTATTGCTT<br>TATTTGTAACCATTATAAGCTGCAATAAACAAGTT |
| 31 | WPRE | AATCAACCTCTGGATTACAAAATTTGTGAAAGATTGACTGGTA<br>TTCTTAACTATGTTGCTCCTTTTACGCTATGTGGATACGCTGCT<br>TTAATGCCTTTGTATCATGCTATTGCTTCCCGTATGGCTTTCATT<br>TTCTCCTCCTTGTATAAATCCTGGTTGCTGTCTCTTTATGAGGA<br>GTTGTGGCCCGTTGTCAGGCAACGTGGCGTGGTGTGCACTGTG<br>TTTGCTGACGCAACCCCCACTGGTTGGGGCATTGCCACCACCT<br>GTCAGCTCCTTTCCGGGACTTTCGCTTTCCCCCTCCCTATTGCC<br>ACGGCGGAACTCATCGCCGCCTGCCTTGCCCGCTGCTGGACAG<br>GGGCTCGGCTGTTGGGCACTGACAATTCCGTGGTGTTGTCGGG<br>GAAATCATCGTCCTTTCCTTGGCTGCTCGCCTGTGTTGCCACCT<br>GGATTCTGCGCGGGACGTCCTTCTGCTACGTCCCTTCGGCCCTC<br>AATCCAGCGGACCTTCCTTCCCGCGGCCTGCTGCCGGCTCTGC<br>GGCCTCTTCCGCGTCTTCGCCTTCGCCCTCAGACGAGTCGGATC<br>TCCCTTTGGGCCGCCTCCCCGC |
| 37 | Full CMV-rtTA4V16 sequence (including ITRs) | CCTGCAGGCAGCTGCGCGCTCGCTCGCTCACTGAGGCCGCCCG<br>GGCAAAGCCCGGGCGTCGGGCGACCTTTGGTCGCCCGGCCTCA<br>GTGAGCGAGCGAGCGCGCAGAGAGGGAGTGGCCAACTCCATC<br>ACTAGGGGTTCCTGCGGCCGCTCGGTCCGCACGATCTCAATTC<br>GGCCATTACGGCCGGATCCGGCTCGAGGAGCTTGGCCCATTGC<br>ATACGTTGTATCCATATCATAATATGTACATTTATATTGGCTCA<br>TGTCCAACATTACCGCCATGTTGACATTGATTATTGACTAGTTA<br>TTAATAGTAATCAATTACGGGGTCATTAGTTCATAGCCCATAT<br>ATGGAGTTCCGCGTTACATAACTTACGGTAAATGGCCCGCCTG<br>GCTGACCGCCCAACGACCCCCGCCCATTGACGTCAATAATGAC<br>GTATGTTCCCATAGTAACGCCAATAGGGACTTTCCATTGACGT<br>CAATGGGTGGAGTATTTACGCTAAACTGCCCACTTGGCAGTAC<br>ATCAAGTGTATCATATGCCAAGTACGCCCCCTATTGACGTCAA<br>TGACGGTAAATGGCCCGCCTGGCATTATGCCCAGTACATGACC<br>TTATGGGACTTTCCTACTTGGCAGTACATCTACGTATTAGTCAT<br>CGCTATTACCATGGTGATGCGGTTTTGGCAGTACATCAATGGG<br>CGTGGATAGCGGTTTGACTCACGGGGATTTCCAAGTCTCCACC<br>CCATTGACGTCAATGGGAGTTTGTTTTGGCACCAAAATCAACG<br>GGACTTTCCAAAATGTCGTAACAACTCCGCCCCATTGACGCAA<br>ATGGGCGGTAGGCGTGTACGGTGGGAGGTCTATATAAGCAGA<br>GCTCGTTTAGTGAACCGTCAGATCGCCTGGAGACGCCATCCAC<br>GCTGTTTTGACCTCCATAGAAGACACCGGGACCGATCCAGCCT<br>CCGCGGCCCCGAATTCACCATGTCCCGCTTGGATAAGAGCAAG<br>GTAATAAATAGCGCACTCGAACTCCTCAACGGCGTGGGCATCG<br>AAGGTCTGACTACTCGAAAGCTCGCCCAGAAATTGGGTGTGGA<br>GCAACCTACATTGTATTGGCATGTCAAGAACAAAAGAGCCCTG<br>CTGGACGCTCTTCCTATTGAAATGCTTGACAGGCATCACACTC<br>ATTCCTGCCCCCTTGAGGTCGAGAGTTGGCAAGATTTTCTCCGA<br>AACAATGCAAAGTCCTACCGCTGCGCACTTTTGTCCCATAGGG<br>ATGGAGCAAAAGTGCACCTGGGAACCAGGCCAACAGAGAAAC<br>AATACGAGACTCTCGAGAACCAGTTGGCTTTCTTGTGCCAACA<br>GGGGTTCTCACTTGAAAATGCCCTTTACGCACTGTCAGCCGTTG<br>GACATTTTACCCTGGGGTGCGTTCTTGAGGAGCAAGAACATCA<br>GGTTGCTAAGGAGGAGCGCGAGACTTCCAACCACTGATTCTATG<br>CCACCTTTGCTGAAACAGGCCATTGAACTTTTCGATAGACAGG<br>GTGCTGAACCTGCCTTTCTCTTCGGGTTGGAGCTGATTATTTGT<br>GGTCTCGAAAACAGCTGAAATGTGAAAGTGGTGGCCCTACTG<br>ACGCCCTCGATGATTTCGACCTGGATATGCTGCCAGCCGATGC<br>ACTTGATGATTTCGATTTGGATATGCTTCCAGCCGACGCACTGG<br>ACGACTTCGATTTGGACATGCTTCCCGGTTAACTAAGTAAGGA<br>TCATCTTAATTAAATCGATAAGGATCTGGCCGCCTCGGCCTAA<br>TCAACCTCTGGATTACAAAATTTGTGAAAGATTGACTGGTATT<br>CTTAACTATGTTGCTCCTTTTACGCTATGTGGATACGCTGCTTT |

TABLE 8-continued

AAV2-CMV-rtTA4 V16 Vector Sequences

| SEQ ID NO: | Component | Sequence |
|---|---|---|
| | | AATGCCTTTGTATCATGCTATTGCTTCCCGTATGGCTTTCATTTT<br>CTCCTCCTTGTATAAATCCTGGTTGCTGTCTCTTTATGAGGAGT<br>TGTGGCCCGTTGTCAGGCAACGTGGCGTGGTGTGCACTGTGTT<br>TGCTGACGCAACCCCCACTGGTTGGGGCATTGCCACCACCTGT<br>CAGCTCCTTTCCGGGACTTTCGCTTTCCCCCTCCCTATTGCCAC<br>GGCGGAACTCATCGCCGCCTGCCTTGCCCGCTGCTGGACAGGG<br>GCTCGGCTGTTGGGCACTGACAATTCCGTGGTGTTGTCGGGGA<br>AATCATCGTCCTTTCCTTGGCTGCTCGCCTGTGTTGCCACCTGG<br>ATTCTGCGCGGGACGTCCTTCTGCTACGTCCCTTCGGCCCTCAA<br>TCCAGCGGACCTTCCTTCCCGCGGCCTGCTGCCGGCTCTGCGGC<br>CTCTTCCGCGTCTTCGCCTTCGCCCTCAGACGAGTCGGATCTCC<br>CTTTGGGCCGCCTCCCCGCCAGACATGATAAGATACATTGATG<br>AGTTTGGACAAACCACAACTAGAATGCAGTGAAAAAAATGCTT<br>TATTTGTGAAATTTGTGATGCTATTGCTTTATTTGTAACCATTA<br>TAAGCTGCAATAAACAAGTTAACAACAACAATTGCATTCATTT<br>TATGTTTCAGGTTCAGGGGGAGATGTGGGAGGTTTTTTAAAGC<br>AAGTAAAACCTCTACAAATGTGGTAACTAGCGCGTGCGGCCGC<br>AGGAACCCCTAGTGATGGAGTTGGCCACTCCCTCTCTGCGCGC<br>TCGCTCGCTCACTGAGGCCGGGCGACCAAAGGTCGCCCGACGC<br>CCGGGCTTTGCCCGGGCGGCCTCAGTGAGCGAGCGAGCGCGCA<br>GCTGCCTGCAGGATCCCAATGGCGCGCCGAGCTTGGCTCGAGC<br>ATGGTCATAGCTGTTTCCTGTGTGAAATTGTTATCCGCTCACAA<br>TTCCACACAACATACGAGCCGGAAGCATAAAGTGTAAAGCCTG<br>GGGTGCCTAATGAGTGAGCTAACTCACATTAATTGCGTTGCGC<br>TCACTGCCCGCTTTCCAGTCGGGAAACCTGTCGTGCCAGCTGC<br>ATTAATGAATCGGCCAACGCGCGGGGAGAGGCGGTTTGCGTAT<br>TGGGCGCTGTTCCGCTTCCTCGCTCACTGACTCGCTGCGCTCGG<br>TCGTTCGGCTGCGGCGAGCGGTATCAGCTCACTCAAAGGCGGT<br>AATACGGTTATCCACAGAATCAGGGGATAACGCAGGAAAGAA<br>CATGTGAGCAAAAGGCCAGCAAAAGGCCAGGAACCGTAAAAA<br>GGCCGCGTTGCTGGCGTTTTTCCATAGGCTCCGCCCCCCTGACG<br>AGCATCACAAAAATCGACGCTCAAGTCAGAGGTGGCGAAACC<br>CGACAGGACTATAAAGATACCAGGCGTTTCCCCCTGGAAGCTC<br>CCTCGTGCGCTCTCCTGTTCCGACCCTGCCGCTTACCGGATACC<br>TGTCCGCCTTTCTCCCTTCGGGAAGCGTGGCGCTTTCTCATAGC<br>TCACGCTGTAGGTATCTCAGTTCGGTGTAGGTCGTTCGCTCCAA<br>GCTGGGCTGTGTGCACGAACCCCCCGTTCAGCCCGACCGCTGC<br>GCCTTATCCGGTAACTATCGTCTTGAGTCCAACCCGGTAAGAC<br>ACGACTTATCGCCACTGGCAGCAGCCACTGGTAACAGGATTAG<br>CAGAGCGAGGTATGTAGGCGGTGCTACAGAGTTCTTGAAGTGG<br>TGGCCTAACTACGGCTACACTAGAAGAACAGTATTTGGTATCT<br>GCGCTCTGCTGAAGCCAGTTACCTTCGGAAAAAGAGTTGGTAG<br>CTCTTGATCCGGCAAACAAACCACCGCTGGTAGCGGTGGTTTT<br>TTTGTTTGCAAGCAGCAGATTACGCGCAGAAAAAAAGGATCTC<br>AAGAAGATCCTTTGATCTTTTCTACGGGGTCTGACGCTCAGTG<br>GAACGAAAACTCACGTTAAGGGATTTTGGTCATGAGATTATCA<br>AAAAGGATCTTCACCTAGATCCTTTTAAATTAAAAATGAAGTT<br>TTAAATCAATCTAAAGTATATATGAGTAAACTTGGTCTGACAG<br>TTAGAAAAACTCATCGAGCATCAAATGAAACTGCAATTTATTC<br>ATATCAGGATTATCAATACCATATTTTTGAAAAAGCCGTTCTG<br>TAATGAAGGAGAAAACTCACCGAGGCAGTTCCATAGGATGGC<br>AAGATCCTGGTATCGGTCTGCGATTCCGACTCGTCCAACATCA<br>ATACAACCTATTAATTTCCCCTCGTCAAAAATAAGGTTATCAA<br>GTGAGAAATCACCATGAGTGACGACTGAATCCGGTGAGAATG<br>GCAAAAGTTTATGCATTTCTTTCCAGACTTGTTCAACAGGCCAG<br>CCATTACGCTCGTCATCAAAATCACTCGCATCAACCAAACCGT<br>TATTCATTCGTGATTGCGCCTGAGCGAAACGAAATACGCGATC<br>GCTGTTAAAAGGACAATTACAAACAGGAATCGAATGCAACCG<br>GCGCAGGAACACTGCCAGCGCATCAACAATATTTTCACCTGAA<br>TCAGGATATTCTTCTAATACCTGGAATGCTGTTTTCCCAGGGAT<br>CGCAGTGGTGAGTAACCATGCATCATCAGGAGTACGGATAAA<br>ATGCTTGATGGTCGGAAGAGGCATAAATTCCGTCAGCCAGTTT<br>AGTCTGACCATCTCATCTGTAACATCATTGGCAACGCTACCTTT<br>GCCATGTTTCAGAAACAACTCTGGCGCATCGGGCTTCCCATAC<br>AATCGATAGATTGTCGCACCTGATTGCCCGACATTATCGCGAG<br>CCCATTTATACCCATATAAATCAGCATCCATGTTGGAATTTAAT<br>CGCGGCCTAGAGCAAGACGTTTCCCGTTGAATATGGCTCATAC<br>TCTTCCTTTTTCAATATTATTGAAGCATTTATCAGGGTTATTGTC<br>TCATGAGCGGATACATATTTGAATGTATTTAGAAAAATAAACA<br>AATAGGGGTTCCGCGCACATTTCCCCGAAAAGTGCCACCTGAC<br>GTCTAAGAAACCATTATTATCATGACATTAACCTATAAAAATA<br>GGCGTATCACGAGGCCCTTTTGTC |

What is claimed:

1. A method for treating non-arteritic anterior ischemic optic neuropathy (NAION) in a subject in need thereof, the method comprising intravitreally administering, to one or both eyes of a subject treated with a tetracycline-class antibiotic before, during and/or after the administering step, pharmaceutically effective amounts of:
   a first adeno-associated virus (AAV) expression vector comprising a first polynucleotide encoding octamer-binding transcription factor 4 (OCT4), sex determining region Y box 2 (SOX2), and Kruppel-like factor 4 (KLF4), but not Myc proto-oncogene (c-Myc), operatively linked to a tetracycline response element (TRE) promoter and flanked by inverted terminal repeats (ITRs), and
   a second adeno-associated virus (AAV) expression vector comprising a second polynucleotide encoding a reverse tetracycline transactivator, operatively linked to a promoter and flanked by inverted terminal repeats (ITRs) wherein the method increases the number of healthy axons, enhances axon survival compared to vehicle treatment, improves retinal ganglion cell (RGC) function, or a combination thereof.

2. The method of claim 1, wherein the method does not reprogram a cell, tissue, or organ to a pluripotent state in the subject.

3. The method of claim 1, comprising administering to the subject the tetracycline-class antibiotic before the adeno-associated virus (AAV) expression vectors.

4. The method of claim 3, comprising administering to the subject the tetracycline-class antibiotic after the adeno-associated virus (AAV) expression vectors.

5. The method of claim 1, wherein the tetracycline-class antibiotic is doxycycline.

6. The method of claim 1, wherein the first polynucleotide encodes a self-cleaving peptide between the OCT4, the SOX2, and/or the KLF4.

7. The method of claim 6, wherein the self-cleaving peptide is a 2A peptide.

8. The method of claim 1, wherein the AAV expression vectors are serotype-2 (AAV2).

9. The method of claim 1, wherein the first polynucleotide comprises nucleic acid elements in the following order:
   a. a first inverted terminal repeat sequence (ITR) sequence;
   b. a Tet-On 3G (TRE3G) promoter sequence;
   c. an OCT4 sequence;
   d. a P2A cleavage sequence;
   e. a SOX2 sequence;
   f. a T2A cleavage sequence;
   g. a KLF4 sequence;
   h. an SV-40-derived terminator sequence; and
   i. a second inverted terminal repeat (ITR) sequence.

10. The method of claim 1, wherein
    i) OCT4 comprises an amino acid sequence having at least 90% identity to SEQ ID NO: 2;
    ii) SOX2 comprises an amino acid sequence having at least 90% identity to SEQ ID NO: 4; and/or
    iii) KLF4 comprises an amino acid sequence having at least 90% identity to SEQ ID NO: 6.

11. The method of claim 1, wherein
    i) the polynucleotide comprises a nucleic acid sequence having at least 90% identity to SEQ ID NO: 1;
    ii) the polynucleotide comprises a nucleic acid sequence having at least 90% identity to SEQ ID NO: 3; and/or
    iii) the polynucleotide comprises a nucleic acid sequence having at least 90% identity to SEQ ID NO: 5.

12. The method of claim 1, wherein the method improves retinal ganglion cell (RGC) function.

13. The method of claim 12, wherein the RGC function is measured by electroretinogram (pERG).

14. The method of claim 1, wherein
    i) OCT4 comprises an amino acid sequence having at least 95% identity to SEQ ID NO: 2;
    ii) SOX2 comprises an amino acid sequence having at least 95% identity to SEQ ID NO: 4; and/or
    iii) KLF4 comprises an amino acid sequence having at least 95% identity to SEQ ID NO: 6.

15. The method of claim 1, wherein
    i) OCT4 comprises the amino acid sequence of SEQ ID NO: 2;
    ii) SOX2 comprises the amino acid sequence of SEQ ID NO: 4; and/or
    iii) KLF4 comprises the amino acid sequence of SEQ ID NO: 6.

16. The method of claim 1, wherein the method restores visual function in the subject.

17. A method for treating non-arteritic anterior ischemic optic neuropathy (NAION) in a subject in need thereof, the method comprising intravitreally administering, to one or both eyes of a subject treated with a doxycycline before, during and/or after the administering step, pharmaceutically effective amounts of:
    a first adeno-associated virus of serotype 2 (AAV2) expression vector comprising a first polynucleotide encoding only three transcription factors, operatively linked to a tetracycline response element (TRE) promoter and flanked by inverted terminal repeats (ITRs); and
    a second adeno-associated virus of serotype 2 (AAV2) expression vector comprising a second polynucleotide encoding only a reverse tetracycline transactivator, operatively linked to a promoter and flanked by inverted terminal repeats (ITRs),
    wherein the only three transcription factors are octamer-binding transcription factor 4 (OCT4), sex determining region Y-box 2 (SOX2), and Kruppel-like factor 4 (KLF4) wherein the method increases the number of healthy axons, enhances axon survival compared to vehicle treatment, improves retinal ganglion cell (RGC) function, or a combination thereof.

18. The method of claim 17, wherein the method does not reprogram a cell, tissue, or organ to a pluripotent state in the subject.

19. The method of claim 17, wherein the method does not induce c-Myc expression in the subject.

20. The method of claim 17, comprising administering to the subject the doxycycline before the adeno-associated virus (AAV) expression.

21. The method of claim 17, comprising administering to the subject the doxycycline after the adeno-associated virus (AAV) expression vectors.

22. The method of claim 17, comprising administering to the subject the doxycycline before and after the adeno-associated virus (AAV) expression vectors.

23. The method of claim 17, wherein the first polynucleotide encodes OCT4, the SOX2, and the KLF4 linked by two self-cleaving peptides.

24. The method of claim 23, wherein the two self-cleaving peptides are each a 2A peptide.

25. The method of claim 17, wherein the first polynucleotide comprises nucleic acid elements in the following order:

a. a first inverted terminal repeat sequence (ITR) sequence;
b. a Tet-On 3G (TRE3G) promoter sequence;
c. an OCT4 sequence;
d. a P2A cleavage sequence;
e. a SOX2 sequence;
f. a T2A cleavage sequence;
g. a KLF4 sequence;
h. an SV-40-derived terminator sequence; and
i. a second inverted terminal repeat (ITR) sequence.

26. The method of claim 25, wherein
i) OCT4 comprises an amino acid sequence having at least 90% identity to SEQ ID NO: 2;
ii) SOX2 comprises an amino acid sequence having at least 90% identity to SEQ ID NO: 4; and
iii) KLF4 comprises an amino acid sequence having at least 90% identity to SEQ ID NO: 6.

27. The method of claim 25, wherein
i) OCT4 comprises an amino acid sequence having at least 95% identity to SEQ ID NO: 2;
ii) SOX2 comprises an amino acid sequence having at least 95% identity to SEQ ID NO: 4; and/or
iii) KLF4 comprises an amino acid sequence having at least 95% identity to SEQ ID NO: 6.

28. A method for treating non-arteritic anterior ischemic optic neuropathy (NAION) in a subject in need thereof, the method comprising intravitreally administering, to one or both eyes of a subject treated with a doxycycline before, during and/or after the administering step, pharmaceutically effective amounts of:
a first adeno-associated virus of serotype 2 (AAV2) expression vector comprising a first polynucleotide encoding only three transcription factors, operatively linked to a Tet-On 3G (TRE3G) promoter, and flanked by inverted terminal repeats (ITRs); and
a second adeno-associated virus of serotype 2 (AAV2) expression vector comprising a second polynucleotide encoding only a reverse tetracycline-controlled transactivator 3 (rtTA3), operatively limited to a cytomegalovirus immediate early promoter (CMV promoter), and flanked by inverted terminal repeats (ITRs),
wherein the only three transcription factors are octamer-binding transcription factor 4 (OCT4), sex determining region Y-box 2 (SOX2), and Kruppel-like factor 4 (KLF4) wherein the method increases the number of healthy axons, enhances axon survival compared to vehicle treatment, improves retinal ganglion cell (RGC) function, or a combination thereof.

29. The method of claim 28, wherein the method improves retinal ganglion cell (RGC) function.

30. The method of claim 29, wherein the RGC function is measured by electroretinogram (pERG).

* * * * *

SEQUENCE LISTING

```
Sequence total quantity: 37
SEQ ID NO: 1              moltype = DNA   length = 1080
FEATURE                   Location/Qualifiers
source                    1..1080
                          mol_type = other DNA
                          organism = Homo sapiens
SEQUENCE: 1
atggcgggac acctggcttc ggatttcgcc ttctcgcccc ctccaggtgg tggaggtgat    60
gggccagggg ggccggagcc gggctggGtt gatcctcgga cctggctaag cttccaaggc   120
cctcctggag ggcaggaat cgggccgggg gttgggccag gctctgaggt gtggggatt    180
ccccatgcc ccccgccgta tgagttctgt gggggatgg cgtactgtgg gccccaggtt    240
ggagtggggc tagtgcccca aggcggcttg gagacctctc agcctgaggg cgaagcagga   300
gtcggggtgg agagcaactc cgatggggcc tccccggagc cctgcaccgt caccccTggt   360
gccgtgaagc tggagaagga gaagctggag caaaacccgg aggagtccca ggacatcaaa   420
gctctgcaga aagaactcga gcaatttgcc aagctcctga agcagaagag gatcacccTg   480
ggatatacac aggccgatgt ggggctcacc ctgggggttc tatttgggaa ggtattcagc   540
caaacgacca tctgccgctt tgaggctctg cagcttagct tcaagaacat gtgtaagctg   600
cggcccttgc tgcagaagtg ggtggaggaa gctgacaaca atgaaaatct tcaggagata   660
tgcaaagcag aaaccctcgt gcaggcccga aagagaaagc gaaccagtat cgagaaccga   720
gtgagaggca acctggagaa tttgttcctg cagtgcccga aacccacact cagcagatc    780
agccacatcg cccagcagct tgggctcgag aaggatgtgg tccgagtgtg gttctgtaac   840
cggcgccaga agggcaagcg atcaagcagc gactatgcac aacgagagga ttttgaggct   900
gctgggtctc ctttctcagg gggaccagtg tcctttcctc tggccccagg gcccCatttg   960
ggtaccccag gctatgggag ccctcacttc actgcactgt actcctcggt cccttTccct  1020
gaggggaag cctttcccc tgtctctgtc accactctgg gctctcccat gcattcaaac   1080

SEQ ID NO: 2              moltype = AA   length = 360
FEATURE                   Location/Qualifiers
source                    1..360
                          mol_type = protein
                          organism = Homo sapiens
SEQUENCE: 2
MAGHLASDFA FSPPPGGGGD GPGGPEPGWV DPRTWLSFQG PPGGPGIGPG VGPGSEVWGI    60
PPCPPPYEFC GGMAYCGPQV GVGLVPQGGL ETSQPEGEAG VGVESNSDGA SPEPCTVTPG   120
AVKLEKEKLE QNPEESQDIK ALQKELEQFA KLLKQKRITL GYTQADVGLT LGVLFGKVFS   180
QTTICRFEAL QLSFKNMCKL RPLLQKWVEE ADNNENLQEI CKAETLVQAR KRKRTSIENR   240
VRGNLENLFL QCPKPTLQQI SHIAQQLGLE KDVVRVWFCN RRQKGKRSSS DYAQREDFEA   300
AGSPFSGGPV SFPLAPGPHF GTPGYGSPHF TALYSSVPFP EGEAFPPVSV TTLGSPMHSN   360

SEQ ID NO: 3              moltype = DNA   length = 951
FEATURE                   Location/Qualifiers
source                    1..951
                          mol_type = other DNA
                          organism = Homo sapiens
SEQUENCE: 3
atgtacaaca tgatggagac ggagctgaag ccgccgggcc cgcagcaaac ttcggggggc    60
ggcggcggca actccaccgc ggcggcggcc ggcggcaacc agaaaaacag cccggaccgc   120
gtcaagcggc ccatgaatgc cttcatggtg tggtcccgcg gcagcggcg caagatgGcc   180
caggagaacc ccaagatgca caactcggtg atcagcaagc gcctgggcgc cgagtggaaa   240
cttttgtcgg agacggagaa gcggccgttc atcgacgagg ctaagcggct gcgagcgctg   300
cacatgaagg agcaccccgga ttataaaatac cggccccggc ggaaaaccaa gacgctcatg   360
aagaaggata agtacacgct gcccggcggg ctgctggccc ccggcggcaa tagcatggcg   420
agcggggtcg gggtgggcgc cggcctgggc gcgggcgtga accagcgcat ggacagttac   480
gcgcacatga acggctggag caacggcagc tacagcatga tgcaggacca gctgggctac   540
ccgcagcacc cgggcctcaa tgcgcacggc gcagcgcaga tgcagcccat gcaccgctac   600
gacgtgagcg ccctgcagta caactccatg accagctcgc agacctacat gaacggctcg   660
cccacctaca gcatgtccta ctcgcagcag ggcaccctcg gcatggctct tggctccatg   720
ggttcggtgg tcaagtccga ggccagctcc agcccccctg tggttacctc ttcctcccac   780
tccagggcgc cctgccaggc cggggacctc cgggacatga tcagcatgta tctccccggc   840
gccgaggtgc cggaacccgc cgcccccagc agacttcaca tgtcccagca ctaccagagc   900
gcccggtgc ccggcacggc cattaacggc acactgcccc tctcacacat g             951

SEQ ID NO: 4              moltype = AA   length = 317
FEATURE                   Location/Qualifiers
source                    1..317
                          mol_type = protein
                          organism = Homo sapiens
SEQUENCE: 4
MYNMMETELK PPGPQQTSGG GGGNSTAAAA GGNQKNSPDR VKRPMNAFMV WSRGQRRKMA    60
QENPKMHNSE ISKRLGAEWK LLSETEKRPF IDEAKRLRAL HMKEHPDYKY RPRRKTKTLM   120
KKDKYTLPGG LLAPGGNSMA SGVGVGAGLG AGVNQRMDSY AHMNGWSNGS YSMMQDQLGY   180
PQHPGLNAHG AAQMQPMHRY DVSALQYNSM TSSQTYMNGS PTYSMSYSQQ GTPGMALGSM   240
GSVVKSEASS SPPVVTSSSH SRAPCQAGDL RDMISMYLPG AEVPEPAAPS RLHMSQHYQS   300
GPVPGTAING TLPLSHM                                                  317

SEQ ID NO: 5              moltype = DNA   length = 1410
FEATURE                   Location/Qualifiers
source                    1..1410
```

```
                              mol_type = other DNA
                              organism = Homo sapiens
SEQUENCE: 5
atggctgtca gcgacgcgct gctcccatct ttctccacgt tcgcgtctgg cccggcggga    60
agggagaaga cactgcgtca agcaggtgcc ccgaataacc gctggcggga ggagctctcc   120
cacatgaagc gacttccccc agtgcttccc ggccgcccct atgacctggc ggcggcgacc   180
gtggccacag acctggagag cggcggagcc ggtgcggctt cgcggcggta gcaacctggcg   240
cccctacctc ggagagagac cgaggagttc aacgatctcc tggacctgga ctttattctc   300
tccaattcgc tgacccatcc tccggagtca gtggccgcca ccgtgtcctc gtcagcgtca   360
gcctcctctt cgtcgtcgcc gtcgagcagc ggccctgcca gcgcgccctc cacctgcagc   420
ttcacctatc cgatccgggc cgggaacgac ccgggcgtgg cgccgggcgg cacgggcgga   480
ggcctcctct atggcaggga gtccgctccc cctccgacgg ctcccttcaa cctggcggac   540
atcaacgacg tgagcccctc gggcggcttc gtggccgagc tcctgcggcc agaattggac   600
ccggtgtaca ttccgccgca gcagccgcag ccgccaggtg gggctgatt gggcaagttc   660
gtgctgaagg cgtcgctgag cgcccctggc agcgagtacg gcagcccgtc ggtcatcagc   720
gtcagcaaag gcagccctga cggcagccac ccggtggtgg tggcgcccta caacggcggg   780
ccgccgcgca cgtgccccaa gatcaagcag gaggcggtct cttcgtgcac ccacttgggc   840
gctggacccc ctctcagcaa tggccaccgg ccggctgcac acgacttccc cctggggcgg   900
cagctcccca gcaggactac cccgaccctg ggtcttgagg aagtgctgag cagcagggac   960
tgtcaccctg ccctgccgct tcctcccggg ttccatcccc accgggggcc caattaccca  1020
tccttcctgc cgatcagat gcagccgcaa gtcccgccgc tccattacca agagctcatg  1080
ccacccggtt cctgcatgcc agaggagccc aagccaaaga gggaagacg atcgtggccc  1140
cggaaaagga ccgccaccca cacttgtgat tacgcgggct gcggcaaaac ctacacaaag  1200
agttcccatc tcaaggcaca cctgcgaacc cacacaggtg agaaaccta ccactgtgac  1260
tgggacggct gtggatggaa attcgcccgc tcagatgaac tgaccaggca ctaccgtaaa  1320
cacacgggc accgccgtt ccagtgccaa aaatgcgacc gagcatttc caggtcgac  1380
cacctcgcct tacacatgaa gaggcatttt                                   1410

SEQ ID NO: 6              moltype = AA   length = 470
FEATURE                   Location/Qualifiers
source                    1..470
                          mol_type = protein
                          organism = Homo sapiens
SEQUENCE: 6
MAVSDALLPS FSTFASGPAG REKTLRQAGA PNNRWREELS HMKRLPPVLP GRPYDLAAAT    60
VATDLESGGA GAACGGSNLA PLPRRETEEF NDLLDLDFIL SNSLTHPPES VAATVSSSAS   120
ASSSSSPSSS GPASAPSTCS FTYPIRAGND PGVAPGGTGG GLLYGRESAP PPTAPFNLAD   180
INDVSPSGGF VAELLRPELD PVYIPPQQPQ PPGGGLMGKF VLKASLSAPG SEYGSPSVIS   240
VSKGSPDGSH PVVVAPYNGG PPRTCPKIKQ EAVSSCTHLG AGPPLSNGHR PAAHDFPLGR   300
QLPSRTTPTL GLEEVLSSRD CHPALPLPPG FHPHPGPNYP SFLPDQMQPQ VPPLHYQELM   360
PPGSCMPEEP KPKRGRRSWP RKRTATHTCD YAGCGKTYTK SSHLKAHLRT HTGEKPYHCD   420
WDGCGWKFAR SDELTRHYRK HTGHRPFQCQ KCDRAFSRSD HLALHMKRHF              470

SEQ ID NO: 7              moltype = DNA   length = 376
FEATURE                   Location/Qualifiers
source                    1..376
                          mol_type = other DNA
                          organism = synthetic construct
SEQUENCE: 7
tttactccct atcagtgata gagaacgtat gaagagttta ctccctatca gtgatagaga    60
acgtatgcag actttactcc ctatcagtga tagagaagtt tactccctat cagtgataga   120
cagtgataga gaacgtatga ccagttact ccctatcagt gatagagaac gtatctcacag   180
tttactccct atcagtgata gagaacgtat atccagttta ctccctatca gtgatagaga   240
acgtataagc tttaggcgtg tacggtgggc gcctataaaa gcagagctcg tttagtgaac   300
cgtcagatcg cctggagcaa ttccacaaca cttttgtctt ataccaactt tccgtaccac   360
ttcctaccct cgtaaa                                                    376

SEQ ID NO: 8              moltype = DNA   length = 57
FEATURE                   Location/Qualifiers
source                    1..57
                          mol_type = other DNA
                          organism = Teschovirus A
SEQUENCE: 8
gccacgaact tctctctgtt aaagcaagca ggagatgttg aagaaaaccc cgggcct       57

SEQ ID NO: 9              moltype = AA   length = 19
FEATURE                   Location/Qualifiers
source                    1..19
                          mol_type = protein
                          organism = Teschovirus A
SEQUENCE: 9
ATNFSLLKQA GDVEENPGP                                                  19

SEQ ID NO: 10             moltype = DNA   length = 54
FEATURE                   Location/Qualifiers
source                    1..54
                          mol_type = other DNA
                          organism = Thosea asigna virus
SEQUENCE: 10
```

```
gagggcaggg gaagtcttct aacatgcggg gacgtggagg aaaatcccgg ccca          54

SEQ ID NO: 11            moltype = AA   length = 18
FEATURE                  Location/Qualifiers
source                   1..18
                         mol_type = protein
                         organism = Thosea asigna virus
SEQUENCE: 11
EGRGSLLTCG DVEENPGP                                                  18

SEQ ID NO: 12            moltype = DNA   length = 135
FEATURE                  Location/Qualifiers
source                   1..135
                         mol_type = other DNA
                         organism = synthetic construct
SEQUENCE: 12
aacttgttta ttgcagctta taatggttac aaataaagca atagcatcac aaatttcaca    60
aataaagcat ttttttcact gcattctagt tgtggtttgt ccaaactcat caatgtatct   120
tatcatgtct ggatc                                                   135

SEQ ID NO: 13            moltype = DNA   length = 4933
FEATURE                  Location/Qualifiers
source                   1..4933
                         mol_type = other DNA
                         organism = synthetic construct
SEQUENCE: 13
ctatgcggca tcagagcaga ttgtactgag agtgcaccat atgcggtgtg aaataccgca    60
cagatgcgta aggagaaaat accgcatcag gcgccattcg ccattcaggc tgcgcaactg   120
ttgggaaggg cgatcggtgc gggcctcttc gctattacgc cagctggcga aggggggatg   180
tgctgcaagg cgattaagtt gggtaacgcc agggttttcc cagtcacgac gttgtaaaac   240
gacggccagt gaattgacgc gtattgggat ccatgattac gccagattta attaaggcct   300
taattaggct cgcgctcgc tcgctcactg aggccgcccg gcaaagccc gggcgtcggg    360
cgacctttgg tcgcccggcc tcagtgagcg agcgagcgcg cagagaggga gtggccaact   420
ccatcactag gggttccttg tagttaatga ttaacccgcc atgctactta tctacgtagc   480
catgctctag gaagatcgga attcttact ccctatcagt gatagagaac gtatgaagag    540
tttactccct atcagtgata gagaacgtat gcagacttta ctcccctatca gtgatagaga   600
acgtataagg agtttactcc ctatcagtga tagagaacgt atgaccagtt tactccctat   660
cagtgataga gaacgtatct acagtttact ccctatcagt gatagagaac gtatatccag   720
tttactccct atcagtgata gagaacgtat aagctttagg cgtgtacggt gggcgcctat   780
aaaagcagag ctcgtttagt gaaccgtcag atcgcctgga gcaattccac aacacttttg   840
tcttatacca actttccgta ccacttccta ccctcgtaaa gcggccgcgc caccatggcg   900
ggacacctgg cttcggattt cgccttctcg ccccctccag gtggtggagg tgatgggcca   960
gggggaccgg agccgggctg ggttgatcct cggacctggc taagcttcca aggccctcct  1020
ggagggccag gaatcgggcc gggggttggg ccaggctctg aggtgtgggg gattccccca  1080
tgccccccgc cgtatgagtt ctgtgggggg atggcgtact gtgggcccca ggttggagtg  1140
gggctagtgc cccaaggcgg cttggagacc tctcagcctg agggcgaagc aggagtcggg  1200
gtggagagca actccgatgg ggcctcccccg gagccctgca ccgtcacccc tggtgccgtg  1260
aagctggaga aggagaagct ggagcaaaac ccggaggagt cccaggacat caaagctctg  1320
cagaaagaac tcgagcaatt tgccaagctc ctgaagcaga gaggatcac cctgggatat  1380
acacaggccg atgtgggct caccctgggg gttctatttg gaaggtatt cagccaaacg  1440
accatctgcc gcttttgaggc tctgcagctt agcttcaaga acatgtgtaa gctgcggccc  1500
ttgctgcaga agtgggtgga ggaagctgac aacaatgaaa atcttcagga gatatgcaaa  1560
gcagaaaccc tcgtgcaggc ccgaaagaga aagcgaacca gtatcgagaa ccgagtgaga  1620
ggcaacctgg agaattttgtt cctgcagtgc ccgaaaccca cactgcagca gatcagccac  1680
atcgcccagc agcttgggct cgagaaggat gtggtccgag tgtggttctg taaccggcga  1740
cagaagggca agcgatcaag cagcgactat gcacaacgag aggattttga ggctgctggg  1800
tctcctttct caggggggacc agtgtcctt cctctggccc cagggcccca ttttggtacc  1860
ccaggctatg ggagccctca cttcactgca ctgtactcct cggtcccttt ccctgagggg  1920
gaagccttc ccctgtctc tgtcaccact ccatgcattc aaacgctagc                1980
ggcagcggcg ccacgaactt ctctctgtta aagcaagcag agatgttga agaaaacccc   2040
gggcctgcat gcatgtacaa catgatggag acggagctga agccgccggg cccgcagcaa  2100
acttcggggg gcggcggcgg caactccacc gcggcggcgg ccggcggcaa ccagaaaaac  2160
agcccggacc gcgtcaagcg gcccatgaat gccttcatgg tgtggtcccg cggcagcgg   2220
cgcaagatgg cccaggagaa cccaagatgc acaactcgga atcagcaa gatgcaggac   2280
gccgagtgga aactttttgtc ggagacggag aagcggccgt tcatcgacga ggctaagcgg  2340
ctgcgagcgc tgcacatgaa ggagcacccg gattataaat accggcccg gcggaaaacc  2400
aagacgctca tgaagaagga taagtacacg ctgcccggcg gctgctggcc ccccggcggc  2460
aatagcatgg cgagcggggt cggggtgggc gccggcctgg gcgcgggcgt gaaccagcga  2520
atggacagtt acgcgcacat gaacggctgg agcaacggca gctacagcat gatgcaggac  2580
cagctgggct acccgcagca cccgggcctc aatgcgcacg gcgcagcgca gatgcagccc  2640
atgcaccgct acgacgtgag cgccctgcag tacaactcca tgaccagctc gcagacctac  2700
atgaacggcc gcccacccta cagcatgtcc tactcgcagc agggcacccc tggcatggct  2760
cttggctcca tgggttcggt ggtcaagtcc gaggccagct ccagcccccc tgtggttacc  2820
tcttcctcca actcccagggc gccggggacc tcgggacat gatcagcatg  2880
tatctccccg gcgccgaggt gccggaaccc gccgccccca gacagcttca catgtccag   2940
cactaccaga gcgccccggt gccggcacg gccattaacg gcacactgcc cctctcacac  3000
atggcatgcg gctccggcga gggcagggga agtcttctaa catgcgggga cgtggaggaa  3060
aatcccggcc cactcgagat ggctgtcagc gacgcgctgc tcccatcttt ctccacgttc  3120
gcgtctggcc cggcgggaag ggagaagaca ctgcgtcaag caggtgcccc gaataaccgc  3180
```

```
tggcgggagg agctctccca catgaagcga cttcccccag tgcttccgg ccgcccctat 3240
gacctggcgg cggcgaccgt ggccacagac ctggagagcg gcggagccgg tgcggcttgc 3300
ggcggtagca acctggcgcc cctacctcgg agagagaccg aggagttcaa cgatctcctg 3360
gacctggact ttattctctc caattcgctg acccatcctc cggagtcagt ggccgccacc 3420
gtgtcctcgt cagcgtcagc ctcctcttcg tcgtcgccgt cgagcagcgg ccctgccagc 3480
gcgccctcca cctgcagctt cacctatccg atccggggccg ggaacgaccc gggcgtggcc 3540
ccgggcggca cgggcggagg cctcctctat ggcagggagt ccgctccccc tccgacgggct 3600
cccttcaacc tggcggacat caacgacgtg agccctcgg gcggcttcgt ggccgagctc 3660
ctgcggccag aattggaccc ggtgtacatt ccgccgcagc agcgcagcc gccaggtggc 3720
gggctgatgg gcaagttcgt gctgaaggcg tcgctgagcg ccctggcag cgagtacggc 3780
agcccgtcgg tcatcagcgt cagcaaaggc agccctgacg gcagccaccc ggtggtggtg 3840
gcgccctaca acgcgggcc gccgcgcacg tgccccaaga tcaagcagga ggcggtctct 3900
tcgtgcaccc acttgggcgc tggacccct ctcagcaatg ccaccggcc ggctgcacac 3960
gacttccccc tggggcggca gctcccccagc aggactaccc cgaccctggg tcttgaggaa 4020
gtgctgagca gcagggactg tcaccctgcc ctgccgcttc ctcccggctt ccatccccac 4080
ccgggggccca attaccccatc cttcctgccc gatcagatgc agccgcaagt cccgccgctc 4140
cattaccaag agctcatgcc acccggttcc tgcatgccag aggagcccaa gccaaagagg 4200
ggaagacgat cgtggcccccg gaaaaggacc gccacccaca cttgtgatta cgcgggctgc 4260
ggcaaaacct acacaaagag ttcccatctc aaggcacacc tgcgaaccca cacaggtgag 4320
aaaccttacc actgtgactg ggacggctgt ggatggaaat tcgcccgctc agatgaactg 4380
accaggcact accgtaaaca cacggggcac cgcccgttcc agtgccaaaa atgcgaccga 4440
gcattttcca ggtcggacca cctcgcctta cacatgaaga ggcattttta aatgactagt 4500
gcgcgcagcg gccgaccatg gcccaacttg tttattgcag cttataatgg ttacaaataa 4560
agcaatagca tcacaaattt cacaaataaa gcatttttt cactgcattc tagttgtggt 4620
ttgtccaaac tcatcaatgt atcttatcat gtctggatct cggtaccgga tccaaattcc 4680
cgataaggat cttcctagag catgctacg tagataagta gcatggcggg ttaatcatta 4740
actacaagga acccctagtg atggagttgg ccactccctc tctgcgcgct cgctcgctca 4800
ctgaggccgg gcgaccaaag gtcgcccgac gcccgggctt tgcccgggcg gcctcagtga 4860
gcgagcgagc gcgcagcctt aattaaccta attcatccca atggcgcgcc gagcttggct 4920
cgagcatggt cat                                                    4933
```

SEQ ID NO: 14        moltype = DNA  length = 3594
FEATURE              Location/Qualifiers
source               1..3594
                       mol_type = other DNA
                       organism = synthetic construct
SEQUENCE: 14

```
atggcgggac acctggcttc ggatttcgcc ttctcgcccc ctccaggtgg tggaggtgat 60
gggccagggg ggccggagcc gggctgggtt gatcctccga cctggctaag cttccaaggc 120
cctcctggag ggccaggaat cgggccgggg gttgggccag gctctgaggt gtggggatt 180
ccccccatgc ccccgccgta tgagttctgt ggggggatgg cgtactgtgg gccccaggtt 240
ggagtggggc tagtgcccca aggcggcttg gagacctctc agcctgaggg cgaagcagga 300
gtcggggtgg agagcaactc cgatgggggcc tccccggacg cctgcaccgt caccccctgg 360
gccgtgaagc tggagaagga gaagctggag caaaacccgg aggagtccca ggacatcaaa 420
gctctgcaga agaactcga gcaatttgcc aagctcctga gcagaagag gatcaccctg 480
ggatatacac aggccgatgt ggggctcacc ctggggggttc tatttgggaa ggtattcagc 540
caaacgacca tctgccgctt tgaggctctg cagcttagct tcaagaacat gtgtaagctg 600
cggcccttgc tgcagaagtg ggtggaggaa gctgacaaca atgaaaatct tcaggagata 660
tgcaaagcag aaaccctcgt gcaggcccga agagaaaagc gaaccagtat cgagaaccga 720
gtgagaggca acctggagaa tttgttcctg cagtgcccga acccacact gcagcagatc 780
agccacatcg cccagcagct tgggctcgag aaggatgtgg tccgagtgtg gttctgtaac 840
cggcgccaga agggcaagcg atcaagcagc gactatgcac aacgagagga ttttgaggct 900
gctgggtctc cttttctcag gggaccagtg tcctttcctc tggccccagg gccccatttt 960
ggtaccccag gctatgggag ccctcacttc actgcactgt actcctcggt cccttttcct 1020
gagggggaag ccttttccccc tgtctctgtc accactctgg gctctcccat gcattcaaac 1080
gctagcggca gcggcgccac gaacttctct ctgttaaagc aagcaggaga tgttgaagaa 1140
aaccccggc ctgcatgcat gtacaacatg atggagacgg agctgaagcc gccgggcccg 1200
cagcaaactt cggggggcgg cggcggcaac tccaccgcgg cggcggccgg cggcaaccag 1260
aaaaacagcc cggcaccgcgt caagcggccc atgaatgcct tcatggtgtg gtcccgcggg 1320
cagcggcgca agatgcccca ggagaacccc aagatgcaca actcggagat cagcaagcgc 1380
ctgggcgccg agtggaaact tttgtcggag acggagaagc ggccgttcat cgacgaggct 1440
aagcggctgc gagcgctgca catgaaggag cacccggatt ataaataccg gcccggcgg 1500
aaaaccaaga cgctcatgaa gaaggataag tacacgctgc ccggcggct gctggcccc 1560
ggcggcaata gcatggcgag cgggtcgggg tgggcgcg gctgggcgc ggcgggtgaac 1620
cagcgcatgg acagttacgc gcacatgaac ggctggagca acggcagcta cagcatgatg 1680
caggaccagc tgggctaccc gcagcacccg ggcctcaatg cgcacggcgc agcgcagatg 1740
cagcccatgc accgctacga cgtgagcgcc ctgcagtaca actccatgac cagctcgcag 1800
acctacatga acggctcgcc cacctacagc atgtcctact cgcaccaggg caccccttgg 1860
atggctcttg gctccatggg ttcggtggtc aagtccgagg ccagctccga cccccctgtg 1920
gttacctctt cctcccactc caggggcgccc tgccaggccg ggacctccg ggacatgatc 1980
agcatgtatc tccccggcgc cgaggtgccg gaacccgccg cccccagcag acttcacatg 2040
tcccagcact accagagcgg cccggtgccc ggcacggcca ttaacggcac actgccctc 2100
tcacacatgg catcgggctc cggcgagggc agggaagtc ttcaacatg cggggacgtg 2160
gaggaaaatc ccggccccact gagatgctt gcacgggcg cgctgctccc atctttctcc 2220
acgttcgcgt ctggccccgg gggaaggag aagacactgt gtcaagcagg tgccccgaat 2280
aaccgctggc gggaggagct ctcccacatg aagcgacttc cccagtgct tccggccgc 2340
ccctatgacc tggcggcggc gaccgtggcc acagacctgg agagcggcgg agccggtgcg 2400
gcttgcggcg gtagcaacct ggcgcccta cctcggagag agaccgagga gttcaacgat 2460
ctcctggacc tggactttat tctctccaat tcgctgaccc atcctccgga gtcagtggcc 2520
```

```
gccaccgtgt cctcgtcagc gtcagcctcc tcttcgtcgt cgccgtcgag cagcggccct 2580
gccagcgcgc cctccaccct cagcttcacc tatccgatcc gggccgggaa cgacccgggc 2640
gtggcgccgg gcggcacggg cggaggcctc ctctatggca gggagtccgc tcccctccg  2700
acggctcct  tcaacctggc ggacatcaac gacgtgagcc cctcgggcgg cttcgtggcc 2760
gagctcctgc ggccagaatt ggaccggtg tacattccgc cgcagcagcc gcagccgcca  2820
ggtggcgggc tgatgggcaa gttcgtgctg aaggcgtcgc tgagcgcccc tggcagcgag 2880
tacggcagcc cgtcggtcat cagcgtcagc aaaggcagcc ctgacggcag ccacccggtg 2940
gtggtggcgc cctacaacgg cgggccgccg cgcacgtgcc ccaagatcaa gcaggaggcg 3000
gtctcttcgt gcacccactt gggcgctgga cccctctca gcaatggcca ccggccggct  3060
gcacacgact tcccctgggg gcggcagctc cccagcagga ctaccccgac cctgggtctt 3120
gaggaagtgc tgagcagcag ggactgtcac cctgccctgc cgcttcctcc cggcttccat 3180
ccccaccgg  ggcccaatta cccatccttc ctgcccgatc agatgcagcc gcaagtcccg 3240
ccgctccatt accaagagct catgccaccc ggttcctgca tgccagagga gcccaagcca 3300
aagaggggaa gacgatcgtg gccccggaaa aggaccgcca cccacacttg tgattacgcg 3360
ggctgcggca aaacctacac aaagagttcc catctcaagg cacacctgcg aacccacaca 3420
ggtgagaaac cttaccactg tgactgggac ggctgtggat ggaaattcgc ccgctcagat 3480
gaactgacca ggcactaccg taaacacacg gggcaccgcc cgttccagtg ccaaaaatgc 3540
gaccgagcat tttccaggtc ggaccacctc gccttacaca tgaagaggca tttt         3594

SEQ ID NO: 15           moltype = DNA   length = 7250
FEATURE                 Location/Qualifiers
source                  1..7250
                        mol_type = other DNA
                        organism = synthetic construct
SEQUENCE: 15
tcgcgcgttt cggtgatgac ggtgaaaacc tctgacacat gcagctcccg gagactgtca 60
cagcttgtct gtaagcggat gccgggagca gacaagcccg tcagggcgcg tcagcgggtg 120
ttggcgggtg tcgggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg gatgtgctgc aaggcgatt aagttgggta acgccagggt 360
tttcccagtc acgacgttgt aaaacgacgg ccagtgaatt gacgcgtatt gggatccatg 420
attacgccag atttaattaa ggccttaatt aggctgcgcg ctcgctcgct cactgaggcc 480
gcccgggcaa agcccgggcg tcgggcgacc tttggtcgcc cggcctcagt gagcgagcga 540
gcgcgcagag agggagtggc caactccatc actagggtt ccttgtagtt aatgattaac 600
ccgccatgct acttatctac gtagccatgc tctaggaaga tcggaattct ttactccta  660
tcagtgatag agaacgtatg aagagtttac tccctatcag tgatagagaa cgtatgcaga 720
cttttactccc tatcagtgat agagaacgta taaggagttt actccctatc agtgatagag 780
aacgtatgac cagtttactc cctatcagtg atagagaact atctacagt ttactcccta  840
tcagtgatag agaacgtata tccagtttac tccctatcag tgatagagaa cgtataagct 900
ttaggcgtgt acggtgggcg cctataaaag cagagctcgt ttagtgaacc gtcagatcgc 960
ctggagcaat tccacaacac ttttgtctta taccaacttt ccgtaccact tcctaccctc 1020
gtaaagcggc cgcgccacca tggcgggaca cctggcttcg gatttcgctt ctcgccccca 1080
tccaggtggt ggaggtgatg ggccagggg gccggagccg gctgggttg atcctcggac 1140
ctggctaagc ttccaaggcc ctcctggagg gccaggaatc gggccggggg ttgggccagg 1200
ctctgaggtg tggggattc ccccatgccc ccgccgtat gagttctgtg ggggatggc   1260
tgactgtggg ccccaggttg gagtggggct agtgccccaa ggcggcttgg agacctctca 1320
gcctgagggc gaagcaggag tcggggtgga gagcaactcc gatggggcct ccccggagcc 1380
ctgcaccgtc acccctggtg ccgtgaagct ggagaaggag aagctggagc aaaacccgga 1440
ggagtcccag gacatcaaag ctctgcagaa agaactcgag caatttgcca agctcctgaa 1500
gcagaagagg atcaccctgg gatatacaca ggcgatgtg ggctcaccc tgggggttct  1560
atttgggaag gtattcagcc aaacgaccat ctgccgcttt gaggctctgc agcttagctt 1620
caagaacatg tgtaagctgc ggccccttgct gcagaagtgg gtgaggaag ctgacaacaa  1680
tgaaaatctt caggagatat gcaaagcaga acccctcgtg caggcccgaa agagaaagcg 1740
aaccgtatc gagaaccgag tgagaggcaa cctggaaatt ttgttcctgc agtgcccgaa  1800
acccacactg cagcagatca gccacatcgc ccagcagctt gggctcgaga aggatgtggt 1860
ccgagtgtgg ttctgtaacc ggcgccagaa gggcaagcga tcaagcagcg actatgcaca 1920
acgagaggat tttgaggctg ctgggtctcc ttctcaggg ggaccagtgt cctttcctct  1980
ggcccaggg ccattttg gtacccagg ctatgggagc cctcacttca ctgactgta  2040
ctcctcggtc cctttccctg aggggaagc cttcccct gtctctgtca ccactctggg  2100
ctctcccatg cattcaaacg ctagcggcag cggccgcacg aacttctctc tgttaaagca 2160
agcaggagat gttgaagaaa accccgggcc tgcatgcatg tacaacatga tggagacgga 2220
gctgaagccg ccgggcccgc agcaaacttc gggggcggc ggcggcaact ccaccgcggc 2280
ggccgccggc ggcaaccaga aaaacgccc ggaccggtc aagcggccca tgaatgcgtt 2340
catggtgtgg tcccgcgggc agcggcgcaa gatggcccag agaaccccca agatgcacaa 2400
ctcggagatc agcaagcgcc tgggcgccga gtggaaactt ttgtcggaga cggagaagcg 2460
gccgttcatc gacgaggcta gcggctgcg agcgctgcac atgaaggagc cccggatta  2520
taaataccgg ccccggcgga aaccaagac gctcatgaag aaggataagt acacgctgcc 2580
cggcggctg ctggccccg gcggcaatag catggcgggc gggtcgggc tgggcgccgg 2640
cctgggcgcg ggcgtgaacc agcgcatgga cagttacgcg cacatgaacg gctggagcaa 2700
cggcagctac agcatgatgc aggaccagct gggctaccg cagcacccgg gcctcaatgc 2760
gcacggcgca gcgcagatgc agcccatgca ccgctacgac gtgagcgccc tgcagtacaa 2820
ctccatgacc agctcgcaga cctacatgaa cggctcgccc acctacagca tgtcctactc 2880
gcagcagggc accccgggca tggctcttgg ctccatggt tcggtggtca agtccgaggc 2940
cagctccagc ccccctgtgg ttacctcttc ctcccactcc agggcgccct gcaggccgg  3000
ggacctccgg gacatgatca gcatgtatct ccccggcgcc gaggtgccgg aaccgccgcc 3060
ccccagcaga cttcacatgt cccagcacta ccagagcggc ccggtgcccg cacggccat  3120
taacggcaca ctgcccctct cacacatggc atcggctcc ggcgagggca gggaagtct   3180
tctaacatgc ggggacgtgg aggaaaatcc cggcccactc gagatggctg tcagcgacgc 3240
```

```
gctgctccca tctttctcca cgttcgcgtc tggcccggcg ggaagggaga agacactgcg  3300
tcaagcaggt gccccgaata accgctggcg ggaggagctc tcccacatga agcgacttcc  3360
cccagtgctt cccggccgcc cctatgacct ggcggcggcg accgtggcca cagacctgga  3420
gagcggcgga gccggtgcgg cttgcggcgg tagcaacctg gcgcccctac ctcggagaga  3480
gaccgaggag ttcaacgatc tcctggacct ggactttatt ctctccaatt cgctgaccca  3540
tcctccggag tcagtggccg ccaccgtgtc ctcgtcagcg tcagcctcct cttcgtcgtc  3600
gccgtcgagc agcggccctg ccagcgcgcc ctccacctgc agcttcacct atccgatccg  3660
ggccgggaac gacccgggcg tggcgccggg cggcacgggc ggaggcctcc tctatgcag   3720
ggagtccgct cccctccga cggctccctt caacctggcg gacatcaacg acgtgagccc  3780
ctcgggcgc ttcgtggccg agctcctgcg gccagaattg gacccggtgt acattccgcc  3840
gcagcagccg cagccgccag gtggcgggct gatgggcaag ttcgtgctga aggcgtcgct  3900
gagcgcccct ggcagcgagt acggcagccc gtcggtcatc agcgtcagca aaggcagccc  3960
tgacggcagc caccccggtgg tggtggcgcc ctacaacggg gggccgccgc gcacgtgccc  4020
caagatcaag caggaggcgg tctcttcgtg cacccacttg ggcgctggac ccctctcag   4080
caatggccac cggccggctg cacacgactt cccctggg cggcagctcc ccagcaggac  4140
taccccgacc ctgggtcttg aggaagtgct gagcagcagg gactgtcacc ctgccctgcc  4200
gcttcctccc ggcttccatc cccacccggg gcccaattac ccatccttcc tgcccgatca  4260
gatgcagccg caagtcccgc cgctccatta ccaagagctc atgccacccg gttcctgcat  4320
gccagaggag cccaagccaa agaggggaag acgatcgtgg ccccggaaaa ggaccgccac  4380
ccacacttgt gattacgcgg gctgcggcaa aacctacaca aagagttccc atctcaaggc  4440
acacctgcga acccacacag gtgagaaacc ttaccactgt gactgggacg gctgtggatg  4500
gaaattcgcc cgctcagatg aactgaccag gcactaccgt aacaacacgg ggcaccgccc  4560
gttccagtgc caaaaatgcg accgagcatt ttccaggtcg gaccacctcg ccttacacat  4620
gaagaggcat ttttaaatga ctagtgcgcg cagcggccga ccatgcccca acttgtttat  4680
tgcagcttat aatggttaca aataaagcaa tagcatcaca aatttcacaa ataaagcatt  4740
tttttcactg cattctagtt gtggtttgtc caaactcatc aatgtatctt atcatgtcat  4800
gatctcggta ccggatccaa attcccgata aggatcttcc tagagcatgg ctacgtagat  4860
aagtagcatg gcgggttaat cattaactac aaggaacccc tagtgatgga gttggccact  4920
ccctctctgc gcgctcgctc gctcactgag gccgggcgac caaaggtcgc ccgacgcccg  4980
ggcttttgccc gggcggcctc agtgagcgag cgagcgcgca gcctaatta acctaattca  5040
tcccaatggc gcgccagct tggctcgagc atggtcatag ctgtttcctg tgtgaaattg  5100
ttatccgctc acaattccac acaacatacg agccggaagc ataaagtgta aagcctgggg  5160
tgcctaatga gtgagctaac tcacattaat tgcgttgcgc tcactgcccg ctttccagtc  5220
gggaaacctg tcgtgccagc tgcattaatg aatcggccaa cgcgcgggga gaggcggttt  5280
gcgtattggg cgctgttccg cttcctcgct cactgactcg ctgcgctcgg tcgttcggct  5340
gcggcgagcg gtatcagctc actcaaaggc ggtaatacgg ttatccacag aatcaggga   5400
taacgcagga aagaacatgt gagcaaaagg ccagcaaaag gccaggaacc gtaaaaaggc  5460
cgcgttgctg gcgtttttcc ataggctccg cccccctgac gagcatcaca aaaatcgacg  5520
ctcaagtcag aggtggcgaa acccgacagg actataaaga taccaggcgt ttccccctgg  5580
aagctccctc gtgcgctctc ctgttccgac cctgccgctt accggatacc tgtccgcctt  5640
tctcccttcg ggaagcgtgg cgctttctca tagctcacgc tgtaggtatc tcagttcggt  5700
gtaggtcgtt cgctccaagc tgggctgtgt gcacgaaccc cccgttcagc ccgaccgctg  5760
cgccttatcc ggtaactatc gtcttgagtc aacccggtaa gacacgactt atcgccact   5820
ggcagcagcc actggtaaca ggattagcag agcgaggtat gtaggcggtg ctacagagtt  5880
cttgaagtgg tggcctaact acggctacac tagaagaaca gtatttggta tctgcgctct  5940
gctgaagcca gttaccttcg gaaaagagt tggtagctct tgatccggca aacaaaccac   6000
cgctggtagc ggtggttttt tgtttgcaa gcagcagatt acgcgcagaa aaaaaggatc  6060
tcaagaagat cctttgatct tttctacggg gtctgacgct cagtggaacg aaaactcacg  6120
ttaagggatt ttggtcatga gattatcaaa aaggatcttc acctagatcc ttttaaatta  6180
aaaatgaagt tttaaatcaa tctaaagtat atatgagtaa acttggtctg acagttagaa  6240
aaactcatcg agcatcaaat gaaactgcaa tttattcaga ttattaatt caataccata   6300
ttttttgaaaa agccgtttct gtaatgaagg agaaaactca ccgaggcagt tccataggat  6360
ggcaagatcc tggtatcggt ctgcgattcc gactcgtcca acatcaatac aacctattaa  6420
tttcccctcg tcaaaataaa ggttatcaag tgagaaatca ccatgagtga cgactgaatc  6480
cggtgagaat ggcaaaagtt tatgcatttc tttccagact tgttcaacag gccagccatt  6540
acgctcgtca tcaaaatcac tcgcatcaac caaaccgtta ttcattcgtg attgcgcctg  6600
agcgaaacga atacgcgat cgctgttaaa aggacaatta caaacaggaa tcgaatgcaa  6660
ccggcgcagg aacactgcca gcgcatcaac aatattttca cctgaatcag gatattcttc  6720
taatacctgg aatgctgttt tcccagggat cgcagtggtg agtaaccatg catcatcagg  6780
agtacggata aaatgcttga tggtcggaag aggcataaat tccgtcagcc agtttagtct  6840
gaccatctca tctgtaacat cattggcaac gctacctttg ccatgtttca gaaacaactc  6900
tggcgcatcg gcttcccat acaatcgata gattgtcgca cctgattgcc cgacattatc   6960
gcgagcccat ttatacccat ataaatcagc atccatgttg aatttaatc gcggcctaga  7020
gcaagcgtt tcccgttgaa tatgctcat actcttcctt tttcaatatt attgaagcat  7080
ttatcagggt tattgtctca tgagcggata catatttgaa tgtatttaga aaaataaaca  7140
aatagggggtt ccgcgcacat ttccccgaaa agtgccacct gacgtctaag aaaccattat  7200
tatcatgaca ttaacctata aaaataggcg tatcacgagg ccctttttgtc             7250

SEQ ID NO: 16           moltype = DNA  length = 141
FEATURE                 Location/Qualifiers
source                  1..141
                        mol_type = other DNA
                        organism = synthetic construct
SEQUENCE: 16
ccttaattag gctgcgcgct cgctcgctca ctgaggccgc ccgggcaaag cccgggcgtc   60
gggcgacctt tggtcgcccg gcctcagtga gcgagcgagc gcgcagagag ggagtggcca  120
actccatcac tagggggttcc t                                           141

SEQ ID NO: 17           moltype = DNA  length = 204
```

```
FEATURE                 Location/Qualifiers
source                  1..204
                        mol_type = other DNA
                        organism = synthetic construct
SEQUENCE: 17
gtgatgcggt tttggcagta catcaatggg cgtggatagc ggtttgactc acggggattt    60
ccaagtctcc accccattga cgtcaatggg agtttgtttt ggcaccaaaa tcaacgggac   120
tttccaaaat gtcgtaacaa ctccgcccca ttgacgcaaa tgggcggtag gcgtgtacgg   180
tgggaggtct atataagcag agct                                          204

SEQ ID NO: 18           moltype = DNA  length = 380
FEATURE                 Location/Qualifiers
source                  1..380
                        mol_type = other DNA
                        organism = synthetic construct
SEQUENCE: 18
gacattgatt attgactagt tattaatagt aatcaattac ggggtcatta gttcatagcc    60
catatatgga gttccgcgtt acataactta cggtaaatgg cccgcctggc tgaccgccca   120
acgacccccg cccattgacg tcaataatga cgtatgttcc catagtaacg ccaatagggc   180
ctttccattg acgtcaatgg gtggagtatt tacgctaaac tgcccacttg gcagtacatc   240
aagtgtatca tatgccaagt acgcccccta ttgacgtcaa tgacggtaaa tggcccgcct   300
ggcattatgc ccagtacatg accttatggg actttcctac ttggcagtac atctacgtat   360
tagtcatcgc tattaccatg                                               380

SEQ ID NO: 19           moltype = DNA  length = 747
FEATURE                 Location/Qualifiers
source                  1..747
                        mol_type = other DNA
                        organism = synthetic construct
SEQUENCE: 19
atgtctagac tggacaagag caaaatcata aacagcgctc tggaattact caatggagtc    60
ggtatcgaag gcctgacgac aaggaaactc gctcaaaagc tgggagttga gcagcctacc   120
ctgtactggc acgtgaagaa caagcgggcc ctgctcgatg ccctgccaat cgagatgctg   180
gacaggcatc atacccacag ctgccccctg gaaggcgagt catggcaaga ctttctgcgg   240
aacaacgcca agtctacacg ctgtgctctc tctcacatc gcgacgggc taaagtgcat   300
ctcggcaccc gcccaacaga gaaacagtac gaaaccctgg aaaatcagct cgcgttcctg   360
tgtcagcaag gcttctccct ggagaacgca ctgtacgctc tgtccgccgt gggccacttt   420
acactgggct gcgtattgga ggaacaggag catcaagtag caaagagga agagagaca   480
cctaccaccg attctatgcc cccacttctg aagcaagcaa ttgagctgtt cgaccggcag   540
ggagccgaac ctgccttcct tttcggcctg gaactaatca tatgtggcct ggagaaacag   600
ctaaagtgcg aaagcggcgg gccgaccgac gcccttgacg atttgacctt agacatgctc   660
ccagccgatg cccttgacga ctttgacctt gatatgctgc ctgctgacgc tcttgacgat   720
tttgaccttg acatgctccc cgggtaa                                       747

SEQ ID NO: 20           moltype = AA  length = 248
FEATURE                 Location/Qualifiers
source                  1..248
                        mol_type = protein
                        organism = synthetic construct
SEQUENCE: 20
MSRLDKSKII NSALELLNGV GIEGLTTRKL AQKLGVEQPT LYWHVKNKRA LLDALPIEML    60
DRHHTHSCPL EGESWQDFLR NNAKSYRCAL LSHRDGAKVH LGTRPTEKQY ETLENQLAFL   120
CQQGFSLENA LYALSAVGHF TLGCVLEEQE HQVAKEERET PTTDSMPPLL KQAIELFDRQ   180
GAEPAFLFGL ELIICGLEKQ LKCESGGPTD ALDDFDLDML PADALDDFDL DMLPADALDD   240
FDLDMLPG                                                            248

SEQ ID NO: 21           moltype = DNA  length = 5435
FEATURE                 Location/Qualifiers
source                  1..5435
                        mol_type = other DNA
                        organism = synthetic construct
SEQUENCE: 21
tcgcgcgttt cggtgatgac ggtgaaaacc tctgacacat gcagctcccg gagactgtca    60
cagccttgtct gtaagcggat gccgggagca gacaagcccg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt gacgcgtatt gggatactat   420
ggttgctttg acgtatgcgg tgtgaaatac cgcacagatg cgtaaggaga aaataccgca   480
tcaggcgccc ctgcaggcag ctgcgcgctc gctcgctcac tgaggccgcc cgggcaaagc   540
ccgggcgtcg ggcgaccttt ggtcgcccgg cctcagtgag cgagcgagcg cgcagagagg   600
gagtggccaa ctccatcact aggggttcct gcggccgctc ggtccgcacg atctcaattc   660
ggcattacg gccggatccg gctcgaggag cttggccat tgtatccatat   720
cataatatgt acatttatat tggctcatgt ccaacattac cgccatgttg acattgatta   780
ttgactagtt attaatagta atcaattacg gggtcattag ttcatagccc atatatggag   840
ttccgcgtta cataacttac ggtaaatggc ccgcctggct gaccgccaa cgaccccgc   900
ccattgacgt caataatgac gtatgttccc atagtaacgc caatagggac tttccattga   960
cgtcaatggg tggagtattt acgctaaact gcccacttgg cagtacatca agtgtatcat  1020
```

```
atgccaagta cgcccnctat tgacgtcaat gacggtaaat ggcccgcctg gcattatgcc    1080
cagtacatga cctnatggga cttncctact tggcagtaca tctacgtatt agtcatcgct    1140
attaccatgg tgatgcggtt ttggcagtac atcaatgggc gtggatagcg gtttgactca    1200
cggggatttc caagtctcca ccccattgac gtcaatggga gtttgttttg gcaccaaaat    1260
caacgggact ttccaaaatg tcgtaacaac tccgccccat tgacgcaaat gggcggtagg    1320
cgtgtacggt gggaggtcta tataagcaga gctcgtttag tgaaccgtca gatcgcctgg    1380
agacgccatc cacgctgttt tgacctccat agaagacacc gggaccgatc cagcctccgc    1440
ggcccccgaat tcaccatgtc tagactggac aagagcaaaa tcataaacag cgctctggaa    1500
ttactcaatg gagtcggtat cgaaggcctg acgacaagga aactcgctca aaagctggga    1560
gttgagcagc ctaccctgta ctggcacgtg aagaacaagc gggccctgct cgatgccctg    1620
ccaatcgaga tgctggacag gcatcatacc cacagctgcc ccctggaagg cgagtcatgg    1680
caagactttg tgcggaacaa cgccaagtca taccgctgtg ctctcctctc acatcgcgac    1740
ggggctaaag tgcatctcgg cacccgccca acagagaaac agtacgaaac cctgaaaat     1800
cagctcgcgt tcctgtgtca gcaaggcttc tccctggaga acgcactgta cgctctgtcc    1860
gccgtgggcc actttacact gggctgcgta ttggaggaac aggagcatca agtagcaaaa    1920
gaggaaagag agacacctac caccgattct atgccccac ttctgaagca agcaattgag     1980
ctgttcgacc ggcagggagc cgaacctgcc ttccttttcg gcctgaact aatcatatgt     2040
ggcctggaga aacagctaaa gtgcgaaagc ggcgggccgg ccgacgccct tgacgatttt   2100
gacttagaca tgctcccagc cgatgccctt gacgactttg accttgatat gctgcctgct    2160
gacgctcttg acgatttga ccttgacatg ctccccgggt aactaagtaa ggatcatctt     2220
aattaaatcg ataaggatct ggccgcctcg gcctaatcaa cctctggatt acaaaatttg    2280
tgaaagattg actggtattc ttaactatgt tgctccttt agcgtatgtg atacgctgc     2340
tttaatgcct ttgtatcatg ctattgcttc ccgtatggct ttcatttct cctccttgta    2400
taaatcctgg ttgctgtctc tttatgagga gttgtggccc gttgtcaggc aacgtggcgt    2460
ggtgtgcact gtgtttgctg acgcaacccc cactggttgg ggcattgcca ccacctgtca    2520
gctcccttcc gggactttcg ctttcccct cctattgcc acggcggaac tcatcgccgc     2580
ctgccttgcc cgctgctgga caggggctcg gctgttgggc actgacaatt ccgtggtgtt    2640
gtcggggaaa tcatcgtcct ttccttggct gctcgcctgt gttgccacct ggattctgcg    2700
cgggacgtcc ttctgctacg tcccttcggc cctcaatcca gcggaccttc cttcccgcgg    2760
cctgctgccg gctctgcggc ctcttccgcg tcttcgcctt cgccctcaga cgagtcggat    2820
ctcccttggg ccgcctccc cgccagacat gataagatac attgatgagt ttggacaaac    2880
cacaactaga atgcagtgaa aaaatgcttt tatttgtgaa atttgtgatg ctattgcttt    2940
atttgtaacc attataagct gcaataaaca agttaacaac aacaattgca ttcattttat    3000
gtttcaggtt cagggggaga tgtgggaggt ttttaaagc aagtaaaacc tctacaaatg    3060
tggtaactag cgcgtgcggc cgcaggaacc cctagtgatg gagttggcca ctccctctct    3120
gcgcgctcgc tcgctcactg aggccggcg accaaaggtc gcccgacgcc cgggctttgc     3180
ccgggcggcc tcagtgagcg agcgagcgcg cagctgcctg caggatccca atggcgcgcc    3240
gagcttggct cgagcatggt catagctgtt tcctgtgtga aattgttatc cgctcacaat    3300
tccacacaac atacgagccg gaagcataaa gtgtaaagcc tggggtgcct aatgagtgag    3360
ctaactcaca ttaattgcgt tgcgctcact gcccgctttc cagtcgggaa acctgtcgtg    3420
ccagctgcat taatgaatcg gccaacgcgc gggagaggc ggtttgcgta ttgggcgctc    3480
ttccgcttcc tcgctcactg actcgctgcg ctcggtcgtt cggctgcggc gagcggtatc    3540
agctcactca aaggcggtaa tacggttatc cacagaatca gggataacg caggaaagaa     3600
catgtgagca aaaggccagc aaaaggccag gaaccgtaaa aaggccgcgt tgctggcgtt    3660
tttccatagg ctccgccccc ctgacgagca tcacaaaaat cgacgctcaa gtcagaggtg    3720
gcgaaacccg acaggactat aaagatacca ggcgtttccc cctggaagct ccctcgtgcg    3780
ctctcctgtt ccgaccctgc cgcttaccgg atacctgtcc gcctttctcc cttcgggaag    3840
cgtggcgctt tctctatagct cacgctgtag gtatctcagt tcggtgtagg tcgttcgctc    3900
caagctgggc tgtgtgcacg aaccccccgt tcagcccgac cgctgcgcct tatccggtaa    3960
ctatcgtctt gagtccaacc cggtaagaca cgacttatcg ccactggcag cagccactgg    4020
taacaggatt agcagagcga ggtatgtagg cggtgctaca gagttcttga agtggtggcc    4080
taactacggc tacactagaa gaacagtatt tggtatctgc gctctgctga agccagttac    4140
cttcggaaaa agagttggta gctcttgatc cggcaaacaa accaccgctg gtagcggtgg    4200
ttttttttgtt tgcaagcagc agattacgcg cagaaaaaaa ggatctcaag aagatccttt    4260
gatcttttct acggggtctg acgctcagtg gaacgaaaac tcacgttaag ggattttggt    4320
catgagatta tcaaaaagga tcttcaccta gatccttta aattaaaaat gaagttttaa    4380
atcaatctaa agtatatatg agtaaacttg gtctgacagt tagaaaaact catcgagcat    4440
caaatgaaac tgcaatttat tcatatcagg attatcaata ccatattttt gaaaaagccg    4500
tttctgtaat gaaggagaaa actcaccgag gcagttccat aggatggcaa gatcctggta    4560
tcggtctgcg attccgactc gtccaacatc aatacaacct attaattcc cctcgtcaaa    4620
aataaggtta tcaagtgaga aatcaccatg agtgacgact gaatccggtg agaatggcaa    4680
aagtttatgc atttctttcc agacttgttc aacaggccag ccattacgct cgtcatcaaa    4740
atcactcgca tcaaccaaac cgttattcat tcgtgattgc gcctgagcga acgaaatac    4800
gcgatcgctg ttaaaaggac aattacaaac aggaatcgaa tgcaaccggc gcaggaacac    4860
tgccagcgca tcaacaatat tttcacctga atcaggatat tcttctaata cctggaatgc    4920
tgttttccca gggatcgcag tggtgagtaa ccatgcatca tcaggagtac ggataaaatg    4980
cttgatggtc ggaagaggca taattccgt cagccagttt agtctgacca tctcatctgt     5040
aacatcattg gcaacgctac ctttgccatg tttcagaaac aactctggcg catcgggctt    5100
cccatacaat cgatagattg tcgcacctga ttgcccgaca ttatcgcgag cccatttata    5160
cccatataaa tcagcatcca tgttggaatt taatcgcggc ctagagcaag acgtttcccg    5220
ttgaatatgg ctcatactct tcctttttca atattattga agcatttatc agggttattg    5280
tctcatgagc ggatacatat ttgaatgtat ttagaaaaat aaacaaatag gggttccgcg    5340
cacatttccc cgaaaagtgc cacctgacgt ctaagaaacc attattatca tgacattaac    5400
ctataaaaat aggcgtatca cgaggccctt ttgtc                              5435
```

SEQ ID NO: 22          moltype = DNA   length = 141
FEATURE                Location/Qualifiers
source                 1..141
                       mol_type = other DNA

```
                        organism = synthetic construct
SEQUENCE: 22
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca  120
actccatcac tagggggttcc t                                           141

SEQ ID NO: 23           moltype = DNA   length = 589
FEATURE                 Location/Qualifiers
source                  1..589
                        mol_type = other DNA
                        organism = synthetic construct
SEQUENCE: 23
aatcaacctc tggattacaa aatttgtgaa agattgactg gtattcttaa ctatgttgct   60
cctttacgc tatgtggata cgctgcttta atgcctttgt atcatgctat tgcttcccgt  120
atggctttca tttctcctc cttgtataaa tcctggttgc tgtctcttta tgaggagttg  180
tggcccgttg tcaggcaacg tggcgtggtg tgcactgtgt ttgctgacgc aaccccccact 240
ggttgggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttcctttc ccgcggcctg ctgccggctc tgcggcctct tccgcgtctt  540
cgccttcgcc ctcagacgag tcggatctcc ctttgggccg cctccccgc               589

SEQ ID NO: 24           moltype = DNA   length = 204
FEATURE                 Location/Qualifiers
source                  1..204
                        mol_type = other DNA
                        organism = synthetic construct
SEQUENCE: 24
gtgatgcggt tttggcagta catcaatggg cgtggatagc ggtttgactc acggggattt   60
ccaagtctcc accccattga cgtcaatggg agtttgtttt ggcaccaaaa tcaacgggac  120
tttccaaaat gtcgtaacaa ctccgcccca ttgacgcaaa tgggcggtag cgtgtacgg   180
tgggaggtct atataagcag agct                                        204

SEQ ID NO: 25           moltype = DNA   length = 380
FEATURE                 Location/Qualifiers
source                  1..380
                        mol_type = other DNA
                        organism = synthetic construct
SEQUENCE: 25
gacattgatt attgactagt tattaatagt aatcaattac ggggtcatta gttcatagcc   60
catatatgga gttccgcgtt acataactta cggtaaatgg cccgcctggc tgaccgccca  120
acgacccccg cccattgacg tcaataatga cgtatgttcc catagtaacg ccaatagggg  180
ctttccattg acgtcaatgg gtggagtatt tacgctaaac tgcccacttg gcagtacatc  240
aagtgtatca tatgccaagt acgccccta ttgacgtcaa tgacggtaaa tggcccgcct  300
ggcattatgc ccagtacatg accttatggg actttcctac ttggcagtac atctacgtat  360
tagtcatcgc tattaccatg                                             380

SEQ ID NO: 26           moltype = DNA   length = 747
FEATURE                 Location/Qualifiers
source                  1..747
                        mol_type = other DNA
                        organism = synthetic construct
SEQUENCE: 26
atgtcccgct tggataagag caaggtaata aatagcgcac tcgaactcct caacggcgtg   60
ggcatcgaag gtctgactac tcgaaagctc gcccagaaat tgggtgtgga gcaacctaca  120
ttgtattggc atgtcaagaa caaaagagcc ctgctgacg ctcttcctat tgaaatgctt   180
gacaggcatc acactcattc ctgccccctt gaggtcgaga gttggcaaga ttttctccga  240
aacaatgcaa agtcctaccg ctgcgcactt ttgtcccata gggatggagc aaaagtgcac  300
ctgggaacca ggccaacaga gaaacaatac gagactctcg agaaccagtt ggctttcttg  360
tgccaacagg ggttctcact tgaaaatgcc ctttacgcac tgtcagccgt ggacattttt  420
accctggggt gcgttcttga ggagcaagaa catcaggttg ctaaggagga gcgcgagact  480
ccaaccactg attctatgcc ccctttgctg aaacaggcca ttgaacttttt cgatagacag  540
ggtgctgaac ctgcctttct cttcgggttg agctgatta tttgtggtct cgaaaaacag  600
ctgaaatgtg aaagtggtgg ccctactgac gccctcgatg atttcgacct ggatatgctg  660
ccagccgatg cacttgatga tttcgatttg gatatgcttc cagccgacgc actggacgac  720
ttcgatttgg acatgcttcc cggttaa                                      747

SEQ ID NO: 27           moltype = AA   length = 248
FEATURE                 Location/Qualifiers
source                  1..248
                        mol_type = protein
                        organism = synthetic construct
SEQUENCE: 27
MSRLDKSKVI NSALELLNGV GIEGLTTRKL AQKLGVEQPT LYWHVKNKRA LLDALPIEML   60
DRHHTHSCPL EVESWQDFLR NNAKSYRCAL LSHRDGAKVH LGTRPTEKQY ETLENQLAFL  120
CQQGFSLENA LYALSAVGHF TLGCVLEEQE HQVAKEERET PTTDSMPPLL KQAIELFDRQ  180
GAEPAFLFGL ELIICGLEKQ LKCESGGPTD ALDDFDLDML PADALDDFDL DMLPADALDD  240
FDLDMLPG                                                           248
```

```
SEQ ID NO: 28        moltype = DNA  length = 5435
FEATURE              Location/Qualifiers
source               1..5435
                     mol_type = other DNA
                     organism = synthetic construct
SEQUENCE: 28
tcgcgcgttt cggtgatgac ggtgaaaacc tctgacacat gcagctcccg gagactgtca   60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt gacgcgtatt gggatactat  420
ggttgctttg acgtatgcgg tgtgaaatac cgcacagatg cgtaaggaga aaataccgca  480
tcaggcgccc ctgcaggcag ctgcgcgctc gctcgctcac tgaggccgcc cgggcaaagc  540
ccgggcgtcg ggcgaccttt ggtcgcccgg cctcagtgag cgagcgagcg cgcagagagg  600
gagtggccaa ctccatcact aggggttcct gcggccgctc ggtccgcacg atctcaattc  660
ggccattacg gccggatccg gctcgaggag cttggcccat tgcatacgtt gtatccatat  720
cataatatgt acatttatat tggctcatgt ccaacattac cgccatgttg acattgatta  780
ttgactagtt attaatagta atcaattacg ggtcattag ttcatagccc atatatggag  840
ttccgcgtta cataacttac ggtaaatggc ccgcctggct gaccgcccaa cgacccccgc  900
ccattgacgt caataatgac gtatgttccc atagtaacgc caatagggac tttccattga  960
cgtcaatggg tggagtattt acgctaaact gcccacttgg cagtacatca agtgtatcat 1020
atgccaagta cgcccctat tgacgtcaat gacggtaaat ggcccgcctg gcattatgcc 1080
cagtacatga ccttatggga cttttcctact tggcagtaca tctacgtatt agtcatcgct 1140
attaccatgg tgatgcggtt ttggcagtac atcaatgggc gtggatagcg gtttgactca 1200
cggggatttc caagtctcca ccccattgac gtcaatggga gtttgttttg gcaccaaaat 1260
caacgggact ttccaaaatg tcgtaacaac tccgccccat tgacgcaaat gggcggtagg 1320
cgtgtacggt gggaggtcta tataagcaga gctcgtttag tgaaccgtca gatcgcctgg 1380
agacgccatc cacgctgttt tgacctccat agaagacacc gggaccgatc cagcctccgc 1440
ggccccgaat tcaccatgtc ccgcttggat aagagcaagg taataaatag cgcactcgaa 1500
ctcctcaacg gcgtgggcat cgaaggtctg actactcgaa agctcgccca gaaattgggt 1560
gtggagcaac ctacattgta ttggcatgtc aagaacaaaa gagccgctgc ggacgctctt 1620
cctattgaaa tgcttgacag gcatcacact cattcctgcc ccccttgaggt cgagagttga 1680
caagattttc tccgaaacaa tgcaaagtcc taccgctgcg cacttttgtc ccataggat 1740
ggagcaaaag tgcacctggg aaccaggcca acagagaaac aatacgagac tctcgagaac 1800
cagttggctt tcttgtgcca acaggggttc tcacttgaaa atgcccttta cgcactgtca 1860
gccgttggac attttaccct ggggtgcgtt cttgaggagc aagaacatca ggttgctaag 1920
gaggagcgcg agactccaac cactgattct atgccacctt tgctgaaaca ggccattgaa 1980
cttttcgata gacagggtgc tgaacctgcc tttctcttcg ggttggagct gattatttgt 2040
ggtctcgaaa acagctgaa atgtgaaagt ggtggcccta ctgacgccct cgatgatttc 2100
gacctggata tgctgccagc cgatgcactt gatgatttcg atttggatat gcttccagcc 2160
gacgcactgg acgacttcga tttgacatg cttcccggtt aactaagtaa ggatcatctt 2220
aattaaatcg ataaggatct ggccgcctcg gcctaatcaa cctctggatt acaaaatttg 2280
tgaaagattg actggtattc ttaactatgt tgctcctttt acgctatgtg gatacgctgc 2340
tttaatgcct ttgtatcatg ctattgcttc ccgtatggct ttcattttct cctccttgta 2400
taaatcctgg ttgctgtctc tttatgagga gttgtggccc gttgtcaggc aacgtggcgt 2460
ggtgtgcact gtgtttgctg acgcaacccc cactggttgg ggcattgcca ccacctgtca 2520
gctccttttc cgggactttcg ctttccccct cctattgcc acggcggaac tcatcgccgc 2580
ctgccttgcc cgctgctgga caggggctcg gctgttgggc actgacaatt ccgtggtgtt 2640
gtcggggaaa tcatcgtcct ttccttggct gctcgcctgt gttgccacct ggattctgcg 2700
cgggacgtcc ttctgctacg tcccttcggc cctcaatcca gcggaccttc cttcccgcgg 2760
cctgctgccg gctctgcggc ctcttccgcg tcttcgcctt cgccctcaga cgagtcggat 2820
ctcccttggg gccgcctccc cgccagacat gataagatac attgatgagt ttggacaaac 2880
cacaactaga atgcagtgaa aaaaatgctt tatttgtgaa atttgtgatg ctattgcttt 2940
atttgtaacc attataagct gcaataaaca agttaacaac aacaattgca ttcattttat 3000
gtttcaggtt cagggggaga tgtgggaggt tttttaaagc aagtaaaacc tctacaaatg 3060
tggtaactag cgcgtgcggc cgcaggaacc cctagtgatg gagttggcca ctccctctct 3120
gcgcgctcgc tcgctcactg aggccgggcg accaaaggtc gcccgacgcc cgggctttgc 3180
ccgggcggcc tcagtgagcg agcgagcgcg cagctgcctg caggatccca atggcgcgcc 3240
gagcttggct cgagcatggt catagctgtt tcctgtgtga aattgttatc cgctcacaat 3300
tccacacaac atacgagccg gaagcataaa gtgtaaagcc tggggtgcct aatgagtgag 3360
ctaactcaca ttaattgcgt tgcgctcact gcccgctttc cagtcgggaa acctgtcggt 3420
ccagctgcat taatgaatcg gccaacgcgc gggagaggc ggtttgcgta ttgggcgctg 3480
ttccgcttcc tcgctcactg actcgctgcg ctcggtcgtt cggctgcggc gagcggtatc 3540
agctcactca aaggcggtaa tacgttatc cacagaatca ggggataacg caggaaagaa 3600
catgtgagca aaaggccagc aaaaggccag gaaccgtaaa aaggccgcgt tgctggcgtt 3660
ttttccatagg ctccgcccc ctgacgagca tcacaaaaat cgacgctcaa gtcagaggtg 3720
gcgaaacccg acaggactat aaagatacca ggcgtttccc cctggaagct ccctcgtgcg 3780
ctctcctgtt ccgaccctgc cgcttaccgg atacctgtcc gcctttctcc cttcgggaag 3840
cgtggcgctt tctcatagct cacgctgtag gtatctcagt tcggtgtagg tcgttcgctc 3900
caagctgggc tgtgtgcacg aaccccccgt tcagcccgac cgctgcgcct tatccggtaa 3960
ctatcgtctt gagtccaacc cggtaagaca cgacttatcg ccactggcag cagccactgg 4020
taacaggatt agcagagcga ggtatgtagg cggtgctaca gagttcttga agtggtggcc 4080
taactacggc tacactagaa gaacagtatt tggtatctgc gctctgctga gccagttacc 4140
ttcggaaaa agagttggta gctcttgatc cggcaaacaa accaccgctg gtagcggtgg 4200
tttttttgtt tgcaagcagc agattacgcg cagaaaaaaa ggatctcaag aagatccttt 4260
gatcttttct acgggtctg acgctcagtg gaacgaaaac tcacgttaag ggattttggt 4320
```

```
catgagatta tcaaaaagga tcttcaccta gatccttta aattaaaaat gaagttttaa  4380
atcaatctaa agtatatatg agtaaacttg gtctgacagt tagaaaaact catcgagcat  4440
caaatgaaac tgcaatttat tcatatcagg attatcaata ccatattttt gaaaaagccg  4500
tttctgtaat gaaggagaaa actcaccgag gcagttccat aggatggcaa gatcctggta  4560
tcggtctgcg attccgactc gtccaacatc aatacaacct attaatttcc cctcgtcaaa  4620
aataaggtta tcaagtgaga atcaccatg agtgacgact gaatccgtg agaatggcaa   4680
aagtttatgc atttctttcc agacttgttc aacaggccag ccattacgct cgtcatcaaa  4740
atcactcgca tcaaccaaac cgttattcat tcgtgattgc gcctgagcga acgaaaatac  4800
gcgatcgctg ttaaaaggac aattacaaac aggaatcgaa tgcaaccggc gcaggaacac  4860
tgccagcgca tcaacaatat tttcacctga atcaggatat tcttctaata cctggaatgc  4920
tgttttccca gggatcgcag tggtgagtaa ccatgcatca tcaggagtac ggataaaatg  4980
cttgatggtc ggaagaggca taaattccgt cagccagttt agtctgacca tctcatctgt  5040
aacatcattg gcaacgctac ctttgccatg tttcagaaac aactctggcg catcgggctt  5100
cccatacaat cgatagattg tcgcacctga ttgcccgaca ttatcgcgag cccatttata  5160
cccatataaa tcagcatcca tgttggaatt taatcgcggc ctagagcaag acgtttcccg  5220
ttgaatatgg ctcatactct tccttttttca atattattga agcatttatc agggttattg  5280
tctcatgagc ggatacatat ttgaatgtat ttagaaaaat aaacaaatag gggttccgcg  5340
cacatttccc cgaaaagtgc cacctgacgt ctaagaaacc attattatca tgacattaac  5400
ctataaaaat aggcgtatca cgaggccctt ttgtc                             5435

SEQ ID NO: 29          moltype = DNA  length = 141
FEATURE                Location/Qualifiers
source                 1..141
                       mol_type = other DNA
                       organism = synthetic construct
SEQUENCE: 29
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc t                                            141

SEQ ID NO: 30          moltype = DNA  length = 122
FEATURE                Location/Qualifiers
source                 1..122
                       mol_type = other DNA
                       organism = synthetic construct
SEQUENCE: 30
taagatacat tgatgagttt ggacaaacca caactagaat gcagtgaaaa aaatgcttta  60
tttgtgaaat ttgtgatgct attgctttat ttgtaaccat tataagctgc aataaacaag  120
tt                                                                 122

SEQ ID NO: 31          moltype = DNA  length = 589
FEATURE                Location/Qualifiers
source                 1..589
                       mol_type = other DNA
                       organism = synthetic construct
SEQUENCE: 31
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aaccccccact  240
ggttggggca ttgccaccac ctgtcagctc ctttccggga ctttcgcttt ccccctccct  300
attgccacgg cggaactcat cgccgcctgc cttgcccgct gctgacagg ggctcggctg   360
ttgggcactg acaattccgt ggtgttgtcg gggaaatcat cgtccttcc ttggctgctc    420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgc              589

SEQ ID NO: 32          moltype = DNA  length = 141
FEATURE                Location/Qualifiers
source                 1..141
                       mol_type = other DNA
                       organism = synthetic construct
SEQUENCE: 32
aggaacccct agtgatgag ttggccactc cctctctgcg cgctcgctcg ctcactgagg   60
ccgggcgacc aaaggtcgcc cgacgcccgg gctttgcccg gcggcctcag tgagcgagc   120
gagcgcgcag ctgcctgcag g                                            141

SEQ ID NO: 33          moltype = DNA  length = 141
FEATURE                Location/Qualifiers
source                 1..141
                       mol_type = other DNA
                       organism = synthetic construct
SEQUENCE: 33
aggaacccct agtgatgag ttggccactc cctctctgcg cgctcgctcg ctcactgagg   60
ccgggcgacc aaaggtcgcc cgacgcccgg gctttgcccg gcggcctcag tgagcgagc   120
gagcgcgcag ctgcctgcag g                                            141

SEQ ID NO: 34          moltype = DNA  length = 141
FEATURE                Location/Qualifiers
```

```
source                  1..141
                        mol_type = other DNA
                        organism = synthetic construct
SEQUENCE: 34
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag ctgcctgcag g                                             141

SEQ ID NO: 35           moltype = DNA  length = 4460
FEATURE                 Location/Qualifiers
source                  1..4460
                        mol_type = other DNA
                        organism = synthetic construct
SEQUENCE: 35
ccttaattag gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc ttgtagttaa tgattaaccc gccatgctac ttatctacgt   180
agccatgctc taggaagatc ggaattcttt actccctatc agtgatagag aacgtatgaa   240
gagtttactc cctatcagtg atagagaacg tatgcagact ttactcccta tcagtgatag   300
agaacgtata aggagtttac tccctatcag tgatagagaa cgtatgacca gtttactccc   360
tatcagtgat agagaacgta tctacagttt actccctatc agtgatagag aacgtatatc   420
cagttactcc cctatcagtg atagagaacg taaagcttt aggcgtgtac ggtgggcgcc    480
tataaaagca gagctcgttt agtgaaccgt cagatcgcct ggagcaattc cacaacactt   540
ttgtcttata ccaactttcc gtaccacttc ctaccctcgt aaagcggccg cgccaccatg   600
gcgggacacc tggcttcgga tttcgccttc tcgccccctc caggtggtgg aggtgatggg   660
ccaggggggc cggagccggg ctgggttgat cctcggaacg ggctaagctt ccaaggccct   720
cctggagggc caggaatcgg gccgggggtt gggccaggct ctgaggtgtg gggagttccc   780
ccatgccccc cgccgtatga gttctgtggg ggatgcgt actgtgggcc ccaggttgga   840
gtgggggcta gtgcccaagg cggcttggag acctctcagc ctgagggcga agcaggagtc   900
ggggtggaga gcaactccga tggggcctcc ccggagccgc gcaccgtcac cctggttgcc   960
gtgaagctgg agaaggagaa gctggagcaa aacccggagg agtcccagga catcaaagct  1020
ctgcagaaag aactcgagca attgccaagc tcctgaagc agaagaggat caccctggga  1080
tatacacagg ccgatgtggg gctcaccctg ggggttctat tgggaaggt attcagccaa  1140
acgaccatct gccgctttga ggctctgcag cttagcttca agaacatgtg taagctgcgg  1200
cccttgctgc agaagtgggt ggaggaagct gacaacaatg aaaatcttca ggagatatgc  1260
aaagcagaaa ccctcgtgca ggcccgaaag agaagcgaa ccagtatcga gaaccgagtg  1320
agaggcaacc tggagaattt gttcctgcag tgcccgaaac ccacactgca gcagatcagc  1380
cacatcgccc agcagcttgg gctcgagaag gatgtggtcc gagtgtggtt ctgtaaccgg  1440
cgccagaagg gcaagcgatc aagcagcgac tatgcacaac gagaggattt tgaggctgct  1500
gggtctcctt tctcaggggg accagtgtcc tttcctctgg ccccaggggcc ccattttggt  1560
accccaggct atgggagccc tcacttcact gcactgtact cctcggtccc tttcctgag  1620
ggggaagcct ttccccctgt ctctgtcacc actctgggct ctcccatgca ttcaaacgct  1680
agcggcacgc gccacgaa cttctctctg ttaaagcaag caggagatgt tgaagaaac  1740
cccgggcctg catgcatgta caacatgatg gagacggagc tgaagccgcc gggcccgcag  1800
caaacttcgg gggcggcgg cggcaactcc accgcggcgg cggccggcgg caaccagaaa  1860
aacagcccgg accgcgtcaa gcggcccatg aatgccttca tggtgtggtc ccgcgggcag  1920
cggcgcaaga tggcccagga gaacccaag atgcacaact cggagatcag caagcgcctg  1980
ggcgccgagt ggaaactttt gtcggagacg gagaagcggc cgttcatcga cgaggctaag  2040
cggctgcgag cgctgcacat gaaggagcac ccgattata aataccgcc ccggcggaaa  2100
accaagacgc tcatgaagaa ggataagtac acgctgcccg gcgggctgct ggcccccggc  2160
ggcaatagca tggcgagcgg ggtcgggggtg ggcgccgggg taggcgggg cgtgaaccag  2220
cgcatggaca gttacgcgca catgaacggc tggagcaacg gcagctacag catgatgcag  2280
gaccagctgg gctacccgca gcacccgggc ctcaatgcgc acggcgcagc gcagatgcag  2340
cccatgcacc gctacgacgt gagcgccctg cagtacaact ccatgaccag ctcgcagacc  2400
tacatgaacg gctcgcccac ctacagcatg tcctactcag agcagggcac cctggcatg  2460
gctcttggct ccatgggttc ggtggtcaag tccgaggcca gctccagccc cctgtggtt  2520
acctcttcct cccactccag ggcgccctgc caggccgggg acctccggga catgatcagc  2580
atgtatctcc ccgcgccga ggtgccgaa cccgccgccc ccagcagact tcacatgtcc  2640
cagcactacc agagcgggcc ggtgcccggc acggccacat acggccacact gccctctca  2700
cacatggcat gcggctccgg cgagggcagg ggaagtcttc taacatgcgg ggacgtggaa  2760
gaaaatcccg gcccactcga gatggctgtc agcgacgcgc tgctcccatc tttctccacg  2820
ttcgcgtctg gcccggcggg aagggagaag acactgcgtc aagcaggtgc cccgaataac  2880
cgctggcggg aggagctctc ccacatgaag cgacttcccc cagtgcttcc cggccgcccc  2940
tatgacctgg cggcggcgac cgtggccaca gacctggagg cggcggcgac cgtggccaca  3000
tgcggcggta gcaacctggc gccctacct cggagagaga ccgaggagtt caacgatctc  3060
ctggacctgg actttattct ctccaattcg ctgacccatc ctccggagtc agtgccgcc  3120
accgtgtcct cgtcagcgtc agcctcctct tgtcgtcgc cgtcgagcag cggccctgcc  3180
agcgcgccct ccacctgcag cttcacctat cgatccgggg ccgggaacga cccgggcgtg  3240
gcgccgggcg gcacgggggg aggcctcctc tatggcaggg agtccgctcc ccctccgacg  3300
gctcccttca acctggcgga catcaacgac gtgagccct cggcggcgctt cgtggccgag  3360
ctcctgcggc cagaattgga cccggtgtac atccgcgcc agcagccgca gcgccaggt  3420
ggcgggctga tgggcaagtt cgtgctgaag cgtcgctga gcgcccctgg cagcgagtac  3480
ggcagcccgt cggtcatcag cgtcagcaaa ggcagccctg acggcagcca cccggtggtg  3540
gtggcgcct acaacggcgg gccgcgcgc acgtgcgcca agatcaagca gaggcggcct  3600
tcttcgtgca cccactggg cgctggaccc cctctcagca atggccaccg gcgggctgca  3660
cacgacttcc ccctggggcg gcagctccca gcaggacta cccgacccct gggtcttgag  3720
gaagtgctga gcagcaggga ctgtcaccct gccctgccgc ttcctcccgg cttccatccc  3780
cacccggggc caattaccc atccttcctg cccgatcaga tgcagccgca gtcccgccg  3840
ctccattacc aagagctcat gccacccggt tcctgcatgc cagaggagcc caagccaaag  3900
```

```
aggggaagac gatcgtggcc ccggaaaagg accgccaccc acacttgtga ttacgcgggc   3960
tgcggcaaaa cctacacaaa gagttcccat ctcaaggcac acctgcgaac ccacacaggt   4020
gagaaacctt accactgtga ctgggacggg tgtggatgga aattcgcccg ctcagatgaa   4080
ctgaccaggc actaccgtaa acacacgggg caccgcccgt tccagtgcca aaaatgcgac   4140
cgagcatttt ccaggtcgga ccacctcgcc ttacacatga agaggcattt ttaaatgact   4200
agtgcgcgca gcggccgacc atggcccaac ttgtttattg cagcttataa tggttacaaa   4260
taaagcaata gcatcacaaa tttcacaaat aaagcatttt tttcactgca ttctagttgt   4320
ggtttgtcca aactcatcaa tgtatcttat catgtctgga tctcggtacc ggatccaaat   4380
tcccgataag gatcttccta gagcatggct acgtagataa gtagcatggc gggttaatca   4440
ttaactacaa ggaacccta                                                4460
```

| SEQ ID NO: 36 | moltype = DNA length = 2735 |
|---|---|
| FEATURE | Location/Qualifiers |
| source | 1..2735 |
| | mol_type = other DNA |
| | organism = synthetic construct |

SEQUENCE: 36
```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgct cggtccgcac gatctcaatt cggccattac    180
ggccggatcc ggctcgagga gcttggccca ttgcatacgt tgtatccata tcataatatg    240
tacatttata ttggctcatg tccaacatta ccgccatgtt gacattgatt attgactagt    300
tattaatagt aatcaattac ggggtcatta gttcatagcc catatatgga gttccgcgtt    360
acataactta cggtaaatgg cccgcctggc tgaccgccca acgacccccg cccattgacg    420
tcaataatga cgtatgttcc catagtaacg ccaatagggg ctttccattg acgtcaatgg    480
gtggagtatt tacgctaaac tgcccacttg gcagtacatc aagtgtatca tatgccaagt    540
acgccccta ttgacgtcaa tgacggtaaa tggcccgcct ggcattatgc ccagtacatg    600
accttatggg actttcctac ttggcagtac atctacgtat tagtcatcgc tattaccatg    660
gtgatgcggt tttggcagta catcaatggg cgtggatagc ggtttgactc acggggattt    720
ccaagtctcc accccattga cgtcaatggg agtttgtttt ggcaccaaaa tcaacgggac    780
tttccaaaat gtcgtaacaa ctccgcccca ttgacgcaaa tgggcggtag gcgtgtacgg    840
tgggaggtct atataagcag agctcgttta gtgaaccgtc agatcgcctg gagacgccat    900
ccacgctgtt ttgacctcca tagaagacac cgggaccgat ccagcctccg cggccccgaa    960
ttccaccatgt ctagactgga caagacaaa atcataaaca gcgctctgga attactcaat   1020
ggagtcggta tcgaaggcct gacgacaagg aaactcgctc aaaagctggg agttgagcag   1080
cctaccctgt actggcacgt gaagaacaag cgggccctgc tcgatgccct gccaatcgag   1140
atgctggaca ggcatcatac ccacagctgc ccctggaag gcgagtcatg gcaagacttt   1200
ctgcggaaca acgccaagtc ataccgctgt gctctcctct cacatcgcga cggggctaaa   1260
gtgcatctcg gcacccgccc aacagagaaa cagtacgaaa ccctggaaaa tcagctcgcg   1320
ttcctgtgtc agcaaggctt ctcccctgga aacgcactgt acgctctgtc cgccgtgggc   1380
cactttacac tgggctgcgt attggaggaa caggagcatc aagtagcaaa agaggaaaga   1440
gagacaccta ccaccgattc tatgccccca cttctgaagc aagcaattga gctgttcgac   1500
cggcagggag ccgaacctgc cttcctttc ggcctgaaac taatcatatg tggcctgagc   1560
aaacagctaa agtgcgaaag cggcgggccg accgacgccc ttgacgattt tgacttagac   1620
atgctcccag ccgatgccct tgacgacttt gaccttgata tgctgcctgc tgacgctctt   1680
gacgattttg accttgacat gctccccggg taactaagta aggatcatct taattaaatc   1740
gataaggatc tggccgcctc ggcctaatca acctctgatt acaaaatttt gtgaaagatt   1800
gactggtatt cttaactatg ttgctccttt tacgctatgt ggatacgctg ctttaatgcc   1860
tttgtatcat gctattgctt cccgtatggc tttcattttc tcctccttgt ataaatcctg   1920
gttgctgtct ctttatgagg agttgtggcc cgttgtcagg caacgtggcg tggtgtgcac   1980
tgtgtttgct gacgcaaccc ccactggttg gggcattgcc accacctgtc agctccttc   2040
cgggactttc gctttccccc tccctattgc cacggcggaa ctcatcgccg cctgccttgc   2100
ccgctgctgg acaggggctc ggctgttggg cactgacaat tccgtggtgt tgtcggggaa   2160
atcatcgtcc tttccttggc tgctcgcctg tgttgccacc tggattctgc gcgggacgtc   2220
cttctgctac gtcccttcgg ccctcaatcc agcggaccTt ccttcccgcg gcctgctgcc   2280
ggctctgcgg cctcttccgc gtcttcgcct tcgccctcag acgagtcgga tctccctttg   2340
ggccgcctcc ccgccagaca tgataagata cattgatgag tttggacaaa ccacaactag   2400
aatgcagtga aaaaaatgct ttatttgtga aatttgtgat gctattgctt tatttgtaac   2460
cattataagc tgcaataaac aagttaacaa caacaattgc attcatttta tgtttcaggt   2520
tcagggggag atgtgggagg ttttttaaag caagtaaaac ctctacaaat gtggtaacta   2580
gcgcgtgcgg ccgcaggaac ccctagtgat ggagttggcc actccctctc tgcgcgctcg   2640
ctcgctcact gaggccgggc gaccaaaggt cgcccgacgc ccgggctttg cccgggcggc   2700
ctcagtgagc gagcgagcgc gcagctgcct gcagg                               2735
```

| SEQ ID NO: 37 | moltype = DNA length = 4946 |
|---|---|
| FEATURE | Location/Qualifiers |
| source | 1..4946 |
| | mol_type = other DNA |
| | organism = synthetic construct |

SEQUENCE: 37
```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgct cggtccgcac gatctcaatt cggccattac    180
ggccggatcc ggctcgagga gcttggccca ttgcatacgt tgtatccata tcataatatg    240
tacatttata ttggctcatg tccaacatta ccgccatgtt gacattgatt attgactagt    300
tattaatagt aatcaattac ggggtcatta gttcatagcc catatatgga gttccgcgtt    360
acataactta cggtaaatgg cccgcctggc tgaccgccca acgacccccg cccattgacg    420
tcaataatga cgtatgttcc catagtaacg ccaatagggg ctttccattg acgtcaatgg    480
gtggagtatt tacgctaaac tgcccacttg gcagtacatc aagtgtatca tatgccaagt    540
```

```
acgccccta ttgacgtcaa tgacggtaaa tggcccgcct ggcattatgc ccagtacatg    600
acttatggg actttcctac ttggcagtac atctacgtat tagtcatcgc tattaccatg    660
gtgatgcggt tttggcagta catcaatggg cgtggatagc ggtttgactc acggggattt    720
ccaagtctcc accccattga cgtcaatggg agtttgtttt ggcaccaaaa tcaacgggac    780
tttccaaaat gtcgtaacaa ctccgcccca ttgacgcaaa tgggcggtag gcgtgtacgg    840
tgggaggtct atataagcag agctcgttta gtgaaccgtc agatcgcctg gagacgccat    900
ccacgctgtt ttgacctcca tagaagacac cgggaccgat ccagcctccg cggcccgaa    960
ttcaccatgt cccgcttgga taagagcaag gtaataaata gcgcactcga actcctcaac   1020
ggcgtgggca tcgaaggtct gactactcga aagctcgccc agaaattggg tgtggagcaa   1080
cctacattgt attggcatgt caagaacaaa agagccctgc tggacgctct tcctattgaa   1140
atgcttgaca ggcatcacac tcattcctgc cccttgagg tcgagagttg gcaagatttt    1200
ctccgaaaca atgcaaagtc ctaccgctgc gcacttttgt cccatagga tggagcaaaa    1260
gtgcacctgg gaaccaggcc aacagagaaa caatacgaga ctctcgagaa ccagttggct   1320
ttcttgtgcc aacaggggtt ctcacttgaa aatgcccttt acgcactgtc agccgttgga   1380
cattttaccc tggggtgcgt tcttgaggag caagaacatc aggttgctaa gaggagcgc    1440
gagactccaa ccactgattc tatgccacct ttgctgaaac aggccattga acttttcgat   1500
agacagggtg ctgaacctgc ctttctcttc gggttggagc tgattatttg tggtctcgaa   1560
aaacagctga aatgtgaaag tggtggccct actgacgccc tcgatgattt cgacctggat   1620
atgctgccag ccgatgcact tgatgatttc gatttggata tgcttccagc cgacgcactg   1680
gacgacttcg atttggacat gcttcccggt taactaagta aggatcatct taattaaatc   1740
gataaggatc tggccgcctc ggcctaatca acctctggat tacaaaattt gtgaaagatt   1800
gactggtatt cttaactatg ttgctccttt tacgctatgt ggatacgctg ctttaatgcc   1860
tttgtatcat gctattgctt cccgtatggc tttcattttc tcctccttgt ataaatcctg   1920
gttgctgtct ctttatgagg agttgtgcc cgttgtcagg caacgtggcg tggtgtgcac    1980
tgtgttttgct gacgcaaccc ccactggttg gggcattgcc accacctgtc agctccttc   2040
cgggactttc gctttccccc tccctattgc cacggcggaa ctcatcgccg cctgccttgc   2100
ccgctgctgg acaggggctc ggctgttggg cactgacaat tccgtggtgt tgtcggggaa   2160
atcatcgtcc tttccttggc tgctcgcctg tgttgccacc tggattctgc gcgggacgtc   2220
cttctgctac gtcccttcgg ccctcaatcc agcggacctt ccttcccgcg gcctgctgcc   2280
ggctctgcgg cctcttccgc gtcttcgcct tcgccctcag acgagtcgga tctcccttg    2340
ggccgcctcc ccgccagaca tgataagata cattgatgag tttggacaaa ccacaactag   2400
aatgcagtga aaaaatgct ttatttgtga aatttgtgat gctattgctt tatttgtaac    2460
cattataagc tgcaataaac aagttaacaa caacaattgc attcatttta tgtttcaggt   2520
tcaggggag atgtgggagg ttttttaaag caagtaaaac ctctacaaat gtggtaacta    2580
gcgcgtgcg ccgcaggaac ccctagtgat ggagttggcc actccctctc tgcgcgctcg    2640
ctcgctcact gaggccgggc gaccaaaggt cgcccgacgc ccgggctttg ccgggcggc    2700
ctcagtgagc gagcgagcgc gcagctgcct gcaggatccc aatggcgcgc cgagcttgc    2760
tcgagcatgg tcatagctgt ttcctgtgtg aaattgttat ccgctcacaa ttccacacaa   2820
catacgagcc ggaagcataa agtgtaaagc ctggggtgcc taatgagtga gctaactcac   2880
attaattgcg ttgcgctcac tgcccgcttt ccagtcggga aacctgtcgt gccagctgca   2940
ttaatgaatc ggccaacgcg cggggagagg cggtttgcgt attgggcgct gttccgcttc   3000
ctcgctcact gactcgctgc gctcggtcgt tcggctgcgg cgagcggtat cagctcactc   3060
aaaggcggta atacggttat ccacagaatc aggggataac gcaggaaaga acatgtgagc   3120
aaaaggccag caaaaggcca ggaaccgtaa aaaggccgcg ttgctggcgt ttttccatag   3180
gctccgcccc cctgacgagc atcacaaaaa tcgacgctca gtcagaggt ggcgaaaccc    3240
gacaggacta taaagatacc aggcgtttcc ccctggaagc tccctcgtgc gctctcctgt   3300
tccgaccctg ccgcttaccg gatacctgtc cgcctttctc ccttcgggaa gcgtggcgct   3360
ttctcatagc tcacgctgta ggtatctcag ttcggtgtag gtcgttcgct ccaagctggg   3420
ctgtgtgcac gaaccccccg ttcagcccga ccgctgcgcc ttatccggta actatcgtct   3480
tgagtccaac ccggtaagac acgacttatc gccactggca gcagccactg gtaacaggat   3540
tagcagagcg aggtatgtag gcggtgctac agagttcttg aagtggtggc ctaactacgg   3600
ctacactaga agaacagtat ttggtatctg cgctctgctg aagccagtta ccttcggaaa   3660
aagagttggt agctcttgat ccggcaaaca aaccaccgct ggtagcggtg gtttttttgt   3720
ttgcaagcag cagattacgc gcagaaaaaa aggatctcaa gaagatcctt tgatcttttc   3780
tacgggtct gacgctcagt ggaacgaaaa ctcacgttaa gggattttgg tcatgagatt    3840
atcaaaaagg atcttcacct agatcctttt aaattaaaaa tgaagtttta aatcaatcta   3900
aagtatatat gagtaaactt ggtctgacag ttagaaaaac tcatcgagca tcaaatgaaa   3960
ctgcaatttta ttcatatcag gattatcaat accatatttt tgaaaaagcc gtttctgtaa   4020
tgaaggagaa aactcaccga gcagttcca taggatggca agatcctggt atcggtctgc    4080
gattccgact cgtccaacat caatacaacc tattaattttc ccctcgtcaa aataaggtt    4140
atcaagtgag aaatcaccat gagtgacgac tgaatccgt gagaatggca aaagtttatg    4200
catttctttc cagacttgtt caacaggcca gccattacgc tcgtcatcaa aatcactcgc    4260
atcaaccaaa ccgttattca ttcgtgattg cgcctgagcg aaacgaaata cgcgatcgct   4320
gttaaaagga caattacaaa caggaatcga atgcaaccgg cgcaggaaca ctgccagcgc   4380
atcaacaata ttttcacctg aatcaggata ttcttctaat acctggaatg ctgttttccc   4440
agggatcgca gtggtgagta accatgcatc atcaggagta cggataaaat gcttgatggt   4500
cggaagagge ataaattccg tcagccagtt tagtctgacc atctcatctg taacatcatt   4560
ggcaacgcta cctttgccat gtttcagaaa caactctggc gcatcgggct tcccatacaa   4620
tcgatagatt gtcgcacctg attgcccgac attatcgcga gcccatttat acccatataa   4680
atcagcatcc atgttggaat ttaatcgcgg cctagagcaa gacgtttccc gttgaatatg    4740
gctcatactc ttccttttc aatattattg aagcatttat cagggttatt gtctcatgag    4800
cggatacata tttgaatgta tttagaaaaa taaacaaata ggggttccgc gcacatttcc   4860
ccgaaaagtg ccacctgacg tctaagaaac cattattatc atgacattaa cctataaaaa   4920
taggcgtatc acgaggcccct tttgtc                                      4946
```